US007534763B2

(12) United States Patent
Qian et al.

(10) Patent No.: US 7,534,763 B2
(45) Date of Patent: May 19, 2009

(54) SUSTAINED RELEASE GLP-1 RECEPTOR MODULATORS

(75) Inventors: Feng Qian, Hillsborough, NJ (US); William R. Ewing, Yardley, PA (US); Claudio Mapelli, Plainsboro, NJ (US); Douglas James Riexinger, Flemington, NJ (US); Ving G. Lee, Hamilton, NJ (US); Richard B. Sulsky, West Trenton, NJ (US); Yeheng Zhu, Stockton, NJ (US); Tasir Shamsul Haque, Yardley, PA (US); Rogelio L. Martinez, Monmouth Junction, NJ (US); Vijay Naringrekar, Princeton, NJ (US); Nina Ni, Kendall Park, NJ (US); Lori S. Burton, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 83 days.

(21) Appl. No.: 11/594,531

(22) Filed: Nov. 8, 2006

(65) Prior Publication Data

US 2007/0099835 A1 May 3, 2007

Related U.S. Application Data

(63) Continuation-in-part of application No. 11/442,017, filed on May 26, 2006, and a continuation-in-part of application No. 11/170,968, filed on Jun. 30, 2005.

(60) Provisional application No. 60/809,134, filed on May 26, 2006, provisional application No. 60/684,805, filed on May 26, 2005, provisional application No. 60/585,358, filed on Jul. 2, 2004.

(51) Int. Cl.
*A61K 38/00* (2006.01)
*C07K 2/00* (2006.01)

(52) U.S. Cl. .......................... 514/2; 530/300
(58) Field of Classification Search ........................ None
See application file for complete search history.

(56) References Cited

U.S. PATENT DOCUMENTS

| 3,674,836 | A | 7/1972 | Creger |
| 3,983,140 | A | 9/1976 | Endo et al. |
| 4,027,009 | A | 5/1977 | Grier et al. |
| 4,231,938 | A | 11/1980 | Monaghan et al. |
| 4,346,227 | A | 8/1982 | Terahara et al. |
| 4,448,784 | A | 5/1984 | Glamkowski et al. |
| 4,450,171 | A | 5/1984 | Hoffman et al. |
| 4,499,289 | A | 2/1985 | Baran et al. |
| 4,613,610 | A | 9/1986 | Wareing |
| 4,647,576 | A | 3/1987 | Hoefle et al. |
| 4,681,893 | A | 7/1987 | Roth |
| 4,686,237 | A | 8/1987 | Anderson |
| 4,759,923 | A | 7/1988 | Buntin et al. |
| 4,871,721 | A | 10/1989 | Biller |
| 4,924,024 | A | 5/1990 | Biller |
| 5,006,530 | A | 4/1991 | Angerbauer et al. |
| 5,011,930 | A | 4/1991 | Fujikawa et al. |
| 5,177,080 | A | 1/1993 | Angerbauer et al. |
| 5,260,440 | A | 11/1993 | Hirai et al. |
| 5,273,995 | A | 12/1993 | Roth |
| 5,354,772 | A | 10/1994 | Kathawala |
| 5,385,929 | A | 1/1995 | Bjorge et al. |
| 5,488,064 | A | 1/1996 | Sher |
| 5,491,134 | A | 2/1996 | Sher et al. |
| 5,506,219 | A | 4/1996 | Robl |
| 5,541,204 | A | 7/1996 | Sher et al. |
| 5,594,016 | A | 1/1997 | Ueno et al. |
| 5,595,872 | A | 1/1997 | Wetterau, II et al. |
| 5,612,359 | A | 3/1997 | Murugesan |
| 5,614,492 | A | 3/1997 | Habener |
| 5,686,104 | A | 11/1997 | Mills et al. |
| 5,691,322 | A | 11/1997 | Robl |
| 5,712,279 | A | 1/1998 | Biller et al. |
| 5,712,396 | A | 1/1998 | Magnin et al. |
| 5,739,135 | A | 4/1998 | Biller et al. |
| 5,753,675 | A | 5/1998 | Wattanasin |
| 5,760,246 | A | 6/1998 | Biller et al. |
| 5,770,615 | A | 6/1998 | Cheng et al. |
| 5,776,983 | A | 7/1998 | Washburn et al. |
| 5,827,875 | A | 10/1998 | Dickson, Jr. et al. |
| 5,885,983 | A | 3/1999 | Biller et al. |
| 5,962,440 | A | 10/1999 | Sulsky |
| 5,998,375 | A | 12/1999 | Thøgersen et al. |
| 6,043,265 | A | 3/2000 | Murugesan et al. |
| 6,548,667 | B2 | 4/2003 | Park et al. |

(Continued)

FOREIGN PATENT DOCUMENTS

EP 0 142 146 5/1985

(Continued)

OTHER PUBLICATIONS

U.S Appl. No. 11/442,017, filed May 26, 2006, Ewing et al.

(Continued)

*Primary Examiner*—Andrew D Kosar
(74) *Attorney, Agent, or Firm*—Brian C. Carey

(57) ABSTRACT

The present invention provides novel pharmaceutical compositions comprising a human glucagon-like peptide-1 (GLP-1)-receptor modulator as an active ingredient in a sustained release formulation.

25 Claims, 17 Drawing Sheets

U.S. PATENT DOCUMENTS

| | | | |
|---|---|---|---|
| 6,737,417 | B2 | 5/2004 | Jo et al. |
| 2002/0019419 | A1 | 2/2002 | De Laszlo et al. |
| 2003/0195157 | A1 | 10/2003 | Natarajan et al. |
| 2004/0127423 | A1 | 7/2004 | Natarajan et al. |
| 2006/0004222 | A1 | 1/2006 | Mathur et al. |
| 2006/0287242 | A1 | 12/2006 | Ewing et al. |

FOREIGN PATENT DOCUMENTS

| | | |
|---|---|---|
| EP | 0 221 025 | 5/1987 |
| FR | 2 596 393 | 10/1987 |
| GB | 2 205 837 | 12/1988 |
| WO | WO 86/03488 | 6/1986 |
| WO | WO 86/07054 | 12/1986 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO 00/34332 | 6/2000 |
| WO | WO 03/033671 A | 4/2003 |
| WO | WO 2004/094461 | 11/2004 |
| WO | WO 2004/096179 | 11/2004 |
| WO | WO 2006/014287 | 2/2006 |
| WO | WO 2006/127948 | 11/2006 |
| WO | WO 2007 017892 | 2/2007 |

OTHER PUBLICATIONS

Ashworth, D.M. et al., "2-Cyanopyrrolidides as Potent, Stable Inhibitors of Dipeptidyl Peptidase IV", Bioorganic & Medicinal Chemistry Letters, vol. 6, No. 10, pp. 1163-1166 (1996).

Ashworth, D.M. et al., "4-Cyanothiazolidides as Very Potent, Stable Inhibitors of Dipeptidyl Peptidase IV", Bioorganic & Medicinal Chemistry Letters, vol. 6, No. 22, pp. 2745-2748 (1996).

Atherton, E. et al., Chapter 1: "The Fluorenylmethoxycarbonyl Amino Protecting Group", The Peptides: Analysis, Synthesis, Biology, vol. 9: Special Methods in Peptide Synthesis, Part C, Academic Press, Inc., publ., Udenfriend, S. et al., eds., pp. 1-38 (1987).

Barany, G. et al., Chapter 1: "Solid-Phase Peptide Synthesis", The Peptides: Analysis, Synthesis, Biology, vol. 2: Special Methods in Peptide Synthesis, Part A, Academic Press, Inc., publ., Gross, E. et al., eds., pp. 1-284 (1979).

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, No. 1, pp. 1-40 (1996).

Burgess, K. et al., "Solid Phase Syntheses of Oligoureas", J. Am. Chem. Soc., vol. 119, No. 7, pp. 1556-1564 (1997).

Byrne, M.M. et al., "Inhibitory effects of hyperglycaemia on fed jejunal motility: potential role of hyperinsulinaemia", European Journal of Clinical Investigation, vol. 28, pp. 72-78 (1998).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", Journal of the American Chemical Society, vol. 98, No. 5, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Davern, P. et al., "Chemical and Biological Reactivity of Sulfamidopenicillins", J. Chem. Soc. Perkin Trans. 2, pp. 381-387 (1994).

Fehder, W.P. et al., "Development and Evaluation of a Chromatographic Procedure for Partial Purification of Substance P with Quantitation by an Enzyme Immunoassay", Clinical and Diagnostic Laboratory Immunology, vol. 5, No. 3, pp. 303-307 (1998).

Fehrentz, J.-A. et al., "An Efficient Synthesis of Optically Active α-(t-Butoxycarbonylamino)-aldehydes from α-Amino Acids", Synthesis, pp. 676-678 (1983).

Fingl, E. et al., Section I: "Introduction", Chapter I: "General Principles", The Pharmacological Basics of Therapeutics, 5$^{th}$ Ed., Macmillan Publishing Co., Inc., publ., Goodman, L.S. et al., eds., pp. 1-46 (1975).

Flint, A. et al., "Glucagon-like Peptide 1 Promotes Satiety and Suppresses Energy Intake in Humans", J. Clin. Invest., vol. 101, No. 3, pp. 515-520 (1998).

Gennaro, A.R., ed., Remington's Pharmaceutical Sciences, 18$^{th}$ Ed., Mack Publishing Company, publ., pp. xv-xvi (table of contents) (1990).

Gennaro, A.R., ed., Remington: Practice of the Science and Pharmacy, 19$^{th}$ Ed., Mack Publishing Company, publ., pp. xv-xvi (table of contents) (1995).

Gennaro, A.R., ed., Remington: Practice of the Science and Pharmacy, vol. 11, 19$^{th}$ Ed., Mack Publishing Company, publ., pp. vii-viii (table of contents) (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Gluschankof, P. et al., "Enzymes processing somatostatin precursors: An Arg-Lys esteropeptidase from the rat brain cortex converting somatostatin-28 into somatostatin-14", Proc. Natl. Acad. Sci. USA, vol. 81, pp. 6662-6666 (1984).

Gutzwiller, J.-P. et al., "Glucagon-like peptide-1: a potent regulator of food intake in humans", Gut, vol. 44, pp. 81-86 (1999).

Hara, S., "Ileal Na$^+$/bile acid cotransporter inhibitors", Drugs of the Future, vol. 24, No. 4, pp. 425-430 (1999).

Holst, J.J., "Glucagon-like Peptide-1, A Gastrointestinal Hormone with a Pharmaceutical Potential", Current Medicinal Chemistry, vol. 6, No. 11, pp. 1005-1017 (1999).

Ito, Y. et al., "Difference in cholesterol-binding and cytolytic activities between listeriolysin O and seeligeriolysin O: a possible role of alanine residue in tryptophan-rich undecapeptide", FEMS Microbiology Letters, vol. 203, pp. 185-189 (2001).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).

King, D.S. et al., "A cleavage method which minimizes side reactions following Fmoc solid phase peptide synthesis", Int. J. Peptide Protein Res., vol. 36, pp. 255-266 (1990).

Krause, B.R. et al., Chapter 6: ACAT Inhibitors: "Physiologic Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-α (PPAR-α) and PPAR-γ: Effect of PPAR-α Activation on Abnormal Lipid Metabolism in Liver of Zucker Fatty Rats", Diabetes, vol. 47, pp. 1841-1847 (1998).

Näslund, E. et al., "Energy intake and appetite are suppressed by glucagon-like peptide-1 (GLP-1) in obese men", International Journal of Obesity, vol. 23, pp. 304-311 (1999).

Nicolosi, R.J. et al., "The ACAT inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, pp. 243-249 (1977).

Rosenblum, S.B. et al., "Discovery of 1-(4-Fluorophenyl)-(3r)-[3-(4-fluorophenyl)-(3S)-hydroxypropyl]-(4S)-(4-hydroxphenyl)-2-azetidinone (SCH58235): A Designed, Potent, Orally Active Inhibitor of Cholesterol Absorption", J. Med. Chem., vol. 41, No. 6, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of the Future, vol. 24, No. 1, pp. 9-15 (1999).

Stewart, J.M. et al., Solid Phase Peptide Synthesis, 2$^{nd}$ Ed., Pierce Chemical Company, publ., pp. vii-xi (table of contents), 92 (1984).

Stoffers, D.A. et al., "Insulinotropic Glucagon-Like Peptide 1 Agonists Stimulate Expression of Homeodomain Protein IDX-1 and Increase Islet Size in Mouse Pancreas", Diabetes, vol. 49, pp. 741-748 (2000).

Stout, D.M. et al., "Inhibitors of Acyl-CoA:Cholesterol $O$-Acyl Transferase (ACAT) as Hypocholesterolemic Agents. 6. The First Water-Soluble ACAT Inhibitor with Lipid-Regulating Activity. Inhibitors of Acyl-CoA:Cholesterol Acyltransferase (ACAT). 7. Development of a Series of Substituted $N$-Phenyl-$N'$-[(1-phenylcyclopentyl)-methyl]ureas with Enhanced Hypocholestrolemic Activity", Chemtracts—Organic Chemistry, vol. 8, pp. 359-362 (1995).

Wettergren, A. et al., "Truncated GLP-1 (Proglucagon 78-107-Amide) Inhibits Gastric and Pancreatic Functions in Man", Digestive Diseases and Sciences, vol. 38, No. 4, pp. 665-673 (1993).

Yamada, M. et al., "A Potent Dipeptide Inhibitor of Dipeptidyl Peptidase IV", Bioorganic & Medicinal Chemistry Letters, vol. 8, pp. 1537-1540 (1998).

Pridel, et al., "Absorption of glucagon-like peptide-1 can be protracted by zinc or protamine", International Journal of Pharmaceutics, XP003937789, vol. 136, pp. 53-59 (1996).

Krayenbühl, et al., "Crystalline protamine insulin", Reports of the Steno Memorial Hospital and the Nordisk Insulin Laboratory, XP009067663, vol. 1, pp. 60-73 (1946).

A

B

A

B

SEM images of A: lyophilized Zn/compound of SEQ ID NO: 9 (Zn: compound of SEQ ID NO: 9=3:1), without mannitol; and B: lyophilized Zn/ compound of SEQ ID NO: 9 (Zn: compound of SEQ ID NO: 9=3:1), with 2.5% w/v mannitol

A

B

SUSTAINED RELEASE GLP-1 RECEPTOR MODULATORS

This application claims priority to U.S. Provisional Patent Application Ser. No. 60/809,134, filed May 26, 2006; is a continuation-in-part of U.S. patent application Ser. No. 11/442,017, filed May 26, 2006, which claims priority to U.S. Provisional Patent Application Ser. No. 60/684,805, filed May 26, 2005; and is a continuation-in-part of U.S. patent application Ser. No. 11/170,968, filed Jun. 30, 2005, which claims priority to U.S. Provisional Application Ser. Nos. 60/684,805, filed May 26, 2005, and 60/585,358, filed Jul. 2, 2004. Each priority application is hereby incorporated by reference in its entirety.

FIELD OF THE INVENTION

The subject matter disclosed and claimed herein relates to sustained release compositions to prolong the delivery of active ingredients to a subject. More particularly, disclosed herein are compositions comprising biologically-active human glucagon-like peptide-1 (GLP-1) receptor modulators formulated for sustained release and methods of making and using the same. These compositions are useful for the amelioration of diabetes and diabetes-associated conditions.

BACKGROUND OF THE INVENTION

GLP-1 is an important gut hormone with regulatory function in glucose metabolism and gastrointestinal secretion and metabolism. Human GLP-1 is a 30 amino acid peptide originating from preproglucagon, which is synthesized for example, in the L-cells in the distal ileum, in the pancreas and in the brain. Processing of preproglucagon to yield GLP-1 (7-36) amide and GLP-2 occurs mainly in the L-cells and the brainstem. GLP-1 is normally secreted in response to the intake of food, particularly carbohydrates and lipids, and it has been identified as a very potent and efficacious stimulator of glucose-dependent insulin release with a reduced risk to induce hypoglycemia. GLP-1 also lowers plasma glucagon concentrations, slows gastric emptying, stimulates insulin biosynthesis and enhances insulin sensitivity (Nauck, *Horm. Metab. Res.*, 29(9):411-416 (1997)) It also enhances the ability of the pancreatic beta-cells to sense and respond to glucose in subjects with impaired glucose tolerance (Byrne, M. M. et al., *Eur. J. Clin. Invest.*, 28(1):72-78 (1998)). The insulinotropic effect of GLP-1 in humans increases the rate of glucose metabolism partly due to increased insulin levels and partly due to enhanced insulin sensitivity (D'Alessio, *J Clin Invest.* 93(5):2263-66 (1994)). Inhibition of glucagon release is thought to be an additional mechanism which contributes to the improvements in glucose homeostasis observed following treatment of type II diabetic patients with GLP-1 (Nauck, M. A. et al., *Diabetologia,* 36(8):741-744 (1993)). These pharmacological properties make GLP-1 a highly desirable therapeutic agent for the treatment of type-II diabetes.

Research has been conducted to develop drug delivery techniques and compositions to allow agent delivery at rates that allow maintenance of drug concentrations at therapeutically effective levels for extended periods of time. For example, one method of making delayed or sustained release formulations involves coating the tablet with a release-delaying coating, or coating individual granules with such a coating, and compressing these coated granules into tablets. However, during preparation of delayed, or sustained release drug formulations, use of relatively high concentrations of soluble polymers may result in slow drug dissolution, poor or variable drug release, poor or variable absorption, and acid instability over the range of the pH environment in the gastrointestinal (GI) tract.

Research has been conducted to develop drug delivery techniques and compositions to allow agent delivery at rates that allow maintenance of drug concentrations at therapeutically effective levels for extended periods of time. For example, biodegradable polymeric drug delivery formulations have been developed and utilized for the controlled in vivo release of drugs. See, e.g., U.S. Pat. Nos. 3,773,919 and 4,767,628. Such biodegradable polymeric formulations are designed to slowly release an entrapped drug by diffusion through a polymer matrix and/or as the biodegradable polymer is depolymerized. International Publication No. WO 94/15587 concerns sustained release ionic molecular conjugates of polyesters and drugs. Since both diffusion and polyester degradation may control the release process, the surface area of the polymeric particles can influence the release profile of the entrapped drug. Thus, such particles should be of similar size and shape to insure reproducible surface area.

Therapy involving the use of GLP-1-type molecules presents a significant problem because the serum half-life of GLP-1 peptides is short. For example, GLP-1 (7-37) has a serum half-life of less than 5 minutes. Thus, there exists a need to extend the half-life of GLP-1 peptides to enhance their therapeutic effect. The subject matter disclosed and claimed herein fulfills this need by providing novel pharmaceutical compositions comprising a metal ion (e.g., zinc) and a GLP-1 receptor modulator adduct in a sustained release formulation. As such, these compositions are useful for the amelioration of diabetes and related conditions. The compositions are appealing to patients and physicians because a sustained release composition requires less frequent administration as compared to other formulations.

SUMMARY OF THE INVENTION

The subject matter described and claimed herein relates to a sustained release pharmaceutical composition or a pharmaceutically-acceptable salt thereof, wherein said pharmaceutical composition comprises: an effective amount of a GLP-1 receptor modulator, or salt thereof, as an active ingredient, wherein said GLP-1 receptor modulator comprises at least ten amino acids, and further comprises at least one biphenylalanine residue, or at least one phenyl-heteroaryl-alanine analog, and a metal ion, a protamine vehicle, or a combination thereof. Additional embodiments include sustained release compositions wherein said GLP-1 receptor modulator is a compound selected from the group consisting of SEQ ID NOs 9, 15, 118, 151, and 158.

The sustained release pharmaceutical compositions may be prepared by a number of particle formation techniques including, but not limited to, spray drying, spray-freeze drying, supercritical fluid precipitation, solvent or pH induced precipitation and/or lyophilization.

A preferred metal ion for use in the GLP-1 sustained release formulations is a divalent metal cation, such as zinc, and may be selected from pharmaceutically acceptable zinc salts including, but not limited to, zinc chloride and zinc acetate. The sustained release pharmaceutical composition is preferably prepared in an aqueous suspension, but may be prepared in any pharmaceutically acceptable vehicle. The sustained release pharmaceutical composition is preferably delivered by subcutaneous injection using a syringe, catheter, or any delivery tool known in the art.

Further embodiments include: a method for treating a patient afflicted with diabetes or a diabetes-associated condition comprising administering a sustained release GLP-1 pharmaceutical composition to a subject in need thereof; and a kit comprising the sustained release GLP-1 pharmaceutical composition.

DETAILED DESCRIPTION OF THE INVENTION

Figure 1:
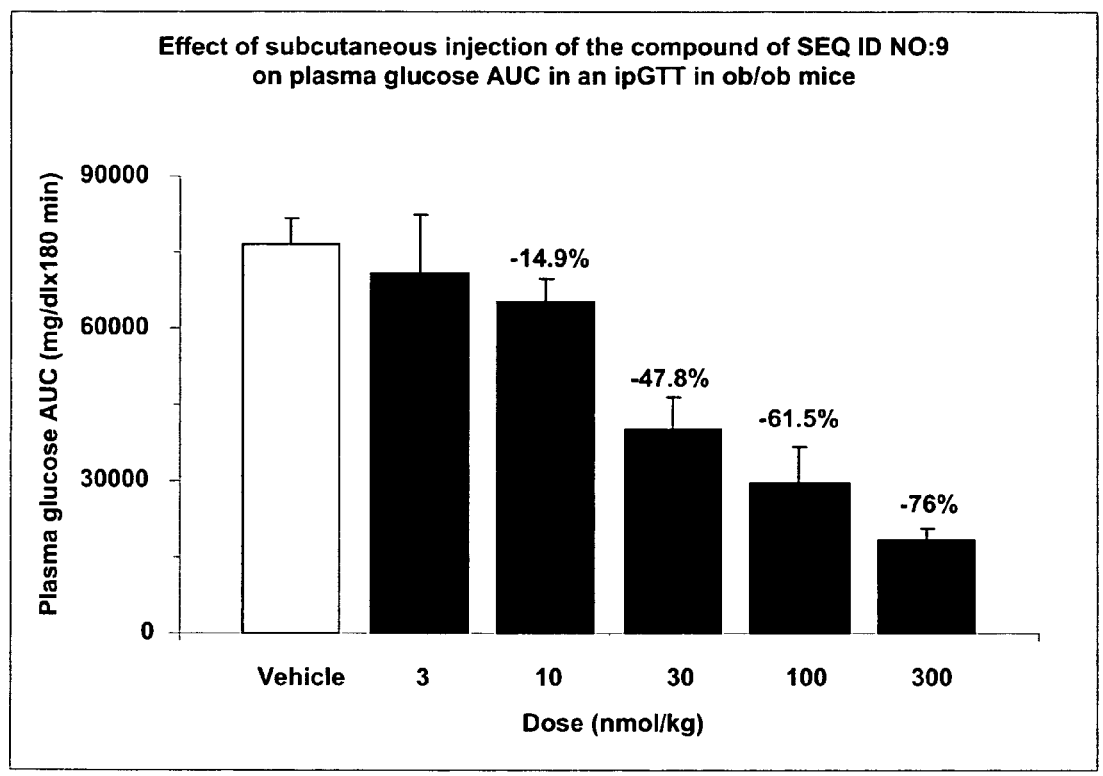
FIG. 1 illustrates the effects of subcutaneous injection of the compound of the SEQ ID NO:9 on plasma glucose in an intraperitoneal glucose tolerance test (ipGTT) in obese ob/ob mice.

Disclosed herein are novel human glucagon-like peptide-1 (GLP-1) peptide receptor modulators provided in sustained release formulations. Such formulations are useful for the amelioration of diseases including diabetes and diabetes-related conditions. In particular, the novel formulations extend the release of GLP-1 receptor modulators through formation of adducts with metal ions such as zinc, manganese, and iron. In one embodiment, a zinc/GLP-1 receptor modulator adduct is formed. In another embodiment, a zinc/GLP-1 receptor modulator adduct is formed in a protamine solution. Preferably, the sustained release formulations are delivered subcutaneously in an aqueous suspension. The sustained release formulation may also be delivered intramuscularly.

The compositions of the present invention exhibit superior in vivo pharmacokinetic properties relative to traditional GLP-1 compositions. These properties include a decrease in solubility, minimal initial burst, constant release rate, and better chemical stability.

DEFINITIONS

The definitions provided herein apply, without limitation, to the terms as used throughout this specification, unless otherwise limited in specific instances.

Amino Acid Abbreviations and Structures

A=L-Ala; ala=D-Ala
Aib=a-aminoisobutyric acid
Bip=L-4,4'-biphenylalanine
D=L-Asp
E=L-Glu
G=Gly
H=L-His
Nle=L-norleucine
Nva=L-norvaline
F=L-Phe
S=L-Ser
T=L-Thr

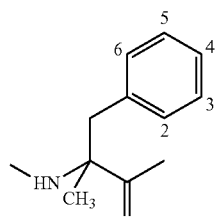
Numbering of the
a-methyl-phenylalanine
(a-Me-Phe) ring carbons
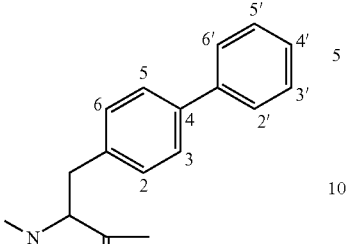
Numbering of the
biphenylalanine
ring carbons
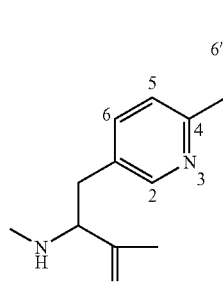
Numbering of the hetero-
biphenylalanine
ring carbons
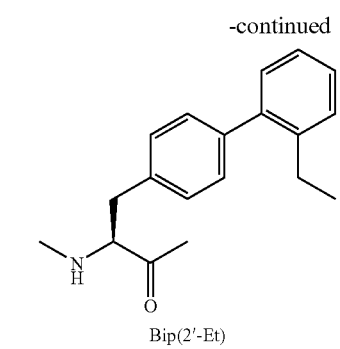
Bip(2'-Et)
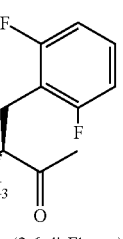
(L)-a-Me-Phe
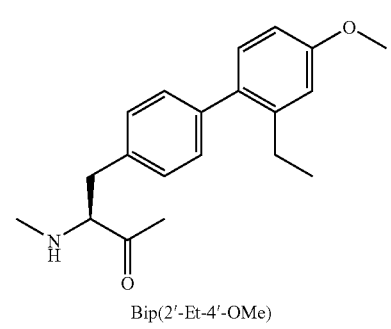
Bip(2'-Et-4'-OMe)
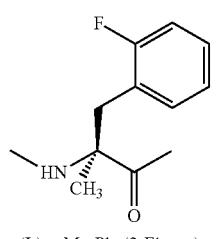
(L)-a-Me-Phe(2-Fluoro)   (L)-a-Me-Phe(2,6-di-Fluoro)
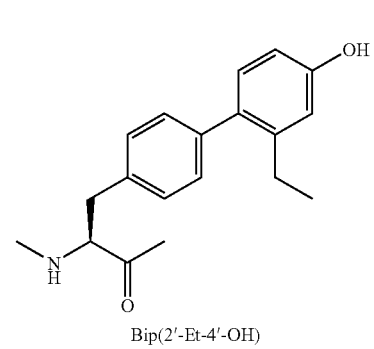
Bip(2'-Et-4'-OH)
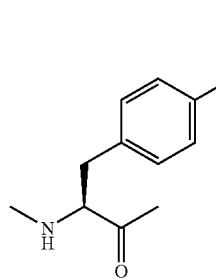
Bip(2'-Me)
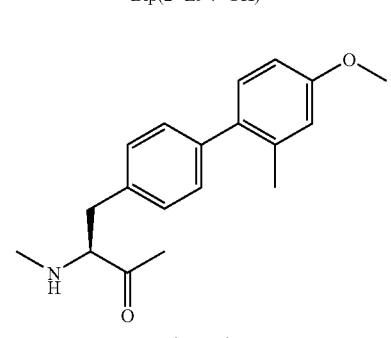
Bip(2'-Me-4'-OMe)
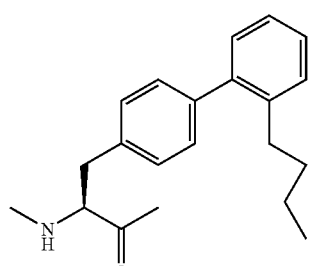
Bip(2'-OBu)
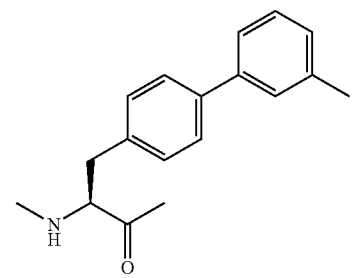
Bip(3',5'-di-Me)

-continued
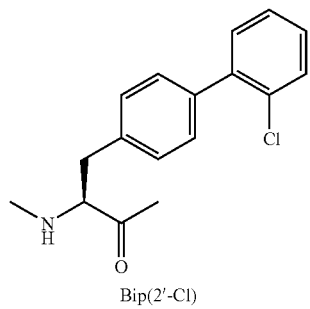
Bip(2'-Cl)
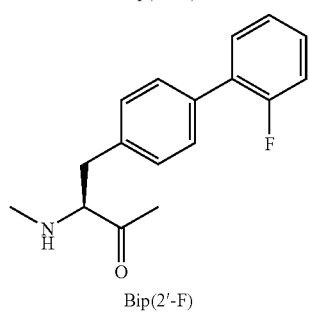
Bip(2'-F)
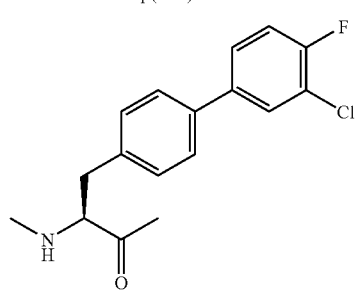
Bip(3'-Cl-4'-F)
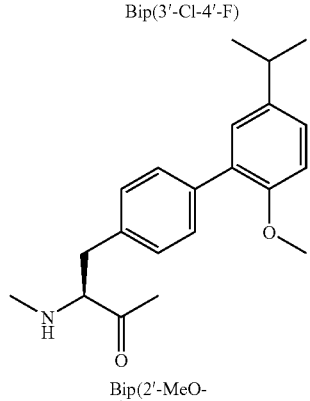
Bip(2'-MeO-5'-isopropyl)
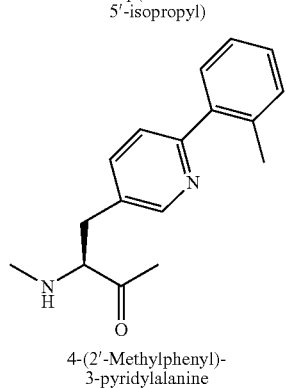
4-(2'-Methylphenyl)-3-pyridylalanine
-continued
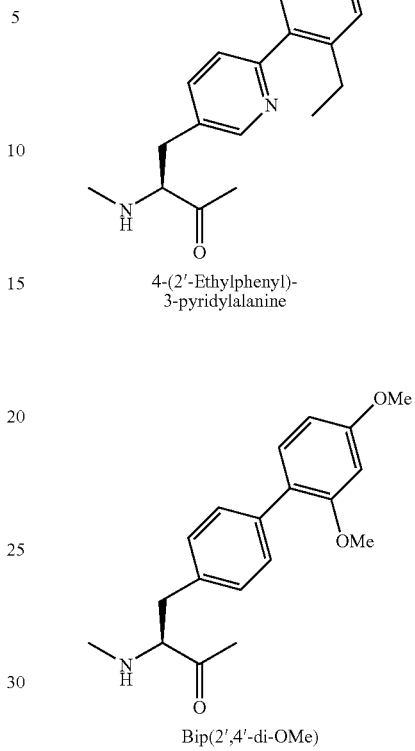
4-(2'-Ethylphenyl)-3-pyridylalanine
Bip(2',4'-di-OMe)
Bip(2'-Me-3'-F)
4-phenyl-3-pyridylalanine -continued
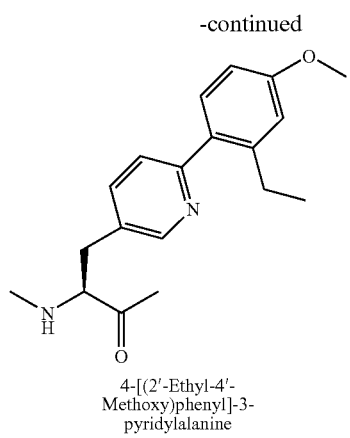
4-[(2'-Ethyl-4'-Methoxy)phenyl]-3-pyridylalanine
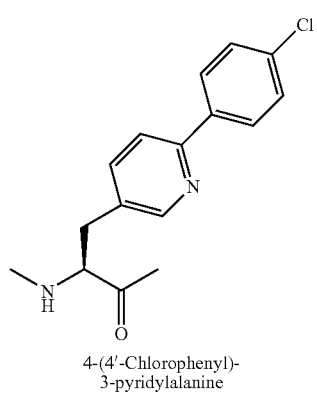
4-(4'-Chlorophenyl)-3-pyridylalanine
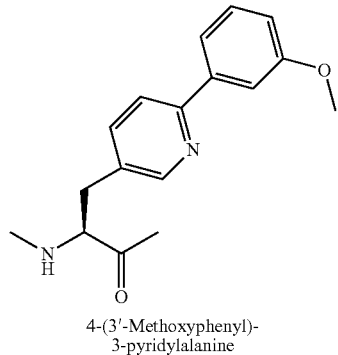
4-(3'-Methoxyphenyl)-3-pyridylalanine
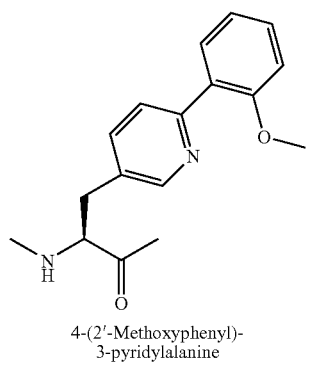
4-(2'-Methoxyphenyl)-3-pyridylalanine
-continued
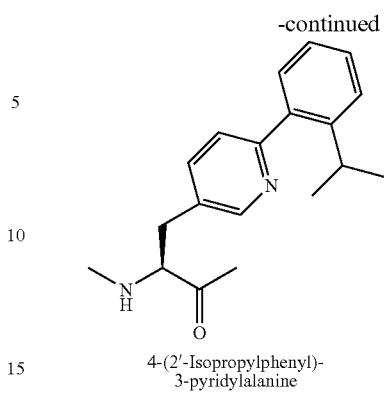
4-(2'-Isopropylphenyl)-3-pyridylalanine
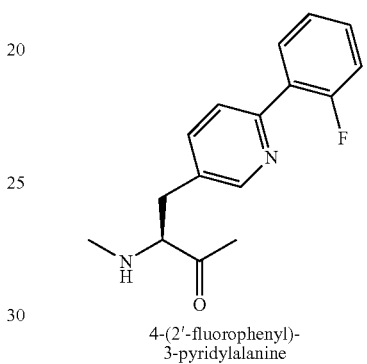
4-(2'-fluorophenyl)-3-pyridylalanine
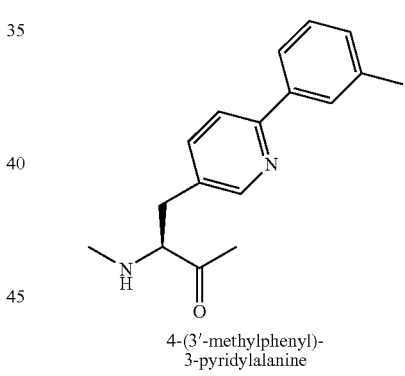
4-(3'-methylphenyl)-3-pyridylalanine
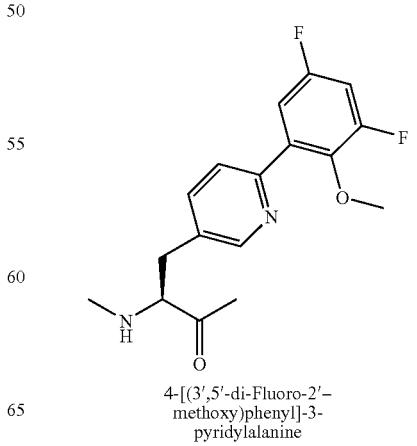
4-[(3',5'-di-Fluoro-2'-methoxy)phenyl]-3-pyridylalanine -continued
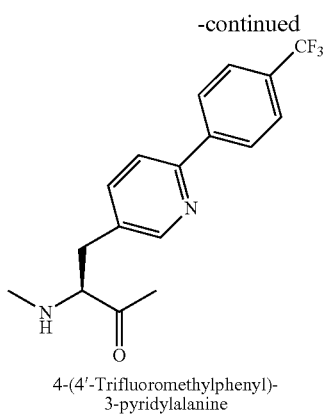
4-(4'-Trifluoromethylphenyl)-
3-pyridylalanine
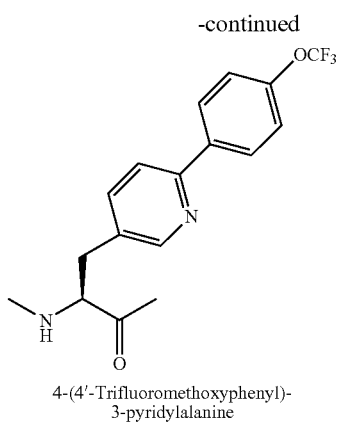
4-(4'-Trifluoromethoxyphenyl)-
3-pyridylalanine
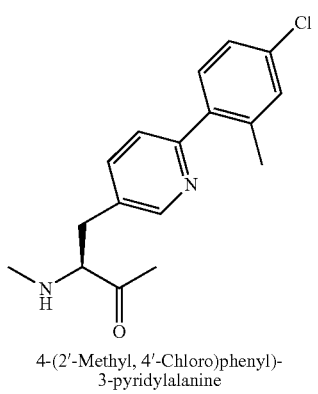
4-(2'-Methyl, 4'-Chloro)phenyl)-
3-pyridylalanine
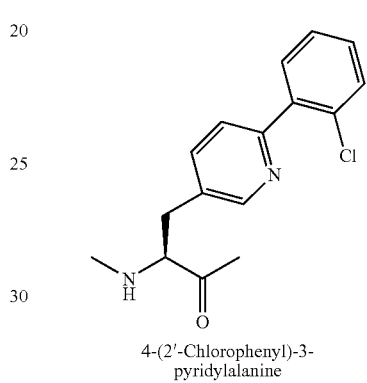
4-(2'-Chlorophenyl)-3-
pyridylalanine
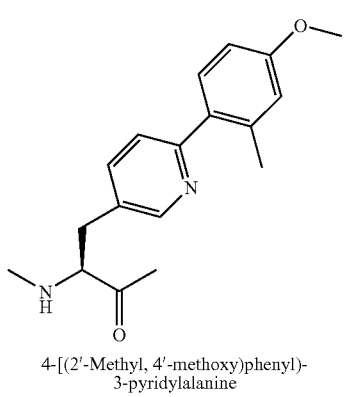
4-[(2'-Methyl, 4'-methoxy)phenyl)-
3-pyridylalanine
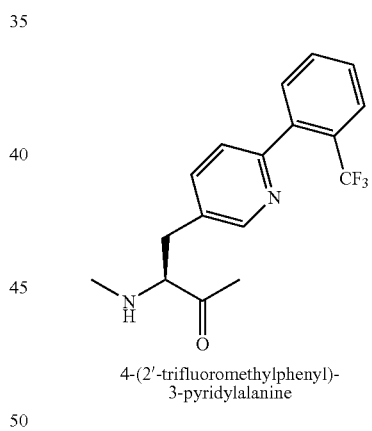
4-(2'-trifluoromethylphenyl)-
3-pyridylalanine
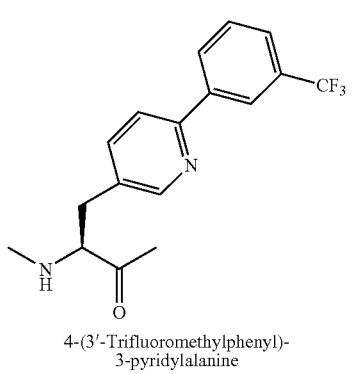
4-(3'-Trifluoromethylphenyl)-
3-pyridylalanine
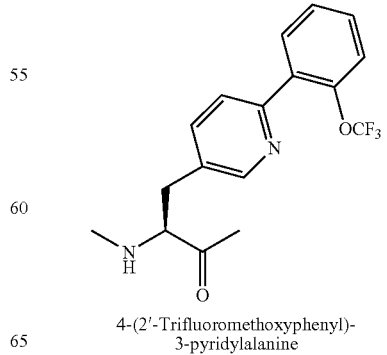
4-(2'-Trifluoromethoxyphenyl)-
3-pyridylalanine -continued
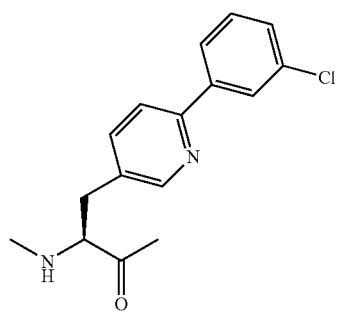
4-(3'-Chlorophenyl)-3-
pyridylalanine
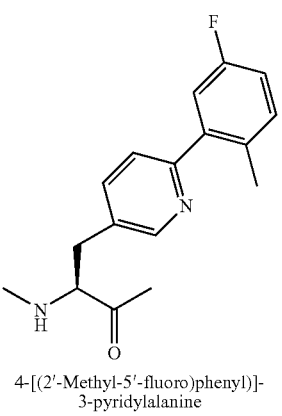
4-[(2'-Methyl-5'-fluoro)phenyl)]-
3-pyridylalanine
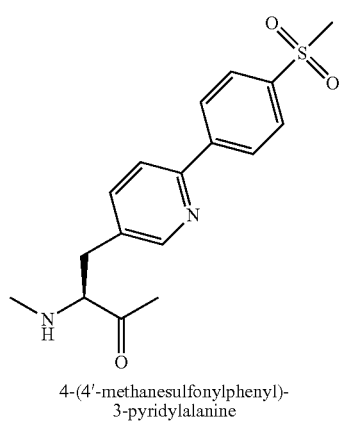
4-(4'-methanesulfonylphenyl)-
3-pyridylalanine
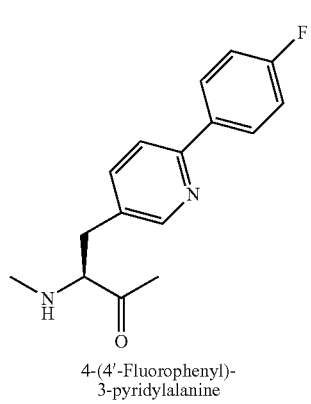
4-(4'-Fluorophenyl)-
3-pyridylalanine
-continued
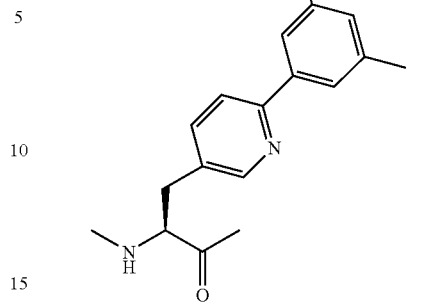
4-(3',5'-dimethylphenyl)-
3-pyridylalanine
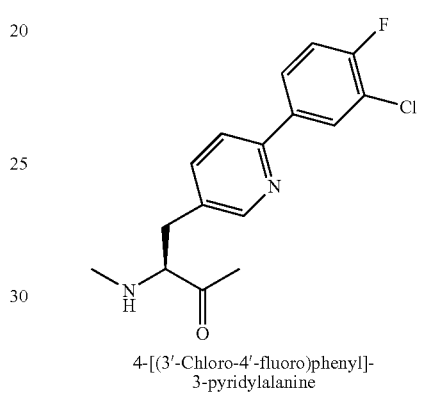
4-[(3'-Chloro-4'-fluoro)phenyl]-
3-pyridylalanine
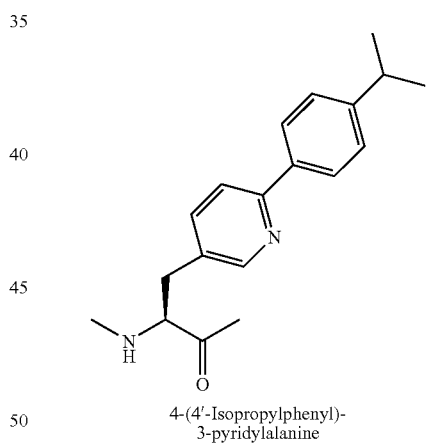
4-(4'-Isopropylphenyl)-
3-pyridylalanine
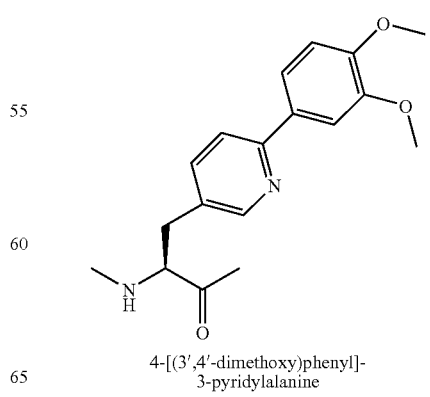
4-[(3',4'-dimethoxy)phenyl]-
3-pyridylalanine -continued
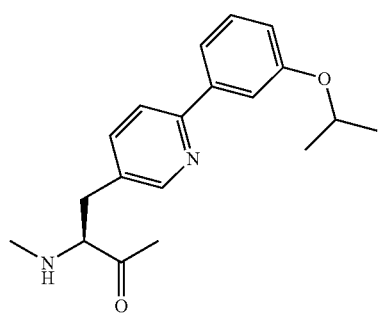
4-(3'-Isopropoxyphenyl)-
3-pyridylalanine
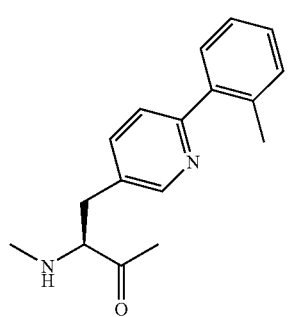
4-(2'-Methylphenyl)-
3-pyridylalanine
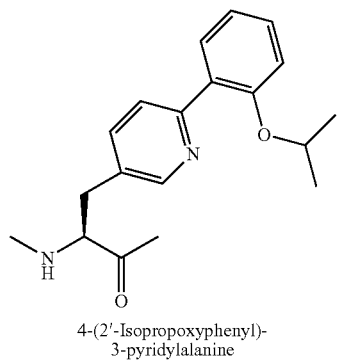
4-(2'-Isopropoxyphenyl)-
3-pyridylalanine
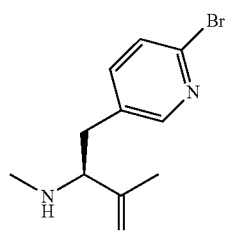
3-(4-Br)pyridylalanine
-continued
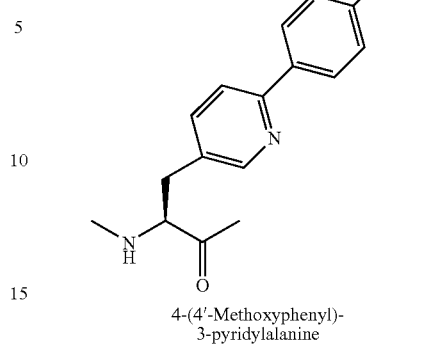
4-(4'-Methoxyphenyl)-
3-pyridylalanine
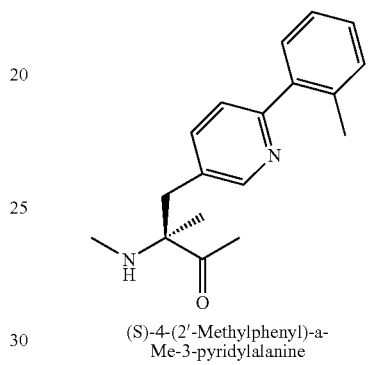
(S)-4-(2'-Methylphenyl)-α-
Me-3-pyridylalanine
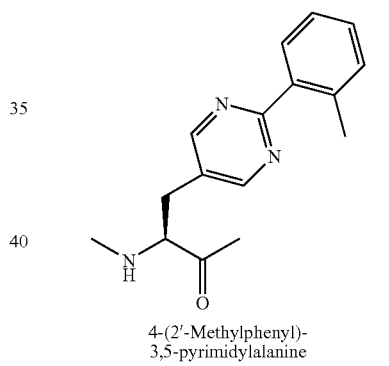
4-(2'-Methylphenyl)-
3,5-pyrimidylalanine
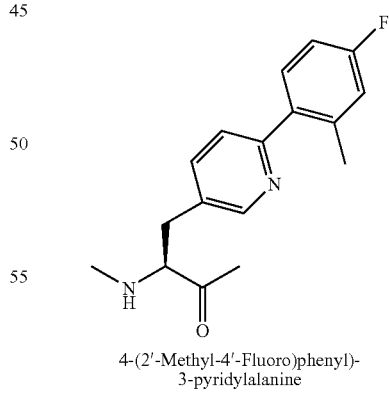
4-(2'-Methyl-4'-Fluoro)phenyl)-
3-pyridylalanine
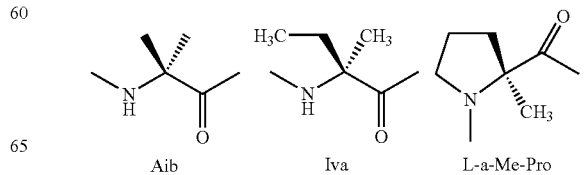
Aib          Iva          L-a-Me-Pro -continued

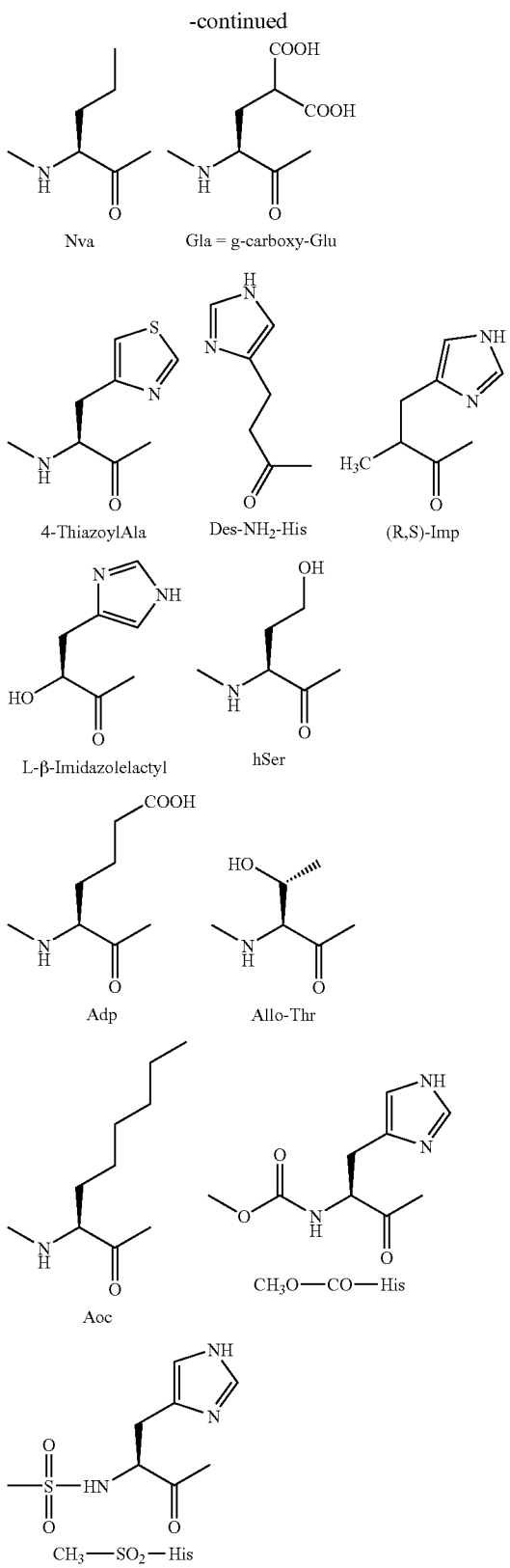

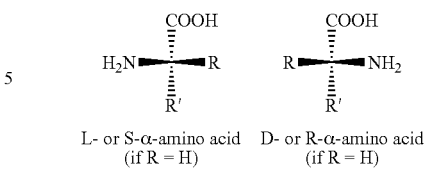

L- or S-α-amino acid  D- or R-α-amino acid
(if R = H)  (if R = H)

Where R and R' are as discussed herein. Unless otherwise indicated, the term "amino acid" as employed herein alone or as part of another group includes, without limitation, an amino group and a carboxyl group linked to the same carbon, referred to as "α" carbon, where R and/or R' can be a natural or an un-natural side chain, including hydrogen. The absolute "S" configuration at the "α" carbon is commonly referred to as the "L" or "natural" configuration. In the case where both the "R" and the "R substituents" equal hydrogen, the amino acid is glycine and is not chiral.

Unless otherwise indicated, the term "amino-alcohol" as employed herein alone or as part of another group includes, without limitation, a natural or non-natural amino acid in which the carboxy group is replaced (reduced) to a methyl alcohol such as valinol, glycinol, alaninol, arylalaninol, heteroarylalaninol.

Unless otherwise indicated, the term "alkyl" as employed herein alone or as part of another group includes, without limitation, both straight and branched chain hydrocarbons, containing 1 to 40 carbons, preferably 1 to 20 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one or more functional groups commonly attached to such chains, such as, but not limited to alkyl, aryl, alkenyl, alkynyl, hydroxy, arylalkyl, cycloalkyl, cycloalkylalkyl, alkoxy, arylalkyloxy, heteroaryloxy, heteroarylalkyloxy, alkanoyl, halo, hydroxyl, thio, nitro, cyano, carboxyl, carbonyl ($\overset{O}{\underset{\shortparallel}{}}$), carboxamido, amino, alkylamino, dialkylamino, amido, alkylamino, arylamido, heterarylamido, azido, guanidino, amidino, phosphonic, phosphinic, sulfonic, sulfonamido, haloaryl, $CF_3$, $OCF_2$, $OCF_3$, aryloxy, heteroaryl, cycloalkylalkoxyalkyl, cycloheteroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "alkenyl" as employed herein alone or as part of another group includes, without limitation, both straight and branched chain hydrocarbons, containing 2 to 40 carbons with one or more double bonds, preferably 2 to 20 carbons with one to three double bonds, more preferably 2 to 8 carbons with one to two double bonds, in the normal chain, such that any carbon may be optionally substituted as described above for "alkyl".

Unless otherwise indicated, the term "alkynyl" as employed herein alone or as part of another group includes, without limitation, both straight and branched chain hydrocarbons, containing 2 to 40 carbons with one or more triple bonds, preferably 2 to 20 carbons with one to three triple bonds, more preferably 2 to 8 carbons with one to two triple bonds, in the normal chain, such that any carbon may be optionally substituted as described above for "alkyl".

Unless otherwise indicated, the term "cycloalkyl" as employed herein alone or as part of another group includes, Those skilled in the art of amino acid and peptide chemistry are aware that an amino acid includes a compound represented by the general structure:

without limitation, saturated or partially unsaturated (containing 1 or 2 double bonds) cyclic hydrocarbon groups containing 1 to 3 rings, appended or fused, including monocyclic alkyl, bicyclic alkyl and tricyclic alkyl, containing a total of 3 to 20 carbons forming the rings, preferably 4 to 7 carbons, forming each ring; which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

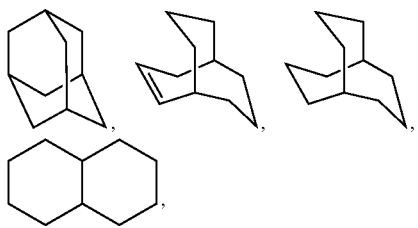

any of which groups may be optionally substituted through any available carbon atoms with 1 or more groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, carboxyl, carbonyl ($\overset{\text{O}}{\text{||}}$), carboxamido, amino, substituted amino wherein the amino includes 1 or 2 substituents (which are alkyl, aryl or any of the other aryl compounds mentioned in the definitions), amido, azido, guanidino, amidino, phosphonic, phosphinic, sulfonic, sulfonamido, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "aryl" as employed herein alone or as part of another group refers, without limitation, to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or heterocycloalkyl rings) and may be optionally substituted through any available carbon atoms with 1 or more groups selected from hydrogen, alkyl, halo, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroaryloxy, hetroarylalkyloxy, hetroarylalkyloxyalkyl, hydroxy, nitro, oxo, cyano, amino, substituted amino wherein the amino includes 1 or 2 substituents (which are alkyl, cycloalkyl, heterocycloalkyl, heteroaryl, or aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, cycloalyklaminocarbonyl, arylaminocarbonyl, heteroarylaminocarbonyl, heteroarylalkylaminocarbonyl alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "arylalkyl" as used herein alone or as part of another group refers, without limitation, to alkyl groups as defined above having an aryl substituent, such as benzyl, phenethyl or naphthylpropyl, wherein said aryl and/or alkyl groups may optionally be substituted as defined above.

The term "alkoxy", "aryloxy", "heteroaryloxy" "arylalkyloxy", or "heteroarylalkyloxy" as employed herein alone or as part of another group includes, without limitation, an alkyl or aryl group as defined above linked through an oxygen atom.

The term "heterocyclo", "heterocycle" "heterocyclyl" or "heterocyclic", as used herein, represents, without limitation, an unsubstituted or substituted stable 4-, 5-, 6- or 7-membered monocyclic ring system which may be saturated or unsaturated, and which consists of carbon atoms and from one to four heteroatoms selected from nitrogen, sulfur, oxygen and/or a SO or $SO_2$ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, tetrahydrofuranyl, tetrahydrothiophenyl pyrrolidinyl, piperidinyl, piperazinyl, oxopyrrolidinyl, oxopiperazinyl, oxopiperidinyl and oxadiazolyl. Optionally a heterocyclo group may be substituted with one or more functional groups, such as those described for "alkyl" or "aryl".

The term "heterocycloalkyl" as used herein alone or as part of another group refers, without limitation, to alkyl groups as defined above having a heterocycloalkyl substituent, wherein said "heterocyclo" and/or alkyl groups may optionally be substituted as defined above.

The term "heteroaryl" as used herein refers, without limitation, to a 5-, 6- or 7-membered aromatic heterocyclic ring which contains one or more heteroatoms selected from nitrogen, sulfur, oxygen and/or a SO or $SO_2$ group. Such rings may be fused to another aryl or heteroaryl ring and include possible N-oxides; Examples of such heteroaryl groups include, but are not limited to, furan, pyrrole, thiophene, pyridine, pyrimidine, pyrazine, pyridazine, isoxazole, oxazole, imidazole and the like. Optionally a heteroaryl group may be substituted with one or more functional groups commonly attached to such chains, such as those described for "allyl" or "aryl".

The term "heteroarylalkyl" as used herein alone or as part of another group refers, without limitation, to alkyl groups as defined above having a heteroaryl substituent, wherein said heteroaryl and/or alkyl groups may optionally be substituted as defined above.

The term "alkyloxycarbonyl" as used herein alone or as part of another group refers, without limitation, to alkyl groups as defined above attached to the oxygen of an —OC(O)— group, for example $CH_3OC(O)$—, $CH_3CH_2OC(O)$— or $CH_2(OH)CH_2OC(O)$—.

The term "aryloxycarbonyl" as used herein alone or as part of another group refers, without limitation, to aryl groups as defined above attached to the oxygen of an —OC(O)— group.

The term "arylalkyloxycarbonyl" as used herein alone or as part of another group refers, without limitation, to aralkyl groups as defined above attached to the oxygen of an —OC(O)— group.

The term "heterocyclyloxycarbonyl" as used herein alone or as part of another group refers, without limitation, to heterocyclyl groups as defined above attached by any carbon atom of the heterocyclyl group to the oxygen of an —OC(O)— group.

The term "heterocycyloxycarbonyl" as used herein alone or as part of another group refers, without limitation, to heterocyclyl groups as defined above attached by any carbon atom of the heterocyclyl group to the oxygen of an —OC(O)— group.

The term "heteroarylalkyloxycarbonyl" as used herein alone or as part of another group refers, without limitation, to heteroarylalkyl groups as defined above attached by any carbon atom of the heterocyclyl group to the oxygen of an —OC(O)— group.

The term "alkylcarbamoyl" as used herein alone or as part of another group refers, without limitation, to alkyl groups as defined above attached to the nitrogen of a —NC(O)— group, for example $CH_3NHC(O)$—, $CH_3CH_2NHC(O)$— or $(CH_3)_2NHC(O)$— and wherein when 2 alkyl groups are present, the alkyl groups can optionally be attached to form a 4, 5, 6 or 7 membered ring, for example,

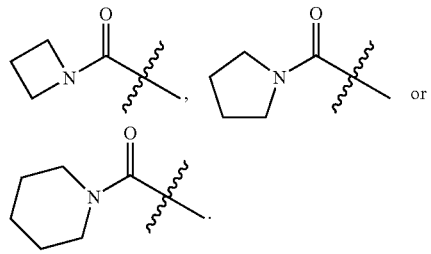

The term "arylalkylcarbamoyl" as used herein alone or as part of another group refers, without limitation, to arylalkyl groups as defined above attached to the nitrogen of a —NC(O)— group.

The term "heterocyclylcarbamoyl" as used herein alone or as part of another group refers, without limitation, to heterocylclyl groups as defined above attached to the nitrogen of an —NC(O)— group.

The term "alkylsulfonyl" as used herein alone or as part of another group refers, without limitation, to alkyl groups as defined above attached to the sulfur of an —S(O)$_2$— group for example $CH_3S(O)_2$—, $CH_3CH_2S(O)_2$— or $(CH_3)_2CH_2S(O)_2$—.

The term "arylsulfonyl" as used herein alone or as part of another group refers, without limitation, to aryl groups as defined above attached to the sulfur of an —S(O)$_2$— group.

The term "arylalkylsulfonyl" as used herein alone or as part of another group refers, without limitation, to arylalkyl groups as defined above attached to the sulfur of an —S(O)$_2$— group.

The term "heteroarylsulfonyl" as used herein alone or as part of another group refers, without limitation, to heteroaryl groups as defined above attached to the sulfur of an —S(O)$_2$— group.

The term "heteroarylalkylsulfonyl" as used herein alone or as part of another group refers, without limitation, to heteroarylalkyl groups as defined above attached to the sulfur of an —S(O)$_2$— group.

The term "receptor modulator" refers to a compound that acts at the GLP-1 receptor to alter its ability to regulate downstream signaling events. Examples of receptor modulators include agonists, antagonists, partial agonists, inverse agonists, allosteric antagonists and allosteric potentiators as defined in standard pharmacology textbooks (e.g. E. M. Ross and T. P. Kenakin in *Goodman and Gilman's The Pharmacological Basis of Therapeutics,* 10th Ed., Chapter 2, pp. 31-43, McGraw Hill, New York (2001)).

One of skill in the art will readily appreciate the meaning of such terms as provided in the present case and in the art.

The term "diabetes and related diseases, related conditions or associated conditions" refers, without limitation, to Type II diabetes, Type I diabetes, impaired glucose tolerance, obesity, hyperglycemia, Syndrome X, dysmetabolic syndrome, diabetic complications, and hyperinsulinemia.

The term "lipid-modulating" or "lipid lowering" agent as employed herein refers, without limitation, to agents that lower LDL and/or raise HDL and/or lower triglycerides and/or lower total cholesterol and/or other known mechanisms for therapeutically treating lipid disorders.

Administration of a therapeutic agent of the invention includes, without limitation, administration of a therapeutically effective amount of the agent of the invention. The term "therapeutically effective amount" as used herein refers, without limitation, to an amount of a therapeutic agent to treat or prevent a condition treatable by administration of a composition of the invention. That amount is the amount sufficient to exhibit a detectable therapeutic or preventative or ameliorative effect. The effect may include, for example and without limitation, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

A "reconstituted" formulation is one which has been prepared by dissolving or suspending a dry powder or lyophilized formulation in a predominantly aqueous carrier such that the GLP-1 receptor modulator is dissolved or homogeneously dispersed in the reconstituted formulation. The reconstituted formulation is suitable for parenteral administration to a patient in need thereof.

An "isotonic" formulation is one which has essentially the same osmotic pressure as human blood. Isotonic formulations will generally have an osmotic pressure from about 250 to 350 mOsmol/Kg$H_2O$. The term "hypertonic" is used to describe a formulation with an osmotic pressure above that of human blood. Isotonicity can be measured using a vapor pressure or ice-freezing type osmometer, for example.

An "acid" is a substance that yields hydrogen ions in aqueous solution. A "pharmaceutically acceptable acid" includes inorganic and organic acids which are non toxic at the concentration and manner in which they are formulated.

A "base" is a substance that yields hydroxyl ions in aqueous solution. "Pharmaceutically acceptable bases" include inorganic and organic bases which are non-toxic at the concentration and manner in which they are formulated.

A "preservative" is an agent that reduces bacterial action, may be optionally added to the formulations herein. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3pentanol, and m-cresol.

A "surfactant" is a surface active molecule containing both a hydrophobic portion (e.g., alkyl chain) and a hydrophilic portion (e.g., carboxyl and carboxylate groups). Surfactant may be added to the formulations of the invention. Surfactants suitable for use in the formulations of the present invention include, but are not limited to, polysorbates (e.g. polysorbates 20 or 80); poloxamers (e.g. poloxamer 188); sorbitan esters and derivatives; Triton; sodium laurel sulfate; sodium octyl glycoside; lauryl-, myristyl-, linoleyl-, or stearyl-sulfobetadine; lauryl-, myristyl-, linoleyl- or stearyl-sarcosine; linoleyl-, myristyl-, or cetyl-betaine; lauramidopropyl-cocamidopropyl-, linoleamidopropyl-, myristamidopropyl-, palmidopropyl-, or isostearamidopropylbetaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethylene glycol, polypropyl glycol, and copolymers of ethylene and propylene glycol (e.g., Pluronics, PF68 etc.).

ABBREVIATIONS

The following abbreviations are employed in the Examples and elsewhere herein:
Ph=phenyl
Bn=benzyl
i-Bu=iso-butyl
i-Pr=iso-propyl
Me=methyl
Et=ethyl
Pr=n-propyl
Bu=n-butyl
TMS=trimethylsilyl
TIS=Triisopropylsilane
$Et_2O$=diethyl ether
HOAc or AcOH=acetic acid
MeCN or $CH_3CN$=acetonitrile
DMF=N,N-dimethylformamide
EtOAc=ethyl acetate
THF=tetrahydrofuran
TFA=trifluoroacetic acid
TFE=α,α,α-trifluoroethanol
$Et_2NH$=diethylamine
NMM=N-methylmorpholine
NMP=N-methylpyrrolidone
DCM=dichloromethane
n-BuLi=n-butyllithium
Pd/C=palladium on carbon
$PtO_2$=platinum oxide
TEA=triethylamine
min=minute(s)
h or hr=hour(s)
L=liter
mL or ml=milliliter
μL=microliter
g=gram(s)
mg=milligram(s)
mol=mole(s)
mmol=millimole(s)
meq=milliequivalent
rt or RT=room temperature
sat or sat'd=saturated
aq.=aqueous
mp=melting point
Bip=biphenylalanine
$LiBH_4$=lithium borohydride
NBS=N-bromo-succinamide
BOP reagent=benzotriazol-1-yloxy-tris-dimethylaminophosphonium hexafluorophosphate (Castro's reagent)
PyBOP reagent=benzotriazol-1-yloxy-tripyrrolidino phosphonium hexafluorophosphate
HBTU=2-(1H-Benzotriazol-1-yl)-1,1,3,3-tetramethyluronim hexafluorophosphate
HATU=O-(7-Azabenzotriazol-1-yl)-1,1,3,3-tetramethyluronim hexafluorophosphate
HCTU=2-(6-Chloro-1-H-benzotriazol-1-yl)-1,1,3,3-tetramethyluronium hexafluorophosphate
DMAP=4-(dimethylamino)pyridine
DIEA=Diisopropylethylamine
EDAC=3-ethyl-3'-(dimethylamino)propyl-carbodiimide hydrochloride (or 1-[(3-(dimethyl)amino)propyl])-3-ethylcarbodiimide hydrochloride)
Fmoc or FMOC=fluorenylmethyloxycarbonyl
Boc or BOC=tert-butyloxycarbonyl
Cbz=carbobenzyloxy or carbobenzoxy or benzyloxycarbonyl
HOBT or $HOBT.H_2O$=1-hydroxybenzotriazole hydrate
Cl—HOBt=6-Chloro-benzotriazole
HOAT=1-hydroxy-7-azabenzotriazole
TLC=thin layer chromatography
HPLC=high performance liquid chromatography
LC/MS=high performance liquid chromatography/mass spectrometry
MS or Mass Spec=mass spectrometry
NMR=nuclear magnetic resonance
Sc or SC=sub-cutaneous
IP or ip=intra-peritoneal
GTT=glucose tolerance test
NBS=N-Bromosuccinimide Peptides of the Invention Disclosed and claimed herein are sustained release compositions comprising a GLP-1 receptor modulator peptide as an active ingredient in a sustained release formulation. Embodiments of peptides that may be used, to make the disclosed sustained release formulations are described below.

Synthesis of Peptides

Synthesis of exemplary peptides to be used for sustained release formulations are described in detail in co-pending priority applications U.S. patent application Ser. No. 11/170,968 and co-pending U.S. patent application Ser. No. 11/442,017, which are incorporated by reference in their entirety.

The GLP-1 peptides, and analogs thereof, may be produced by chemical synthesis using various solid-phase techniques such as those described in G. Barany and R. B. Merrifield, *The Peptides: Analysis, Synthesis, Biology*, Vol. 2, "Special Methods in Peptide Synthesis, Part A", pp. 3-254, E. Gross and J. Meienhofer, eds., Academic Press, New York, 1980; and in J. M. Stewart and J. D. Young, *Solid Phase Peptide Synthesis*, 2nd Ed., Pierce Chemical Co., Rockford, Ill. (1984).

A desired peptide synthesis strategy is based on the Fmoc (9-Fluorenylmethylmethyloxycarbonyl) group for temporary protection of the α-amino group, in combination with the tert-butyl group for temporary protection of the amino acid side chains (see for example E. Atherton and R. C. Sheppard, "The Fluorenylmethoxycarbonyl Amino Protecting Group", in *The Peptides: Analysis, Synthesis, Biology*, Vol. 9, "Special Methods in Peptide Synthesis, Part C", pp. 1-38, S. Undenfriend and J. Meienhofer, eds., Academic Press, San Diego (1987)).

Peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively. Alternatively, in cases where a C-terminal amino alcohol is present, the C-terminal residue may be attached to 2-Methoxy-4-alkoxybenzyl alcohol resin (SASRIN™, Bachem Bioscience, Inc., King of Prussia, Pa.) and, after completion of the peptide sequence assembly, the resulting peptide alcohol is released with $LiBH_4$ in THF (see J. M. Stewart and J. D. Young, supra, p. 92).

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins, which are required as precursors to the final peptides, utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of the first and subsequent amino acids can be accomplished using HOBT or HOAT active esters produced from DIC/HOBT, HBTU/HOBT, BOP, PyBOP, or from DIC/HOAT, HATU/HOAT, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is achieved by reacting the Fmoc-protected amino acid with the resin in dichloromethane and DIEA. If necessary, a small amount of DMF may be added to facilitate dissolution of the amino acid.

The synthesis of the 11-mer peptide analogs can be carried out by using a peptide synthesizer, such as an Advanced Chemtech Multiple Peptide Synthesizer (MPS396) or an Applied Biosystems Inc. peptide synthesizer (ABI 433A). If the MPS396 was used, up to 96 peptides were simultaneously synthesized. If the ABI 433A synthesizer was used, individual peptides were synthesized sequentially. In both cases the stepwise solid phase peptide synthesis was carried out utilizing the Fmoc/t-butyl protection strategy described herein.

The non-natural, non-commercial, amino acids present at positions ten and eleven of the 11-mer peptides described herein were incorporated into the peptide chain in one of two methods. In the first approach, a Boc- or Fmoc-protected non-natural amino acid was prepared in solution using appropriate organic synthetic procedures. The resulting derivative was then used in the step-wise synthesis of the peptide. Alternatively the required non-natural amino acid was built on the resin directly using synthetic organic chemistry procedures. When a non-natural non-commercial amino acid was needed for incorporation at positions six, or at any other amino acid position of the 11-mer peptides, the required Fmoc-protected non-natural amino acid was synthesized in solution. Such a derivative was then used in stepwise solid phase peptide synthesis.

The peptidyl-resin precursors for their respective peptides may be cleaved and deprotected using any standard procedure (see, for example, King, D. S. et al., *Int. J. Pept. Protein Res.*, 36(3):255-266 (1990)). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with $Et_2O$ or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

Recombinant Methods of Synthesis

An alternative synthesis method utilizes recombinant DNA technology to express GLP-1 molecules in prokaryotic and eukaryotic cells. Prokaryotes most frequently are represented by various strains of bacteria. The bacteria may be gram positive or gram negative although typically gram-negative bacteria such as *E. coli* are preferred. Other microbial strains may also be used.

Several strategies may be employed to introduce non-naturally occurring amino acids into proteins. It is possible to augment the protein biosynthetic machinery of a cell to accommodate genetically encoded amino acids using orthogonal tRNA/aminoacyl tRNA synthetase (O-tRNA/O-RS) pairs (See, e.g., U.S. Pat. No. 7,045,337). These methods can be used with non-natural amino acids that provide novel spectroscopic, chemical or structural properties to peptides. The methods may introduce various side chain substituents and are applicable to both prokaryotic (e.g., Eubacteria, Archaeabacteria) and eukaryotic (e.g., yeast, mammalian, plant, or insect) systems.

In general, recombinant methods are useful for the site specific incorporation of non-naturally occurring amino acids via selector codons, e.g., stop codons, four base codons, and the like. The non-naturally occurring amino acid is added to the genetic repertoire, rather than substituting for one of the twenty common amino acids. An example of a recombinant method provides translation systems, e.g., cells, that include an orthogonal tRNA (O-tRNA), an orthogonal aminoacyl tRNA synthetase (O-RS), and a non-naturally occurring amino acid, where the O-RS aminoacylates the O-tRNA with the non-naturally occurring amino acid, and the cell uses the components to incorporate the non-naturally occurring amino acid into a growing polypeptide chain.

Specific Peptide Embodiments

The efficacy of 11-mer GLP-1 peptides, in non-sustained release formulation, has been evaluated in a glucose tolerance test in ob/ob mice to assess relative in vivo efficacy. These experiments are described in Example 29 below. The peptides demonstrate superior potency in this efficacy model of glucose reduction and superior pharmacokinetics (as measured by subcutaneous injection in dogs, described in Examples 30 and 34), relative to a peptide exemplified by reference Compound I. These data are illustrated in Tables 1 and 2. The structures of the peptides reported in Tables I and II are as follows:

Compound I

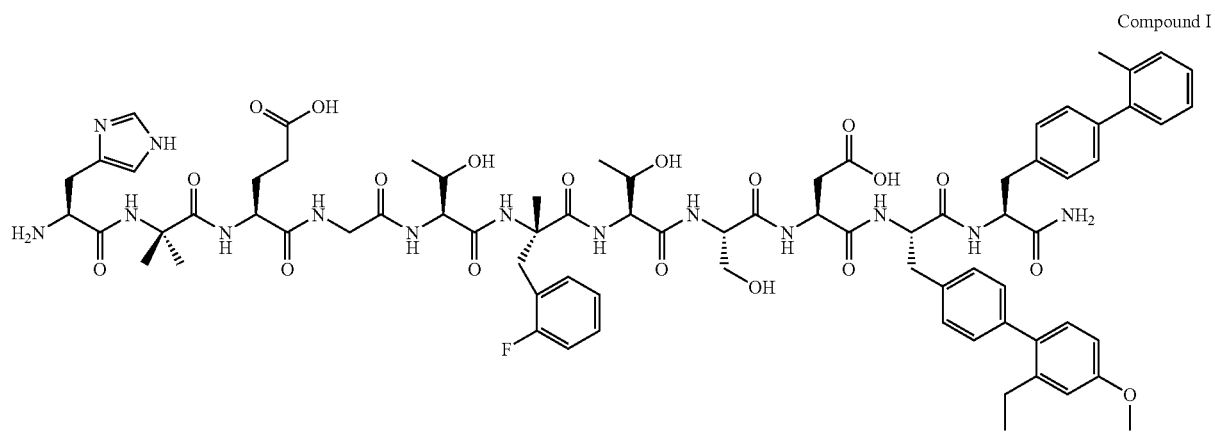

SEQ ID NO: 9

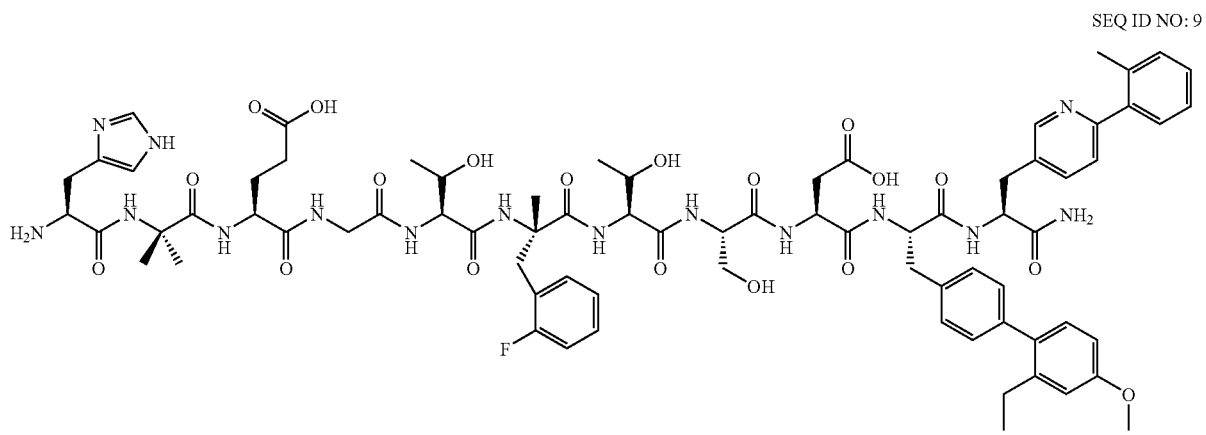

SEQ ID NO: 118

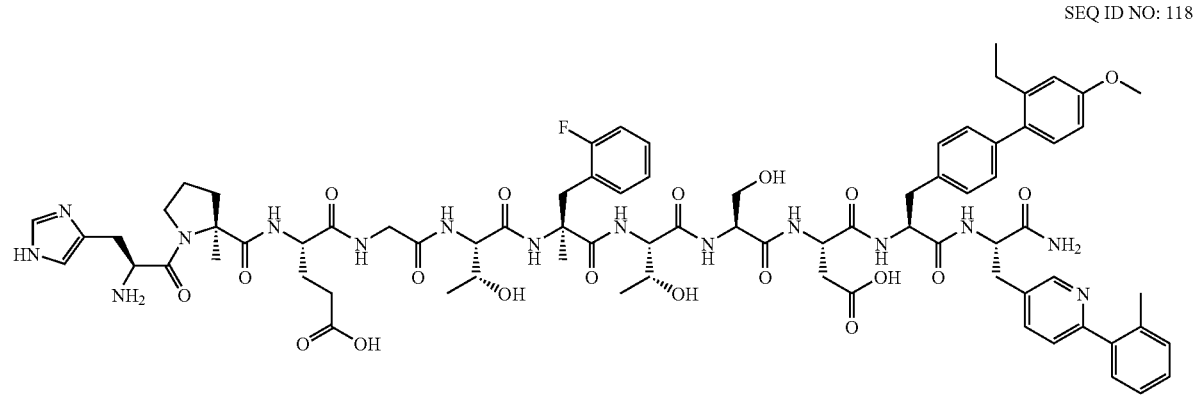

SEQ ID NO: 133
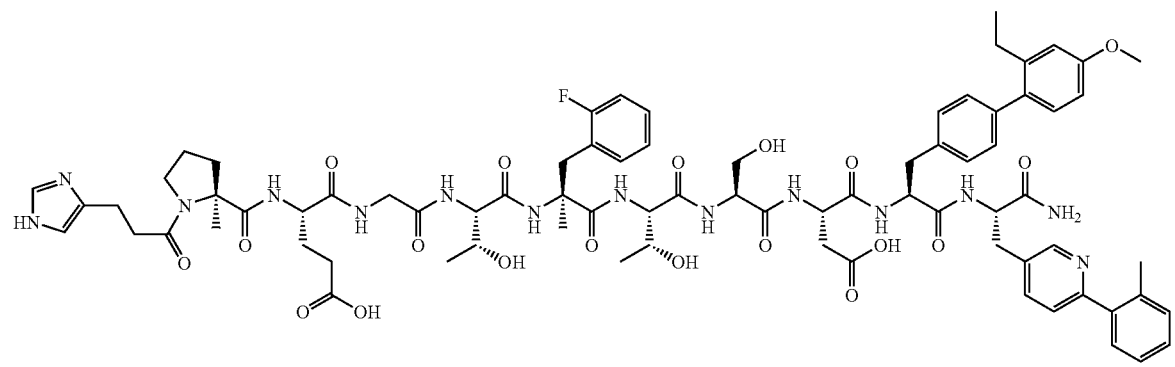
SEQ ID NO: 139
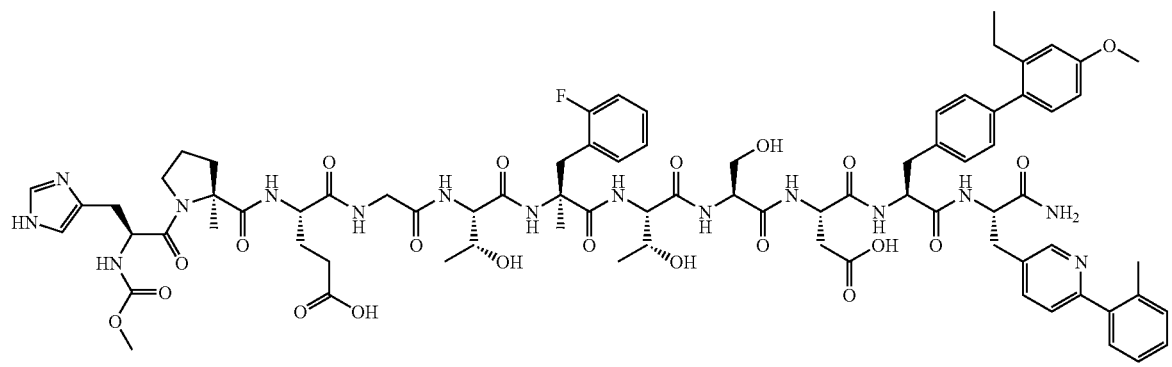
SEQ. ID NO: 151
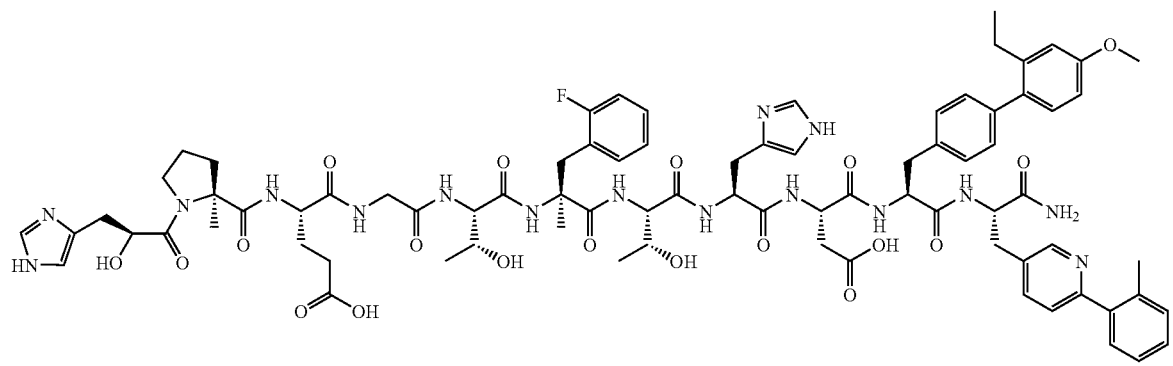
SEQ ID NO: 158
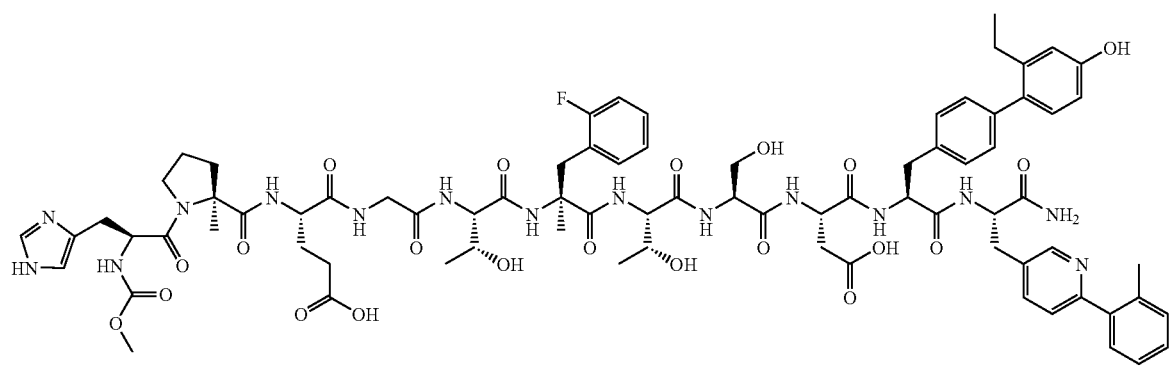

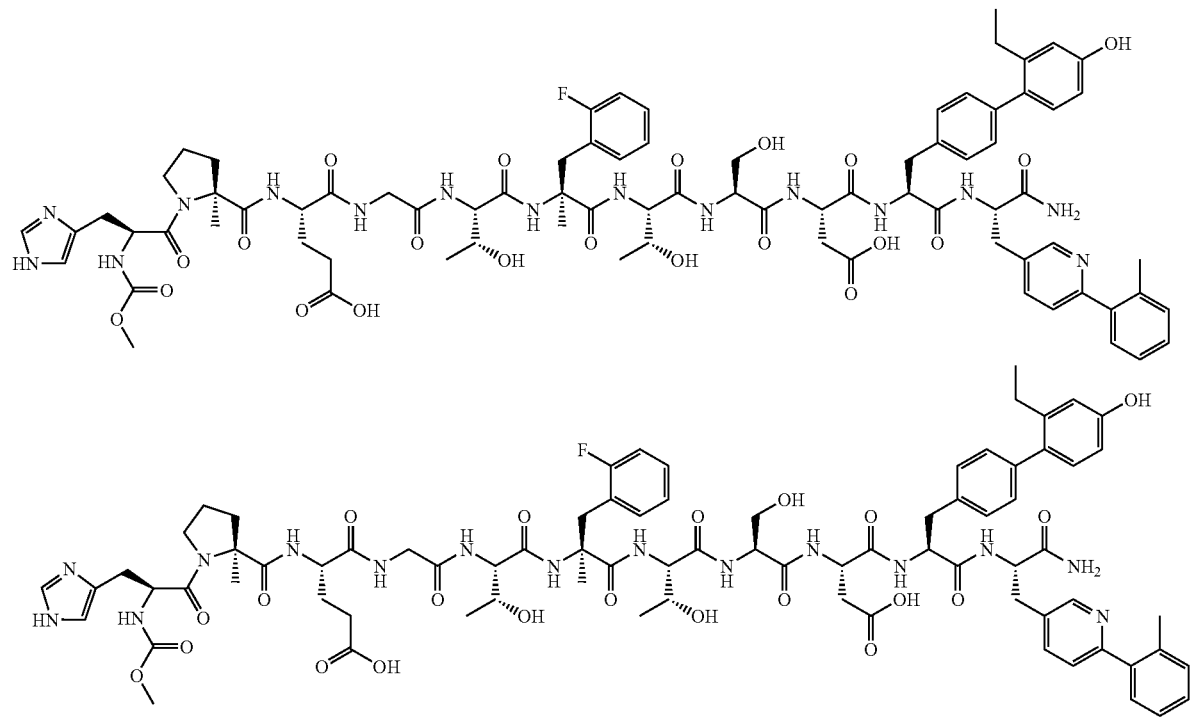

SEQ ID NO: 158

TABLE I

| Compound/<br>SEQ ID NO: | Potency in ob/ob mice | Exposure/dose<br>during ipGTT<br>in ob/ob mice<br>(nM * h/nmol/kg) | Exposure<br>in dogs*<br>(sc@67 μg/kg) |
|---|---|---|---|
| Compound I | ED50 = 50 nmoles/kg | 22 | 89 nM * h |
| 9 | ED50 = 5 nmoles/kg | 18 | 452 nM * h |
| 118 | ED50 = 2.5 nmoles/kg | 4.4 | 4020 nM * h |
| 151 | ED50 = 1 nmoles/kg | 16 | 1566 nM * h |
| 158 | ED50 = 2 nmoles/kg | 11 | 1467 nM * h |

*Compound I and the compound of SEQ ID NO: 118 were dosed in propylene glycol/pH 7.4 phosphate buffer (1:1); Compounds of SEQ ID Nos: 9, 151 and 158 were dosed in 0.2 M Tris buffer (pH 8.0).

TABLE II

| Compound/<br>SEQ ID NO | Potency in ob/ob mice:<br>% AUC Reduction in<br>Plasma Glucose in an IP<br>Glucose Tolerance Test<br>after SC Injection of<br>Compound* | Exposure in<br>dogs***<br>(sc@67 μg/kg) |
|---|---|---|
| Compound I | −15% (p = 0.247, NS)<br>(10 nmol/kg) | 89 nM * h |
| 9 | −68% (p < 0.0001)<br>(10 nmol/kg) | 1230 nM * h |
| 118 | −70% (p < 0.001)<br>(10 nmol/kg) | 4020 nM * h |
| 130 | −72% (p < 0.0001)<br>(10 nmol/kg) | 541 nM * h |
| 149 | −54%(p < 0.0001)<br>(10 nmol/kg) | 940 nM * h |
| 140 | −73% (p < 0.001)<br>(10 nmol/kg) | 283 nM * h |
| 120 | −68% (p < 0.0001)<br>(10 nmol/kg) | 1116 nM * h |
| 139 | −63% (p < 0.01)<br>(10 nmol/kg) | 1603 nM * h |
| 119 | −61% (p < 0.0001)<br>(5 nmol/kg) | 1257 nM * h |
| 150 | −38% (p < 0.05)<br>(10 nmol/kg) | 979 nM * h |

*AUC = area under the curve. AUC values are calculated using the fasting plasma glucose value as the baseline in each individual animal. The percentage change in the AUC is calculated relative to the AUC for the vehicle-treated group in the same study. The p values given are determined by comparison to the vehicle-treated group using analysis of variance (ANOVA) followed by Fisher's post-hoc test
**NS = non-statistically significant
***Dosing vehicle: propylene glycol/pH 7.4 phosphate buffer (1:1).

Sustained release formulations of the compound of SEQ ID NO: 9 were characterized, tested, and showed a decrease in solubility and an increase in bioavailabilty. See Examples 31-34.

Synthesis of Sustained Release Formulations

Disclosed herein are sustained release formulations of GLP-1 receptor modulator peptides. The sustained release formulations are made by forming a metal ion/GLP-1 receptor modulator adduct. In one embodiment, the metal ion/GLP-1 receptor modulator adduct is formed by mixing a solution of metal ion with a solution of GLP-1 receptor modulator until a precipitate forms. Metal ions include zinc, manganese, and iron. Preferably, the metal ion is zinc or zinc acetate. The metal ion/GLP-1 receptor modulator adduct is then purified, for example by vacuum drying or spray drying.

In one embodiment, the metal ion/GLP-1 receptor modulator adduct is formed in a protamine solution. Protamine is a positively charged polypeptide (MW~4300 Da) so it forms a less soluble adduct with negatively charged GLP-1 peptides and, therefore, extends release following administration. Protamine formulations using the compound of SEQ ID NO:9 may be prepared as follows: (1) A pre-formed protamine/compound of SEQ ID NO:9 adduct may be suspended in an injectable medium; (2) a compound of SEQ ID NO:9 may be suspended in protamine solution; or (3) two separate compounds of SEQ ID NO:9 solution/suspension and protamine solutions may be co-administered to the same injection site.

The approach used to make the SEQ ID NO:9 formulation can be readily applied to other GLP-1 peptides such as those of SEQ ID NO's: 118, 119, 120, 130, 139, 140, 149, 150, 151, and 158, as well as the peptides described in co-pending U.S. patent application Ser. No. 11/170,968 and co-pending U.S. patent application Ser. No. 11/442,017, which are incorporated by reference in their entirety.

Pharmaceutical Compositions

The sustained release formulations described herein may further comprise pharmaceutical compositions including a GLP-1 receptor modulator compound with a pharmaceutically acceptable carrier, diluent or solvent. The active ingredient (i.e., an 11-mer GLP-1 peptide) in such formulations may comprise from about 0.1 to about 99.99 weight percent. "Pharmaceutically acceptable carrier" means any carrier, diluent or excipient which is compatible with the other ingredients of the formulation and not deleterious to the recipient.

The formulation is preferably administered with a pharmaceutically acceptable carrier selected on the basis of the selected route of administration and standard pharmaceutical practice. The formulation may be introduced in dosage forms according to standard practices in the field of pharmaceutical preparations. Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

Parenteral administration is preferred. For parenteral administration, the formulation may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

A preferred embodiment of the compositions disclosed and claimed herein is an aqueous pharmaceutical suspension of a GLP-1 receptor modulator that may include one or more surfactants, suspending agents, thickening agents, preservatives and/or antioxidants.

The suspension may comprise a co-precipitated, lyophilized, or spray dried zinc adduct in a Zn:GLP-1 modulator ratio of from about 1:10 to about 50:1, with a weight to volume ratio of surfactants, suspending agents, and/or thickening agents, of from 0% to about 30%. The Zn:GLP-1 modulator ratio may be further defined as between about 0.5:1 to 10:1 and the weight to volume ratio of surfactants, suspending agents, and/or thickening agents of from 0% to about 30%. Furthermore, the Zn:GLP-1 receptor modulator ratio may be between about 1.5:1 to about 5:1, and the weight to volume ratio of surfactants may be from 0% to about 1%, the suspending agents from 0% to about 5%, and/or a thickening agents may be from 0% to about 1%.

Suitable surfactants include phospholipids (e.g., lecithin), cationic surfactants (e.g., myristylgammapicolinium chloride), anionic surfactants and non-ionic surfactants (e.g., polysorbate 80).

Suitable suspending and/or density adjusting agents include polyvinylpyrrolidone compounds and polyethylene glycols. Examples of polyethylene glycols include those having a molecular weight from about 300 to about 6000, e.g., polyethylene glycol 3350 and polyethylene glycol 4000. Polyvinylpyrrolidone (PVP) compounds include PVP K12, K17, K25 and K30.

Suitable thickening or viscosity agents include well known cellulose derivatives (e.g., methylcellulose, carboxymethylcellulose, hydroxyethylcellulose and hydroxypropylmethylcellulose), gelatin and acacia.

Suitable antioxidants include ascorbic acid derivatives (e.g., ascorbic acid, erythorbic acid, sodium ascorbate), thiol derivatives (e.g. thioglycerol, cysteine, acetylcysteine, cysteine, dithioerythreitol, dithiothreitol, glutathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiareticacid.

Suitable preservatives are for instance phenol, chlorobutanol, benzylalcohol, methyl paraben, propyl paraben, benzalkonium chloride and cetylpyridinium chloride.

In addition, certain embodiments of the compositions disclosed and claimed herein may also include tonicity-adjusting agents. Exemplary tonicity adjusting agents include sodium chloride, sodium sulfate, dextrose, mannitol and glycerol.

The compounds and compositions described herein may take the form of salts. The term "salts", embraces addition salts of free acids or free bases which are compounds of the invention. The term "pharmaceutically-acceptable salt" refers to salts which possess toxicity profiles within a range that affords utility in pharmaceutical applications. Suitable pharmaceutically-acceptable acid addition salts may be prepared from an inorganic acid or from an organic acid. Examples of inorganic acids include hydrochloric, hydrobromic, hydroiodic, nitric, carbonic, sulfuric and phosphoric acid. Appropriate organic acids may be selected from aliphatic, cycloaliphatic, aromatic, aralphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, salicyclic, 4-hydroxybenzoic, phenylacetic, mandelic, pamoic, methanesulfonic, ethanesulfonic, benzenesulfonic, pantothenic, trifluoromethanesulfonic, 2-hydroxyethanesulfonic, toluenesulfonic, sulfanilic, cyclohexylaminosulfonic, stearic, alginic, γ-hydroxybutyric, galactaric and galacturonic acid.

Suitable pharmaceutically-acceptable base addition salts include for example, metallic salts including alkali metal, alkaline earth metal and transition metal salts such as, for example, calcium, magnesium, potassium, sodium and zinc salts. Pharmaceutically-acceptable base addition salts also include organic salts made from basic amines such as, for example, N,N'-dibenzylethylenediamine, chloroprocaine, choline, diethanolamine, ethylenediamine, meglunine (N-methylglucamine) and procaine.

All of these salts may be prepared by conventional means from the corresponding compound by reacting, for example, the appropriate acid or base with a the compound according to the peptide sequence of the invention.

Combinations

Optionally, the formulations described herein can be used alone, in combination with other compounds/compositions described herein, or in combination with one or more other therapeutic agent(s), e.g., an antidiabetic agent or other pharmaceutical.

The formulations described herein may be employed in combination with other GLP-1 receptor modulators (e.g., agonists or partial agonists, such as a peptide agonist) or other suitable therapeutic agents useful in the treatment of the aforementioned disorders including: anti-diabetic agents; anti-hyperglycemic agents; hypolipidemic/lipid lowering agents; anti-obesity agents (including appetite suppressants/modulators) and anti-hypertensive agents. In addition, the formulations described herein may be combined with one or more of the following therapeutic agents; infertility agents, agents for treating polycystic ovary syndrome, agents for treating growth disorders, agents for treating frailty, agents for treating arthritis, agents for preventing allograft rejection in transplantation, agents for treating autoimmune diseases, anti-AIDS agents, anti-osteoporosis agents, agents for treating immunomodulatory diseases, antithrombotic agents, agents for the treatment of cardiovascular disease, antibiotic agents, anti-psychotic agents, agents for treating chronic inflammatory bowel disease or syndrome and/or agents for treating anorexia nervosa.

Examples of suitable anti-diabetic agents for use in combination with the formulations described herein include biguanides (e.g., metformin or phenformin), glucosidase inhibitors (e.g,. acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), DPP-IV inhibitors, and SGLT2 inhibitors.

Other suitable thiazolidinediones include Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include muraglitazar (Bristol-Myers Squibb), AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), and in U.S. application Ser. No. 09/644,598, filed Sep. 18, 2000, the disclosure of which is incorporated herein by reference, employing dosages as set out therein, which formulations designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable DPP4 inhibitors that may be used in combination with the formulations described herein include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, LAF237, saxagliptin, MK0431, TSL-225 (tryptophyl-1,2,3,4-tetrahydroisoquinoline-3-carboxylic acid (disclosed by Yamada et al, Bioorg. & Med. Chem. Lett. 8 (1998) 1537-1540, 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996) employing dosages as set out in the above references.

Suitable meglitinides include nateglinide (Novartis) or KAD1229 (PF/Kissei).

Examples of other suitable glucagon-like peptide-1 (GLP-1,) compounds that may be used in combination with the formulations described herein include GLP-1(1-36) amide, GLP-1(7-36) amide, GLP-1(7-37) (as disclosed in U.S. Pat. No. 5,614,492 to Habener), as well as AC2993 (Amylin), LY-315902 (Lilly) and NN2211 (Novo Nordisk).

Examples of suitable hypolipidemic/lipid lowering agents for use in combination with the formulations described herein include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885, 983 and U.S. Pat. No. 5,962,440, all of which are incorporated by reference herein.

The HMG CoA reductase inhibitors which may be employed in combination with the formulations described herein include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No.0142146 A2, and quinoline and pyridine derivatives, as disclosed in U.S. Pat. Nos. 5,506,219 and 5,691,322.

Desired hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the formulations described herein.

The squalene synthetase inhibitors include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl) phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination with the formulations described herein include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with the formulations described herein include those disclosed in Drugs of the Future 24, 9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitors for use in combination with the formulations described herein include SCH48461 (Schering-Plough), as well as those disclosed in Atherosclerosis 115, 45-63 (1995) and J. Med. Chem. 41, 973 (1998).

Examples of suitable ileal Na+/bile acid cotransporter inhibitors for use in combination with the formulations described herein include compounds as disclosed in Drugs of the Future, 24, 425-430 (1999).

The lipoxygenase inhibitors which may be employed in combination with the formulations described herein include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "1 5-Lipoxygenase and its Inhibition: A Novel Therapeutic Target for Vascular Disease", Current Pharmaceutical Design, 1999, 5, 11-20.

Examples of suitable anti-hypertensive agents for use in combination with the formulations described herein include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the formulations described herein include a NPY receptor antagonist, a NPY-Y2 or NPY-Y4 receptor agonist, Oxyntomodulin, a MCH antagonist, a GHSR antagonist, a CRH antagonist, a beta 3 adrenergic agonist, a lipase inhibitor, a serotonin (and dopamine) reuptake inhibitor, a thyroid receptor beta drug, a CB-1 antagonist and/or an anorectic agent.

The beta 3 adrenergic agonists which may be optionally employed in combination with the formulations described herein include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064, with AJ9677, L750,355 and CP331648 being preferred.

Examples of lipase inhibitors which may be optionally employed in combination with the formulations described herein include orlistat or ATL-962 (Alizyme), with orlistat being preferred.

The serotonin (and dopamine) reuptake inhibitor which may be optionally employed in combination with the formulations described herein may be sibutramine, topiramate (Johnson & Johnson) or axokine (Regeneron), with sibutramine and topiramate being preferred.

Examples of thyroid receptor beta compounds which may be optionally employed in combination with the formulations described herein include thyroid receptor ligands, such as those disclosed in WO97/21993 (U. Cal SF), WO99/00353 (KaroBio) and WO 00/039077 (KaroBio), with compounds of the KaroBio applications being preferred.

Examples of CB-1 antagonists which may be optionally employed in combination with the formulations described herein include CB-1 antagonists and rimonabant (SR141716A).

Examples of NPY-Y2 and NPY-Y4 receptor agonists include PYY(3-36) and Pancreatic Polypeptide (PP), respectively.

The anorectic agent which may be optionally employed in combination with the formulations described herein include dexamphetamine, phentermine, phenylpropanolamine or mazindol, with dexamphetamine being preferred.

Examples of suitable anti-psychotic agents include clozapine, haloperidol, olanzapine (Zyprexa®), Prozac® and aripiprazole (Abilify®).

The aforementioned patents and patent applications are incorporated herein by reference.

The above other therapeutic agents, when employed in combination with the formulations described herein may be used, for example, in those amounts indicated in the Physician's Desk Reference, as in the patents set out above or as otherwise determined by one of ordinary skill in the art.

Administration of Pharmaceutical Compositions

Various delivery systems are known and can be used to administer the pharmaceutical compositions of the invention, e.g., encapsulation in liposomes, microparticles, microcapsules, etc. Methods of introduction include but are not limited to intradermal, intramuscular, intraperitoneal, intravenous, subcutaneous, intranasal, and oral routes. The formulations may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions into the central nervous system by any suitable route, including intraventricular and intrathecal injection; intraventricular injection may be facilitated by an intraventricular catheter, for example, attached to a reservoir, such as an ommaya reservoir.

Those skilled in the art of treating diabetes and related conditions can determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraoccular, intravenous, or intestinal administration.

The formulations disclosed herein may be administered simultaneously, by the same or different routes, or at different times during treatment. The specific dose of polypeptide to obtain therapeutic benefit for treatment of will, of course, be determined by the particular circumstances of the individual patient including, the size, weight, age and sex of the patient, the nature of the disease, and the route of administration of the compound. For example, a daily dosage of from about 0.01 to about 50 mg/kg/day may be utilized, more preferably from about 0.05 to about 25 mg/kg/day. Particularly preferred are doses from about 0.5 to about 10.0 mg/kg/day, for example, a dose of about 5.0 mg/kg/day. The dose may be given over multiple administrations, for example, two administrations of 2.5 mg/kg. Higher or lower doses are also contemplated.

The subject being treated with the pharmaceutical composition is monitored throughout the treatment to determine the progress of the treatment. Continued monitoring allows the clinician to determine if therapy is effective and if administration should continue.

The dosage regimen for the formulations will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.01 ng to 10.0 mg per min per Kg body weight.

Dosage forms (pharmaceutical compositions) suitable for administration may contain from about 0.01 milligram to about 500 milligrams of active ingredient per dosage unit. In these pharmaceutical compositions the active ingredient will ordinarily be present in an amount of about 0.5-95% by weight based on the total weight of the composition.

Suitable pharmaceutical carriers are described in Remington: "The Science and Practice of Pharmacy", Nineteenth Edition, Mack Publishing Company, 1995, a standard reference text in this field. Specific examples of sustained release formulations are provided in the Examples below.

Kits

Another embodiment described is a kit comprising the sustained release GLP-1 formulations and preferably provides instructions for its use for the treatment of a patient suffering from diabetes or a diabetic related condition. The kit comprises a container. Suitable containers include, for example, bottles, vials, syringes and test tubes. The container may be formed from a variety of materials such as glass, plastic or metals.

The container may be adapted to store a lyophilized or liquid formulation. The label on, or associated with, the container may provide directions for reconstitution and/or use. For example, the label may indicate that the sustained release formulation is to be diluted to a specific concentration. The label may further indicate that the formulation is intended for subcutaneous administration. The container holding the formulation may be a multi-use vial, which allows for repeat administrations (e.g. from 2-6 administrations) of, for example, a subcutaneous formulation. Alternatively, the container may be a pre-filled syringe containing, for example, a subcutaneous formulation.

The kit may further comprise a second container comprising, for example, a suitable carrier for the lyophilized formulation.

The kit may further include materials including a variety of buffers, diluents, filters, needles, syringes, and package inserts with instructions for use.

Silicone free syringes are preferably utilized for surfactant free drug product, such as upon reconstitution of lyophilized drug product and/or transfer of the solutions from the vial to the intravenous bag and may be co-packaged with the drug product vial.

Numerous modifications and variations of the subject matter disclosed and claimed herein are possible in light of the above teachings. It is therefore understood that within the subject matter recited in the appended claims may be practiced otherwise than as specifically described herein.

The subject matter described and claimed herein is not to be limited in scope by the specific embodiments provided. Functionally equivalent methods and components, in addition to those shown and described herein, will become apparent to those skilled in the art from the foregoing description and accompanying drawings. Such modifications are intended to fall within the scope of the appended claims. All references cited herein are hereby incorporated by reference in their entirety.

EXAMPLES

The GLP-1 receptor modulator peptides used in sustained release formulations have the general structure:

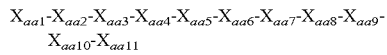

Several of the Examples that follow describe the synthesis of preferred GLP-1 receptor modulators and refer to various substituents of the above referenced structure.

Example 1

Simultaneous Solid Phase Peptide Synthesis of 11-mer Peptides

Dipeptidyl resin, containing, amino acid at positions ten and eleven of the 11-mer GLP-1 modulators, was prepared using the following manual procedure in a batchwise mode before continuing peptide chain elongation utilizing the automated simultaneous synthesis protocol on an MPS-396 peptide synthesizer.

An amount of 9-Fmoc-aminoxanthen-3-yloxy-Merrifield resin (Sieber amide resin; loading: 0.5 to 0.7 mmol/g) sufficient to synthesize several 11-mer analogs, was swelled by washing with DMF (4×10 mL/g, 5 minutes). The Fmoc group was then removed using two treatments, 5 and 15 minutes each respectively, with 20% piperidine in DMF (10 mL/g). The resin was washed with DMF (4×10 mL/g) and NMP (4×10 mL/g). A 0.5 M solution of Fmoc-L-4-(2'-Methylphenyl)-3-pyridylalanine-OH (HCl salt)(1.1 eq.), (or of any other amino acid represented by Formula IVa), PyBOP (1.1 eq.) and DIEA (3.3 eq.) in NMP was added to the resin. The resin was then shaken or vortexed for 16-24 hours. Coupling completion was monitored using a qualitative ninhydrin test. The resin was drained, washed with NMP (3×10 mL/g) and DMF (3×10 mL/g), and treated for 90 minutes with 10% acetic anhydride in DCM (10 mL/g). After DCM washes (4×10 mL/g), a second manual coupling cycle using a DIC/HOAt mediated was then performed, starting from the removal of the Fmoc group with 20% piperidine in DMF, and using a Fmoc-protected biphenylalanine analog in the coupling step. This synthesis scheme produced the desired Fmoc-protected dipeptidyl-Sieber amide resin.

Such dipeptidyl-resins required for the synthesis of a set of designed analogs were then used in the automated MPS synthesis of up to 96 peptides per run in the following manner. The dipeptidyl-resins were loaded as suspensions in dichloromethane/DMF (60:40) into the 96-well reactor of an Advanced ChemTech MPS 396 synthesizer in volumes corresponding to 0.01-0.025 mmol (20-50 mg) of resin per reactor well. The reactor was placed on the instrument and drained. The wells were then washed with DMF (0.5-1.0 mL, 3×2 min) and subjected to the number of automated coupling cycles required to assemble the respective peptide sequences as determined by the pre-programmed sequence synthesis table.

The detailed stepwise synthesis protocol used for a typical 0.025 mmol/well simultaneous synthesis of 96 compounds is described below. This protocol was adapted for the simultaneous synthesis of arrays of analogs ranging from 12 to 96 per individual run. The general synthesis protocol is depicted in Scheme 1.

SCHEME 1
Automated Synthesis of GLP-1 Receptor Modulator Peptide Analogs

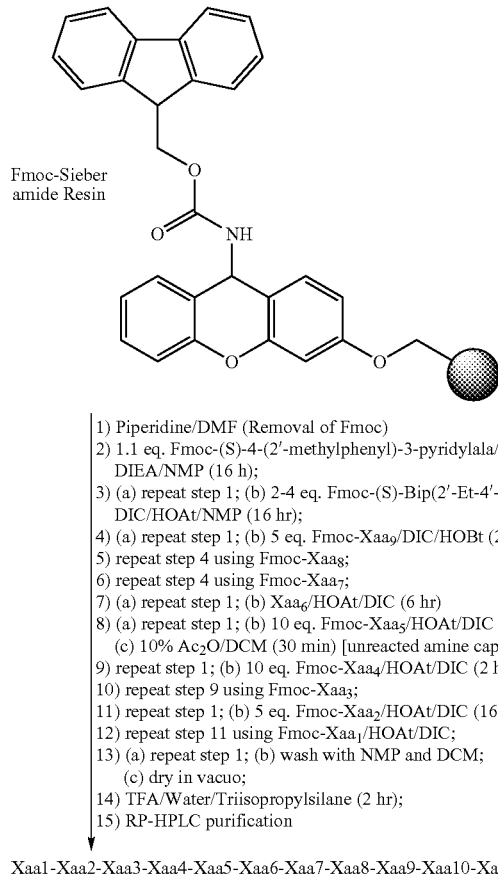

1) Piperidine/DMF (Removal of Fmoc)
2) 1.1 eq. Fmoc-(S)-4-(2'-methylphenyl)-3-pyridylala/PyBOP/ DIEA/NMP (16 h);
3) (a) repeat step 1; (b) 2-4 eq. Fmoc-(S)-Bip(2'-Et-4'-OMe)/ DIC/HOAt/NMP (16 hr);
4) (a) repeat step 1; (b) 5 eq. Fmoc-Xaa$_9$/DIC/HOBt (2 hr);
5) repeat step 4 using Fmoc-Xaa$_8$;
6) repeat step 4 using Fmoc-Xaa$_7$;
7) (a) repeat step 1; (b) Xaa$_6$/HOAt/DIC (6 hr)
8) (a) repeat step 1; (b) 10 eq. Fmoc-Xaa$_5$/HOAt/DIC (4 hr);
   (c) 10% Ac$_2$O/DCM (30 min) [unreacted amine capping step];
9) repeat step 1; (b) 10 eq. Fmoc-Xaa$_4$/HOAt/DIC (2 hr);
10) repeat step 9 using Fmoc-Xaa$_3$;
11) repeat step 1; (b) 5 eq. Fmoc-Xaa$_2$/HOAt/DIC (16 hr);
12) repeat step 11 using Fmoc-Xaa$_1$/HOAt/DIC;
13) (a) repeat step 1; (b) wash with NMP and DCM;
    (c) dry in vacuo;
14) TFA/Water/Triisopropylsilane (2 hr);
15) RP-HPLC purification Xaa1-Xaa2-Xaa3-Xaa4-Xaa5-Xaa6-Xaa7-Xaa8-Xaa9-Xaa10-Xaa11

Prior to starting the synthesis, the following reagent solutions were prepared and placed on the instrument as required: 1.5 M (15%) piperidine in DMF; 0.5 M DIEA in NMP; 0.36 M DIC in NMP; 1 M (10%) acetic anhydride in DMF. The required Fmoc-protected amino acids were prepared as 0.36 M solutions in 0.36 M HOAt/NMP and placed into the appropriate positions in the 32-position amino acid rack.

The Fmoc-protected dipeptidyl-resin prepared above was deprotected by treating with 20% piperidine in DMF (1.0 mL; 1×5 minutes; 1×15 minutes). The resin was then washed with NMP (8×1.0 mL).

Coupling of the next amino acid, typically Fmoc-Asp (OtBu)-OH or another Fmoc-amino acid with appropriate orthogonal protection if required, was carried out by manual addition of a solution of the appropriate Fmoc-amino acid (0.075 mmol, 3.0 eq.), HCTU (0.075 mmol, 3.0 eq.) and DIEA (0.15 mmol, 6.0 eq.) in NMP (1 mL) to all wells. The coupling was allowed to proceed for 3 hrs. After reactor draining by nitrogen pressure (3-5 psi) and washing the wells with NMP (4×1.0 mL).

The next coupling cycle started with the removal of the Fmoc group as described above, and involved the coupling of either Fmoc-Ser(tBu)-OH or of a different Fmoc-amino acid as required by the sequence substitutions desired at this position. The coupling was carried out in a manner identical to that described for Fmoc-Asp(OtBu)-OH. The next coupling step was carried out in the same way to incorporate either Fmoc-Thr(tBu)-OH or any of the other selected Fmoc-amino acids into this sequence position as required.

The next Fmoc-amino acid (for example Fmoc-α-methyl-Phe-OH or an analog thereof) was coupled as follows: after Fmoc deprotection in the usual manner, the Fmoc-amino acid (1-5 eq.), HOAt (1-5 eq.) and DIC (1-5 eq.) were added manually as a solution in NMP (1.0 mL) and the coupling was allowed to proceed for 16-24 hrs. The coupling was not repeated in this case. After the usual post-coupling washes, the peptidyl-resins were capped with acetic anhydride as described herein.

The next coupling step involved either Fmoc-Thr(tBu)-OH or substitution analogs as required by sequence replacements at this position. The coupling was performed as described for the initial MPS coupling of Fmoc-Asp(OtBu)-OH and its analogs, except that 10 eq. of Fmoc-Thr(tBu)-OH or substitution analogs was used and the coupling was allowed to proceed for 16 hrs and the coupling reagents used were DIC/HOAt in NMP. After the usual post-coupling washes, the peptidyl-resins were capped with 10% acetic anhydride in DCM (1×1 mL×60 mins.).

The identical coupling protocol described for the coupling of Fmoc-Asp(OtBu)-OH was used was repeated for the next three amino acid residues. Fmoc-His(Trt)-OH was coupled as the Fmoc-Thr(tBu)-OH residue described in the paragraph above in order to complete the sequence assembly of the desired 11-mer peptide analogs. For the coupling of commercially and non-commercially available non-natural amino acids needed at a certain sequence position, a single coupling protocol similar to that described above for the novel amino acid at position 6 ($X_{aa6}$) was used.

Finally, the Fmoc group was removed with 20% piperidine in DMF as described above, and the peptidyl-resins were washed with DMF (4×1.0 mL) and DCM (4×1.0 mL). They were then dried on the reactor block by applying a constant pressure of nitrogen gas (5 psi) for 10-15 min.

A. Cleavage/Deprotection

The desired peptides were cleaved/deprotected from their respective peptidyl-resins by treatment with a TFA cleavage mixture as follows. A solution of TFA/DCM/tri-isopropylsilane (70:28:2) (1.0 mL) was added to each well in the reactor block, which was then vortexed for 10 mins. This was repeated twice more and the TFA solutions from the wells were collected by positive pressure into pre-tared vials located in a matching 96-vial block on the bottom of the reactor. The vials were capped and gently vortexed for an additional 90 minutes. The vials were uncapped and concentrated in a SpeedVac™ (Savant) to a volume of about 0.2 mL. The crude peptides were then precipitated by the addition of diisopropyl ether (3 mL) and being briefly vortexed. The precipitates were pelleted by centrifugation and the supernatants were decanted. The vials were dried in a SpeedVac™ (Savant) to yield the crude peptides, typically in >100% yields (20-40 mgs). The crude peptides dissolved directly in 2 mL of 0.6% ammonium hydroxide for purification by preparative HPLC as follows.

B. Preparative HPLC Purification of the Crude Peptides

Preparative HPLC was carried out either on a Waters Model 4000 or a Shimadzu Model LC-8A liquid chromatograph. Each solution of crude peptide was injected into a YMC S5 ODS (20×100 mm) column and eluted using a linear gradient of MeCN in water, both buffered with 0.1% TFA. A typical gradient used was from 20% to 50% 0.1% TFA/MeCN in 0.1% TFA/water over 15 min. at a flow rate of 14 mL/min with effluent UV detection at 220 nm. The desired product eluted well separated from impurities, typically after 10-11 min., and was usually collected in a single 10-15 mL fraction on a fraction collector. The desired peptides were obtained as amorphous white powders by lyophilization of their HPLC fractions.

C. HPLC Analysis of the Purified Peptides

After purification by preparative HPLC as described above, each peptide was analyzed by analytical RP-HPLC on a Shimadzu LC-10AD or LC-10AT analytical HPLC system consisting of: a SCL-10A system controller, a SIL-10A autoinjector, a SPD10AV or SPD-M6A UV/VIS detector, or a SPD-M10A diode array detector. A YMC ODS S3 (4.6×50 mm) column was used and elution was performed using one of the following gradients: 10-70% B in A over 8 min, 2.5 mL/min. (method A); 5-80% B in A over 8 min, 2.5 mL/min. (method B); 5-70% B in A over 8 min., 2.5 mL/min. (method C); 25-75% B in A over 8 min, 2.5 mL/min (method D); 20-75% B in A over 8 min, 2.5 mL/min. (method E); 15-70% B in A over 8 min, 2.5 mL/min. (method F); 10-90% B in A over 8 min, 2.5 mL/min. (method G); 20-65% B in A over 8 min, 2.5 mL/min. (method H); 5-90% B in A over 8 min., 2.0 mL/min. (method I); 5-90% B in A over 8 min., 2.5 mL/min. (method J); 20-80% B in A over 8 min., 2.5 mL/min. (method K); 10-100% B in A over 8 min., 2.5 mL/min. (method L); 10-75% B in A over 8 min., 2.5 mL/min. (method M). Mobile phase A: 0.1% TFA/water; mobile phase B: 0.1% TFA/acetonitrile. The purity was typically >90%.

D. Characterization by Mass Spectrometry

Peptides were characterized by electrospray mass spectrometry (ES-MS) either in flow injection or LC/MS mode. Finnigan SSQ7000 single quadrupole mass spectrometers (ThermoFinnigan, San Jose, Calif.) were used in all analyses in positive and negative ion electrospray mode. Full scan data was acquired over the mass range of 300 to 2200 amu for a scan time of 1.0 second. The quadrupole was operated at unit resolution. For flow injection analyses, the mass spectrometer was interfaced to a Waters 616 HPLC pump (Waters Corp., Milford, Mass.) and equipped with an HTS PAL autosampler (CTC Analytics, Zwingen, Switzerland). Samples were injected into a mobile phase containing 50:50 water:acetonitrile with 0.1% ammonium hydroxide. The flow rate for the analyses was 0.42 mL/min. and the injection volume 6 µl. A ThermoSeparations Constametric 3500 liquid chromatograph (ThermoSeparation Products, San Jose, Calif.) and HTS PAL autosampler were used for LC/MS analyses. Chromatographic separations were achieved employing a Luna $C_{18}$, 5 micron column, 2×30 mm (Phenomenex, Torrance, Calif.). The flow rate for the analyses was 1.0 mL/min and column effluent was split, so that the flow into the electrospray interface was 400 µl/min. A linear gradient from 0% to 100% B in A over 4 minutes was run, where mobile phase A was 98:2 water:acetonitrile with 10 mM ammonium acetate and mobile phase B was 10:90 water:acetonitrile with 10 mM ammonium acetate. The UV response was monitored at 220 nm. The samples were dissolved in 200 µl 50:50 H2O:MeCN (0.05% TFA). The injection volume was 5 µl.

In all cases, the experimentally measured molecular weight was within 0.5 Daltons of the calculated mono-isotopic molecular weight.

Example 2

A. General Procedure for the Synthesis of N-acylated 11-mer Peptide Analogs (Scheme 2)

The synthesis of the N-acylated 11-mer peptide analogs was started from the protected 11-mer peptidyl-resin intermediate (1) (0.015 mmol), prepared as described herein, as shown in Scheme 2. The Fmoc group was removed using the procedure described herein, and the resulting resin intermediate 2 was coupled with the relevant Fmoc-protected amino acid or carboxylic acid using the coupling protocol described in the general method described herein. In cases where the appropriate anhydride was available, the N-acylation was performed using 5 eq. of the anhydride in NMP. The resulting N-acylated 11-mer analogs (3) were cleaved/deprotected and purified by prep. HPLC by the general method described herein.

SCHEME 2
Synthesis of Residue #1 Substituted/Derivatized
11-mer Peptide Analogs

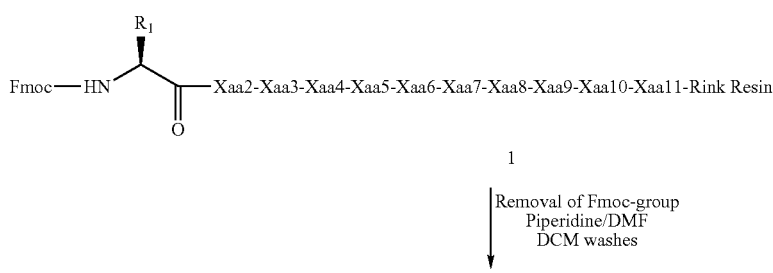

-continued

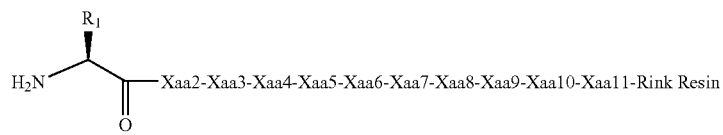

2

1. Fmoc-AA/Carboxylic acid, DIC, HOAt, NMP; or (R-CO)$_2$O, NMP
2. Removal of Fmoc
3) TFA/H$_2$O/Triisopropylsilane

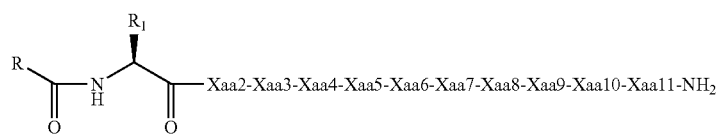

3

B. General Procedure for the Synthesis of N-carbamate Derivatives of 11-mer Peptide Analogs The synthesis of N-carbamate derivatives of 11-mer peptide analogs may be started from the protected 11-mer peptidyl-resin intermediate (1) (0.015 mmol), prepared as described herein. The Fmoc group is removed using the procedure described herein, and the resulting resin intermediate 2 is allowed to react with the relevant chloroformate in the presence of an appropriate base such as a tertiary amine, or with a di-carbonate or an activated carbonate such as p-nitrophenyl or phenyl or hydroxy-succinimidyl carbonate.

C. General Procedure for the Synthesis of N-urea Derivatives of 11-mer Peptide Analogs The synthesis of N-urea derivatives of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant isocyanate prepared, for example, as in K. Burgess et al., J. Am. Chem. Soc. 1997, 119, 1556-1564; alternatively, the resin intermediate 2 may be allowed to react with the relevant carbamoyl chloride. Similarly, N-urea derivatives of 10-mer peptide analogs may be prepared starting from a protected 10-mer peptidyl-resin intermediate, Fmoc removal and reaction of the resulting peptidyl-resin intermediate with the relevant isocyanate or carbamyl chloride.

D. General Procedure for the Synthesis of N-sulfonamides of 11-mer Peptide Analogs The synthesis of N-sulfonamides of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant sulfonyl chloride. Similarly, N-sulfonamides of 10-mer peptide analogs may be prepared starting from a protected 10-mer peptidyl-resin intermediate, Fmoc removal and reaction of the resulting peptidyl-resin intermediate with the relevant sulfonyl chloride.

E. General Procedure for the Synthesis of N-sulfonylurea Derivatives of 11-mer Peptide Analogs The synthesis of N-sulfonylurea derivatives of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant sulfamoyl chloride $R_4R_5N$—$SO_2$—Cl to yield a sulfonyl urea intermediate (see, for example, P. Davern et al. J. Chem. Soc., Perkin Trans. 2, 1994 (2), 381-387). Similarly, N-sulfonyl urea derivatives of 10-mer peptide analogs may be prepared starting from a protected 10-mer peptidyl-resin intermediate, Fmoc removal and reaction of the resulting peptidyl-resin intermediate with the relevant sulfamoyl chloride $R_4R_5N$—$SO_2$—Cl.

Example 3

Solid Phase Synthesis of 11-mer Peptide Analogs Using an Applied Biosystems Model 433A Peptide Synthesizer Following is the general description for the solid phase synthesis of typical 11-mer peptide analogs, using an upgraded Applied Biosystems Model 433A peptide synthesizer. The upgraded hardware and software of the synthesizer enabled conductivity monitoring of the Fmoc deprotection step with feedback control of coupling. The protocols allowed a range of synthesis scale from 0.05 to 1.0 mmol.

The incorporation of the two non-natural C-terminal amino acid was described above in connection with simultaneous synthesis of 11-mer analogs. Such a Fmoc-protected dipeptidyl resin was used in this ABI synthesis. The Fmoc-protected dipeptidyl-resin (0.1 mmol) was placed into a vessel of appropriate size on the instrument, washed 6 times with NMP and deprotected using two treatments with 22% piperidine/NMP (2 and 8 min. each). One or two additional monitored deprotection steps were performed until the conditions of the monitoring option were satisfied (<10% difference between the last two conductivity-based deprotection peaks). The total deprotection time was 10-12 min. The deprotected dipeptidyl-resin was washed 6 times with NMP and then coupled with the next amino acid. The procedure is illustrated by the example used in the next step.

Thus, Fmoc-Asp(OtBu)-OH was coupled next using the following method: Fmoc-Asp(OtBu)-OH (1 mmol, 10 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP, and subjected to 8 additional deprotection/coupling cycles as described above in order to complete the assembly of the desired sequence. The Fmoc-amino acids sequentially used were: Fmoc-Ser(tBu)-OH, Fmoc-Thr(tBu)-OH, Fmoc-α-methyl-Phe(2-Fluoro)-OH or analog thereof, Fmoc-Thr(tBu)-OH, Fmoc-Gly-OH, Fmoc-Glu(OtBu)-OH, Fmoc-Aib-OH and Fmoc-His(Trt)-OH. Finally, the Fmoc group was removed with 22% piperidine in NMP as described above, and the peptidyl-resin was washed 6 times with NMP and DCM, and dried in vacuo.

Alternatively, a modified coupling protocol was used in which the Fmoc-protected amino acid (0.26 mmol) was activated by subsequent addition of 0.5 M HOAt in DMF (0.52 mL) and DIC (40 μL), transferred to the reaction vessel manually and allowed to couple for 14-18 hrs.

A. Cleavage/Deprotection

The desired peptide was cleaved/deprotected from its respective peptidyl-resin by treatment with a solution of TFA/water/tri-isopropylsilane (96:2:2) (3.0 mL) for 2 hrs. The resin was filtered off, rinsed with TFA (1.0 mL), and the combined TFA filtrates were added to 35 mL of Et$_2$O. The resulting precipitate was collected by centrifugation and finally dried, to yield 232 mg of crude peptide product as a white solid. This was purified by preparative HPLC as described herein. The gradient used was from 15% to 45% 0.1% TFA/MeCN in 0.1% TFA/water over 40 min. The fractions containing pure product were pooled and lyophilized, to yield 28.4 mg (18% recovery) of pure product.

Example 4

Synthesis of Biphenylalanine and Phenyl-Heteroaryl-Alanine Analogs at Position-$X_{aa}$10 and Position-$X_{aa}$11 Represented by Formulas II and IVa For those analogs wherein position-$X_{aa}$10 and position-$X_{aa}$11 residues were represented by substituted amino acid analogs represented by Formulas II and IVa, i.e., biphenylalanine analogs (Bip analogs) or phenyl-heteroaryl-alanine analogs, their incorporation into the peptide chain was carried out in one of the following two approaches.

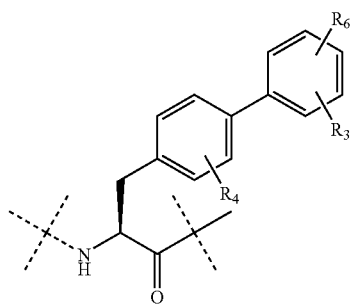

Formula II

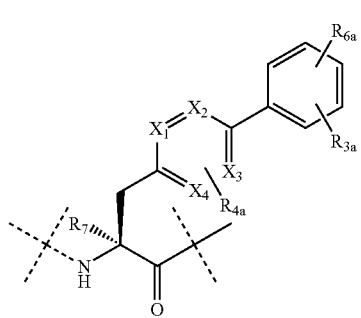

Formula IVa

A. Approach A: Solid Phase Suzuki Condensation

In approach A, solid phase Suzuki condensation was practiced to prepare the required modified biphenylalanine or phenyl-heteroaryl-alanine residue in a manner suitable for carrying out subsequent solid phase peptide synthesis to obtain the target peptides. When the amino acid at position-$X_{aa}$11 in the target peptide was represented by a modified biphenylalanine or phenyl-heteroaryl-alanine residue, it was prepared as shown in Scheme 3. After removal of the Boc α-amine protecting group, chain elongation was continued using multiple peptide synthesis as described in the previous section to obtain the desired 11-mer peptides or its derivatives thereof When the modified biphenylalanine analog was in position $X_{aa}$10 of the target peptides, the required amino acid was prepared using a suitable dipeptide precursor on solid support as shown in Scheme 4 (below).

The resulting dipeptidyl segment containing the required modified biphenylalanine derivative was then used to carry out the synthesis of the target 11-mer peptide or its derivatives thereof. When both position-$X_{aa}$10 and position-$X_{aa}$11 required novel biphenylalanine or phenyl-heteroaryl-alanine residues, two sequential solid phase Suzuki reactions were carried out as shown in Scheme 5 (below).

1. General Procedure for Preparation of SynPhase™ Lanterns Containing Amino Acids Represented by Formula IVa at Position-$X_{aa}11$ (Suzuki Couplings)

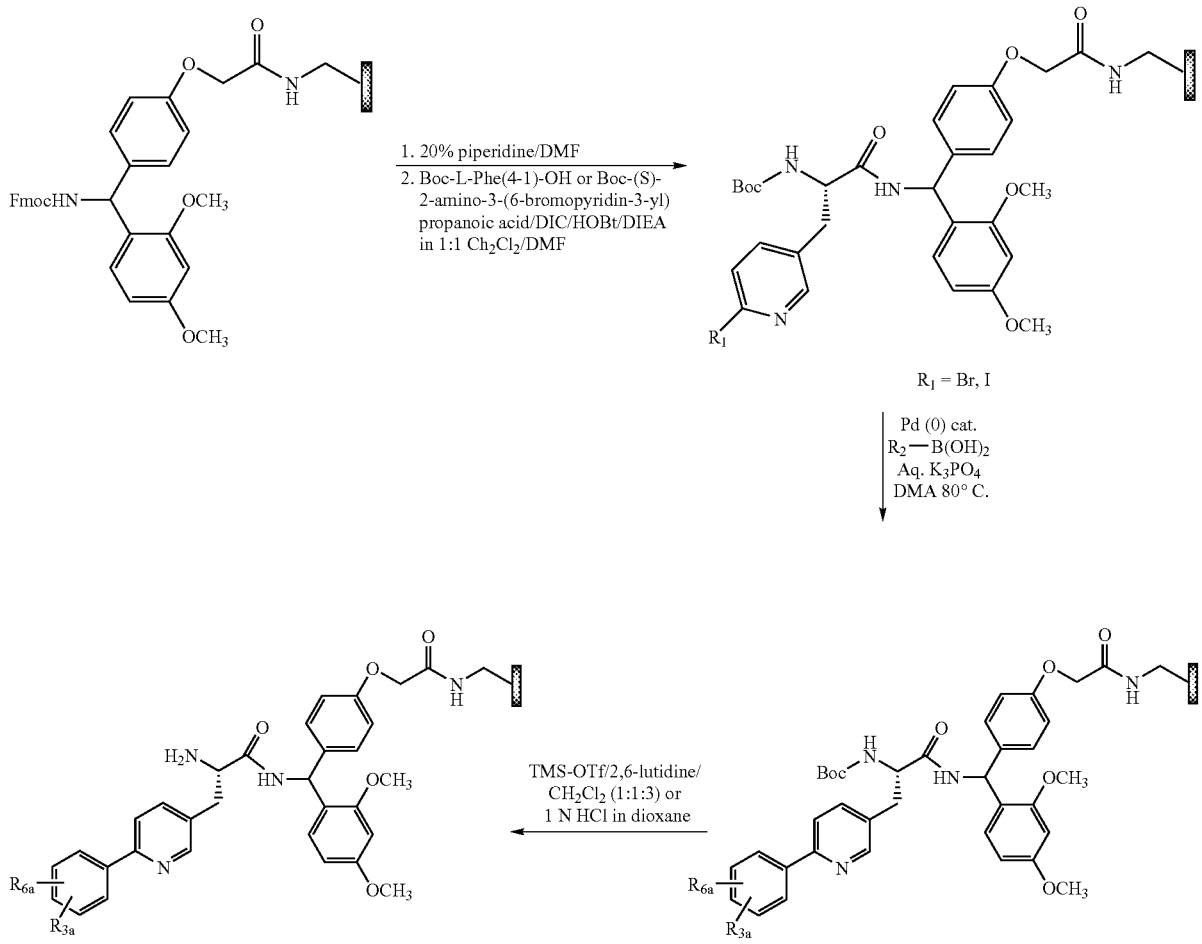

◪ = SynPhase™ Lantern, grafted polystyrene surface
$R_2\text{—}B(OH)_2$ = aryl- or heteroaryl-boronic acid.
$R_3$, $R_4$, $R_6$, $R_{3a}$, and $R_{6a}$ are represented by the side chains described in Formulas II and IVa.

a. General Procedure A

SynPhase™ Lanterns (A-series (0.075 mmole/lantern) or D-series (0.035 mmole/lantern), from Mimotopes) derivatized with an N-Boc-(S)-2-amino-3-(6-bromopyridin-3-yl) propanoic acid residue or N-Boc-L-4-iodophenylalanine residue either attached directly via a Knorr linkage (Boc-amino acid-resin) or via an amino acid-Knorr linkage (Boc-dipeptide-resin) were placed into 13×100 mm glass culture tubes with screw caps. (The following procedure was used for D-series lanterns. Similar ratios of reactants were used for reactions involving A-series lanterns.) Aryl- or heteroaryl-boronic acids (0.140 mmole, 4 equivalents) were dissolved in 0.30 ml of N,N-dimethylacetamide. The resulting solutions were added to the lanterns in the 13×100 mm glass culture tubes.

Potassium phosphate (0.280 mmole, 8 equivalents, 0.14 ml of a 2 M aqueous solution) was added to the aryl- or heteroaryl-boronic acid solution, followed by 0.10 ml of an N,N-dimethylacetamide solution containing 4.0 mg of tetrakis(triphenylphosphine)palladium(0) catalyst (ca. 10 mole %, 0.0035 mmol). The resulting mixtures were blanketed with nitrogen, and the reaction vessels were tightly capped and maintained at 80° C. for 17-20 hours while placed on an orbital shaker. The lanterns were transferred to a filter apparatus, and washed with 3×1 ml of N,N-dimethylacetamide and 3×1 ml of dichloromethane (per lantern, minimum of 3 minutes/wash cycle) prior to Boc group cleavage (see General Procedure below).

b. General Procedure B

The reactions were performed as in General Procedure A except a different catalyst was employed. For this procedure, the dichlorobis(triphenylphosphine) palladium(II) was used as the catalyst. For the D-series lantern scale reactions, ca. 10 mol % (0.0035 mol) catalyst was used.

2. Procedures for Cleavage of the Boc Group a. Method A (The following procedure applies to D-series lanterns, 0.035 mmol/lantern. A similar, appropriately scaled procedure was used for A-series lanterns, 0.075 mmol/lantern.) The Boc-protected lanterns prepared as described in General Procedures A or B were treated with 0.5 ml of a reagent solution consisting of trimethylsilyl trifluoromethanesulfonate, 2,6-lutidine and dichloromethane (1:1:3 by volume). After 2 such reagent treatments for 1 hour each with mild agitation, the resins were washed with 4×1.0 ml of dichloromethane, 3×1.0 ml of N,N-dimethylformamide, and 3×1.0 ml dichloromethane. The lanterns were then subjected to the next acylation (coupling reaction) in the peptide synthesis sequence.

b. Method B

The Boc-protected lanterns prepared as described in General Procedures A or B were treated with 0.5 ml of 1 N HCl in anhydrous 1,4-dioxane for 1 hour at room temperature with mild agitation. The lanterns were washed with 2×1.0 ml of 1,4-dioxane, 2×1.0 ml of 10% N,N-diisopropylethylamine in N,N-dimethylacetamide (vol:vol), 3×1.0 ml of N,N-dimethylacetamide, and 3×1.0 ml of dichloromethane to provide the free amino-lanterns ready for the next acylation (coupling reaction) step.

Example 5

General Procedure for Preparation of a Lantern Containing a Modified Biphenylalanine Residue at Position-$X_{aa}10$ The General Procedures described above (A and B) for Suzuki coupling were utilized to obtain the required dipeptidyl lantern containing modified Phe at position-$X_{aa}10$ starting with the amino acid (at position-$X_{aa}11$) bound to SynPhase™ Lantern as shown in Scheme 4.

SCHEME 4

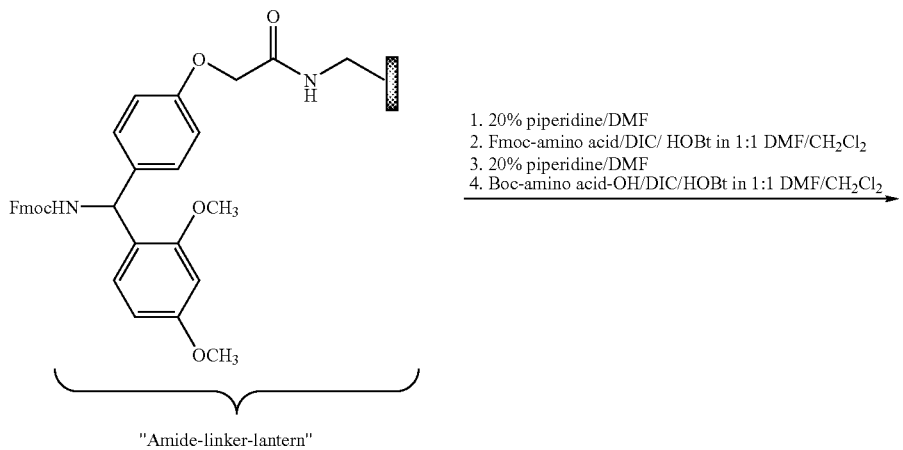

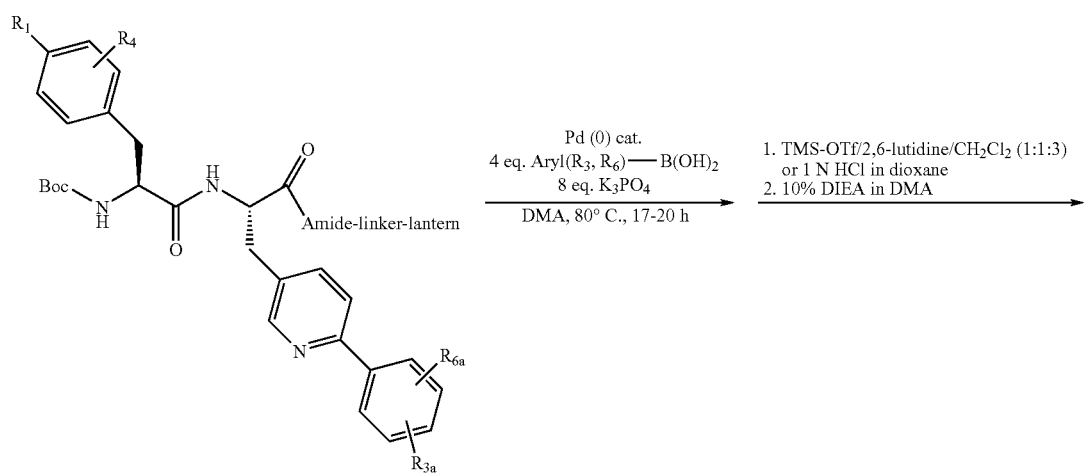

-continued

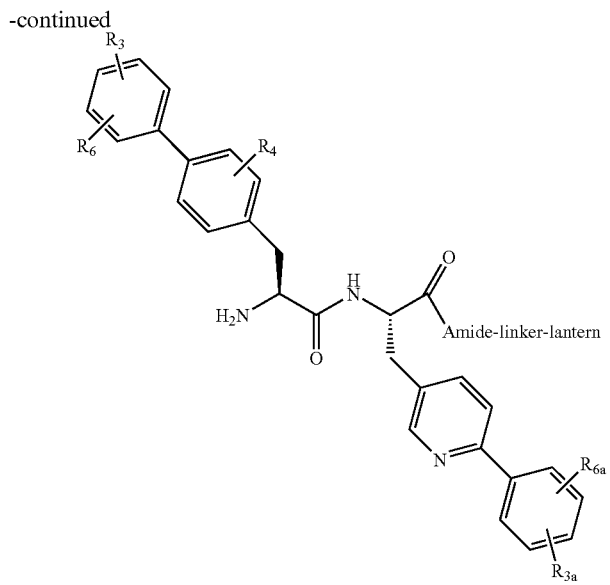

$R_3$, $R_4$, $R_6$, $R_{3a}$, and $R_{6a}$ are represented by the side chains described in Formulas II and IVa.

Example 6

General Procedure for Preparation of Lantern Containing Amino Acids Represented by Formula II and Formula IVa at Both Positions-$X_{aa}10$ and -$X_{aa}11$ Utilizing the procedures described above for position-$X_{aa}11$ modified analogs (Scheme 1) and carrying out the Suzuki coupling procedure two successive times produced dipeptidyl lanterns containing modified phenylalanine and phenyl-heteroaryl alanine residues at both positions-$X_{aa}10$ and -$X_{aa}11$ as illustrated in Scheme 5, below.

Example 7

General Procedures for Acylation/Elongation of Peptides on SynPhase™ Lanterns

A. Procedure for Fmoc-Deprotection

A D-series SynPhase™ Lantern (0.035 mmol/lantern loading) was added to 0.5 ml 8:2 N,N-dimethylformamide/piperidine (vol:vol). Mild agitation was applied. After 1 h, the lantern was washed with 3×1.0 ml N,N-dimethylformamide and 3×1.0 ml dichloromethane, allowing lantern to soak at least 3 min/wash.

B. Procedure for Acylation/Amino Acid Coupling (Scheme 6)

A side chain and a-amine protected amino acid (0.105 mmol) was dissolved in 0.5 ml 1:1 N,N-dimethylformamide/dichloromethane. To this solution was added N-hydroxybenzotriazole (0.105 mmol), N,N-diisopropylethylamine (0.315 mmol), and N,N'-diisopropylcarbodiimide (0.105 mmol). The amino acid solution was allowed to sit for 10 minutes, after which a D-series lantern containing α-amine deprotected peptide (0.035 mmol/lantern) was added to the solution. The vial was capped and gently agitated for 16-20 h. The lantern was then washed with 3×1.0 ml N,N-dimethylformamide and 3×1.0 ml dichloromethane, letting lantern soak for 3-5 min/wash cycle.

SCHEME 5

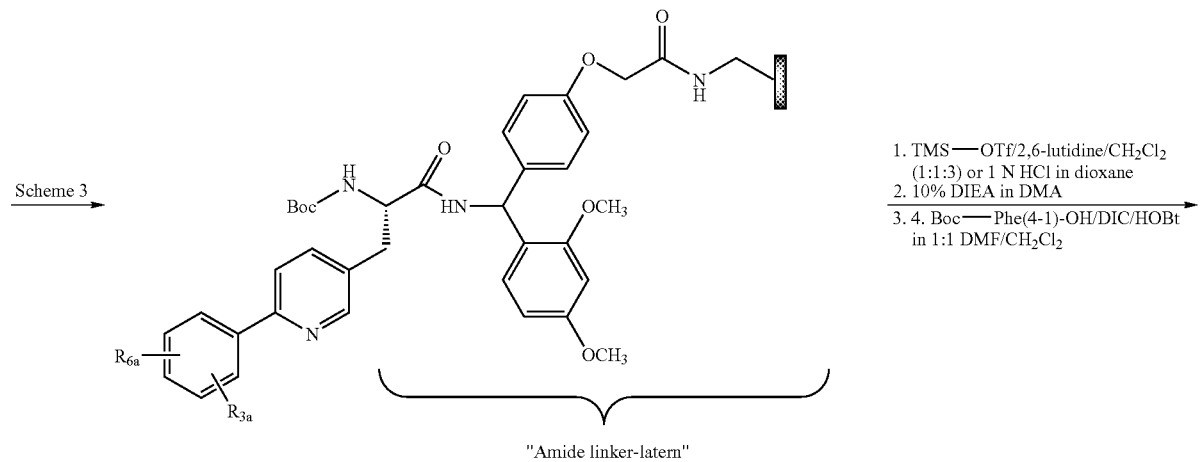

"Amide linker-latern"

-continued
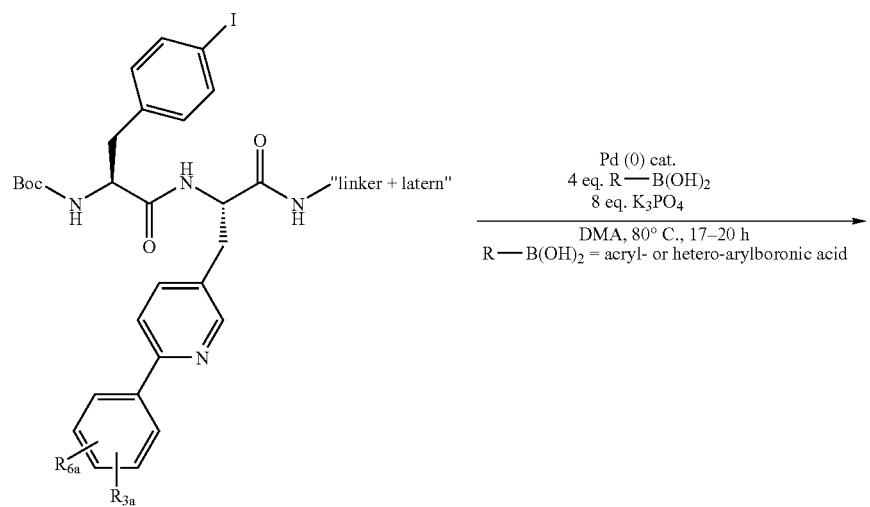
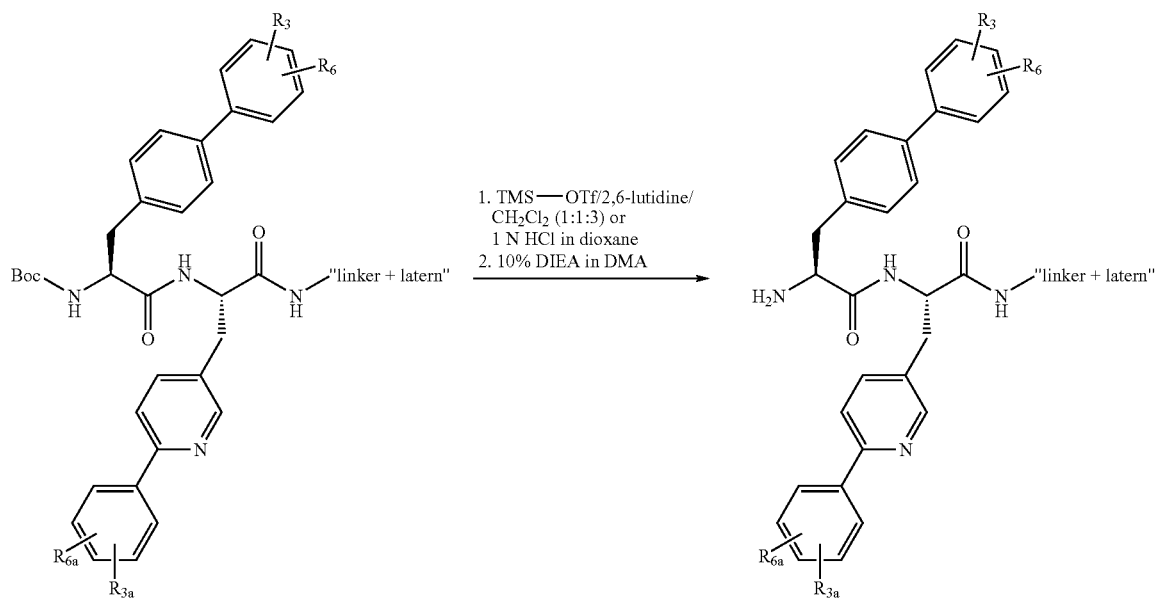
$R_3$, $R_6$, $R_{3a}$, and $R_{6a}$ are represented by the side chains described in Formulas II and IVa.

SCHEME 6
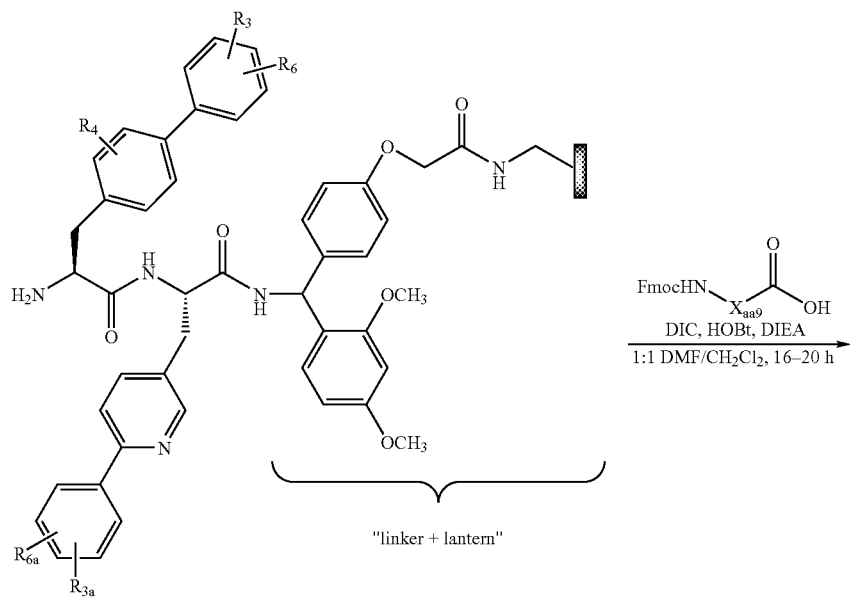
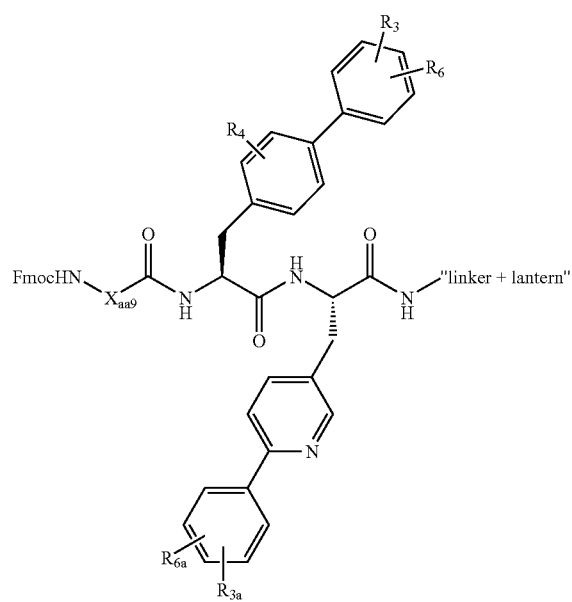
$R_3$, $R_4$, $R_6$, $R_{3a}$, and $R_{6a}$ are represented by the side chains described in Formulas II and IVa.

Example 8

General Procedure for Preparation of Peptides Via Fragment Condensation

In approach A, solid phase Suzuki condensation was practiced to prepare the required amino acids represented by Formula II Formula IVa at positions $X_{aa}10$ and $X_{aa}11$, as described in Example 4. The dipeptide was cleaved from support, with either simultaneous (procedure A) or subsequent (procedure B) removal of the N-terminal α-amine protecting group. The dipeptide was then coupled to a fully side chain-protected 9 amino acid peptide (vide infra). Subsequent deprotection of side chains and purification resulted in the desired 11-mer peptide products.

A. Approach A: Solution Phase Fragment Condensation

In Approach A, solid phase Suzuki condensations and acylations were performed (as described in Example 7) to prepare the desired dipeptides bound to SynPhase™ Lanterns, with the N-terminal α-amine either Boc-protected or Fmoc-protected. The dipeptides were cleaved from the Lantern support under acidic conditions. In the case of Boc-protected N-terminal α-amines, the acidic cleavage afforded simultaneous deprotection of the α-amine as shown in Scheme 7, and these were either purified or carried directly into the fragment coupling sequence.

The dipeptides containing Fmoc-protected N-terminal α-amines were cleaved under acidic conditions and the N-terminal α-amine was deprotected in solution, as shown in Scheme 8. These dipeptides were purified, then carried into the fragment coupling sequence.

1. Procedures for Cleavage of Dipeptides from SynPhase™ Lanterns a. Procedure A (Boc-protected Dipeptides; see Scheme 7)

The D-series SynPhase™ Lantern was placed in a 1 dram glass vial. A solution of 1:1 trifluoroacetic acid/dichloromethane (0.5 ml) was added to the vial. The vial was capped, and mildly agitated on an orbital shaker (100 rpm) for 2 h. The cleavage solution was transferred to a fresh vial, and an additional 0.5 ml 1:1 trifluoroacetic acid/dichloromethane was added to the lantern. The vial was again capped, and mildly agitated on an orbital shaker (100 rpm) for 2 h. The second cleavage solution was added to the first, and the lantern was rinsed with dichloromethane. The rinse was added to the cleavage solutions, and solvent was evaporated to yield the dipeptide as the trifluoroacetic acid salt of the α-amine.

SCHEME 7

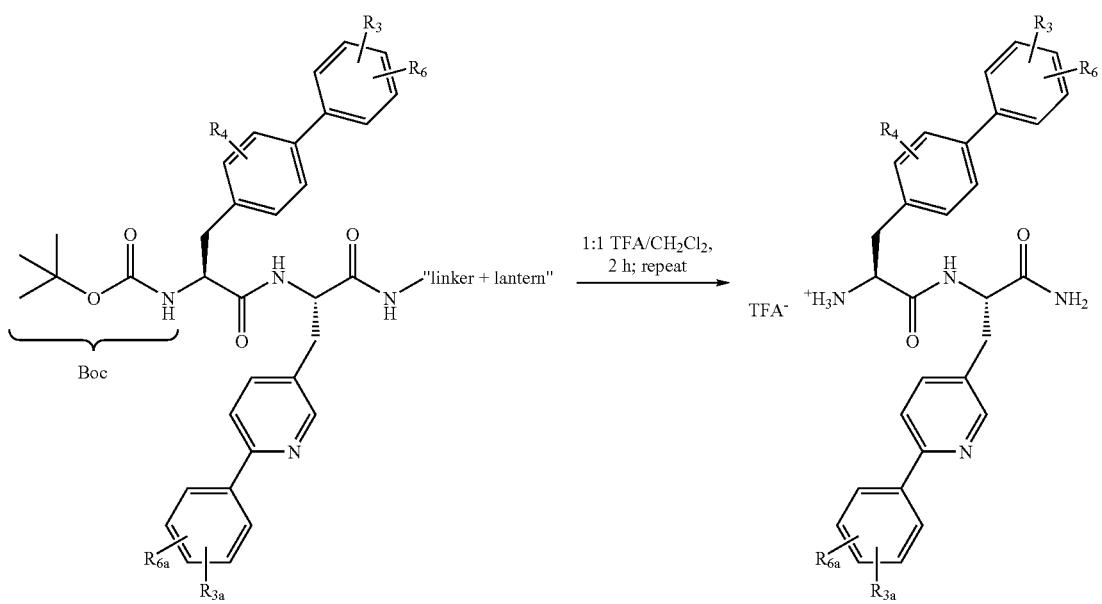

$R_3$, $R_4$, $R_6$, $R_{3a}$, and $R_{6a}$ are represented by the side chains described in Formulas IIa and IVa.

b. Procedure B (Fmoc-protected Dipeptides; Scheme 8)

The Fmoc-protected dipeptide was cleaved from the SynPhase™ Lantern as described above in Procedure A. The lanterns were rinsed with dichloromethane, and solvent was evaporated from the combined rinse/cleavage solutions. To the resulting residue (in a 1 dram vial) was added 0.40 ml 8:2 dimethylformamide/piperidine (vol:vol). The vial was capped and allowed to react for 45 min. The remaining solvent was evaporated off, and the resulting product was purified by HPLC, using a C-18 column and $CH_3CN/H_2O/TFA$ solvent system to yield (after evaporation of solvent) the dipeptide as the trifluoroacetic acid salt of the α-amine.

SCHEME 8

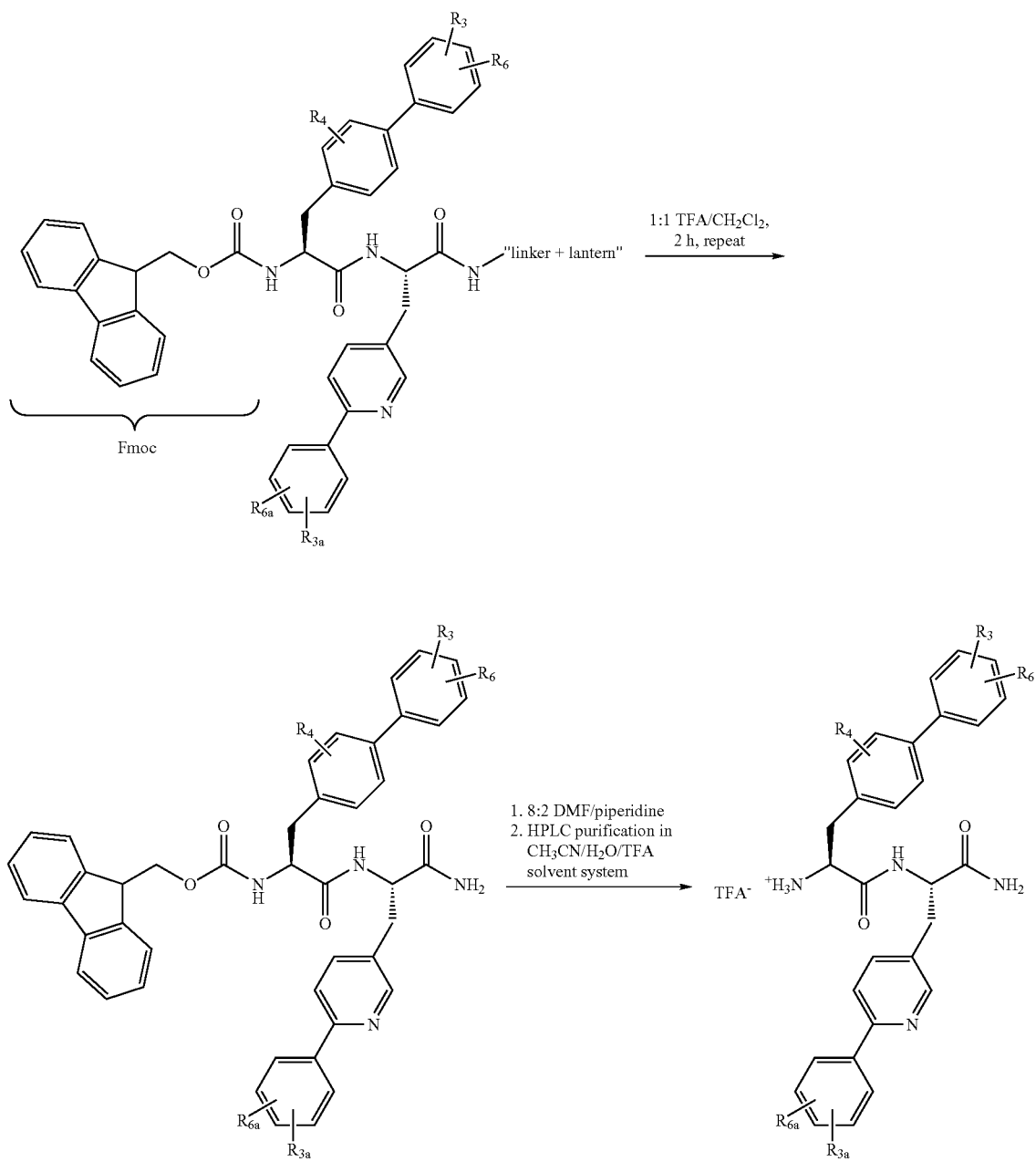

$R_3$, $R_4$, $R_6$, $R_{3a}$, and $R_{6a}$ are represented by the side chains described in Formulas II and IVa.

2. Procedure for Solid Phase Synthesis of Side Chain Protected 9-mer Peptide C-terminal Carboxylic Acid (Scheme 9A)

A solution of Fmoc-(L)-Ser(tBu)-OH (5 eq.), 0.5 M HOAt/DMF (5 eq.) and DIC (5 eq.) in NMP (5 mL) was vortexed with (L)-Asp(OtBu)-2-chloro chlorotrityl resin (3.0 g, 2.16 mmol) for 18 hrs at RT. After several washes with NMP, the Fmoc group was removed by treatment with 1.5 M piperidine/DMF twice (5 min and 10 min). These coupling and deprotection steps were repeated seven times to assemble the desired sequence, except that 1.1 eq. and 1.5 eq. of Fmoc-α-Me-Phe(2-R-6-R")-OH and Boc-(L)-His(Trt)-OH were used, respectively, for their couplings, and that HATU/HOAt and DIEA (4 eq.) were used for coupling Fmoc-Thr(tBu)-OH onto (S)-α-Me-Phe(2-R-6-R")-peptidyl-resin.

Upon assembly completion, the peptidyl-resin was washed with DCM and then the protected 9-mer peptide C-terminal carboxylic acid was released from the resin by treatment with DCM/AcOH/TFE (8:1:1, v:v:v) for 1 hr at RT. The resin was filtered off and the filtrate was evaporated to dryness, redissolved in AcCN/water (2:1) and lyophilized twice, to yield 2.777 g of 81% pure product, which was used in the subsequent fragment coupling step with no further purification.

SCHEME 9A

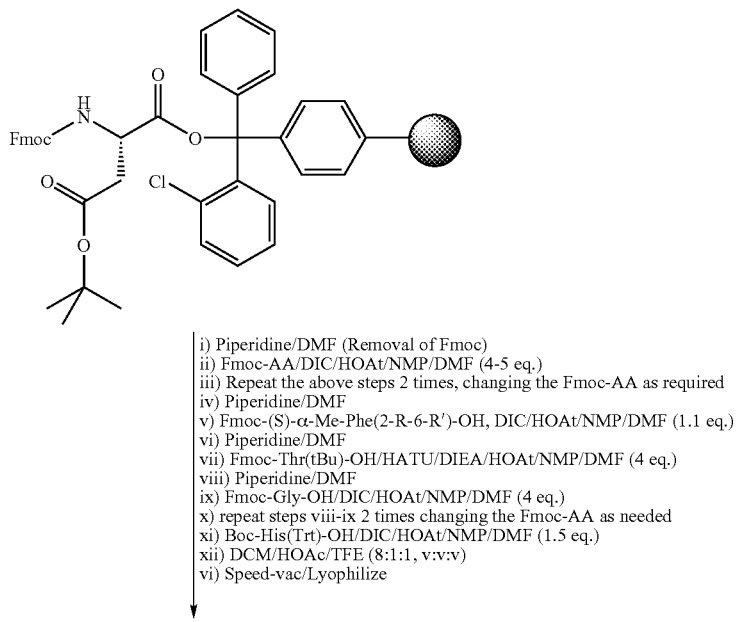

i) Piperidine/DMF (Removal of Fmoc)
ii) Fmoc-AA/DIC/HOAt/NMP/DMF (4-5 eq.)
iii) Repeat the above steps 2 times, changing the Fmoc-AA as required
iv) Piperidine/DMF
v) Fmoc-(S)-α-Me-Phe(2-R-6-R')-OH, DIC/HOAt/NMP/DMF (1.1 eq.)
vi) Piperidine/DMF
vii) Fmoc-Thr(tBu)-OH/HATU/DIEA/HOAt/NMP/DMF (4 eq.)
viii) Piperidine/DMF
ix) Fmoc-Gly-OH/DIC/HOAt/NMP/DMF (4 eq.)
x) repeat steps viii-ix 2 times changing the Fmoc-AA as needed
xi) Boc-His(Trt)-OH/DIC/HOAt/NMP/DMF (1.5 eq.)
xii) DCM/HOAc/TFE (8:1:1, v:v:v)
vi) Speed-vac/Lyophilize

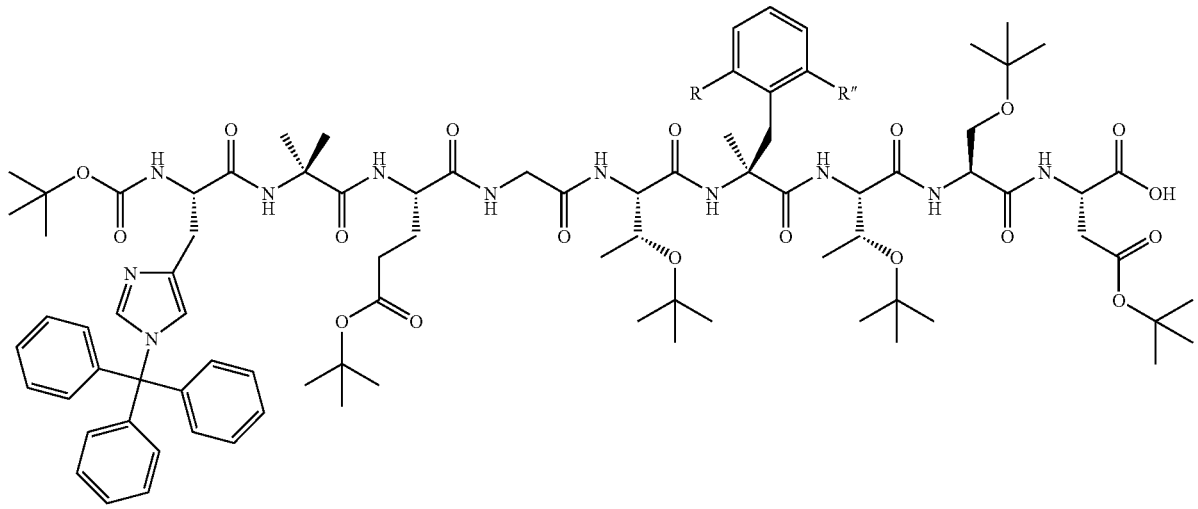

3. Procedure for Solid Phase Synthesis of Side Chain Protected N-methoxycarbonyl 9-mer Peptide C-terminal Carboxylic Acid (Scheme 9B)

The N-Fmoc side chain protected 8-mer peptidyl-(o-Cl)-Trityl resin (3.5 mmol) was prepared as described above (Scheme 9A). After Fmoc removal and DMF washes, the peptidyl-resin (3.5 mmol) was treated with N-α-Methyloxycarbonyl-N-im-Trityl-L-Histidine (2.4 g, 5.33 mmol) in 0.546 M HOAt in DMF (9.8 mL, 5.33 mmol), followed by addition of DMF (10 mL) and DIC (0.633 mL, 5.33 mmol). After stirring for 72 hours, the N-derivatized 9-mer peptidyl-resin was washed with DMF (4×50 mL) and DCM (2×50 mL), and the protected 9-mer peptide C-terminal carboxylic acid was released from the resin by treatment with DCM/AcOH/TFE (8:1:1, v:v:v) for 3 hours at RT. The resin was filtered off and the filtrate was evaporated to dryness, redissolved in AcCN/water (1:1.4) and lyophilized twice, to yield 4.05 g of 71% pure product, which was used in the subsequent fragment coupling steps with no further purification.

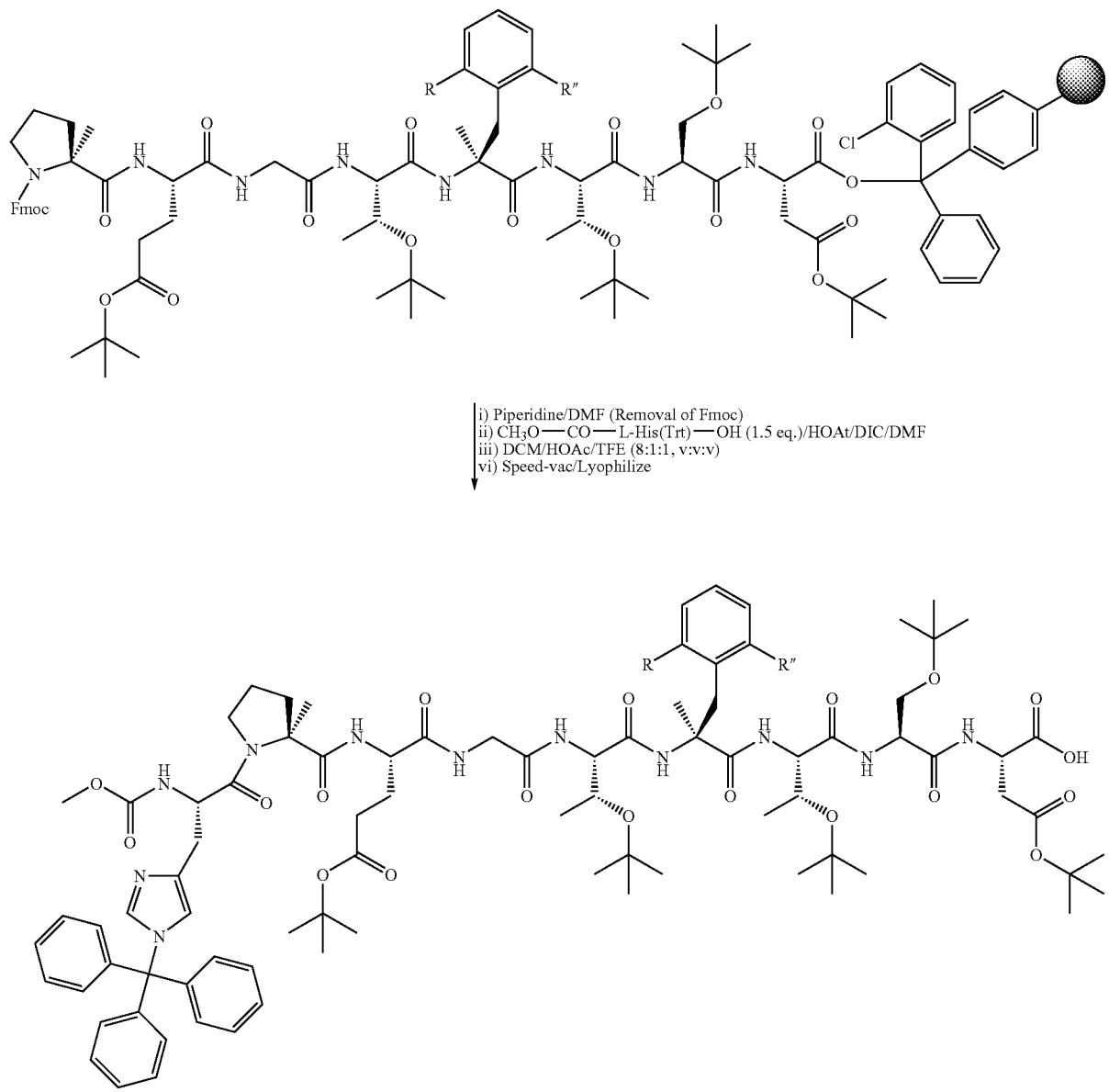

SCHEME 9B i) Piperidine/DMF (Removal of Fmoc)
ii) CH₃O—CO—L-His(Trt)—OH (1.5 eq.)/HOAt/DIC/DMF
iii) DCM/HOAc/TFE (8:1:1, v:v:v)
vi) Speed-vac/Lyophilize 4. Procedure for Solution Phase Fragment Coupling Reaction These reactions were performed both in a single-compound format in 1 dram vials, and in a parallel array of compounds in a 2 ml 96-well plate. The following description (shown in Scheme 10) applies to the single-compound case, but is entirely analogous to the reactions performed in the 96-well plate.

The TFA-salt of the dipeptide (0.01 mmol) was dissolved in 0.25 ml THF containing 0.5% N,N-diisopropylethylamine in a 1.5 ml glass vial. Macroporous carbonate resin (MP-carbonate, 0.03 mmol, Argonaut Technologies) was added to the vial. The vial was capped and agitated for 2 h at room temperature. The solution was filtered, and excess solvent was removed by evaporation.

A solution of 0.15 ml of 9:1 chloroform/N,N-dimethylformamide containing the side chain protected 9-mer peptide C-terminal carboxylic acid (0.008 mmol) and N-hydroxybenzotriazole (HOBt, 0.008 mmol) was added to the vial containing the dipeptide amine. Diisopropylcarbodiimide (DIC, 0.08 mmol) was added in a solution of 0.05 ml 9:1 chloroform/N,N-dimethylformamide. The vial was capped, and the reaction was stirred on an orbital shaker at room temperature for 16 h. Remaining solvent was evaporated from the vial.

The 11-mer peptide side chains and N-terminal α-amine were deprotected with 0.40 ml 97.5:2.5 trifluoroacetic acid/triisopropylsilane (TFA/TIS) for 1 h. The remaining solvent was evaporated away, and the 11-mer peptide products were then purified by HPLC, using a CH₃CN/H₂O/TFA solvent system, and triggering effluent collection by the detection of desired product mass.

SCHEME 10
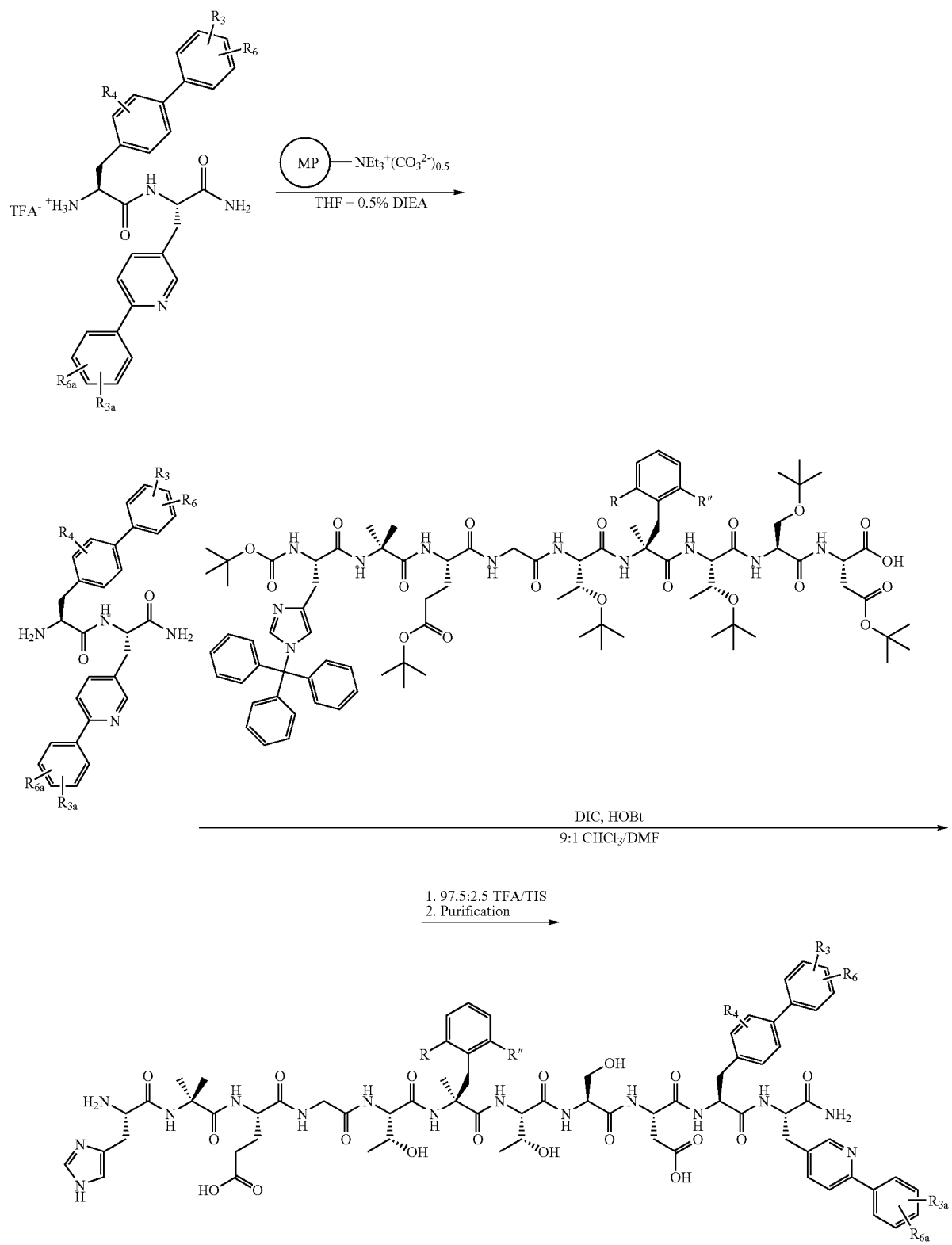
R, R" = H, or F
R3, R4, R6, R3a, and R6a are represented by the side chains described in Formulas II and IVa.

B. Approach B: Synthesis of Fmoc-amino Acids Analogs Represented by Formulas II and IVa Using Suzuki Coupling in Solution The below examples illustrate the synthesis of several Fmoc-amino acids analogs represented by Formulas II and IVa, which were then utilized for the solid phase synthesis of 11-mers and other peptide analogs as described in Example 1.

Example 9

Synthesis of Fmoc-(S)-2'-ethyl-4'-methoxy-biphenylalanine [Fmoc-(S)-Bip(2'-Et-4'-OMe)]

The following Scheme 11 describes the synthesis of Fmoc-(S)-2'-ethyl-4'-methoxy-biphenylalanine.

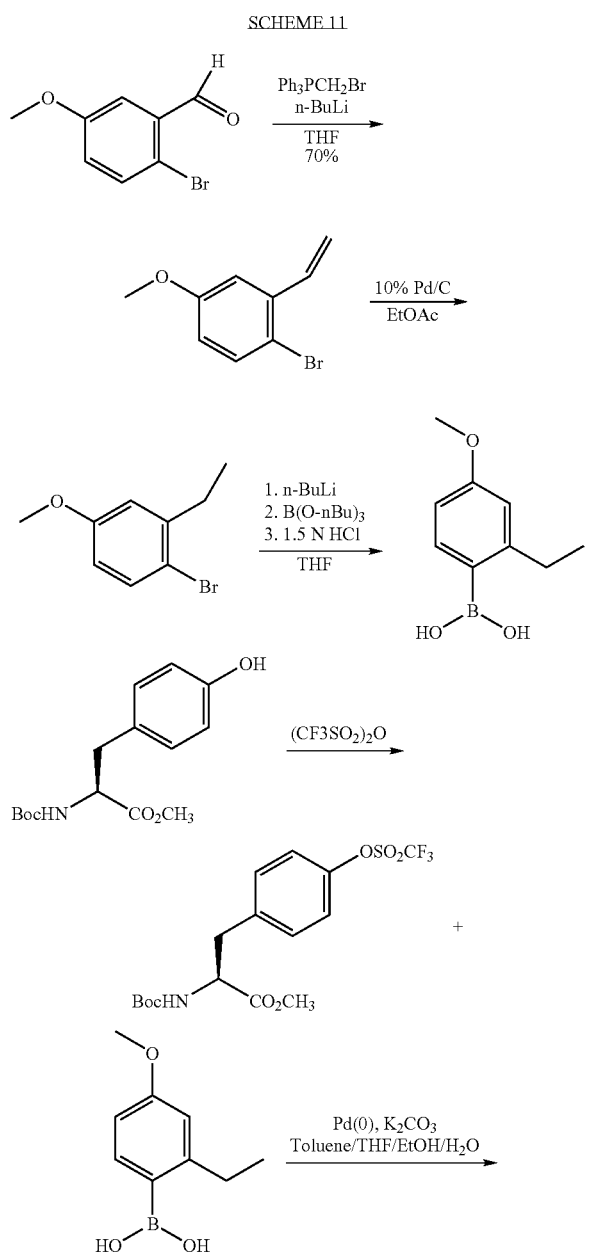

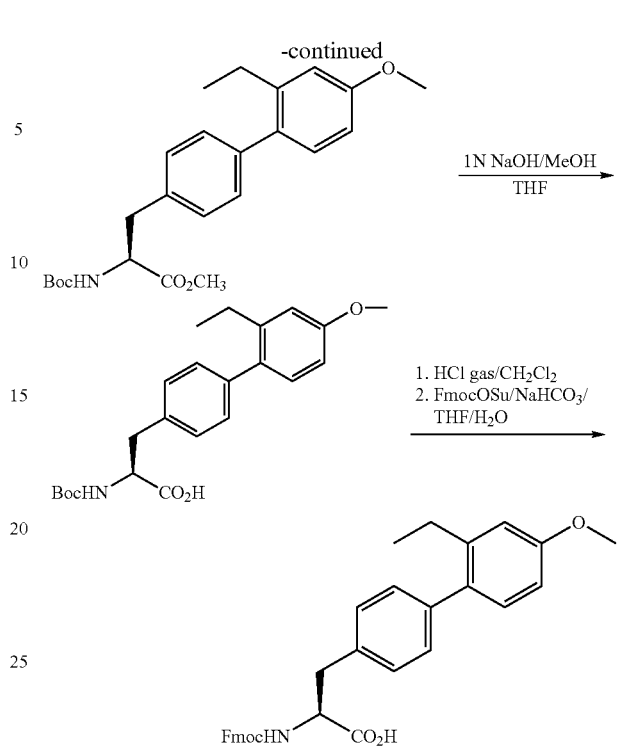

A. Boc-L-Tyrosine-O-triflate

To a solution of 25 g (85 mmol) of Boc-L-tyrosine methyl ester, and 36.25 g (339 mmol, 4 eq.) of 2,6-lutidine in 200 mL of dry DCM, kept at −40° C. under $N_2$, was added slowly 47.74 mg (169.5 mmol, 2 eq.) of triflic anhydride in DCM (100 ml) over 30 minutes. The solution was stirred at −40° C. for an additional 2 hours. HPLC analysis indicated that the reaction was complete. The reaction was quenched by addition of 20 mL of water. The layers were separated, and the organic layer was washed with 3×200 ml of 1N HCl, 200 ml of saturated Na2CO3, 200 ml of water and 200 mL of brine. The organic layer was dried over magnesium sulfate, filtered and dried in vacuo to give the crude product as a red oil. It was subjected to silica gel flash chromatography (300 g silica gel, 0 to 50% EtOAc in hexanes gradient). The product-containing fractions were concentrated in vacuo to give the desired compound (27 g, 75% yield) as a white solid.

B. 2-Ethyl-4-methoxy-phenylboronic acid

1. Method A

A suspension of methyl triphenylphosphoniumbromide (199.5 g, 0.465 mol) in dry THF (800 ml) was purged for 10 min. and cooled to 10° C. n-Butyl lithium (169 ml, 0.465 mol, 2.75 M solution) was added slowly over 30 min. and stirred for 1 hr. 2-Bromo-5-methoxy benzaldehyde (100 g, 0.465 mol) in dry THF (300 ml) was added slowly over a period of 30 min. After the addition, the reaction mixture was stirred for 1 hr. Petroleum ether (2 L) was added and the reaction mixture was stirred for an additional 30 min. The reaction mixture was filtered over a silica gel pad. The pad was washed with diethyl ether. The combined organic washes were concentrated below 30° C. and the crude product was purified by 60-120 silica gel chromatography using 100% pet ether as eluent. Yield: 92 g, 90%, as pale yellow liquid.

2,2'-Bipyridyl (24.3 g, 0.15 mol) and 2-bromo-5-methoxystyrene (65 g, 0.31 mol) in ethyl acetate (650 ml) were cooled to 0° C. The solution was purged and 10% palladium on carbon (16.25 g, 25%) was added under a stream of nitrogen. The reaction mixture was stirred under 2 kg pressure in a Parr shaker for 3 days under hydrogen. The reaction progress was monitored by HPLC. The reaction mixture was filtered through Celite and the filtrate was washed with 5% solution of potassium bisulfate, dried over sodium sulfate and concentrated below 30° C. Yield: 60 g, 91%, as pale yellow liquid.

A solution of 4-bromo-3-ethyl anisole (94 g, 0.437 mol) in THF (900 ml) was cooled to −78° C. n-Butyl lithium (249 ml, 0.55 mol) was added drop wise at the same temperature. Stirring was continued for 1 hr at −78° C. Tri-n-butyl borate (177 ml, 0.655 mol) was added slowly at −78° C. The cooling bath was removed, the reaction mixture was allowed to warm to 0° C. and was quenched with 1.5 N hydrochloric acid at 0° C. The organic layer was separated. The aqueous layer was extracted with ethylacetate and the combined organic layers were washed with brine and concentrated. The residue obtained was stirred in pet-ether for 30 min. The solid obtained was filtered and dried under vacuum. Yield: 65 g, 82%, as a white solid.

2. Method B (see Scheme 12)

To a mixture of 3-Ethylphenol (50 g, 0.4 mol, 98% pure, Fluka) and $K_2CO_3$ (283 g, 2.05 mol) in dry acetone (500 ml) was added methyliodide (290 g, 2.05 mol). The reaction mixture was transferred to an autoclave and refluxed at 70° C. overnight. The reaction mixture was filtered through a Celite pad. The pad was washed with acetone and the combined filtrate and washes were concentrated. The product was dissolved in DCM, filtered and evaporated to dryness. Yield: 50 g, 90%, as a brown liquid.

3-Ethylanisole (50 g, 0.3676 mol) and N-bromosuccinimide (72 g, 0.4 mol) in acetonitrile (1 L) were stirred for 8 hr under dark at RT. The reaction mixture was concentrated below 40° C. and the residue obtained was redissolved in $CCl_4$ and filtered. The filtrate was concentrated and the product was purified by fractional distillation. Yield: 35 g, 43%, as pale yellow liquid.

The 4-bromo-3-ethyl anisole was converted to the corresponding boronic acid as described in Method A. For the purpose of reaction scale up, the conversion of 4-bromo-3-ethyl anisole to 2-ethyl-4-methoxy-boronic acid may be accomplished using a Grignard method. Such method involves formation of the Grignard reagent by reaction of 4-bromo-3-ethyl anisole with Mg (1.1 eq.) in THF, followed by reaction of the resulting Grignard intermediate with tri-n-butyl- or trimethylborate as described in Method A.

SCHEME 12

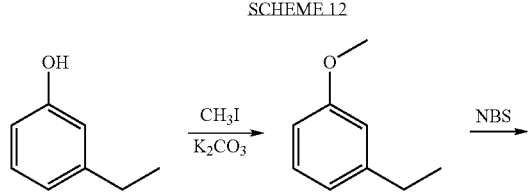

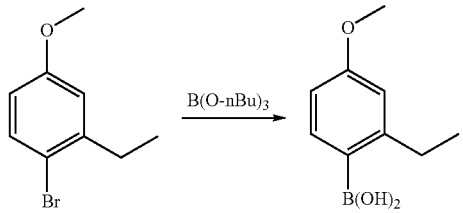

C. Fmoc-(S)-2'-ethyl-4'-methoxy-biphenylalanine

Boc-L-Tyrosine-O-triflate (81 g, 0.19 mol) in dry toluene (600 ml) was purged for 10 min with nitrogen. $K_2CO_3$ (36 g, 0.26 mol) in 200 ml of water was added followed by 2-Ethyl-4-Methoxy-phenylboronic acid (36 g, 0.2 mol) and the reaction mixture was purged for 10 min using nitrogen. $Pd(PPh_3)_4$ (16.18 g, 0.014 mol), ethanol (200 ml) and THF (400 ml) were added and the reaction mixture was heated to 100° C. with stirring for 4 hr. The reaction mixture was concentrated under vacuum and the residue was dissolved in DCM (1.0 L). The organic layer was washed with 10% sodium hydroxide solution, 15% of citric acid solution, dried over sodium sulfate and concentrated. The crude product was purified by 60-120-mesh silica gel column chromatography with 10% of ethyl acetate in pet-ether. Yield: 50 g, 65%, as a yellow liquid.

To a mixture of the methyl ester of Boc-(S)-2'-ethyl-4'-methoxy-biphenylalanine (60 g, 0.146 mol) in THF (450 ml) and methanol (85 ml) was added sodium hydroxide (24 g, 0.58 mol) in 85 ml of water. The reaction mixture was stirred at RT overnight, concentrated and the residue was dissolved in water (100 ml) and washed with diethyl ether. The aqueous layer was acidified to pH 1 using 20% citric acid and extracted with ethyl acetate. The extract was washed with brine, dried over sodium sulfate and evaporated to dryness. Yield: 55 g, 94%, as colorless liquid.

Boc-(S)-2'-ethyl-4'-methoxy-biphenylalanine (55 g, 0.138 mol) was dissolved in dry DCM (1 lit) and dry HCl gas was purged at RT for 6 hr. The solid product obtained was filtered and dried under vacuum. Yield: 46 g, 100%.

To the free amino acid hydrochloride salt (30 g, 0.089 mol) in THF (700 ml) was added $NaHCO_3$ (29 g, 0.358 mol) in water (240 ml). Fmoc-OSu (30 g, 0.089 mol) was added portion wise over a period of 30 min. The reaction mixture was stirred overnight at RT. The THF was removed under vacuum and water (2.0 L) was added. The clear solution was extracted with ether to remove any impurities. The aqueous solution was acidified to pH 1 and extracted with ethyl acetate. The organic layer was washed with water and brine, and was evaporated to dryness. Yield: 37 g, 80%.

Example 10

Synthesis of (2S)-2-(((9H-Fluoren-9-yl)methoxy)carbonylamino)-3-(6-o-tolylpyridin-3-yl)propanoic acid hydrochloride [Fmoc-(S)-4-(2'-methylphenyl)-3-pyridylalanine hydrochloride]

The following Scheme 13 describes the synthesis of (2S)-2-(((9H-fluoren-9-yl)methoxy)carbonylamino)-3-(6-o-tolylpyridin-3-yl)propanoic acid hydrochloride:

SCHEME 13

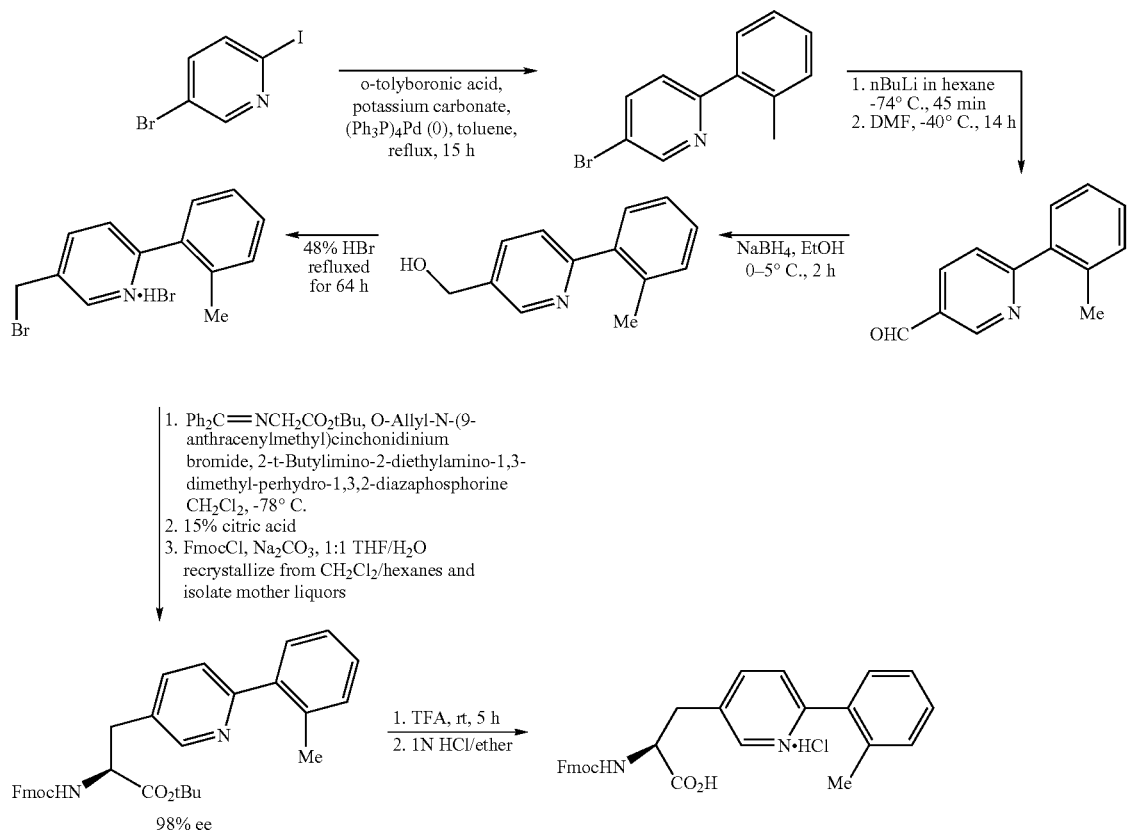

A. 5-Bromo-2-o-tolylpyridine

To an argon-purged and evacuated slurry of 910 mg (3.21 mmol) of 5-bromo-2-iodopyridine and 436 mg (3.21 mmol, 1.0 eq.) of 2-o-tolylboronic acid in 8 mL of toluene and 3.2 mL of 2 M aqueous sodium carbonate, was added 36 mg (0.032 mmol, 0.01 eq) of tetrakis(tri-phenylphosphine) palladium. The reaction mixture was purged and evacuated with argon twice more and then set to reflux under argon for 15 h. The reaction was cooled and partitioned between water and EtOAc. The layers were separated, and the aqueous layer extracted once more with EtOAc. The organic extracts were combined, dried over magnesium sulfate, filtered, concentrated and dried in vacuo to give the crude product as an orange oil. Purification by silica gel chromatography (7:3 CH$_2$Cl$_2$/hexanes) provided the title compound as a yellow oil, 666 mg, 84% yield.

B. 6-o-Tolylnicotinaldehyde

To a stirred solution of 125 mg of the above compound (0.50 mmol) in THF (2.0 mL) under argon at −74° C. was added 220 μL of nBuLi solution in hexane (2.5 M, 0.55 mmol, 1.1 eq) over 5 min, the temperature not allowed to rise above −71° C. A light green solution formed, which became dark green after 30 min. After 45 min, 49.4 μL (0.61 mmol, 1.2 eq) of DMF was added and the reaction allowed to warm to −40° C. After 14 h, a bright orange solution had formed. The reaction was quenched with 10% citric acid and the mixture stirred rapidly for 20 min at room temperature. The resulting bright yellow solution was extracted twice with EtOAc. The organic extracts were combined, dried over MgSO$_4$, filtered and concentrated to give a yellow oil. The crude mixture thus obtained was purified by silica gel chromatography using ethyl acetate/dichloromethane (1:24) as eluant, (2.5×10 cm column), to give white solid, mp 82-84° C., 90.3 mg, 91% yield.

C. (6-o-Tolylpyridin-3-yl)methanol

To a solution of 1.070 g (5.43 mmol) of 6-o-tolylnicotinaldehyde in 19 mL of ethanol at 0-5° C., was added 287 mg(7.5 mmol, 1.4 eq.) of sodium borohydride. After 2 h, the reaction mixture was quenched with saturated sodium bicarbonate solution and, after 30 min, partitioned between dichloromethane and brine. The organic extract was dried over magnesium sulfate and concentrated to give the indicated product as a colorless oil, 1.08 g, 100% yield.

D. 5-(Bromomethyl)-2-o-tolylpyridine hydrobromide

A solution of 4.49 g (22.5 mmol) of (6-o-tolylpyridin-3-yl)methanol in 75 mL of 48% hydrobromic acid was heated to reflux for 64 h. The reaction mixture was partially cooled and excess hydrobromic acid was removed by vacuum distillation (110° C.@2 Torr) until a tan solid residue remained in the flask. Distillation was carried out using a large KOH pellet trap placed between the distillation apparatus and the vacuum pump. The solid residue was slurried in diethyl ether, filtered and dried under a nitrogen stream to give 7.38 g of product, 95% yield.

E. (2S)-tert-butyl 2-(diphenylmethyleneamino)-3-(6-o-tolylpyridin-3-yl)propanoate To a stirred mixture of 800 mg (2.33 mmol) of 5-(bromomethyl)-2-o-tolylpyridine hydrobromide, 689 mg (2.33 mmol, 1.0 equivalent) of tert-butyl 2-(diphenylmethyleneamino)acetate and 141 mg (0.233 mmol, 0.1 equivalent) of O-allyl-N-(9-anthracenylmethyl) cinchonidinium bromide in 14 mL of dichloromethane at −78° C. under argon was added 1.687 mL (5.83 mmol, 2.5 eq) of 2-t-butylimino-2-diethylamino-1,3-dimethyl-perhydro-1,3,2-diazaphosphorine over 5 min. The reaction mixture was stirred at −78° C. for 10 h and then allowed to warm to room temperature in situ. The mixture was directly purified by silica gel chromatography using ethyl acetate/dichloro-methane (1:4) as eluant (5×10 cm column), to give tan oil, 1.10 g, 100% yield.

F. (2S)-tert-Butyl 2-(((9H-fluoren-9-yl)methoxy)carbonylamino)-3-(6-o-tolylpyridin-3-yl)propanoate To a stirred solution of 1.10 g (2.33 mmol) of (2S)-tert-butyl 2-(diphenylmethyleneamino)-3-(6-o-tolylpyridin-3-yl)propanoate in 9 mL of THF at room temperature under argon was added 2.795 g (14.54 mmol, 6.5 equivalents) of citric acid in 9 mL of water. After 20 h, the reaction mixture was diluted with water (5 mL) and washed twice with ether (10 mL). The aqueous phase was then brought to pH 9 with solid sodium carbonate and extracted twice with dichloromethane.

The dichloromethane extracts were combined, dried with sodium sulfate and concentrated. The resulting oil was dissolved in 10 mL of THF and treated with 7.2 mL of 10% sodium carbonate solution and then 703 mg (2.56 mmol, 1.1 equivalents) of 9-fluorenylmethyloxycarbonylchloride at room temperature. After 14 h, the reaction mixture was extracted twice with dichloromethane, dried with sodium sulfate, filtered, concentrated and purified by chromatography on silica gel using ethyl acetate/dichloromethane (1:19) as eluant (2.5×10 cm column), to give colorless oil, 1.082 g, 91% yield. Recrystallization from 20 mL of 7:1 hexanes/dichloromethane provided a white solid, 287 mg. The mother liquors were concentrated to provide an amorphous white solid, the title compound, 779 mg, 63% yield. Chiral HPLC analysis (4.6×250 mm AD column, 38:1:1 heptane:methanol:ethanol as eluant 1 m]L/min flow rate) indicated 98% ee.

G. (2S)-2-(((9H-Fluoren-9-yl)methoxy)carbonylamino)-3-(6-o-tolylpyridin-3-yl)propanoic acid hydrochloride A solution of 1.75 g (3.19 mmol) of (2S)-tert-butyl 2-(((9H-fluoren-9-yl)methoxy)carbonylamino)-3-(6-o-tolylpyridin-3-yl)propanoate in TFA (5.0 mL), protected from the atmosphere by a calcium chloride-filled drying tube was stirred at room temperature for two hours. The reaction mixture was concentrated in vacuo at less than 40° C. and the resulting orange oil was dissolved in 10 mL of ether to which a solution of 5 mL of 1 M HCl/ether was added. The resulting white solid was filtered and washed with ether to give the desired compound as a white powder, 1.65 g, 100% yield.

Example 11

Synthesis of (2S)-2-(((9H-Fluoren-9-yl)methoxy)carbonylamino)-4-(6-bromopyridin-3-yl)propanoic Acid Hydrochloride The following Scheme 14 describes the synthesis of 3-(((9H-fluoren-9-yl)methoxy)carbonylamino)-3-(6-bromopyridin-3-yl)propanoic acid hydrochloride:

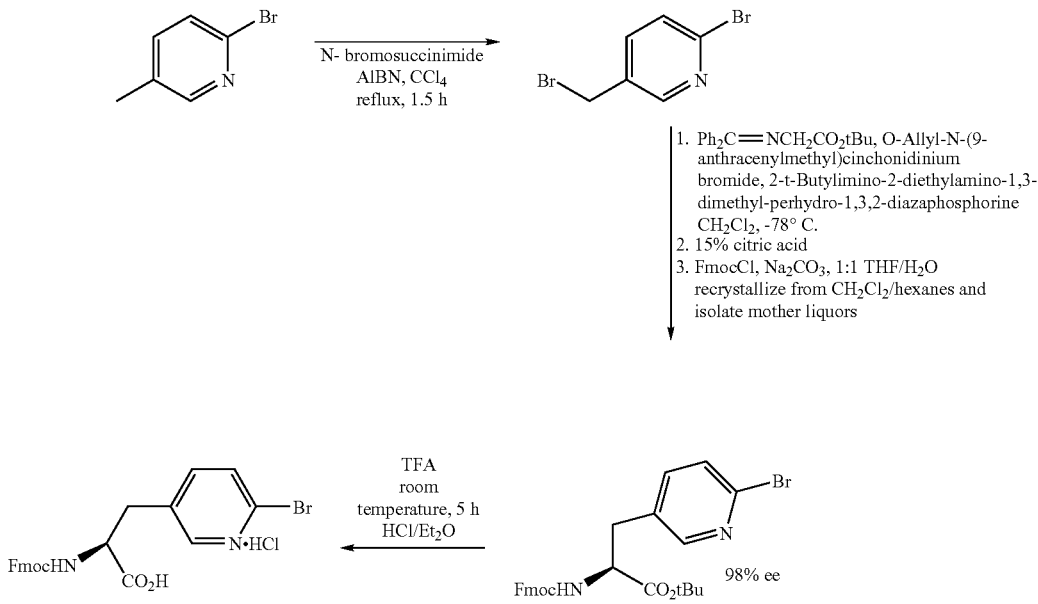

A. 2-Bromo-5-(bromomethyl)pyridine

To a stirred slurry of 10.320 g (60.0 mmol) of 5-methyl-2-bromopyridine and 5.339 g (30.0 mmol, 0.5 eq) of recrystallized N-bromosuccinimide in 150 mL of carbon tetrachloride was added 200 mg of AIBN. The reaction mixture was purged twice with argon and evacuated and set to reflux under argon. After 90 min, the reaction mixture was cooled to room temperature, filtered and the filtrate concentrated to give a yellow oil. Proton NMR indicated that the mixture contains 53% (mol) unreacted 5-methyl-2-bromopyridine, 43% of the title product and 4% of 2-bromo-5-(dibromomethyl)pyridine. The mixture was used immediately without further purification for the following procedure.

B. (S)-tert-Butyl 2-(((9H-fluoren-9-yl)methoxy)carbonylamino)-3-(6-bromopyridin-3-yl)propanoate To a stirred mixture of 2-bromo-5-(bromomethyl)pyridine (nominally 26.4 mmol), 7.798 g (26.4 mmol, 1.0 equivalents) of tert-butyl 2-(diphenylmethyleneamino)acetate and 1.60 g (2.64 mmol, 0.1 equivalent) of O-allyl-N-(9-anthracenylmethyl) cinchonidinium bromide in 100 mL of dichloromethane at −78° C. under argon was added 11.46 mL (39.6 mmol, 1.5 eq) of 2-t-butylimino-2-diethylamino-1,3-dimethyl-perhydro-1,3,2-diazaphosphorine over 5 min. The reaction mixture was stirred at −78° C. for 7 h and then allowed to warm to room temperature in situ. The reaction mixture was then concentrated, redissolved in 75 mL of THF and treated with citric acid (22 g) in 75 mL of water. After stirring vigorously for 7 h, the mixture was extracted twice with ether (75 mL). The organic extracts were combined and washed once with water (25 mL). The aqueous extracts were combined and brought to pH 8 with solid sodium carbonate. The aqueous solution was used without further treatment for the next reaction.

C. (S)-tert-Butyl 2-(((9H-fluoren-9-yl)methoxy)carbonylamino)-3-(6-bromopyridin-3-yl)propanoate The aqueous solution from above was added to a solution of 7.545 g (27.5 mmol, 1.04 equivalents) of 9-fluorenylmethyloxycarbonylchloride in 75 mL of THF at room temperature. After 14 h, the reaction mixture was extracted twice with ethyl acetate, dried with magnesium sulfate, filtered, concentrated and purified by chromatography on silica gel using ethyl acetate/dichloro-methane (1:24) as eluant (12×25 cm column), to give colorless oil, 7.25 g, 91% yield. Recrystallization from 120 mL of 5:1 hexanes/dichloromethane gave a small amount of a white solid, which was filtered off. The mother liquors were concentrated to provide an amorphous white solid, the title compound, 4.96 g, 62% yield. Chiral HPLC analysis (4.6×250 mm AD column, 38:1:1 heptane:methanol: ethanol as eluant 1 mL/min flow rate) indicated 97.2% ee.

D. 2-(((9H-Fluoren-9-yl)methoxy)carbonylamino)-3-(6-bromopyridin-3-yl)propanoic acid hydrochloride A solution of 1.02 g (1.95 mmol) of (2S)-tert-butyl 2-(((9H-fluoren-9-yl)methoxy)carbonylamino)-3-(6-bromopyridin-3-yl)propanoate in TFA (3.0 mL), protected from the atmosphere by a calcium chloride-filled drying tube was stirred at room temperature for two hours. The reaction mixture was concentrated in vacuo at less than 35° C. and the resulting orange oil was dissolved in 3 mL of dichloromethane to which a solution of 6 mL of 1 M HCl/ether was added. The resulting white solid was filtered and washed with ether to give the title compound as a white powder, 845 mg, 86% yield.

Example 12

Synthesis of (2S) 2-(((9H-Fluoren-9-yl)methoxy) carbonylamino)-3-(6-(2-ethylphenyl)pyridin-3-yl) propanoic acid hydrochloride [Fmoc-(S)-4-(2'-ethylphenyl)-3-pyridylalanine]

The following Scheme 15 describes the synthesis of (2S)-2-(((9H-fluoren-9-yl)methoxy)carbonylamino)-3-(6-(2-ethylphenyl)pyridine-3-yl)propanoic acid hydrochloride:

SCHEME 15

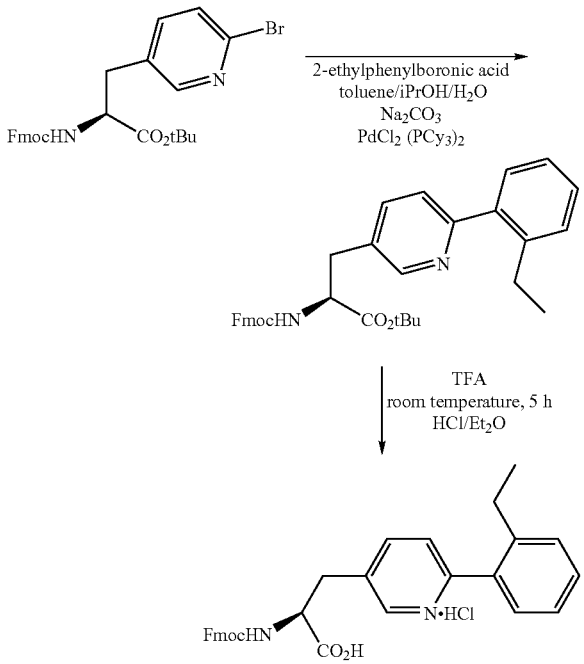

A. ((S)-tert-Butyl 2-(((9H-fluoren-9-yl)methoxy) carbonylamino)-3-(6-(2-ethylphenyl)pyridin-3-yl) propanoate To a stirred slurry of 1.75 g (3.35 mmol) of (S)-tert-butyl 2-(((9H-fluoren-9-yl)methoxy)carbonylamino)-3-(6-bromopyridin-3-yl) propanoate and 1.005 g (6.70 mmol, 2 eq.) of 2-ethylphenylboronic acid in 50 mL of 1:1 isopropanol/toluene was added 25.0 mL of 2 M aqueous sodium carbonate solution. The reaction mixture was purged twice with argon and evacuated and then 124 mg (0.167 mmol, 0.05 equivalents) of bis(tricyclohexylphosphine)palladium (II) chloride was added and the mixture was again purged with argon and evacuated. The rapidly stirred mixture was heated at 80° C. under argon. After 20 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (1:9) as eluant (5×15 cm column), gave the desired compound as a colorless oil, 1.25 g, 77% yield.

B. (2S) 2-(((9H-Fluoren-9-yl)methoxy)carbonylamino)-3-(6-(2-ethylphenyl)pyridine-3-yl)propanoic acid hydrochloride A solution of 1.53 g (2.79 mmol) of (2S)-tert-butyl 2-(((9H-fluoren-9-yl)methoxy)carbonylamino)-4-(6-(2-ethylphenyl)pyridine-3-yl)propanoate in TFA (5.0 mL), protected from the atmosphere by a calcium chloride-filled drying tube was stirred at room temperature for two hours. The reaction mixture was concentrated in vacuo at less than 35° C. and the resulting orange oil was dissolved in ether to which a solution of 6 mL of 1 M HCl/ether was added. The resulting white solid was filtered and washed with ether to give the desired product as a white powder, 1.38 g, 93% yield.

Example 13

Synthesis of (2S) 2-(((9H-Fluoren-9-yl)methoxy)carbonylamino)-3-(6-(2-ethyl-4-methoxy)phenyl)pyridin-3-yl)propanoic acid hydrochloride [Fmoc-(S)-4-[(2'-ethyl-4'-methoxy)phenyl]-3-pyridylalanine]

The following Scheme 16 describes the synthesis of (2S)-2-(((9H-fluoren-9-yl)methoxy)carbonylamino)-3-(6-(2-ethyl-4-methoxy)phenyl)pyridin-3-yl)propanoic acid hydrochloride:

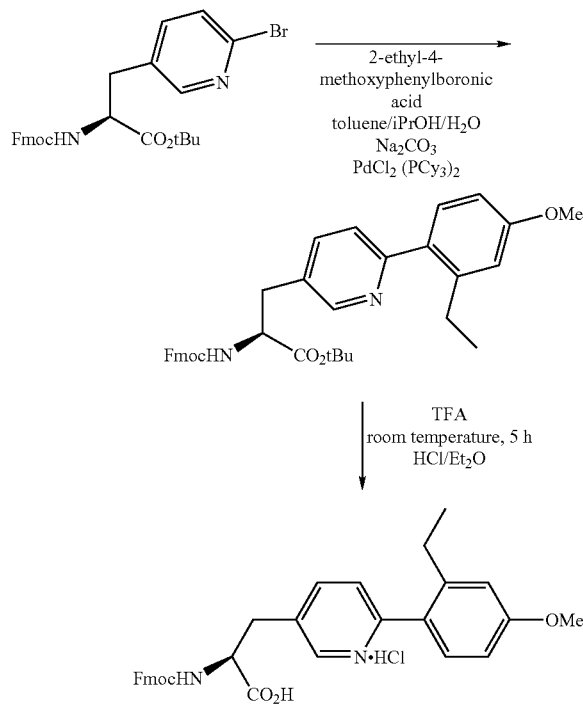

A. (S)-tert-Butyl 2-(((9H-fluoren-9-yl)methoxy)carbonylamino)-3-(6-(2-ethyl-4-methoxyphenyl)pyridine-3-yl)propanoate To a stirred slurry of 613 mg (1.17 mmol) of (S)-tert-butyl 2-(((9H-fluoren-9-yl)methoxy)carbonylamino)-3-(6-bromopyridin-3-yl)propanoate and 422 mg (2.34 mmol, 2 eq.) of 2-ethylphenylboronic acid in 20 mL of 1:1 isopropanol/toluene was added 10.0 mL of 2 M aqueous sodium carbonate solution. The reaction mixture was purged twice with argon and evacuated and then 43.2 mg (0.059 mmol, 0.05 equivalents) of bis(tricyclohexylphosphine)palladium (II) chloride was added and the mixture was again purged with argon and evacuated. The rapidly stirred mixture was heated at 80° C. under argon. After 9 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (3:17) as eluant (5×15 cm column), gave the expected compound as a colorless oil, 401 mg, 59% yield.

B. (2S)2-(((9H-Fluoren-9-yl)methoxy)carbonylamino)-3-(6-(2-ethyl-4-methoxyphenyl)pyridine-3-yl)propanoic acid hydrochloride A solution of 401 mg (0.69 mmol) of(2S)-tert-butyl 2-(((9H-fluoren-9-yl)methoxy)carbonylamino)-3-(6-(2-ethyl-4-methoxyphenyl)pyridine-3-yl)propanoate in TFA (2.0 mL), protected from the atmosphere by a calcium chloride-filled drying tube was stirred at room temperature for two hours. The reaction mixture was concentrated in vacuo at less than 30° C. and the resulting orange oil was dissolved in ether to which a solution of 2 mL of 1 M HCl/ether was added. The resulting white solid was filtered and washed with ether to give the desired product as a white powder, 336 mg, 84% yield.

Example 14

Alternative Synthesis of (S)-tert-Butyl 2-(((9H-fluoren-9-yl)methoxy)carbonylamino)-3-(6-(2-methylphenyl)pyridin-3-yl)propanoate [Fmoc-(S)-4-(2'-methylphenyl)-3-pyridylalanine tert-Butyl ester]

The following Scheme 17 describes the alternate synthesis of (S)-tert-Butyl 2-(((9H-fluoren-9-yl)methoxy)carbonylamino)-3-(6-(2-methylphenyl)pyridin-3-yl)propanoate:

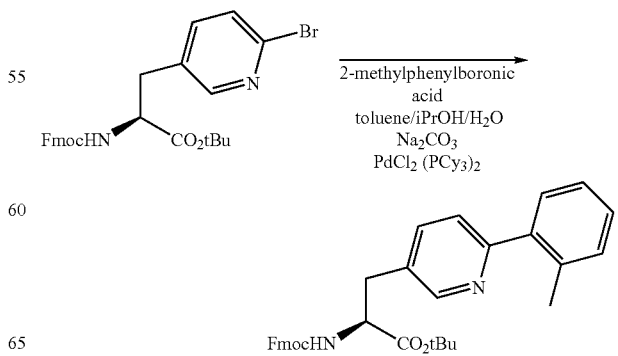

A. (S)-tert-Butyl 2-(((9H-fluoren-9-yl)methoxy)carbonylamino)-3-(6-(2-methylphenyl)pyridin-3-yl)propanoate To a stirred slurry of 1.75 g (3.35 mmol) of (S)-tert-butyl 2-(((9H-fluoren-9-yl)methoxy)carbonylamino)-3-(6-bromopyridin-3-yl)propanoate and 913 mg (6.70 mmol, 2 eq.) of 2-methylphenylboronic acid in 50 mL of 1:1 isopropanol/toluene was added 25.0 mL of 2 M aqueous sodium carbonate solution. The reaction mixture was purged twice with argon and evacuated and then 124 mg (0.167 mmol, 0.05 equivalents) of bis(tricyclohexylphosphine)palladium (II) chloride was added and the mixture again purged with argon and evacuated.

The rapidly stirred mixture was set to heating at 80° C. under argon. After 20 h, the reaction mixture was cooled to room temperature and partially concentrated to remove isopropanol. The residue was partitioned between ethyl acetate and water and the aqueous phase was extracted once more with ethyl acetate. The organic extracts were combined, dried over magnesium sulfate, filtered and concentrated to give a brown oil. Purification by chromatography on silica gel using ethyl acetate/dichloromethane (1:9) as eluant (5×15 cm column), gave the desired compound as a colorless oil, 1.81 g, 90% yield.

Example 15

Synthesis of Fmoc-(S)-2'-ethyl-4'-hydroxy-biphenylalanine [Fmoc-(S)-Bip(2'-Et-4'-OH)]

The following Scheme 18 describes the synthesis of Fmoc-(S)-2'-ethyl-4'-hydroxy-biphenylalanine [Fmoc-(S)-Bip(2'-Et-4'-OH)]:

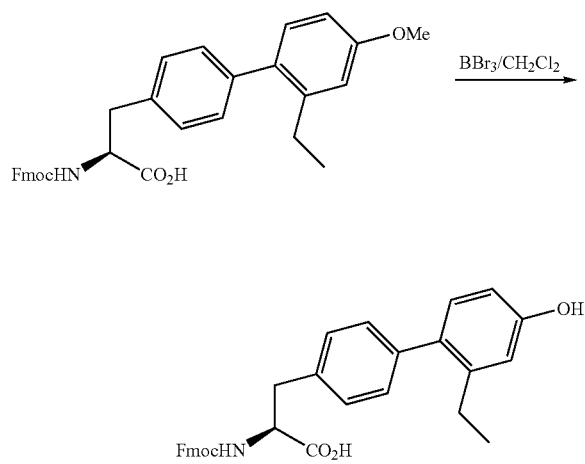

SCHEME 18

To a stirred solution of 4.46 g (8.55 mmol) of (S)-2-(((9H-fluoren-9-yl)methoxy)carbonylamino)-3-(2'-ethyl-4'-methoxybiphenyl-4-yl)propanoic acid [Fmoc-Bip(2'-Et-4'-OMe)-OH] in dichloromethane (34 mL) at −12° C. under argon was added a solution of 21.4 mL of 1 M borontribromide in dichloromethane (21.2 mmol) over the course of 20 min. The reaction mixture was stirred and allowed to warm to room temperature in situ as a gray slurry formed. After 3 h, the reaction mixture was added slowly to 300 mL of rapidly stirring water at room temperature. After 1 h, the reaction mixture was extracted twice with dichloromethane (100 mL portions). The organic extracts were combined, dried (MgSO$_4$), filtered and evaporated to provide a tan foam, 4.65 g. The desired product was purified by reverse phase HPLC (Luna 5µ C18 30×100 mm column, 50% to 100% gradient (10 min) (900:100:1 to 100:900:1 water/acetonitrile/TFA) as elutant; Flow rate at 40 mL/min. UV detection at 220 nm). Partial evaporation of the pooled fractions provided a gummy material which was decanted from the remaining solution, washed with water, redissolved in dichloromethane, dried (MgSO$_4$), filtered and evaporated to provide the product as a white amorphous solid, 3.50 g, 81% yield. HPLC/MS: retention time=5.52 min [Zorbax SB C18 (4.6×75 mm) column; 0% to 100% gradient (8 min) (90:10:0.1 to 10:90:0.1 water/AcCN/TFA as elutant). Flow rate at 2.5 mL/min. UV detection at 220 nm.]; [M+H]$^+$=508. $^1$H NMR (DMSO-d$_6$): δ 12.77 (br s, 1H), 9.29 (s, 1H), 7.86 (d, J=7.7 Hz, 1H), 7.78 (d, J=8.8 Hz, 1H), 7.65 (t, J=7.1 Hz, 2H), 7.38 (m, 2H), 7.28 (m, 4H), 7.11 (d, J=7.7 Hz, 2H), 6.85 (d, J=8.2 Hz, 1H), 6.65 (d, J=2.2 Hz, 1H), 6.57 (dd, J=2.2, 8.3 Hz, 1H), 4.20 (m, 5H), 3.32 (br s, 1H), 3.10 (dd, J=4.4, 13.8 Hz, 1H), 2.90 (dd, J=10.5, 13.2 Hz, 1H), 2.37 (q, J=7.7 Hz, 2H), 0.91 (t, J=7.7 Hz, 3H).

2.28 g of the above product was further purified by chiral HPLC (CHIRALPAK® AD, 10 µm, 50×500 mm column, isocratic elution (n-heptane/acetonitrile/methanol/TFA, 839:80:80:1); flow rate at 60 mL/min. UV detection at 217 nm.). Evaporation of the pooled fractions, followed by re-evaporation with chloroform (3×20 mL) provided the product as an off-white amorphous solid, 2.17 g, 95% yield. Reverse phase HPLC: retention time=21.42 mins. [YMC ODS-A C18 3 µm (4.6×150 mm) column; 10% to 100% B gradient (30 min) (Buffer A: 0.1% trifluoroacetic acid in water, Buffer B: 0.1% trifluoroacetic acid in acetonitrile). Flow rate at 1 mL/min. UV detection at 217 nm.]. MS analysis: [M+NH$_3$]$^+$=525.3 and [M−H]$^-$=506.2. Chiral HPLC analysis: >99% ee, retention time=12.17 mins [CHIRALPAK® AD, 10 µm, 4.6×250 mm column, isocratic elution (n-heptane/acetonitrile/methanol/TFA, 799:100:100:1); flow rate at 1 mL/min. UV detection at 217 nm.]. [α]$^{25}_D$=−12.6 (c=1.0 in DMF).

Example 16

Synthesis of (2S)-tert-butyl 2-(((9H-fluoren-9-yl)methoxy)carbonylamino)-3-(6-(2-ethylphenyl)pyridazin-3-yl)propanoate [Fmoc-(S)-4-(2'-ethylphenyl)-2,3-pyridazylalanine]

The following Sc0heme 19 describes the synthesis of (2S)-tert-butyl 2-(((9H-fluoren-9-yl)methoxy)carbonylamino)-3-(6-(2-ethylphenyl)pyridazin-3-yl)propanoate:

SCHEME 19

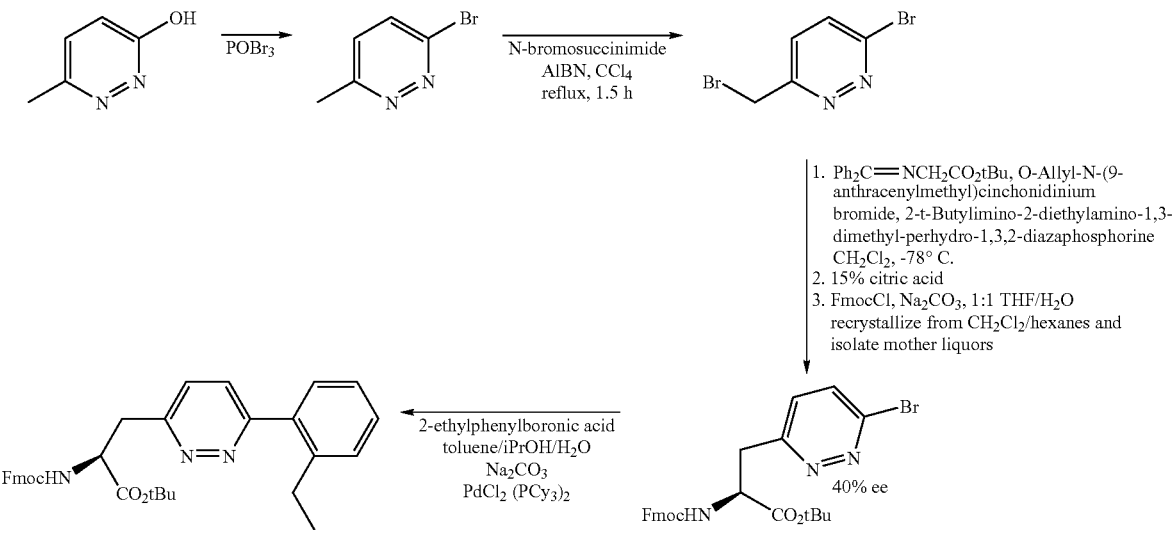

A. 3-Bromo-6-methylpyridazine

A mixture of 2.20 g of 3-methyl-6-pyrazinol (20.0 mmol) and 13.06 g of phosphorous oxybromide (45.6 mmol, 2.3 equivalents) was stirred and heated to 130 deg C. (pre-heated oil bath) for 50 min. The solid reaction mixture was cooled in an ice bath and ~20 g of chipped ice was added. The resulting solution was chilled in an ice bath and 50% KOH was added to neutralize. The resulting solid was collected, washed with water and air-dried for 15 h. Purification by silica gel chromatography using ether/dichloromethane (3:17) as eluant (5×15 cm column), provided the title compound as a light yellow solid, 1.37 g, 39% yield.

B. 3-Bromo-6-(bromomethyl)pyridazine

A solution of 1.00 g (5.78 mmol) of 3-bromo-6-methylpyridazine and 1.03 g (5.79 mmol, 1.0 eq) of recrystallized N-bromosuccinimide in 20 mL of carbon tetrachloride was added 95 mg of AIBN. The reaction mixture was purged twice with argon and evacuated and set to reflux under argon. After 3 h, the reaction mixture was cooled to room temperature, filtered and the filtrate was concentrated to give a yellow oil. The mixture was directly purified by silica gel chromatography using hexanes/dichloromethane (1:9) as eluant (5×12 cm column), to give a colorless oil, 444 mg, 30% yield.

C. (S)-tert-Butyl 2-(((9H-fluoren-9-yl)methoxy)carbonylamino)-3-(6-bromopyridazin-3-yl)propanoate To a stirred mixture of 374 mg (1.48 mmol) of 3-bromo-6-(bromomethyl)pyridazine, 439 mg (1.48 mmol, 1.0 equivalent) of tert-butyl 2-(diphenylmethyleneamino)acetate and 112 mg (0.186 mmol, 0.12 equivalent) of O-allyl-N-(9-anthracenylmethyl) cinchonidinium bromide in 4 mL of dichloromethane at −78° C. under argon was added 0.645 mL (2.23 mmol, 1.5 eq) of 2-t-butylimino-2-diethylamino-1,3-dimethyl-perhydro-1,3,2-diazaphosphorine over 5 min. The reaction mixture was stirred at −78° C. for 1 h and then allowed to warm to −40° C. in situ. After 16 h, the mixture was directly purified by silica gel chromatography using ethyl acetate/dichloro-methane (1:9) as eluant (5×10 cm column), to give a yellow oil, 540 mg, 78% yield.

To a stirred solution of the above product in 10 mL of THF at room temperature under argon was added 10 mL of 15% aqueous citric acid. After 16 h, the reaction mixture was diluted with water (5 mL) and washed twice with ether (10 mL).

The aqueous phase was then brought to pH 9 with solid sodium carbonate and extracted twice with dichloromethane. The dichloromethane extracts were combined, dried with sodium sulfate and concentrated. The resulting oil was dissolved in 5 mL of THF and treated with 5 mL of 10% sodium carbonate solution and then 480 mg (1.86 mmol, 1.3 eq.) of 9-fluorenylmethyloxycarbonylchloride at room temperature. After 6 h, the reaction mixture was extracted twice with dichloromethane, dried with sodium sulfate, filtered, concentrated and purified by chromatography on silica gel using ethyl acetate/dichloromethane (1:5) as eluant (5×15 cm column), to give a colorless oil, 507 mg, 65% yield. Chiral HPLC analysis (4.6×250 mm AD column, 38:1:1 heptane:methanol:ethanol as eluant, 1 mL/min flow rate) indicated 40% ee.

D. (2S)-tert-Butyl 2-(((9H-fluoren-9-yl)methoxy)carbonylamino)-3-(6-(2-ethylphenyl)pyridazin-3-yl)propanoate To a stirred slurry of 507 mg (0.967 mmol) of (S)-tert-butyl 2-(((9H-fluoren-9-yl)methoxy)carbonylamino)-3-(6-bromopyridazin-3-yl)propanoate and 290 mg (1.93 mmol, 2 eq.) of 2-ethylphenylboronic acid in 16 mL of 1:1 isopropanol/toluene was added 8.0 mL of 2 M aqueous sodium carbonate solution. The reaction mixture was purged twice with argon and evacuated and then 35.7 mg (0.048 mmol, 0.05 equivalents) of bis(tricyclohexylphosphine) palladium (II) chloride was added and the mixture was again purged with argon and evacuated. The rapidly stirred mixture was heated at 90° C. under argon.

After 8 h, the reaction mixture was cooled to room temperature and partially concentrated to remove isopropanol. The residue was partitioned between ethyl acetate and water and the aqueous phase was extracted once more with ethyl acetate. The organic extracts were combined, concentrated and the residue was redissolved in 2 mL of THF. To this solution was added 300 mg (1.17 mmol) of 9-fluorenylmethylchloroformate and 100 µL of triethylamine. After 21 h, the reaction mixture was diluted with ethyl acetate and washed once with brine. The organic phase was dried over magnesium sulfate, filtered and concentrated. Purification by chromatography on silica gel using ethyl acetate/dichloromethane (1:2) as eluant (2.5×15 cm column), gave the desired compound as a colorless oil, 428 mg, 81% yield.

Example 17

Synthesis of (2S)-2-(tert-Butoxycarbonylamino)-3-(5-o-tolylpyridin-2-yl)propanoic acid [Boc-(S)-4-(2'-methylphenyl)-2-pyridylalanine)]

The following Scheme 20 describes the synthesis of (2S)-2-(tert-butoxycarbonylamino)-3-(5-o-tolylpyridin-2-yl)propanoic acid:

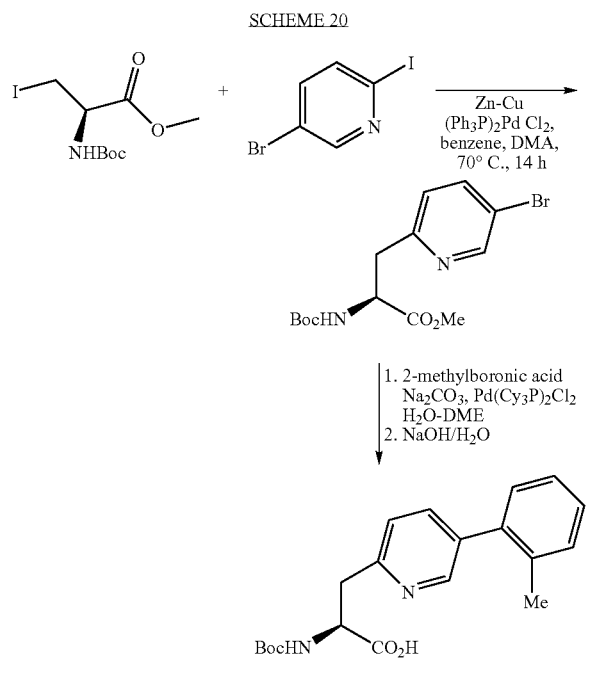

A. (S)-Methyl 2-(tert-butoxycarbonylamino)-3-(5-bromopyridin-2-yl)propanoate

An argon-purged and evacuated slurry of 210 mg of zinc-copper couple (prepared as in Organic Synthesis Collective Volume 5, page 855) and 580 mg (1.76 mmol) of 3-iodoalanine were dissolved in 7 mL of benzene to which was added 0.5 mL of N,N-dimethylacetamide. The slurry was sonicated in a sealed flask for 40 min, and then 500 mg (1.76 mmol, 1.0 eq.) of 5-bromo-2-iodopyridine and 82 mg (0.11 mmol, 0.06 eq.) of bis(tri-phenylphosphine) palladium dichloride were added.

The reaction mixture was purged and evacuated with argon twice more and then heated at 70° C. under argon for 15 h. The reaction was cooled and partitioned between water and EtOAc. The layers were separated, and the aqueous layer was extracted once more with EtOAc. The organic extracts were combined, dried over magnesium sulfate, filtered, concentrated and dried in vacuo to give the crude product as a yellow oil. Purification by silica gel chromatography CH₂Cl₂/hexanes (3:1)as eluant (2.5×15 cm column), provided the expected compound as a yellow oil, 288 mg, 46% yield.

B. (2S)-2-(tert-Butoxycarbonylamino)-3-(5-o-tolylpyridin-2-yl)propanoic Acid

To a stirred slurry of 285 mg (0.79 mmol) of (S)-methyl 2-(tert-butoxycarbonylamino)-3-(5-bromopyridin-2-yl)propanoate and 162 mg (1.19 mmol, 1.5 eq.)of 2-methylphenylboronic acid in 7 mL of 1,2-dimethoxyethane was added 168 mg (1.59 mmol, 2.0 eq.) of sodium carbonate and 0.5 mL of water. The reaction mixture was purged twice with argon and evacuated and then 29 mg (0.040 mmol, 0.05 eq.) of bis (tricyclohexylphosphine) palladium (II) chloride was added and the mixture again purged with argon and evacuated. The rapidly stirred mixture was heated at 80° C. under argon.

After 14 h, the reaction mixture was cooled to room temperature and 4 mL of 1 N sodium hydroxide solution was added. The reaction mixture was heated to 70 deg C. for 1 h. After cooling to room temperature the mixture was extracted once with ether. The aqueous phase was acidified to pH 3 with 10% sodium bisulfate solution and then extracted twice with DCM. The DCM extracts were combined, dried over magnesium sulfate, filtered and concentrated to give a yellow semi-solid. Purification by preparative reverse-phase HPLC (YMC ODS S5 30×100 mm column, 10% to 90% acetonitrile/water gradient [10 min], 0.1% TFA) gave (after concentration) the desired product as a white amorphous solid, 46.5 mg, 17% yield.

Example 18

The following Scheme 18 describes the general synthesis of analogs of (2 S)-2-(((9H-fluoren-9-yl)methoxy)carbonylamino)-3-(6-phenyl)pyridin-3-yl)propanoate.

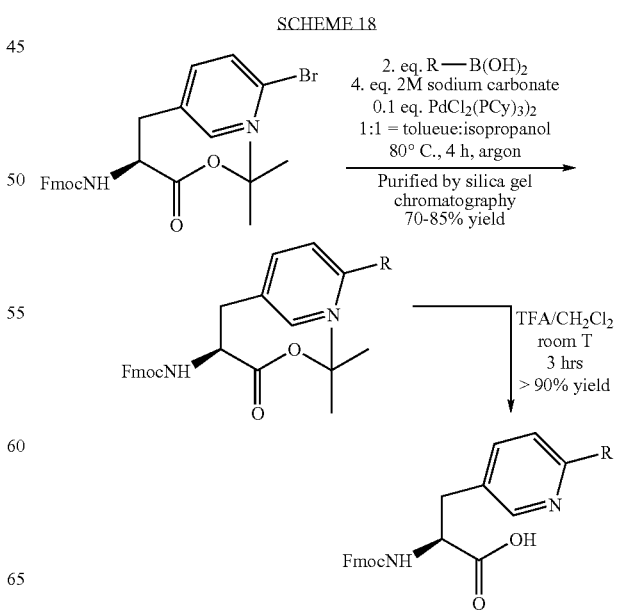

-continued

R—B(OH)₂ = aryl- or hetero-arylboronic acid

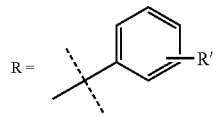

A. (2S)-tert-Butyl 2-(((9H-fluoren-9-yl)methoxy)carbonylamino)-3-[6-(3-Chloro-4-fluoro)phenyl)pyridin-3-yl)]propanoate To a round bottom flask was added 300 mg Fmoc-L-bromo-3-pyridylalanine (0.573 mmol), 200 mg 3-chloro-4-fluorophenylboronic acid (1.145 mmol, 2 eq.), 1.145 mL 2M sodium carbonate solution (2.29 mmol, 4 eq.), 5 mL toluene, 5 mL isopropylnol and 42 mg PdCl2(PCy)3)2 (0.0573 mmol, 0.1 eq.). The reaction solution was purged with argon before it was brought to 80° C. for 5 hrs. The reaction was cooled to room temperature and diluted with 50 mL EtOAc. The solution was washed with water (30 mL) and brine (20 mL), dried over magnesium sulfate, filtered and concentrated. The crude oil was subjected to silica gel chromatography (12 gm silica gel, 0-40% EtOAc/Hexanes gradient) to give 245 mg of the desired compound (75% yield)as an oil.

B. (2S)-2-(((9H-fluoren-9-yl)methoxy)carbonylamino)-3-(6-[(3-chloro-4-fluoro)phenyl)pyridin-3-yl)propanoic Acid To a solution of (2S)-tert-butyl 2-(((9H-fluoren-9-yl)methoxy)carbonylamino)-3-(6-[(3-chloro-4-fluoro)phenyl)pyridin-3-yl)propanoate (240 mg, 0.429 mmol) and 3 mL dichloromethane was added TFA (3 mL). The reaction was stirred at room temperature for 5 hrs. The solvent was evaporated to dryness and the residue was subjected to prep-HPLC (methanol-water gradient, 0.1% TFA). Concentration of the fractions containing the product yielded 200 mg (93% yield) of the desired compound as the TFA salt.

Example 19

A. Synthesis of the Compound of SEQ ID NO:9

The desired dipeptidyl resin containing (S)-4-(2'-Methylphenyl)-3-pyridylalanine as the $X_{aa11}$ amino acid and (S)-(2'-Ethyl-4'-Methoxy) biphenylalanine as the $X_{aa10}$ amino acid was prepared as described in Example 1. Peptide chain elongation was then completed utilizing the coupling protocols described in Example 1 for amino acids $X_{aa1}$-$X_{aa9}$. The resulting peptidyl-resin was dried and treated with 2 mL of TFA/TIS/water (96:2:2) for 1.5 hrs. The resin was filtered off and washed with TFA (1×1 ml). The combined filtrates were added to diethyl ether (30 mL), briefly vortexed and then held at −15° C. for 1 hour. The precipitated solid was collected by centrifugation and dried in a speed-vac. The crude product was purified by preparative HPLC as follows: the crude peptide was dissolved in 1 mL of 0.1 M sodium bicarbonate, 2 mL of water and 1 mL of acetonitrile. The peptide was loaded onto a YMC column (SH-343-10P), 250×20 mm I.D., containing ODS-A 10 μm packing material. The column was equipped with a guard column, YMC (G-340-10P), 50×20 mm I.D., containing ODS 10 μm packing. The peptide was eluted with a gradient of 0.1% TFA/MeCN in 0.1% TFA/water, 20% to 45% over 50 minutes, at a flow rate of 15 ml/min. The appropriate fractions collected were pooled and lyophilized to give a 98.6% pure peptide with a HPLC retention time of 14.4 minutes under the following conditions: gradient, 10% to 70% solvent B in A over 20 minutes at 1 mL/min. Solvent A: 0.1% TFA in water, Solvent B: 0.1% TFA in acetonitrile. Column: YMC ODS-A 100×4.6 mm, 3 μm particle size, 12 nm pore size. Mass spectroscopy: ESI $(M+H)^+=1528.9$ and $(M+2H)/2=765.3$.

B. Synthesis of the Compound of SEQ ID NO:118

A sample of the $X_{aa4}$-$X_{aa11}$ peptidyl-resin (0.067 mmole) described above was vortexed with a solution of Fmoc-L-Glu(OtBu)-OH (5 eq.), residue $X_{aa3}$, and 0.5M HOAt (5 eq.) in DMF, pre-vortexed for 5 minutes, and DIC (5 eq.) for 18 hours. The resin was drained, washed with DMF (4×3 mL).

The resin bound peptide (0.034 mmole) was deprotected and coupled with Fmoc-[(S)-α-Me-Pro]-OH (5 eq.) as described previously for residue $X_{aa3}$ to afford the resin bound Fmoc-[$X_{aa2}$-$X_{aa11}$]-peptide.

The resin (0.017 mmole)was deprotected and coupled with Boc-L-His(Trt)-OH (5 eq.) as described for residue $X_{aa2}$.

The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated to yield 39 mg of crude peptide product as an oily solid. This was purified by preparative HPLC using a gradient of 0.1% TFA/AcCN in 0.1% TFA/water, from 5% to 65% over 20 min. The fractions containing pure product were pooled and lyophilized, to yield 5.4 mg (18.9% recovery) of the compound of SEQ ID NO:118.

C. Synthesis of the Compound of SEQ ID NO:119

A sample of the Fmoc-[$X_{aa3}$-$X_{aa11}$]-peptidyl-Sieber resin (0.015 mmole), described in the previous synthesis, was vortexed with a solution of Fmoc-[N-methyl-(D)-Ala]-OH (5 eq.) and 0.5M HOAt (5 eq.) in DMF, pre-vortexed for 5 minutes, and DIC (5 eq.) for 4 hours. The resin was drained and washed with DMF (4×3 mL). The Fmoc group was removed by treating with 20% piperidine in DMF (3 mL) for 5 and 15 minutes. The resin was washed with DMF (8×3 mL) and then coupled with Boc-L-His(Trt)-OH (5 eq.) as described in the previous synthesis. The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated. The resulting oily solid was dissolved in (1:1) acetonitrile/water (2 mL) and purified by preparative HPLC using a gradient used of 0.1% TFA/MeCN in 0.1% TFA/water, from 5% to 65% over 20 min. The fractions containing pure product were pooled and lyophilized, to yield 5.2 mg (18.5% recovery) of the compound of SEQ ID NO:119.

D. Synthesis of the Compound of SEQ ID NO:120

A sample of Fmoc-deprotected [$X_{aa10}$-$X_{aa11}$]-dipeptidyl-Sieber resin (0.05 mmol), prepared as described previously, was subjected to 9 additional coupling cycles using the Fast-Moc™ protocol of an Applied Biosystems 433A Peptide Synthesizer as described in Example 3.

The Fmoc-protected dipeptidyl-resin (0.05 mmol) was placed into a vessel of appropriate size on the instrument, washed 6 times with NMP and deprotected using two treatments with 20% piperidine/NMP (2 and 8 min. each). One additional monitored deprotection step was performed until the conditions of the monitoring option were satisfied. The total deprotection time was 10-12 min. The deprotected dipeptidyl-resin was washed 6 times with NMP and then coupled with the next amino acid. The procedure is illustrated by the example used in the next step.

Fmoc-L-Asp(OtBu)-OH was coupled next using the following method: Fmoc-L-Asp(OtBu)-OH (1 mmol, 20 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP and the coupling protocol was repeated. This was subjected to 5 additional deprotection/coupling cycles as described above in order to complete the assembly of the desired $X_{aa4}$-$X_{aa11}$ sequence. The Fmoc-amino acids sequentially coupled were: Fmoc-(L)-His(Trt)-OH, Fmoc-(L)-Thr(tBu)-OH, Fmoc-(S)-2-fluoro-α-Me-Phe-OH, Fmoc-(L)-Thr(tBu)-OH and Fmoc-Gly-OH. Finally, the peptidyl-resin was washed 6 times with NMP and DCM. The Fmoc-protected dipeptidyl-resin (0.025 mmole) was added to a ACT 396 multiple peptide synthesizer in a slurry of N,N-dimethylformamide/dichloromethane (55:45). The resin was washed 2 times with DMF and deprotected using two treatments with 1.5 M piperidine/DMF as described in Example 1. Fmoc-L-Glu(OtBu)-OH (4.0 eq.) was activated by subsequent addition of 0.5 M HOAt in DMF (4.0 eq.) and DIC (4.0 eq.), transferred to the reaction vessel manually and allowed to couple for 2 hrs. The resin was rinsed with NMP (4×0.5 mL) with vortexing for 1 min. After deprotection of the Fmoc group as described for the previous coupling, Fmoc-[(S)-α-Me-Pro]-OH was coupled as follows: Fmoc-[(S)-α-Me-Pro]-OH (2.4 eq.) was activated by subsequent addition of 0.5 M HOAt in DMF (2.4 eq.), diluted with NMP (0.12 mL), and of DIC (2.4 eq.). The solution was transferred to the reaction vessel manually and allowed to couple for 18 hrs. The resin was rinsed with NMP. After deprotection of the Fmoc group, Fmoc-(L)-His(Trt)-OH was coupled by adding manually a solution of the amino acid (4 eq.) in 0.5 M HOAt in DMF (4 eq.), diluted with NMP (0.2 mL), and DIC (4 eq.) to the reaction vessel. The coupling reaction was allowed to couple for 18 hrs. The resin was rinsed with NMP. The Fmoc group was removed as described for the previous coupling. The TFA cleavage/deprotection of the peptide was performed as described in Example 1. This was purified by preparative HPLC using a gradient of 0.1% TFA/MeCN in 0.1% TFA/water, from 10% to 60% over 20 min. The fractions containing a pure product were pooled and lyophilized, to yield 21.7 mg (42% recovery) of 94% pure Compound 120; HPLC retention time, 4.88 min, under the following conditions: gradient, from 5-80% 0.1% TFA/MeCN in 0.1% TFA/water over 10 min, flow rate 2.5 mL/min; column: YMC S5 ODS (4.6×50 mm); ESI: $(M+H)^+=1604.9$ amu.

E. Synthesis of the Compound of SEQ ID NO:133

A sample of the Fmoc-deprotected [$X_{aa2}$-$X_{aa11}$]-peptidyl-Sieber resin (0.017 mmole), described in the previous synthesis, was vortexed with a solution of des-amino-His(Trt)-OH (5 eq) and HATU (5 eq.) in 0.5 HOAt in DMF (5 eq.), and a solution of 2M DIEA in NMP (5 eq.) for 18 hours. The resin was drained and washed with DMF (6×2 mL) and DCM (3×2 mL). The desired peptide was cleaved/deprotected from its respective peptidyl-resin by treatment with a solution of TFA/water/tri-isopropylsilane (94:3:3) (5.0 mL) for 3 hrs. The resin was filtered off, rinsed with TFA (1.0 mL), and the combined TFA filtrates were evaporated. The resulting oily solid (32 mg) was dissolved in (1:1) acetonitrile/water (2 mL) and purified by preparative HPLC using a gradient of 0.1% TFA/MeCN in 0.1% TFA/water, from 5% to 65% over 20 min. The fractions containing pure product were pooled and lyophilized, to yield 7.4 mg (24.6% recovery) of the compound of SEQ ID NO:133.

F. Synthesis of the Compound of SEQ ID NO:121

A sample of Fmoc-deprotected [$X_{aa10}$-$X_{aa11}$]-dipeptidyl-Sieber resin (0.05 mmol), prepared as described previously, was subjected to 9 additional coupling cycles using the Fast-Moc™ protocol of an Applied Biosystems 433A Peptide Synthesizer as described in Example 3.

The Fmoc-protected dipeptidyl-resin (0.05 mmol) was placed into a vessel of appropriate size on the instrument, washed 6 times with NMP and deprotected using two treatments with 20% piperidine/NMP (2 and 8 min. each). One additional monitored deprotection step was performed until the conditions of the monitoring option were satisfied. The total deprotection time was 10-12 min. The deprotected dipeptidyl-resin was washed 6 times with NMP and then coupled with the next amino acid. The procedure is illustrated by the example used in the next step.

Fmoc-L-Asp(OtBu)-OH was coupled next using the following method: Fmoc-L-Asp(OtBu)-OH (1 mmol, 20 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP and the coupling protocol was repeated. This was subjected to 5 additional deprotection/coupling cycles as described above in order to complete the assembly of the desired $X_{aa4}$-$X_{aa11}$ sequence. The Fmoc-amino acids sequentially coupled were: Fmoc-(L)-His(Trt)-OH, Fmoc-(L)-Thr(tBu)-OH, Fmoc-(S)-2-fluoro-α-Me-Phe-OH, Fmoc-(L)-Thr(tBu)-OH and Fmoc-Gly-OH. Finally, the peptidyl-resin was washed 6 times with NMP and DCM. The Fmoc-protected dipeptidyl-resin (0.025 mmole) was added to a ACT 396 multiple peptide synthesizer in a slurry of N,N-dimethylformamide/dichloromethane (55:45). The resin was washed 2 times with DMF and deprotected using two treatments with 1.5 M piperidine/DMF as described in Example 1. Fmoc-L-Glu(OtBu)-OH (4.0 eq.) was activated by subsequent addition of 0.5 M HOAt in DMF (4.0 eq.) and DIC (4.0 eq.), transferred to the reaction vessel manually and allowed to couple for 2 hrs. The resin was rinsed with NMP (4×0.5 mL) with vortexing for 1 min. After deprotection of the Fmoc group as described for the previous coupling, Fmoc-[(S)-α-Me-Pro]-OH was coupled as follows: Fmoc-[(S)-α-Me-Pro]-OH (2.4 eq.) was activated by subsequent addition of 0.5 M HOAt in DMF (2.4 eq.), diluted with NMP (0.12 mL), and of DIC (2.4 eq.). The solution was transferred to the reaction vessel manually and allowed to couple for 18 hrs. The resin was rinsed with NMP. After deprotection of the Fmoc group, Fmoc-(L)-His(Trt)-OH was coupled by adding manually a solution of the amino acid (4 eq.) in 0.5 M HOAt in DMF (4 eq.), diluted with NMP (0.2 mL), and DIC (4 eq.) to the reaction vessel. The coupling reaction was allowed to couple for 18 hrs. The resin was rinsed with NMP. The Fmoc group was removed as described for the previous coupling. The TFA cleavage/deprotection of the peptide was performed as described in Example 1. This was purified by preparative HPLC using a gradient of 0.1% TFA/MeCN in 0.1% TFA/water, from 10% to 60% over 20 min. The fractions containing a pure product were pooled and lyophilized, to yield 21.7 mg (42% recovery) of 91% pure Compound 121, as determined by HPLC; retention time 20.8 minutes, using the following conditions: gradient, 10% to 60% solvent B in A over 25 minutes at 1 mL/min. Solvent A: 0.1% TFA in water, Solvent B: 0.1% TFA in acetonitrile. Column: YMC ODS-A 150×4.6 mm, 3 μm particle size, 12 nm pore size. Mass spectroscopy: ESI $(M+H)^+=1568.9$ and $(M+2H)/2=785.2$.

Example 20

Synthesis of (R,S)-3-(1-(2,4-dinitrophenyl)-imidazol-4-yl)-2-methylpropionic acid [α-Methyl-β-[1-(2,4-dinitrophenyl)-imidazol-4-yl]propionic acid][3-(1H-imidazol-4-yl)-2-methylpropionic cid may be abbreviated as Imp, see "Amino Acid Abbreviations and Structures", above]

A. 1-Tosyl-4(5)-hydroxymethylimidazole

The following procedure was adapted from Agr. Biol. Chem., 38 (5), 1097-1099, 1974. To a solution of $Na_2CO_3$ (8.4 g., 0.08 mole) in water (40 mL) was added 4-(hydroxymethyl)imidazole hydrochloride (2.7 g, 0.02 mole,). Upon complete dissolution, a solution of p-toluenesulfonyl chloride (4.58 g, 0.024 mole) in ethyl acetate (30 mL) was added drop wise over a 5 minute period. The reaction mixture was allowed to stir for 5 hours. The layers were separated and more ethyl acetate was added (20 mLs). The organic phase was washed with 0.1 M $Na_2CO_3$ (2×20 mL), water (1×20 mL) and then saturated NaCl (1×20 mL). The ethyl acetate was treated with 2 g of $MgSO_4$ and 1 g of activated charcoal for 10 minutes. The solids were removed by filtration through a celite pad and the solvent removed on a rotavap. The residue began to crystallize. Fresh ethyl acetate was added (10 mL) and the solution was warmed with a heat gun to redissolve the solids. The product crystallized overnight at room temperature. The crystalline material was collected, washed with ethyl acetate (5 mL) and then ethyl ether (10 mL), and dried in vacuo to a constant weight of 3.59 g.

B. 1-Tosyl-4(5)-acetoxymethylimidazole

1-Tosyl-4(5)-hydroxymethylimidazole (2.52 g, 10 mmole) was dissolved in chloroform (10 ml). To this was added triethylamine (2.02 g, 20 mmole) drop wise at room temperature, followed by drop wise addition of acetic anhydride (1.33 g, 13 mmole) over 15 minutes. The mixture was stirred at room temperature and monitored by LC/MS for four days. The chloroform was removed by reduced pressure and the residue was dissolved in ethyl acetate (60 ml). The organic layer was washed successively with 0.1 M sodium bicarbonate, water and then saturated sodium chloride, all 1×40 ml each. The organic layer was treated with activated charcoal and magnesium sulfate simultaneously and then filtered through a celite pad. The solvent was removed by reduced pressure and the resultant residue was dissolved in warm ethyl acetate (10 ml). To this solution was slowly added 20 ml of diethyl ether. The solution was left to crystallize overnight at room temperature. The crystals were collected, washed with diethyl ether (2×10 ml) and dried in vacuo overnight to yield 1.55 g.

C. Methyl-α-carbomethoxy-α-methyl-β-4-(1-tosylimidazole)-propionate

The following procedure was adapted from Synthetic Communications, 19(7&8), 1157-1165, 1989. A solution of 1-Tosyl-4(5)-acetoxymethylimidazole (0.3516 g, 1.2 mmole) and dimethyl methylmalonate (0.1485 g, 1.0 mmole) in acetonitrile (2 ml) was added to a stirred suspension of powdered KOH (0.1694 g, 3.0 mmole) and tetrabutylammonium bromide (0.0496 g, 0.15 mmole) in acetonitrile (1 ml). The reaction was complete after 40 mins, as determined by HPLC analysis. The reaction mixture was poured into ethyl ether (100 ml), filtered through a celite pad and the solvents were removed by evaporation under reduced pressure. The residual oil was dissolved in 30 ml of ethyl acetate and washed with 0.1 M $NaHCO_3$ (1×15 ml), saturated NaCl (1×15 ml) and dried over $MgSO_4$. The solvent was removed under reduced pressure and the resultant oil was left in a desiccator in vacuum for 3 days to yield 0.207 g.

D. α-Methyl-β-4-imidazole Propionic Acid

Methyl-α-carbomethoxy-α-methyl-β-4-(1-tosylimidazole)-propionate (0.186 g, 0.5 mmole) was dissolved in 2 ml of methanol. To this was added 1.5 ml of 1.0 N NaOH and the reaction was allowed to stir overnight. After purification by preparative HPLC, the product obtained by lyophilization (0.1366 g) was dissolved with 5 ml of 1.0 N NaOH and heated at 100° C. for 2 hours in a 16×100 mm screw-cap tube sealed with a PTFE lined cap, followed by addition of 2 ml of concentrated HCl and heating at 145° C. for 6 hours. The desired decarboxylated product was formed. The entire solution was filtered and loaded onto a YMC G-340-10P ODS 50×20 mm preparative HPLC column. The product was eluted with a gradient of 0% to 60% 0.1% TFA/MeCN in 0.1% TFA/water over 60 minutes. The fractions corresponding to 11 to 13 minutes in the gradient were pooled, frozen and lyophilized to give 32 mg of product.

E. α-Methyl-β-[1-(2,4-dinitrophenyl)-imidazol-4-yl] propionic Acid

To a solution of α-Methyl-β-4-imidazole propionic acid (0.0305 g, 0.114 mmoles) and sodium bicarbonate (0.0617 g, 0.734 mmole) in water (1 mL) (pH 8.04) was added a solution of 2,4-dinitrofluorobenzene (0.0323 g, 0.174 mmole) in MeCN (1.0 mL). The reaction mixture was vortexed overnight. The MeCN was removed under reduced pressure and the residue was re-dissolved in 2 mL of water, filtered and loaded onto a Phenomenex Luna C18(2) 5 μm 100×21.2 mm preparative HPLC column in two aliquots of 1.5 and 0.5 mL each. The product was eluted with a gradient of 0% to 80% 0.1% TFA/MeCN in 0.1% TFA/water over 40 minutes. The fractions corresponding to 12.5 to 14.5 minutes in the gradient were pooled and dried in a Savant SpeedVac™ overnight. Additional product was recovered by dissolving the water-insoluble crude product in DMSO, followed by preparative HPLC as described above. The combined fractions produced 31 mg of pure product after lyophilization.

Example 21

Synthesis of the Compound of SEQ ID NO:165 and SEQ ID NO:166

(R,S)-3-(1-(2,4-dinitrophenyl)-imidazol-4-yl)-2-methylpropionic acid was coupled to the relevant $X_{aa}2$-$X_{aa}11$-peptidyl-Sieber resin as follows:

To a solution of (R,S)-3-(1-(2,4-dinitrophenyl)-imidazol-4-yl)-2-methylpropionic acid (0.0267 g, 0.083 mmoles), 6-Cl-HOBt (0.0151 g, 0.089 mmoles) and HCTU (0.0360 g, 0.087 mmoles) in 1 mL of NMP/DCM (3:1) was added DIEA (0.0315 g, 0.244 mmole); the solution was briefly vortexed and then added to the relevant Fmoc deprotected $X_{aa}2$-$X_{aa}11$-peptidyl-Sieber resin prepared as described in Example 19. The coupling was allowed to proceed for 16 hours. The peptidyl-resin was washed with NMP then DCM (3×1.5 mL×1 min) and then treated with 10% acetic anhydride in DCM, 1×2 mL×90 minutes, followed by DCM then DMF washes (3×1.5 mL×1 min). The peptidyl-resin was treated with 10% thiophenol in DMF (1.5 mL) for 1 hr and washed with DMF and DCM (4×1.5 mL×1 min). The peptidyl-resin was then treated with TFA/DCM/TIS (3:1.9:0.1) (1 mL) for 10 min and filtered. The filtrates were collected and gently vortexed for another hr. The TFA mixture was concentrated in a speed-vac to about 0.5 mL and added to 4 mL of MTBE. After 1 hr the precipitated product was collected by centrifugation, washed and then dried to give 0.0841 g of crude product. This was purified by preparative HPLC as follows: the crude peptide was dissolved and injected into a Phenomenex Luna C18(2) (5 μm, 250×30 mm) column and eluted using a linear gradient from 20% to 50% 0.1% TFA/MeCN in 0.1% TFA/water over 40 min at a flow rate of 15 mL/min with effluent UV detection at 217 nm. The fractions containing the desired product pooled and lyophilized to give 26.7 mg of 97.5% pure peptide; HPLC retention time, 21.2 min. under the following conditions: gradient, 10% to 60% solvent B in A over 25 minutes at 1 mL/min. Solvent A: 0.1% TFA in water, Solvent B: 0.1% TFA in MeCN. Column: YMC ODS-A 150×4.6 mm, 3 μm particle size, 12 nm pore size. Mass spectroscopy: ESI $(M+H)^+=1527.9$ and $(M+2H)/2=764.9$.

Preparative chiral HPLC purification of the peptide:

The diastereomeric peptide mixture (10 mg) was dissolved in MeCN/MeOH. The solution was loaded onto a Chirobiotic V 2.2×50 cm, 5 μm column and eluted with MeCN/MeOH/ $N(CH_2CH_3)_3/CH_3COOH$: 65/35/0.5/0.5 at 20 mL/min. Isomer A was collected between 29 and 35 minutes. Isomer B was collected between 36 and 44 min. A second run was made as described above. The fractions containing Isomer A were combined, concentrated to about 5 mL, diluted with water/MeCN (4:1) and the solution was lyophilized. Isomer B was processed in the same manner. The resultant residues were converted to TFA salts by preparative HPLC. Each peptide was injected into a Phenomenex Luna C18(2) 5 μm 100×21.2 mm column and eluted using a linear gradient from 20% to 50% 0.1% TFA/MeCN in 0.1% TFA/water over 40 min. at a flow rate of 10 mL/min with effluent UV detection at 217 nm. The fractions containing the desired product were pooled, frozen and lyophilized to give 6.0 mg 100% pure Isomer A, HPLC retention time 21.28 min. under the following conditions: gradient, 10% to 60% solvent B in A over 25 minutes at 1 mL/min. Solvent A: 0.1% TFA in water, Solvent B: 0.1% TFA in MeCN. Column: YMC ODS-A 150×4.6 mm, 3 μm particle size, 12 nm pore size. Mass spectroscopy: ESI $(M+H)^+=1527.6$ and $(M+2H)/2=764.7$. In a similar manner 4.9 mg of 100% pure peptide Isomer B was obtained; HPLC retention time, 21.3 min. under the following conditions: gradient, 10% to 60% solvent B in A over 25 minutes at 1 mL/min. Solvent A: 0.1% TFA in water, Solvent B: 0.1% TFA in MeCN. Column: YMC ODS-A 150×4.6 mm, 3 μm particle size, 12 nm pore size. Mass spectroscopy: ESI $(M+H)^+=1527.5$ and $(M+2H)/2=764.6$.

Example 22

Synthesis of the Compound of SEQ ID NO: 151

The synthesis was initiated on an Advanced ChemTech Model 90 Synthesizer in a 50 ml reactor starting with 2.67 g (0.56 mmole/g, 1.5 mmole) of Sieber Amide resin. The general deprotection/coupling repetitive cycle used for the stepwise assembly was as follows:

1. DMF wash 1×20 ml×1 min.
2. 20% piperidine in DMF 1×20 ml×5 min.
3. 20% piperidine in DMF 1×20 ml×15 min.
4. DMF washes 3×20 ml×1 min.
5. NMP washes 4×20 ml×1 min.
6. Coupling step (see below).
7. DMF washes 4×15 ml×1 min.
8. Kaiser Ninhydrin test or cleavage/deprotection with HPLC and mass spectral analyses.

The Fmoc group was removed from the Sieber Amide resin using steps 1 to 5 above. N-α-Fmoc-4-(2'-Methylphenyl)-3-pyridylalanine (0.73 g, 1.50 mmole), PyBOP (0.78 g, 1.50 mmole) and HOBt (0.39 g, 1.50 mmole) were dissolved in NMP (5 ml) and the solution was then added to the resin followed by the addition of DIEA (0.39 g, 3.05 mmole). The coupling mixture was vortexed for 16 hours. The resin was treated with 10% acetic anhydride in DCM (1×50 mL×60 mins.), washed with DCM (4×50 ml×1 min.) and dried in vacuo for overnight. An Fmoc determination test gave a substitution of 0.456 mmole/gram. The synthesis was continued with 3.11 g (1.42 mmole) of resin. Following resin deprotection, a solution of N-α-Fmoc-(L)-Bip(2'-Et-4'-OMe)-OH (0.98 g, 1.9 mmole), HCTU (0.78 g, 1.9 mmole) in NMP (5 ml) was added to the resin, followed by the addition of DIEA (0.48 g, 3.80 mmole), and the mixture was vortexed for 16 hrs. After washing with NMP, a Kaiser ninhydrin test was negative. Following deprotection of the resin, N-α-Fmoc-L-Aspartic acid β-t-butyl ester (0.6487 g, 1.24 mmole) was coupled for 48 hrs using HCTU (1.03 g, 2.49 mmole) and DIEA (0.65 g, 5.03 mmole) in NMP (10 ml). Following deprotection of the resin, N-α-Fmoc-N-im-trityl-L-Histidine (3.85 g, 6.25 mmole) was coupled for 16 hours using 0.546 M HOAt in DMF (11.5 mL, 6.3 mmole) and DIC (0.96 mL, 6.3 mmole). The protocol was repeated to couple N-α-Fmoc-O-t-butyl-L-Threonine (2.5 g, 6.30 mmole) to the resin. After resin deprotection, N-α-Fmoc-α-methyl-2-fluoro-L-Phenylalanine (0.78 g, 1.86 mmole) in 0.546M HOAt in DMF (3.4 mL, 1.87 mmole) was added to the resin followed by DIC (0.24 g, 1.87 mmole) in DMF (3.5 ml), and coupling was allowed to proceed for 4 hours. After resin deprotection, N-α-Fmoc-O-t-butyl-L-Threonine (4.97 g, 12.50 mmole) was coupled for 16 hours using a solution of 0.546 M HOAt in DMF (25 mL, 12.50 mmole) and DIC (1.58 g, 12.52 mmole). The resin was capped with 10% acetic anhydride in DMF (20 mL) for 1 hour and washed with DMF (4×20 mL). The Fmoc group was removed, and N-Fmoc-Glycine (1.11 g, 3.75 mmole) was coupled for 90 min. as described for the previous N-α-Fmoc-L-Aspartic acid β-t-butyl ester coupling step, followed by N-α-Fmoc-L-glutamic acid γ-t-butyl ester (1.60 g, 3.75 mmole) in the same manner. A portion of the peptidyl-resin (0.030 mmole) was deprotected and N-α-Fmoc-α-methyl-L-proline (21.2 mg, 0.06 mmole) was coupled for 16 hours using 0.546 M HOAt in DMF (0.110ml, 0.83 mmole) and DIC (7.6 mg, 0.06 mmole) in DMF (0.1 ml). Finally, L-β-(N-1-Trityl)imidazolelactic acid (39.8 mg, 0.10 mmole) and HATU (38 mg, 0.10 mmole) in NMP (0.9 mL) was added to a portion of peptidyl-resin (0.01 mmole) followed by addition of DIEA (17.4 mL, 0.10 mmole). After vortexing for one hour and washing with NMP, the coupling was repeated as described above and allowed to proceed for 48 hours. The resin-bound peptide was treated with TFA/TIS/water (94:3:3) (2 mL) for 2.5 hours, followed by two rinses of TFA/TIS/water (94:3:3) (2×1 mL each). The combined filtrates were concentration in vacuo to yield 18.1 mg (92%) of crude peptide. This was dissolved in 2 mL of (1:1) acetonitrile/water and the solution was loaded onto a Luna [C18(2), 5 μm] Phenomenex column, 250×21.2 mm I.D. The column was eluted with a gradient of 15% to 55% solvent B in solvent A over 50 minutes at a flow rate of 15 ml/min. Solvent A: 0.1% TFA in water. Solvent B: 0.1% TFA in AcCN. The fractions containing a pure product were pooled and lyophilized to give 4.2 mg of the compound of SEQ ID NO:151.

Example 23

Synthesis of (S)-3-(N-1-Trityl-imidazol-4-yl)-2-hydroxypropanoic Acid (L-β-(N-1-Trityl)imidazolelactic Acid)

The following Scheme 22 describes the synthesis of (S)-3-(N-1-Trityl-imidazol-4-yl)-2-hydroxypropanoic acid:

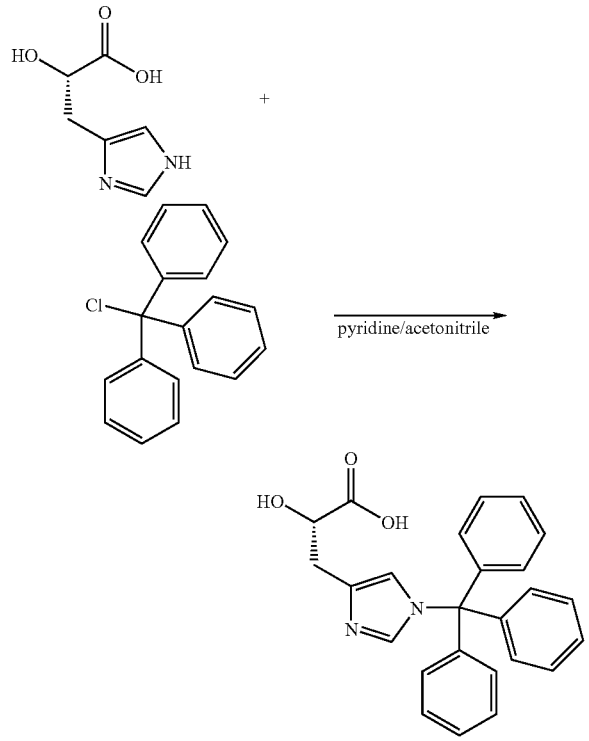

(S)-3-(1H-imidazol-4-yl)-2-hydroxypropanoic acid (0.5265 g, 3.0 mmole) and trityl chloride (1.2991 g, 4.7 mmole) were charged to a 100 mL flask. Pyridine/acetonitrile 1:1 (20 mL) was added under stirring. The flask was heated in an oil bath at 50° to 55° C. for 4 hours. The solvents were removed to near dryness on a rotovap. To the residue was added equal volumes of water and ethyl acetate (30 mL each). The mixture was stirred for about 20 minutes. The resultant solid was collected by filtration, washed with water (2×10 mL), then with ethyl acetate (2×10 mL) and dried in vacuo. Yield: 0.6953 g (58%).

Example 24

Synthesis of (S)-3-(N-1-(2,4-dinitrophenyl)imidazol-4-yl)-2-hydroxypropanoic Acid (L-β-(N-1-(2,4-dinitrophenyl)imidazolelactic Acid)

The following Scheme 23 describes the synthesis of (S)-3-(N-1-(2,4-dinitrophenyl)imidazol-4-yl)-2-hydroxypropanoic acid:

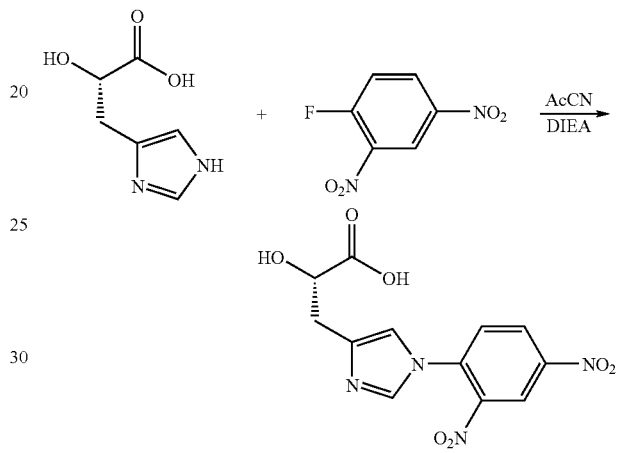

(S)-3-(1H-imidazol-4-yl)-2-hydroxypropanoic acid monohydrate (0.8971 g, 5.2 mmole), acetonitrile (60 mL), DIEA (1.3438 g, 10.4 mmole) and 1-fluoro-2,4-dinitrobenzene (0.9564 g, 5.1 mmole) were charged to a round bottom flask, covered with aluminum foil and stirred overnight. The reaction mixture was filtered and the solvent was removed under reduced pressure. The oily residue was triturated with diisopropyl ether (2×20 mL) and was then dissolved in chloroform (20 mL) and re-evaporated from chloroform and AcCN. Addition of DCM (60 mL) produced a precipitate, which was stirred at RT after adding more DCM (30 mL). The solid product was collected, washed with DCM (2×10 mL) and dried in vacuo overnight. Yield: 1.37 g (83%).

Example 25

Synthesis of the Compound of SEQ ID NO: 158

A. Method A: Fragment Coupling (Scheme 10)

The synthesis was performed manually in an 8 ml reactor starting with 0.1896 g (0.56 mmole/g, 0.11 mmole) of Sieber Amide resin. The following cycles were used to remove the Fmoc group from the resin:

1. DMF wash 1×2 ml×5 mins.
2. 20% piperidine in DMF 1×2 ml×5 mins.
3. 20% piperidine in DMF 1×2 ml×15 mins.
4. DMF washes 8×2 ml×1 min.

N-α-Fmoc-4-(2'-Methylphenyl)-3-pyridylalanine HCl salt (0.0549 g, 0.11 mmole) and PyBOP (0.0667 g, 0.13 mmole) were dissolved in DMF (1 ml). This solution was added to the deprotected resin, followed by DIEA (0.0423 g, 0.33 mmole) in DMF (1 mL). The resin was vortexed for 3.5 hours, washed with DMF and DCM (4×2 mL×1 min). The resin was treated with 10% acetic anhydride in DCM (2 mL) overnight, washed with DCM (6×2 ml×1 min.) and dried in vacuo for 1 hour. Yield: 0.2508 g. An Fmoc determination test gave a substitution of 0.35 mmole/gram. 0.083 g (0.029 mmol) of the resin was used in the next step.

Following deprotection of the resin using the above cycles 1 to 4, a solution of N-α-Fmoc-(L)-Bip(2'-Et-4'-OH)—OH (0.0251 g, 0.049 mmole), HOBt (0.0084 g, 0.055 mmole) and DIC (0.0067 g, 0.053 mmole) in DMF (1 ml) was added to the resin. After vortexing for 16 hours, the peptidyl-resin was washed with DMF then DCM (4×1 mL×1 min.). The Fmoc group was removed as using steps 1 to 3 above followed by DMF then DCM washes (4×1 mL×1 min.).

The peptide-resin was treated with trifluoroacetic acid/triisopropylsilane/water 96:2:2 (2×1 mL×10 mins.). The filtrates were collected and concentrated in vacuo to a residue which was triturated with diisopropyl ether and centrifuged to yield a solid product. This was washed with diisopropyl ether and dried in vacuo to give 0.0244 g of dipeptide. The dipeptide was dissolved in 0.2% DIEA in THF (1 mL) and treated for 2 hours with macroporous triethylammonium methylpolystyrene carbonate resin (0.0682 g, 0.211 mmole, Argonaut Technologies). The resin beads were removed and washed with 0.2% DIEA in THF (2×1 mL). The combined filtrate and wash solution was dried in vacuo. To the resulting residue was added a solution of the side-chain protected N-methyloxycarbonyl $X_{aa}1$-$X_{aa}9$ 9-mer peptide (55.8 mg, 0.035 mmole), HOBt (5.47 mg, 0.036 mmole) and DIC (6 μL, 0.035 mmole) in CHCl3/DMF 9:1 (1 mL). The resultant solution was vortexed overnight. After solvent removal in vacuo, the resulting residue was treated with 2% triisopropylsilane in trifluoroacetic acid (1 mL) for 90 minutes after which diisopropyl ether (20 mL) was added. The precipitated solid was dried and dissolved in 2 mL of 1.5% ammonium hydroxide. The pH was adjusted to ~9.5 with acetic acid. This solution was loaded onto a Luna [C18(2), 5 μm] Phenomenex column, 250×21.2 mm I.D. The column was eluted with a gradient of 20% to 50% solvent B over 60 minutes at a flow rate of 15 ml/min. Solvent A: 0.1% TFA in water. Solvent B: 0.1% TFA in AcCN. The fractions containing a pure product were pooled and lyophilized to give 5.5 mg of the Compound of SEQ ID NO:158.

A different fragment coupling procedure for the synthesis of the Compound of SEQ ID NO:158 followed the method described in Scheme 10B. The synthesis was performed manually in an 8 ml reactor starting with 0.1182 g (0.47 mmole/g, 0.056 mmole) of N-α-Fmoc-4-(2'-Methylphenyl)-3-pyridylalanyl-Sieber Amide resin prepared as described earlier in this Example. The cycles used to remove the Fmoc group from the resin were the same as those described above. N-α-Fmoc-(L)-Bip(2'-Et-4'-OH)-OH (0.0419 g, 0.083 mmole) was coupled to the resin as described above. Following resin treatment with 10% acetic anhydride in DCM (2 mL) for 30 minutes, DCM washes (6×2 ml×1 min.) and removal of the Fmoc group, a solution of the side-chain protected N-methyloxycarbonyl $X_{aa}1$-$X_{aa}9$ 9-mer peptide (0.1347 g, 0.084 mmole), HOBt (0.0130 g, 0.085 mmole) and DIC (0.0118 g, 0.94 mmole) in DCM (0.1 mL) and DMF (0.45 mL) was added to the deprotected dipeptidyl-resin and the mixture was vortexed for 4.5 hours. The resin was washed with DMF and DCM (4×2 mL×1 min.), and then treated with 2% triisopropylsilane, 2% water in trifluoroacetic acid (5×1 mL×3 mins.); the filtrates were collected and allowed to stand for 75 minutes. The solvents were removed in vacuo and the resultant residue triturated with diisopropyl ether (20 mL) to yield the crude peptide as a solid (0.0818 g). This was purified as described above, except that the gradient used was 25% to 35% solvent B in solvent A over 120 minutes at a flow rate of 15 ml/min. Solvent A: 0.1% TFA in water; solvent B: 0.1% TFA in AcCN. The fractions containing a pure product were pooled and lyophilized to give 19 mg of the Compound of SEQ ID NO:158.

B. Method B: Stepwise Elongation (Scheme 1)

The synthesis was performed on an Advanced ChemTech Model 90 Synthesizer in a 50 ml reactor starting with 1.46 g (0.72 mmole/g, 1.05 mmole) of Sieber Amide resin. The general deprotection/coupling repetitive cycle used for the stepwise assembly was as follows:

1. DMF wash 1×15 ml×1 min.
2. 20% piperidine in DMF 1×15 ml×5 min.
3. 20% piperidine in DMF 1×15 ml×15 min.
4. DMF washes 4×15 ml×1 min.
5. NMP washes 4×15 ml×1 min.
6. Coupling step (see below).
7. DMF washes 4×15 ml×1 min.
8. DCM washes 4×15 ml×1 min.
9. Kaiser Ninhydrin test or cleavage/deprotection with HPLC and mass spectral analyses.

The Fmoc group was removed from the Sieber Amide resin using steps I to 5 above. N-α-Fmoc-4-(2-Methylphenyl)-3-pyridylalanine HCl salt (1.0977 g, 2.13 mmole), PyBOP (1.0972 g, 2.11 mmole) and HOBt monohydrate (0.3228 g, 2.11 mmole) were dissolved in DMF (8 ml). DIEA (0.8052 g, 6.23 mmole) was added to the solution, which was then added to the resin. The coupling mixture was vortexed for 16 hours. The resin was treated with 10% acetic anhydride in DCM (1×15 mL×60 mins.), washed with DCM (6×15 ml×1 min.) and dried in vacuo for 6 hours. Yield: 1.6816 g. An Fmoc determination test gave a substitution of 0.48 mmole/gram. The synthesis was continued with 0.8602 g (0.41 mmole) of resin. Following resin deprotection, a solution of N-α-Fmoc-(L)-Bip(2'-Et-4'-OH)-OH (0.2660 g, 0.524 mmole), HOBt (0.0796 g, 0.520 mmole) and DIC (0.0647 g, 0.513 mmole) in DMF (8 ml) was added to the resin and the mixture was vortexed for 16 hrs. After washing with DMF and DCM, a Kaiser ninhydrin test was negative. Following deprotection of the resin, N-α-Fmoc-L-Aspartic acid β-t-butyl ester (0.6487 g, 1.24 mmole) was coupled for 45 min. using HOBt (0.1893 g, 1.24 mmole) and DIC (0.1566 g, 1.24 mmole) in DMF/DCM (1:1) (6 ml). The same coupling cycle was repeated with N-α-Fmoc-O-t-butyl-L-Serine (0.4750 g, 1.24 mmole) and N-α-Fmoc-O-t-butyl-L-Threonine (0.4924 g, 1.24 mmole). After resin deprotection, N-α-Fmoc-α-methyl-2-fluoro-L-Phenylalanine (0.3497 g, 0.834 mmole) was coupled for 1 hour using HOBt (0.1271 g, 0.830 mmole) and DIC (0.1044 g, 0.827 mmole) in DMF/DCM (1:1) (6 ml). After resin deprotection, N-α-Fmoc-O-t-butyl-L-Threonine (1.6413 g, 4.14 mmole) was coupled for 16 hours using a solution of 0.5 M HOAt in DMF (8.3 mL, 4.15 mmole) and DIC (0.5240 g, 4.15 mmole). After DMF and DCM washes, 3 mg of wet resin was treated with 1 ml of TFA/TIS/water (96:2:2) for 1.5 hours. The resin was filtered off and the solvents were removed in a speed-vac. The residue was dissolved in 2 ml of water/acetonitrile (1:1). HPLC and MS analyses showed no uncoupled peptide. The Fmoc group was removed, and N-Fmoc-Glycine (0.3691 g, 1.24 mmole) was coupled for 1 hr as described for the previous N-α-Fmoc-L-Aspartic acid β-t-butyl ester coupling step, followed by N-α-Fmoc-L-glutamic acid γ-t-butyl ester (0.5297 g, 1.24 mmole) in the same manner. N-α-Fmoc-α-methyl-L-proline (0.2902 g, 0.83 mmole) was then coupled for 3.5 hours using HOBt (0.1271 g, 0.83 mmole) and DIC (0.1042 g, 0.83 mmole) in DMF/DCM 1:1 (6 ml). Finally, N-α-Fmoc-N-im-trityl-L-Histidine (2.5564 g, 4.13 mmole) was coupled for 12 hours as described for the N-α-Fmoc-O-t-butyl-L-Threonine coupling to the N-α-Fmoc-α-methyl-2-fluoro-L-Phenylalanine. A deprotected peptide sample released from the peptidyl-resin as described above showed some uncoupled peptide by MS. The Fmoc group was manually removed and, after DMF and DCM washes, a solution of N-(methyloxycarbonyloxy)succinimide (0.2163 g, 1.25 mmole) in DCM (6 mL) was added and the mixture was vortexed for 16 hours. The peptide-resin was washed with DCM (4×10 ml×1 min.). A Kaiser ninhydrin test was negative. The N-methyloxycarbonyl-derivatized peptidyl-resin was treated with TFA/TIS/water (96:2:2) (10 mL) for 10 minutes, followed by two additional treatments with 5 mL each. The combined filtrates were left to stand for an additional 2 hours at RT. Following concentration in vacuo to about 4 mL, the solution was added drop wise to diethyl ether (50 ml) with stirring. The resulting solid was collected by filtration, washed with diethyl ether (2×5 ml) and dried in vacuo to yield 0.691 g (92%) of crude peptide. This was purified by preparative HPLC using the procedures described in Method A of this Example.

Example 26

Synthesis of N-(methyloxycarbonyloxy)succinimide [2,5-(dioxopyrrolidin-1-yl) Methyl Carbonate]

The following Scheme 24 describes the synthesis of N-(methyloxycarbonyloxy) succinimide [2,5-(dioxopyrrolidin-1-yl) methyl carbonate]:

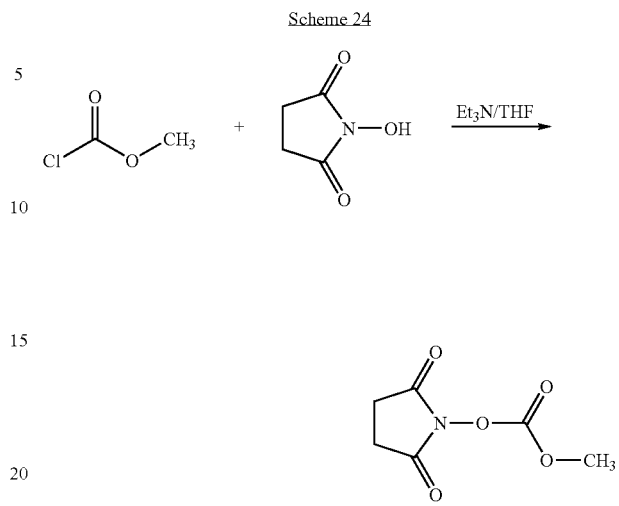

Scheme 24

To a stirred solution of 64.61 g (0.561 mol) of N-hydroxysuccinimide and 58.95 g (0.624 mol) of methyl chloroformate in THF (900 mL) at −5° C. under argon was added 82.6 mL (0.593 mol) of triethylamine at a rate such that the temperature remained below +3° C. The reaction mixture was stirred and allowed to warm to RT. After 15 h, the resulting slurry was filtered and the solids were washed with THF (100 mL). The filtrate was evaporated under reduced pressure to give a white solid. Recrystallization from EtOAc/hexanes (2:1, 150 mL) provided the desired product as white crystals, mp 84-86° C., 79.4 g, 82% yield.

Example 27

Utilizing the synthetic methods described herein, exemplary 11-mer peptides are set forth in Table 3.

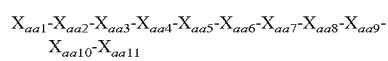

TABLE 3

| SEQ ID No. | X$_{aa1}$ | X$_{aa2}$ | X$_{aa3}$ | X$_{aa4}$ | X$_{aa5}$ | X$_{aa6}$ | X$_{aa7}$ | X$_{aa8}$ | X$_{aa9}$ | X$_{aa10}$ | X$_{aa11}$—NH$_2$ |
|---|---|---|---|---|---|---|---|---|---|---|---|
| 1. | H | Aib | E | G | T | L-α-Me-Phe(2-Fluoro) | T | S | D | Bip(2'-Me) | 4-(2'-pyridyl)Phenylalanine-NH$_2$ |
| 2. | H | Aib | E | G | T | L-α-Me-Phe(2-Fluoro) | T | S | D | Bip(3',5'-di-Me) | 4-(2'-pyridyl)Phenylalanine-NH$_2$ |
| 3. | H | Aib | E | G | T | L-α-Me-Phe(2-Fluoro) | T | S | D | Bip(2'-OBu) | 4-(2'-pyridyl)Phenylalanine-NH$_2$ |
| 4. | H | Aib | E | G | T | L-α-Me-Phe(2-Fluoro) | T | S | D | Bip(2'-Me) | 4-(4'-pyridyl)Phenylalanine-NH$_2$ |
| 5. | H | Aib | E | G | T | L-α-Me-Phe(2-Fluoro) | T | S | D | Bip(2'-Cl) | 4-(4'-pyridyl)Phenylalanine-NH$_2$ |
| 6. | H | Aib | E | G | T | L-α-Me-Phe(2-Fluoro) | T | S | D | Bip(2'-methoxy-5'-isopropyl) | 4-(4'-pyridyl)Phenylalanine-NH$_2$ |
| 7. | H | Aib | E | G | T | L-α-Me-Phe(2-Fluoro) | T | S | D | 4-(2'-Ethylphenyl)-3-pyridylalanine | Bip(2'-Me)—NH$_2$ |
| 8. | H | Aib | E | G | T | L-α-Me-Phe(2-Fluoro) | T | S | D | 4-[(2'-Ethyl-4'-methoxy)phenyl]3-pyridylalanine | Bip(2'-Me)—NH$_2$ |
| 9. | H | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 10. | H | Aib | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 11. | Des-NH$_2$-His | Aib | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 12. | Des-NH$_2$-His | Aib | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 13. | H | Aib | E | G | T | L-α-Me-Phe(2-Fluoro) | T | S | D | 4-(2'-ethylphenyl)-3-pyridylalanine | 4-(2'-Methylphenyl)-3-pyridylalanine-NH$_2$ |
| 14. | H | Aib | E | G | T | L-α-Me-Phe(2,6-di-Fluoro) | T | S | D | 4-(2'-ethylphenyl)-3-pyridylalanine | 4-(2'-Methylphenyl)-3-pyridylalanine-NH$_2$ |
| 15. | H | Aib | E | G | T | L-α-Me-Phe(2-Fluoro) | T | S | D | Bip(2'-Et-4'-OMe) | 4-[3-(4-Methyl)pyridyl)]phenylalanine-NH$_2$ |
| 16. | H | Aib | E | G | T | L-α-Me-Phe(2,6-di-Fluoro) | T | S | D | Bip(2'-Et-4'-OMe) | 4-[3-(4-Methyl)pyridyl)]phenylalanine-NH$_2$ |
| 17. | H | Aib | E | G | T | L-α-Me-Phe(2-Fluoro) | T | S | D | Bip(2'-Et-4'-OMe) | 4-(3-Pyridazyl)phenylalanine-NH$_2$ |
| 18. | H | Aib | E | G | T | L-α-Me-Phe(2,6-di-Fluoro) | T | S | D | Bip(2'-Et-4'-OMe) | 4-(3-Pyridazyl)phenylalanine-NH$_2$ |
| 19. | H | Aib | E | G | T | L-α-Me-Phe(2-Fluoro) | T | S | D | Bip(2'-Et-4'-OMe) | 4-[3-(4-Me,6-OMe)pyridyl)] |

TABLE 3-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$—NH$_2$ |
|---|---|---|---|---|---|---|---|---|---|---|---|
| 20. | H | Aib | E | G | T | L-α-Me-Phe(2,6-di-Fluoro) | T | S | D | 4-[3-(4'-Methyl)pyridyl]phenylalanine | phenylalanine-NH$_2$ Bip(2'-Me)—NH$_2$ |
| 21. | H | Aib | E | G | T | L-α-Me-Phe(2-Fluoro) | T | S | D | 4-[(4'-Me-6'-OMe)-3-pyridyl]phenylalanine | Bip(2'-Me)—NH$_2$ |
| 22. | H | Aib | E | G | T | L-α-Me-Phe(2,6-di-Fluoro) | T | S | D | 4-[(4'-Me-6'-OMe)-3-pyridyl]phenylalanine | Bip(2'-Me)—NH$_2$ |
| 23. | H | Aib | E | G | T | L-α-Me-Phe(2,6-di-Fluoro) | T | S | D | Bip(2'-Et-4'-OMe) | 4-[2(1H)Pyridonyl]phenylalanine-NH$_2$ |
| 24. | H | Aib | E | G | T | L-α-Me-Phe(2-Fluoro) | T | S | D | Bip(2'-Et-4'-OMe) | Bip(8-Quinoline)-NH$_2$ |
| 25. | H | Aib | E | G | T | L-α-Me-Phe(2-Fluoro) | T | S | D | Bip(2'-Et-4'-OMe) | Bip(3-Quinoline)-NH$_2$ |
| 26. | H | Aib | E | G | T | L-α-Me-Phe(2-Fluoro) | T | S | D | Bip(2'-Et-4'-OMe) | Bip(6-Quinoline)-NH$_2$ |
| 27. | H | Aib | E | G | T | L-α-Me-Phe(2-Fluoro) | T | S | D | Bip(2'-Et-4'-OMe) | Bip(5-Quinoline)-NH$_2$ |
| 28. | H | Aib | E | G | T | L-α-Me-Phe(2-Fluoro) | T | S | D | Bip(2'-Et-4'-OMe) | 4-(3-(6-OMe)pyridyl)phenylalanine-NH$_2$ |
| 29. | H | Aib | E | G | T | L-α-Me-Phe(2-Fluoro) | T | S | D | Bip(2'-Et-4'-OMe) | 4-(3-(2-Methoxy)pyridyl)phenylalanine-NH$_2$ |
| 30. | H | Aib | E | G | T | L-α-Me-Phe(2-Fluoro) | T | S | D | Bip(2'-Et-4'-OMe) | 4-(3'-pyridyl)phenylalanine-NH$_2$ |
| 31. | Des-NH$_2$-His | Aib | E | G | T | L-α-Me-Phe(2,6-di-Fluoro) | T | S | D | 4-(2'-ethylphenyl)-3-pyridylalanine | 4-(2'-Methylphenyl)-3-pyridylalanine-NH$_2$ |
| 32. | H | Aib | E | G | T | L-α-Me-Phe(2-Fluoro) | T | S | D | 4-(5-Quinoline)phenylalanine | Bip(2'-Me)—NH$_2$ |
| 33. | H | Aib | E | G | T | L-α-Me-Phe(2-Fluoro) | T | S | D | 4-[3-(2'-OMe)pyridyl]phenylalanine | Bip(2'-Me)—NH$_2$ |
| 34. | H | Aib | E | G | T | L-α-Me-Phe(2-Fluoro) | T | S | D | 4-(6-Quinoline)phenylalanine | Bip(2'-Me)—NH$_2$ |
| 35. | H | Aib | E | G | T | L-α-Me-Phe(2-Fluoro) | T | S | D | 4-(4'-pyridyl)phenylalanine | Bip(2'-Me)—NH$_2$ |
| 36. | H | Aib | E | G | T | L-α-Me-Phe(2-Fluoro) | T | S | D | 4-[4'-(3',5'-dimethylisoxazole)]phenylalanine | Bip(2'-Me)—NH$_2$ |
| 37. | H | Aib | E | G | T | L-α-Me-Phe(2-Fluoro) | T | S | D | Bip(2'-Et-4'-OMe) | 4-(2-trifluoromethylphenyl)-3-pyridylalanine-NH$_2$ |
| 38. | H | Aib | E | G | T | L-α-Me-Phe(2-Fluoro) | T | S | D | Bip(2'-Et-4'-OMe) | 4-(2-methyl-5-fluorophenyl)-3-pyridylalanine-NH$_2$ |
| 39. | H | Aib | E | G | T | L-α-Me-Phe(2-Fluoro) | T | S | D | Bip(2'-Et-4'-OMe) | 4-(4-methanesulfonylphenyl)-3-pyridylalanine-NH$_2$ |

TABLE 3-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$—NH$_2$ |
|---|---|---|---|---|---|---|---|---|---|---|---|
| 40. | H | Aib | E | G | T | L-α-Me-Phe | T | S | D | Bip(2'-Et-4'-OMe) | 4-(2'-Methylphenyl)-3-pyridylalanine-NH$_2$ |
| 41. | H | Aib | E | G | T | L-α-Me-Phe(2-Fluoro) | T | S | D | Bip(2'-Et) | 4-(2'-Methylphenyl)-3-pyridylalanine-NH$_2$ |
| 42. | H | Aib | E | G | Nle | L-α-Me-Phe(2-Fluoro) | T | S | D | Bip(2'-Et-4'-OMe) | 4-(2'-Methylphenyl)-3-pyridylalanine-NH$_2$ |
| 43. | H | Aib | E | G | T | L-α-Me-Phe(2-Fluoro) | T | S | D | Bip(2'-Et-4'-OMe) | 4-[(2'-Cl,4'-CF3)-3'-pyridyl]phenylalanine-NH$_2$ |
| 44. | H | Aib | E | G | T | L-α-Me-Phe(2,6-di-Fluoro) | T | S | D | Bip(2'-Et-4'-OMe) | 4-[3'-(2'-CN-6'-Me)pyridyl]phenylalanine-NH$_2$ |
| 45. | H | Aib | E | G | T | L-α-Me-Phe(2,6-di-Fluoro) | T | S | D | Bip(2'-Cl) | 4-(2'-Methylphenyl)-3-pyridylalanine-NH$_2$ |
| 46. | H | Aib | E | G | T | L-α-Me-Phe(2,6-di-Fluoro) | T | S | D | Bip(2',4'-di-OMe) | 4-(2'-Methylphenyl)-3-pyridylalanine-NH$_2$ |
| 47. | H | Aib | E | G | T | L-α-Me-Phe(2,6-di-Fluoro) | T | S | D | 4-(3-pyridyl)phenylalanine | 4-(2'-Methylphenyl)-3-pyridylalanine-NH$_2$ |
| 48. | H | Aib | E | G | T | L-α-Me-Phe(2,6-di-Fluoro) | T | S | D | 4-(4-pyridyl)phenylalanine | 4-(2'-Methylphenyl)-3-pyridylalanine-NH$_2$ |
| 49. | H | Aib | E | G | T | L-α-Me-Phe(2,6-di-Fluoro) | T | S | D | Bip(2'-Me-3'-F) | 4-(2'-Methylphenyl)-3-pyridylalanine-NH$_2$ |
| 50. | H | Aib | E | G | T | L-α-Me-Phe(2-Fluoro) | T | S | D | Bip(2'-F) | 4-(2'-Methylphenyl)-3-pyridylalanine-NH$_2$ |
| 51. | H | Aib | E | G | T | L-α-Me-Phe(2,6-di-Fluoro) | T | S | D | 4-[3'-(2'-Cl-6'-CF3)pyridyl]phenylalanine | 4-(2'-Methylphenyl)-3-pyridylalanine-NH$_2$ |
| 52. | H | Aib | E | G | T | L-α-Me-Phe(2,6-di-Fluoro) | T | S | D | 4-(2'-ethylphenyl)-3-pyridylalanine | Bip(2'-Cl)—NH$_2$ |
| 53. | H | Aib | E | G | T | L-α-Me-Phe(2,6-di-Fluoro) | T | S | D | 4-(2'-ethylphenyl)-3-pyridylalanine | Bip(3'-Cl-4'-F)—NH$_2$ |
| 54. | H | Aib | E | G | Nva | L-α-Me-Phe(2-Fluoro) | T | S | D | Bip(2'-Et-4'-OMe) | 4-(2'-Methylphenyl)-3-pyridylalanine-NH$_2$ |
| 55. | H | Aib | E | G | T | L-α-Me-Phe(2,6-di-Fluoro) | T | S | D | 4-(2'-ethylphenyl)-3-pyridylalanine | Bip(3',5'-di-Me)—NH$_2$ |
| 56. | H | Aib | E | G | T | L-α-Me-Phe(2,6-di-Fluoro) | T | S | D | 4-(2'-ethylphenyl)-3-pyridylalanine | 4-(2,3'-pyridazyl)phenylalanine-NH$_2$ |
| 57. | H | Aib | E | G | T | L-α-Me-Phe(2-Fluoro) | T | S | D | Bip(2'-Et-4'-OMe) | 4-(2'-ethylphenyl)-3-pyridylalanine-NH$_2$ |

TABLE 3-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$—NH$_2$ |
|---|---|---|---|---|---|---|---|---|---|---|---|
| 58. | H | Aib | E | G | T | L-α-Me-Phe(2,6-di-Fluoro) | T | S | D | 4-(2'-ethylphenyl)-3-pyridylalanine | 4-[3'-(2'-Cl-6'-CF3)pyridyl]phenylalanine-NH$_2$ |
| 59. | H | Aib | E | G | T | L-α-Me-Phe(2,6-di-Fluoro) | T | S | D | 4-(2'-ethylphenyl)-3-pyridylalanine | 4-[3'-(2'-CN-6'-Me)pyridyl]phenylalanine-NH$_2$ |
| 60. | H | Aib | E | G | T | L-α-Me-Phe(2,6-di-Fluoro) | T | S | D | 4-[3'-(4'-Me)pyridyl]phenylalanine | Bip(2'-Cl)—NH$_2$ |
| 61. | H | Aib | E | G | T | L-α-Me-Phe(2,6-di-Fluoro) | T | S | D | 4-[3'-(4'-Me)pyridyl]phenylalanine | Bip(3'-Cl-4'-F)—NH$_2$ |
| 62. | H | Aib | E | G | T | L-α-Me-Phe(2,6-di-Fluoro) | T | S | D | 4-[3'-(4'-Me)pyridyl]phenylalanine | Bip(3',5'-di-Me)—NH$_2$ |
| 63. | H | Aib | E | G | T | L-α-Me-Phe(2,6-di-Fluoro) | T | S | D | 4-[3'-(4'-Me)pyridyl]phenylalanine | Bip(2'-Me-4'-OMe)—NH$_2$ |
| 64. | H | Aib | E | G | T | L-α-Me-Phe(2,6-di-Fluoro) | T | S | D | 4-[3'-(4'-Me)pyridyl]phenylalanine | Bip(2'-Me-3'-F)—NH$_2$ |
| 65. | H | Aib | E | G | T | L-α-Me-Phe(2,6-di-Fluoro) | T | S | D | 4-[3'-(4'-Me)pyridyl]phenylalanine | Bip(2'-F)—NH$_2$ |
| 66. | H | Aib | E | G | T | L-α-Me-Phe(2,6-di-Fluoro) | T | S | D | 4-[3'-(4'-Me)pyridyl]phenylalanine | Bip(2'-Cl)—NH$_2$ |
| 67. | H | Aib | E | G | T | L-α-Me-Phe(2,6-di-Fluoro) | T | S | D | 4-[(4'-Me-6'-OMe)-3-pyridyl]phenylalanine | Bip(3',4'-di-OMe)—NH$_2$ |
| 68. | H | Aib | E | G | T | L-α-Me-Phe(2,6-di-Fluoro) | T | S | D | 4-[(4'-Me-6'-OMe)-3-pyridyl]phenylalanine | 4-(2-pyridyl)phenylalanine-NH$_2$ |
| 69. | H | Aib | E | G | T | L-α-Me-Phe(2,6-di-Fluoro) | T | S | D | 4-[(4'-Me-6'-OMe)-3-pyridyl]phenylalanine | Bip(2'-Me-4'-OMe)—NH$_2$ |
| 70. | H | Aib | E | G | T | L-α-Me-Phe(2,6-di-Fluoro) | T | S | D | 4-[(4'-Me-6'-OMe)-3-pyridyl]phenylalanine | 4-(2'-Methylphenyl)-3-pyridylalanine-NH$_2$ |
| 71. | H | Aib | E | G | T | L-α-Me-Phe(2,6-di-Fluoro) | T | S | D | Bip(2'-Et) | 4-(2'-ethylphenyl)-3-pyridylalanine-NH$_2$ |
| 72. | H | Aib | E | G | T | L-α-Me-Phe(2,6-di-Fluoro) | T | S | D | 4-[3'-Methyl)pyridyl]phenylalanine | 4-(2'-Methylphenyl)-3-pyridylalanine-NH$_2$ |
| 73. | H | Aib | E | G | T | L-α-Me-Phe(2,6-di-Fluoro) | T | S | D | Bip(2'-Et-4-OMe) | 4-(4'-pyridyl)-phenylalanine-NH$_2$ |

TABLE 3-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$—$NH_2$ |
|---|---|---|---|---|---|---|---|---|---|---|---|
| 74. | H | Aib | E | G | T | L-α-Me-Phe(2-Fluoro) | T | S | D | Bip(2'-Et-4'-OMe) | 4-(3'-quinoline)phenylalanine-NH$_2$ |
| 75. | H | Aib | E | G | T | L-α-Me-Phe(2-Fluoro) | T | S | D | Bip(2'-Et-4'-OMe) | 4-(3'-(2-Methoxy)pyridyl)phenylalanine-NH$_2$ |
| 76. | H | Aib | E | G | T | L-α-Me-Phe(2-Fluoro) | T | S | D | Bip(2'-Et-4'-OMe) | 4-phenyl-3-pyridylalanine-NH$_2$ |
| 77. | H | Aib | E | G | T | L-α-Me-Phe(2-Fluoro) | T | S | D | Bip(2'-Et-4'-OMe) | 4-(3',5'-dimethylphenyl)-3-pyridylalanine-NH$_2$ |
| 78. | H | Aib | E | G | T | L-α-Me-Phe(2-Fluoro) | T | S | D | Bip(2'-Et-4'-OMe) | 4-[(3'-chloro-4'-fluoro)phenyl]-3-pyridylalanine-NH$_2$ |
| 79. | H | Aib | E | G | T | L-α-Me-Phe(2-Fluoro) | T | S | D | Bip(2'-Et-4'-OMe) | 4-[(3',4'-dimethoxy)phenyl]-3-pyridylalanine-NH$_2$ |
| 80. | H | Aib | E | G | T | L-α-Me-Phe(2-Fluoro) | T | S | D | Bip(2'-Et-4'-OMe) | 4-[(2'-ethyl-4'-methoxy)phenyl]-3-pyridylalanine-NH$_2$ |
| 81. | L-β-Imidazole lactyl | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 82. | H | Aib | E | G | T | L-α-Me-Phe(2-Fluoro) | T | S | D | Bip(2'-Et-4'-OMe) | 2-(5-o-Tolyl)thienylalanine-NH$_2$ |
| 83. | H | Aib | E | G | T | L-α-Me-Phe(2-Fluoro) | T | S | D | Bip(2'-Et-4'-OMe) | 2-[(5-(3'-Methoxyphenyl)thienyl]thienylalanine-NH$_2$ |
| 84. | H | Aib | E | G | T | L-α-Me-Phe(2-Fluoro) | T | S | D | Bip(2'-Et-4'-OMe) | 2-[(5-(3',5'-di-Methyl)phenyl]thienylalanine-NH$_2$ |
| 85. | H | Aib | E | G | T | L-α-Me-Phe(2-Fluoro) | T | S | D | Bip(2'-Et-4'-OMe) | 2-[(5-(3'-Cl,5'-F)phenyl]thienylalanine-NH$_2$ |
| 86. | H | Aib | E | G | T | L-α-Me-Phe(2-Fluoro) | T | S | D | Bip(2'-Et-4'-OMe) | 4-(3'-Isopropoxyphenyl)-3-pyridylalanine-NH$_2$ |
| 87. | H | Aib | E | G | T | L-α-Me-Phe(2-Fluoro) | T | S | D | Bip(2'-Et-4'-OMe) | 4-(2'-Methyl,5'-Fluorophenyl)-3-pyridylalanine-NH$_2$ |
| 88. | H | Aib | E | G | T | L-α-Me-Phe(2-Fluoro) | T | S | D | Bip(2'-Et-4'-OMe) | 4-(2'-Isopropoxyphenyl)-3-pyridylalanine-NH$_2$ |
| 89. | H | Aib | E | G | T | L-α-Me-Phe(2-Fluoro) | T | S | D | Bip(2'-Et-4'-OMe) | 3-(4-Br)pyridylalanine-NH$_2$ |
| 90. | H | Aib | E | G | T | L-α-Me-Phe(2-Fluoro) | T | S | D | Bip(2'-Et-4'-OMe) | 4-(4'-Methoxyphenyl)-3-pyridylalanine-NH$_2$ |
| 91. | H | Aib | E | G | T | L-α-Me-Phe(2-Fluoro) | T | S | D | Bip(2'-Et-4'-OMe) | 4-(2'-Methyl,4'-Fluorophenyl)-3-pyridylalanine-NH$_2$ |

TABLE 3-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$—NH$_2$ |
|---|---|---|---|---|---|---|---|---|---|---|---|
| 92. | H | Aib | E | G | T | L-α-Me-Phe(2-Fluoro) | T | S | D | Bip(2'-Et) | 4-(2'-Methylphenyl)-3-pyridylalanine-NH$_2$ |
| 93. | H | Aib | E | G | T | L-α-Me-Phe(2-Fluoro) | T | S | D | Bip(2'-Et-4'-OMe) | 4-(2'-Trifluoromethoxyphenyl)-3-pyridylalanine-NH$_2$ |
| 94. | H | Aib | E | G | T | L-α-Me-Phe(2-Fluoro) | T | S | D | Bip(2'-Et-4'-OMe) | 4-(4'-Trifluoromethoxyphenyl)-3-pyridylalanine-NH$_2$ |
| 95. | H | Aib | E | G | T | L-α-Me-Phe(2-Fluoro) | T | S | D | Bip(2'-Et-4'-OMe) | 3-pyridylalanine-NH$_2$ |
| 96. | H | Aib | E | G | T | L-α-Me-Phe(2-Fluoro) | T | S | D | Bip(2'-Et-4'-OMe) | 4-(2'-Methyl,4'-Chlorophenyl)-3-pyridylalanine-NH$_2$ |
| 97. | H | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 98. | H | Aib | E | G | T | L-α-Me-Phe(2-Fluoro) | T | S | D | Bip(2'-Me-4'-OMe) | 4-(4'-Trifluoromethylphenyl)-3-pyridylalanine-NH$_2$ |
| 99. | H | Aib | E | G | T | L-α-Me-Phe(2-Fluoro) | T | S | D | Bip(2'-Et-4'-OMe) | 4-(4'-Fluorophenyl)-3-pyridylalanine-NH$_2$ |
| 100. | H | Aib | E | G | T | L-α-Me-Phe(2-Fluoro) | T | S | D | Bip(2'-Et-4'-OMe) | 4-(2'-Trifluoromethylphenyl)-3-pyridylalanine-NH$_2$ |
| 101. | H | Aib | E | G | T | L-α-Me-Phe(2-Fluoro) | T | S | D | Bip(2'-Et-4'-OMe) | 4-(2'-Chlorophenyl)-3-pyridylalanine-NH$_2$ |
| 102. | H | Aib | E | G | T | L-α-Me-Phe(2-Fluoro) | T | S | D | Bip(2'-Et-4'-OMe) | 4-(3'-Chlorophenyl)-3-pyridylalanine-NH$_2$ |
| 103. | H | Aib | E | G | T | L-α-Me-Phe(2-Fluoro) | T | S | D | Bip(2'-Et-4'-OMe) | 4-(4'-Isopropylphenyl)-3-pyridylalanine-NH$_2$ |
| 104. | H | Aib | E | G | T | L-α-Me-Phe(2-Fluoro) | T | S | D | Bip(2'-Et-4'-OMe) | 4-(3',5'-dimethylisoxazol-4'-yl)-3-pyridylalanine-NH$_2$ |
| 105. | H | Aib | E | G | T | L-α-Me-Phe(2-Fluoro) | T | S | D | Bip(2'-Et-4'-OMe) | 4-[(2'-Methyl-4'-methoxy)phenyl]-3-pyridylalanine-NH$_2$ |
| 106. | H | Aib | E | G | T | L-α-Me-Phe(2-Fluoro) | T | S | D | Bip(2'-Et-4'-OMe) | 4-(4'-Trifluoromethylphenyl)-3-pyridylalanine-NH$_2$ |
| 107. | H | Aib | E | G | T | L-α-Me-Phe(2-Fluoro) | T | S | D | Bip(2'-Et-4'-OMe) | 4-(4'-Chlorophenyl)-3-pyridylalanine-NH$_2$ |
| 108. | H | Aib | E | G | T | L-α-Me-Phe(2-Fluoro) | T | S | D | Bip(2'-Et-4'-OMe) | 4-(4'-Pyridyl)-3-pyridylalanine-NH$_2$ |
| 109. | H | Aib | E | G | T | L-α-Me-Phe(2-Fluoro) | T | S | D | Bip(2'-Et-4'-OMe) | 4-(3'-Methoxyphenyl)-3-pyridylalanine-NH$_2$ |

TABLE 3-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$—NH$_2$ |
|---|---|---|---|---|---|---|---|---|---|---|---|
| 110. | H | Aib | E | G | T | L-α-Me-Phe(2-Fluoro) | T | S | D | Bip(2'-Et-4'-OMe) | 4-(6'-Methoxypyridin-3'-yl)-3-pyridylalanine-NH$_2$ |
| 111. | H | Aib | E | G | T | L-α-Me-Phe(2-Fluoro) | T | S | D | Bip(2'-Et-4'-OMe) | 4-(2'-Isopropylphenyl)-3-pyridylalanine-NH$_2$ |
| 112. | H | Aib | E | G | T | L-α-Me-Phe(2-Fluoro) | T | S | D | Bip(2'-Et-4'-OMe) | 4-(2'-Methoxyphenyl)-3-pyridylalanine-NH$_2$ |
| 113. | H | Aib | E | G | T | L-α-Me-Phe(2-Fluoro) | T | S | D | Bip(2'-Et-4'-OMe) | 4-[(3',5'-di-Fluoro-2'-methoxy)phenyl]-3-pyridylalanine-NH$_2$ |
| 114. | H | Aib | E | G | T | L-α-Me-Phe(2-Fluoro) | T | S | D | Bip(2'-Et-4'-OMe) | 4-(3'-methylphenyl)-3-pyridylalanine-NH$_2$ |
| 115. | H | Aib | E | G | T | L-α-Me-Phe(2-Fluoro) | T | S | D | Bip(2'-Et-4'-OMe) | 4-(2'-fluorophenyl)-3-pyridylalanine-NH$_2$ |
| 116. | H | Aib | E | G | T | L-α-Me-Phe(2,6-di-Fluoro) | T | S | D | Bip(2'-Et-4'-OMe) | 4-(2'-fluorophenyl)-3-pyridylalanine-NH$_2$ |
| 117. | H | Aib | E | G | T | L-α-Me-Phe(2,6-di-Fluoro) | T | S | D | Bip(2'-Et-4'-OMe) | 4-(3'-Methoxyphenyl)-3-pyridylalanine-NH$_2$ |
| 118. | H | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 119. | H | N—Me-(D)-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 120. | H | (S)-α-Me-Pro | E | G | T | L-α-Me-Phe(2-Fluoro) | T | H | D | Bip(2'-Et-4'-OMe) | 4-(2'-Methoxyphenyl)-3-pyridylalanine-NH$_2$ |
| 121. | H | (S)-α-Me-Pro | E | G | T | L-α-Me-Phe(2-Fluoro) | T | S | D | Bip(2'-Et-4'-OMe) | (S)-4-(2'-Methylphenyl)-α-Me-3-pyridylalanine-NH$_2$ |
| 122. | H | Aib | E | G | T | L-α-Me-Phe(2-Fluoro) | T | S | D | Bip(2'-Et-4'-OMe) | (S)-4-(2'-Methylphenyl)-α-Me-3-pyridylalanine-NH$_2$ |
| 123. | H | (S)-α-Me-Pro | E | G | T | L-α-Me-Phe(2-Fluoro) | T | H | D | Bip(2'-Et-4'-OMe) | 4-(2'-Methylphenyl)-3-pyridylalanine-NH$_2$ |
| 124. | H | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 125. | H | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH$_2$ |
| 126. | H | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH$_2$ |
| 127. | H | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-NH$_2$ |
| 128. | H | (S)-α-Me-Pro | E | G | T | L-α-Me-Phe(2,6-di-Fluoro) | T | S | D | Bip(2'-Et-4'-OMe) | 4-(2'-Fluorophenyl)-3-pyridylalanine-NH$_2$ |

TABLE 3-continued

| SEQ ID No. | $X_{aa1}$ | $X_{aa2}$ | $X_{aa3}$ | $X_{aa4}$ | $X_{aa5}$ | $X_{aa6}$ | $X_{aa7}$ | $X_{aa8}$ | $X_{aa9}$ | $X_{aa10}$ | $X_{aa11}$—NH$_2$ |
|---|---|---|---|---|---|---|---|---|---|---|---|
| 129. | H | N—Me-(L)-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 130. | H | Aib | E | G | T | L-α-Me-Phe(2-Fluoro) | T | S | D | Bip(2'-Et-4'-OMe) | 4-(2'-Methylphenyl)-3,5-pyrimidylalanine-NH$_2$ |
| 131. | H | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 132. | H | (S)-α-Me-Pro | E | G | T | L-α-Me-Phe(2-Fluoro) | T | S | D | Bip(2'-Et) | 4-(2'-Ethylphenyl)-3-pyridylalanine-NH$_2$ |
| 133. | Des-NH$_2$-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 134. | Des-NH$_2$-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 135. | Des-NH$_2$-His | (S)-α-Me-Pro | E | G | T | L-α-Me-Phe(2-Fluoro) | T | S | D | Bip(2'-Et-4'-OMe) | 4-(2'-Fluorophenyl)-3-pyridylalanine-NH$_2$ |
| 136. | Des-NH$_2$-His | (S)-α-Me-Pro | E | G | T | L-α-Me-Phe(2-Fluoro) | T | S | D | Bip(2'-Et-4'-OMe) | 4-(3'-Methoxyphenyl)-3-pyridylalanine-NH$_2$ |
| 137. | (R)-Imp | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 138. | (S)-Imp | Aib | E | G | T | L-α-Me-Phe(2-Fluoro) | T | S | D | Bip(2'-Et-4'-OMe) | 4-(2'-Methylphenyl)-3-pyridylalanine-NH$_2$ |
| 139. | CH3O—CO-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 140. | CH3O—CO-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 141. | CH3O—CO-His | N—Me-(D)-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 142. | CH3O—CO-His | N—Me-(D)-Ala | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 143. | CH3SO2-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 144. | CH3SO2-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |
| 145. | L-Lactyl-His | (S)-α-Me-Pro | E | G | T | L-α-Me-Phe(2-Fluoro) | T | S | D | Bip(2'-Et-4'-OMe) | 4-(2'-Methylphenyl)-3-pyridylalanine-NH$_2$ |
| 146. | L-Lactyl-His | (S)-α-Me-Pro | E | G | T | L-α-Me-Phe(2,6-di-Fluoro) | T | S | D | Bip(2'-Et-4'-OMe) | 4-(2'-Methylphenyl)-3-pyridylalanine-NH$_2$ |

TABLE 3-continued

| SEQ ID No. | X$_{aa1}$ | X$_{aa2}$ | X$_{aa3}$ | X$_{aa4}$ | X$_{aa5}$ | X$_{aa6}$ | X$_{aa7}$ | X$_{aa8}$ | X$_{aa9}$ | X$_{aa10}$ | X$_{aa11}$—NH$_2$ |
|---|---|---|---|---|---|---|---|---|---|---|---|
| 147. | H | Aib | E | G | T | L-α-Me-Phe(2-Fluoro) | T | S | D | Bip(2'-Et-4'-OMe) | 4-(3',5'-di-Me)phenyl-3-pyridylalanine-NH$_2$ |
| 148. | H | Aib | E | G | T | L-α-Me-Phe(2-Fluoro) | T | H | D | Bip(2'-Et-4'-OMe) | 4-(2'-Methylphenyl)-3-pyridylalanine-NH$_2$ |
| 149. | H | D-Ala | E | G | T | L-α-Me-Phe(2-Fluoro) | T | S | D | Bip(2'-Et-4'-OMe) | 4-(2'-Methylphenyl)-3-pyridylalanine-NH$_2$ |
| 150. | H | Aib | H | G | T | L-α-Me-Phe(2-Fluoro) | T | S | D | Bip(2'-Et-4'-OMe) | 4-(2'-Methylphenyl)-3-pyridylalanine-NH$_2$ |
| 151. | L-β-Imidazole-lactyl | (S)-α-Me-Pro | E | G | T | L-α-Me-Phe(2-Fluoro) | T | H | D | Bip(2'-Et-4'-OMe) | 4-(2'-Methyl phenyl)-3-pyridyl alanine-NH$_2$ |
| 152. | L-β-Imidazole-lactyl | (S)-α-Me-Pro | E | G | T | L-α-Me-Phe (2-Fluoro) | T | S | D | Bip(2'-Et-4'-OMe) | 4-(2'-Methyl phenyl)-3-pyridyl alanine-NH$_2$ |
| 153. | L-β-Imidazole-lactyl | (S)-α-Me-Pro | E | G | T | L-α-Me-Phe (2-Fluoro) | T | H | D | Bip(2'-Et-4'-OH) | 4-(2'-Methyl phenyl)-3-pyridyl alanine-NH$_2$ |
| 154. | L-β-Imidazole-lactyl | (S)-α-Me-Pro | E | G | T | L-α-Me-Phe (2-Fluoro) | T | S | D | Bip(2'-Et-4'-OH) | 4-(2'-Methyl phenyl)-3-pyridyl alanine-NH$_2$ |
| 155. | L-β-Imidazole-lactyl | N—Me-D-Ala | E | G | T | L-α-Me-Phe (2-Fluoro) | T | H | D | Bip(2'-Et-4'-OH) | 4-(2'-Methyl phenyl)-3-pyridyl alanine-NH$_2$ |
| 156. | L-β-Imidazole-lactyl | N—Me-D-Ala | E | G | T | L-α-Me-Phe (2-Fluoro) | T | S | D | Bip(2'-Et-4'-OH) | 4-(2'-Methyl phenyl)-3-pyridyl alanine-NH$_2$ |
| 157. | CH$_3$O—CO— | (S)-α-Me-Pro | E | G | T | L-α-Me-Phe (2-Fluoro) | T | H | D | Bip(2'-Et-4'-QH) | 4-(2'-Methyl phenyl)-3-pyridyl alanine-NH$_2$ |
| 158. | CH$_3$O—CO— | (S)-α-Me-Pro | E | G | T | L-α-Me-Phe (2-Fluoro) | T | S | D | Bip(2'-Et-4'-OH) | 4-(2'-Methyl phenyl)-3-pyridyl alanine-NH$_2$ |
| 159. | CH$_3$O—CO— | N—Me-D-Ala | E | G | T | L-α-Me-Phe (2-Fluoro) | T | H | D | Bip(2'-Et-4'-OH) | 4-(2'-Methyl phenyl)-3-pyridyl alanine-NH$_2$ |
| 160. | CH$_3$O—CO— | N—Me-D-Ala | E | G | T | L-α-Me-Phe (2-Fluoro) | T | S | D | Bip(2'-Et-4'-OH) | 4-(2'-Methyl phenyl)-3-pyridyl alanine-NH$_2$ |
| 161. | CH$_3$O—CO—His | Aib | E | G | T | L-α-Me-Phe (2-Fluoro) | T | H | D | Bip(2'-Et-4'-OH) | 4-(2'-Methyl phenyl)-3-pyridyl alanine-NH$_2$ |
| 162. | CH$_3$O—CO—His | Aib | E | G | T | L-α-Me-Phe (2-Fluoro) | T | S | D | Bip(2'-Et-4'-OH) | 4-(2'-Methyl phenyl)-3-pyridyl alanine-NH$_2$ |
| 163. | H | Aib | E | G | T | L-α-Me-Phe(2,6-di-Fluoro) | T | S | D | 4-[(2'-Cl-4'-CF3)-3'-pyridyl]-phenylalanine | 4-(2'-Methylphenyl)-3-pyridylalanine-NH2 |
| 164. | H | Aib | E | G | T | L-α-Me-Phe (2-Fluoro) | T | S | D | Bip(2'-Et-4'-OMe) | 4-(3'-(2'-Methoxy)pyridyl)phenylalanine-NH$_2$ |
| 165. | (R)-Imp | Aib | E | G | T | L-α-Me-Phe (2-Fluoro) | T | H | D | Bip(2'-Et-4'-OMe) | 4-(2'-Methylphenyl)-3-pyridylalanine-NH2 |
| 166. | (S)-Imp | Aib | E | G | T | L-α-Me-Phe (2-Fluoro) | T | H | D | Bip(2'-Et-4'-OMe) | 4-(2'-Methylphenyl)-3-pyridylalanine-NH2 |

Example 28

Cyclic AMP Determination

The GLP-1 receptor is a G-protein coupled receptor. GLP-1 (7-36)-amide, the biologically active form, binds to the GLP-1 receptor and through signal transduction causes activation of adenylyl cyclase and increases intracellular cAMP concentrations. To monitor agonism of peptide compounds in stimulating the GLP-1 receptor, adenylyl cyclase activity was monitored by assaying for intracellular cAMP content. Full-length human glucagon-like peptide 1 receptor was stably expressed in CHO-K1 cells and clonal lines were established. The clones were screened for the greatest increase in cAMP content in response to a saturating dose of GLP-1 and clone CHO-GLP1R-19 was selected.

Cells were cultured in Ham's F12 nutritional media (Gibco #11765-054), 10% FBS, 1× L-Glutamine, 1× Pen/Strep, and 0.4 mg/ml G418. CHO-GLP-1R-19 cells (20,000 in 100 µl of media) were plated into each well of a 96-well tissue culture microtiter plate and incubated overnight in a 5% $CO_2$ atmosphere at 37° C. On the day of the assay, cells were washed once with 100 µl of phosphate-buffered saline (PBS). A Biomek 2000 was used to serially dilute all peptides prior to beginning the assay. Serial dilutions were carried out in 100% DMSO. Peptide plates were created prior to the initiation of the assay using a Platemate Plus; 1.5 uL of compound was transferred to a V bottom plate and 150 uL of assay buffer supplemented with 100 µM 3-isobutyl-1-methylxanthine (a nonselective phosphodiesterase inhibitor) was added to the plate to give a 1:100 dilution and a 1% final concentration of DMSO.

In order to create a cAMP standard curve, a serial dilution of cAMP in the range 0.2-25.6 pmol/well was made up in lysis reagent 1 (Amersham cAMP SPA kit). 50 µl of each cAMP standard was added by hand and 70 µl of mix reagent (Amersham cAMP SPA kit) was added using the multidrop. The plates were then sealed and counted on a Trilux counter after 15 hours. This standard curve was used to convert CPM to pmol of cAMP.

A. cAMP Assay Protocol on the Platemate Plus

Cell plates and peptide plates were loaded onto the Platemate. The media was aspirated from the wells and discarded. 100 uL per well of the peptide/buffer mixture were then added from the peptide plates to initiate the assay. After 30 minutes of incubation the peptide/buffer was removed and 50 uL of the lysis reagent 1 solution was added per well. The plate was kept for one hour at RT or overnight if refrigerated and sealed. 70 uL of the cAMP detection reagent (premixed $^{125}$I-cAMP analog, anti-cAMP antibody and anti-rabbit antibody conjugated to SPA beads—all from the Amersham cAMP SPA kit) was added using the multidrop and the plates were sealed. After 15 hours the plates were counted on a Trilux scintillation counter.

Dose dependence for compounds was determined at half-log concentrations in duplicate. Ten nM GLP-1 served as a reference standard for determination of maximal activity. A standard curve was determined using known amounts of cyclic AMP. The amounts of cAMP synthesized by the treated cells were determined from the cyclic AMP standard curve, and the percent of the maximal GLP-1 stimulated activity was calculated and plotted against log compound concentration. The data were analyzed by nonlinear regression curve fitting (4 parameter sigmoidal dose-response curve) to determine the $EC_{50}$ of the compounds. By way of example, peptides of the present invention have $EC_{50}$ values in the range of 0.0005 nM to 10 nM, more preferably in the range of 0.0005 nM to 0.200 nM.

Example 29

In Vivo Studies

Peptides were dissolved in an appropriate vehicle at a concentration in nmol/ml equivalent to the dose that was to be administered in nmol/kg so that each mouse would receive the same volume/weight of dosing solution. Male C57BL/6J-ob/ob mice (10 weeks old) were randomized into groups of 6 mice per group based on fed plasma glucose and body weight. After an overnight fast, mice were weighed and placed in the experimental lab. After 30 min in the environment, the mice were bled via tail tip at −30 min and immediately injected subcutaneously (sc) with vehicle or the peptide dissolved in vehicle (0.1 ml solution/100 g body weight). At time 0 the mice were bled and then injected intraperitoneally with 50% glucose (2 g/kg) to initiate the intraperitoneal glucose tolerance test (ipGTT). The mice were bled 30, 60, 120 and 180 min after the glucose injection. Blood samples were drawn into potassium EDTA, placed on ice during the study and subsequently centrifuged for 10 min at 3000 rpm at 4° C. Plasma samples were diluted 11-fold for glucose analysis in the Cobas System. Another 5 µl plasma sample was diluted 5-fold with 20 µl of Sample Diluent (Insulin ELISA assay kit, Crystal Chem Inc.) and stored at −20° C. for subsequent analysis using the Ultra Sensitive Mouse Insulin ELISA kit (Crystal Chem Inc.).

Figure 2:
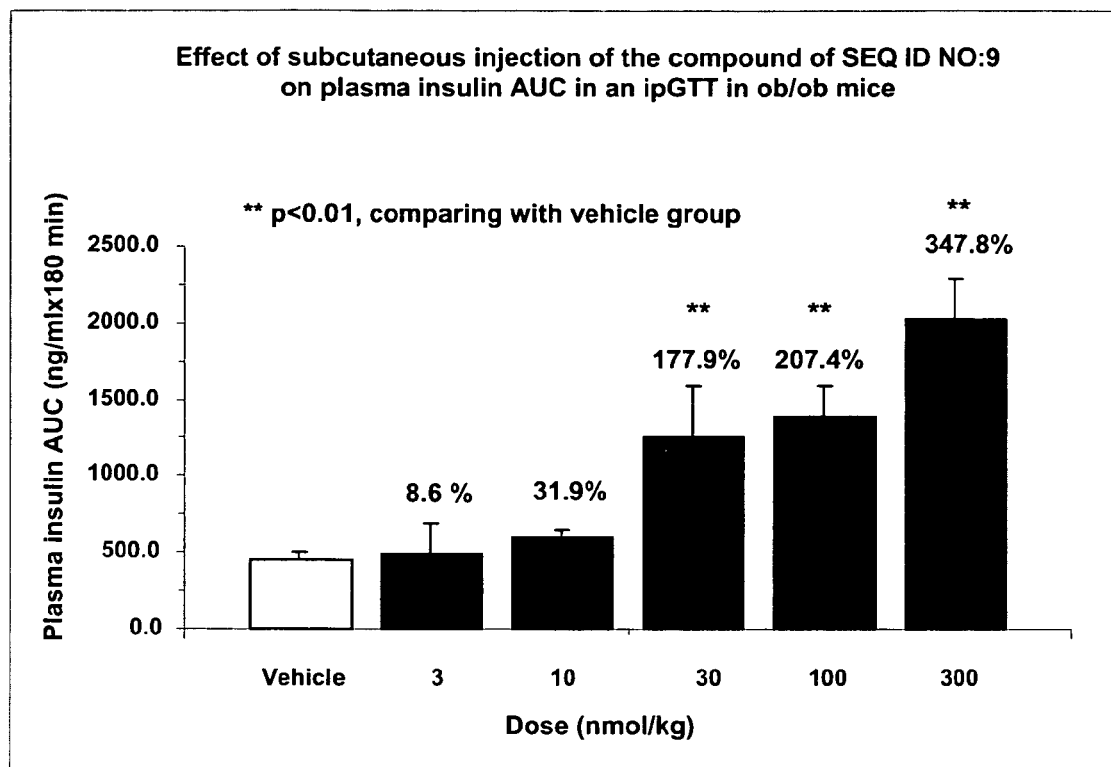
FIG. 2 illustrates the effects of subcutaneous injection of the compound of the SEQ ID NO:9 on plasma insulin in an ipGTT in ob/ob mice.

The in vivo glucose lowering properties for the compound of SEQ ID NOs: 9 and 118 in ob/ob mice (a mouse model of insulin resistance) are described above. Subcutaneous administration of peptide I attenuated the postprandial glucose excursion curve in an intraperitoneal glucose tolerance test (ipGTT), with the plasma glucose area under the curve (AUC) decreasing in a dose-dependent manner between 0 and 180 minutes (FIG. 1). The ED50 of compound I was determined to be 50 nmoles/kg. There was a concomitant and statistically significant dose-dependent increase in postprandial plasma insulin levels in these animals (FIG. 2). The correlation between changes in plasma glucose and insulin in animals treated with the compound of SEQ ID NO:9 (FIG. 1 and FIG. 2) suggests that the glucose lowering effect is mediated by stimulation of insulin release by the compound of SEQ ID NO:9.

Figure 3:
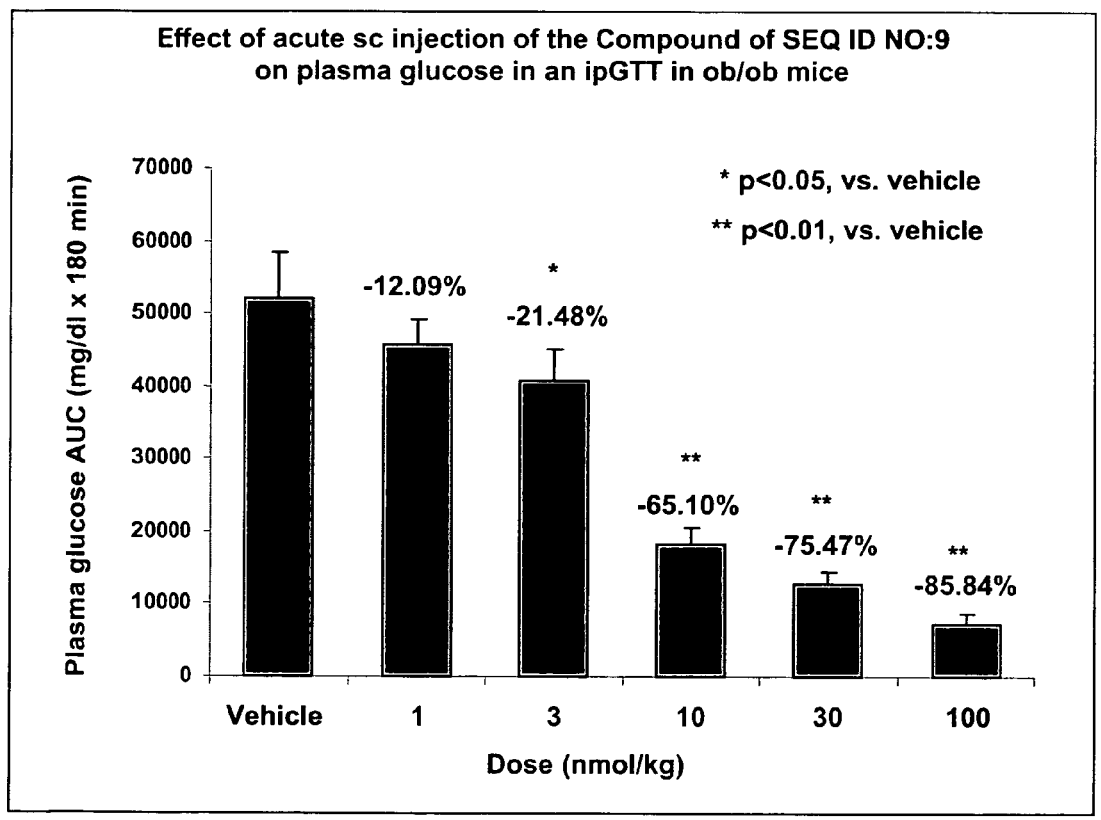
FIG. 3 illustrates the effects of subcutaneous injection of the compound of SEQ ID NO:9 on plasma glucose in an ipGTT in ob/ob mice.
Figure 4:
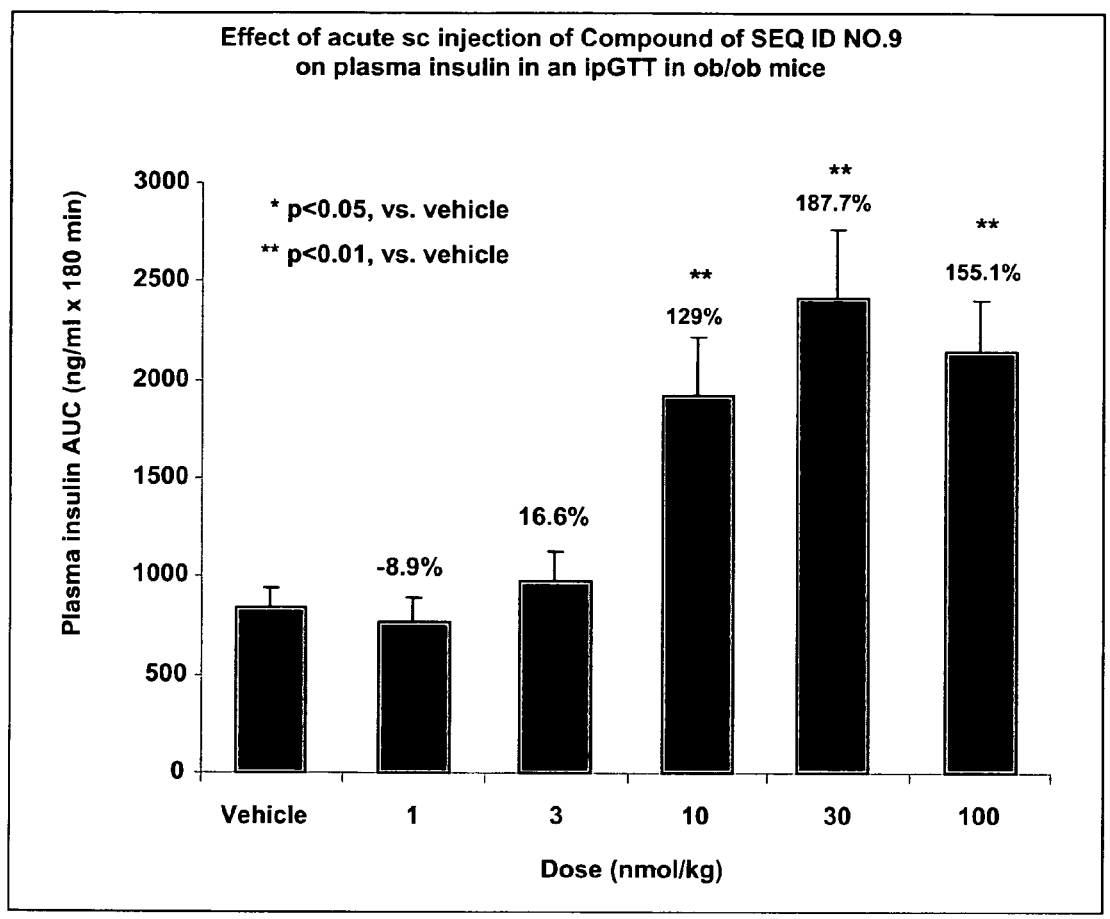
FIG. 4 represents the effect of acute subcutaneous injection of the compound of SEQ ID NO.9 on plasma insulin in an ipGTT in ob/ob mice.

More significantly and unexpectedly, the compounds of SEQ ID NOs: 9, 118, 151 and 158 produced a time-dependent (between 0 and 180 or 210 minutes) statistically significant decrease in postprandial plasma glucose following subcutaneous administration in ob/ob mice (FIGS. 3, 5, 6 and 7). The effect of the compound of SEQ ID NO: 9 on postprandial glucose was dose-dependent between 1-100 nmol/kg and plasma glucose AUC decreased 85.8% at 100 nmol/kg dose (FIG. 3). The ED50 for the compound of SEQ ID NO: 9 was determined to be 5 nmoles/kg. The effect of the compound of SEQ ID NO: 9 on plasma glucose is also accompanied by a significant increase in postprandial insulin in these animals (FIG. 4). The effect on insulin appears to be dose-dependent with a maximum increase of 187.7% in AUC at 30 nmol/kg dose (FIG. 4).

Figure 5:
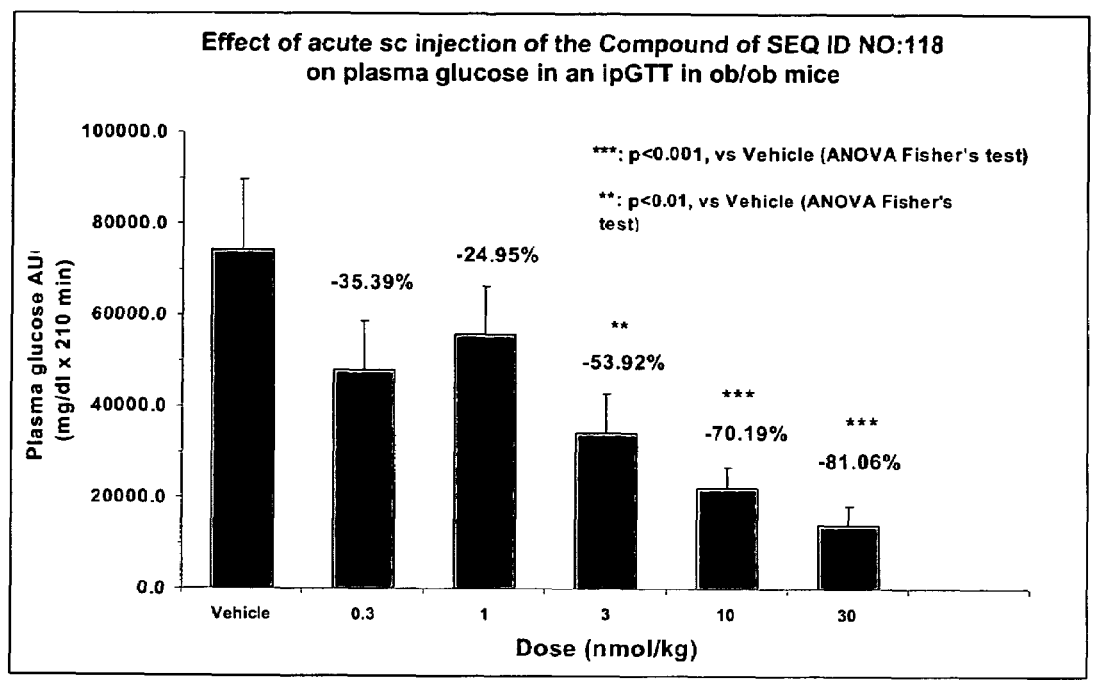
FIG. 5 illustrates the effects of subcutaneous injection of the compound of SEQ ID NO:118 on plasma glucose in an ipGTT in ob/ob mice.
Figure 6:
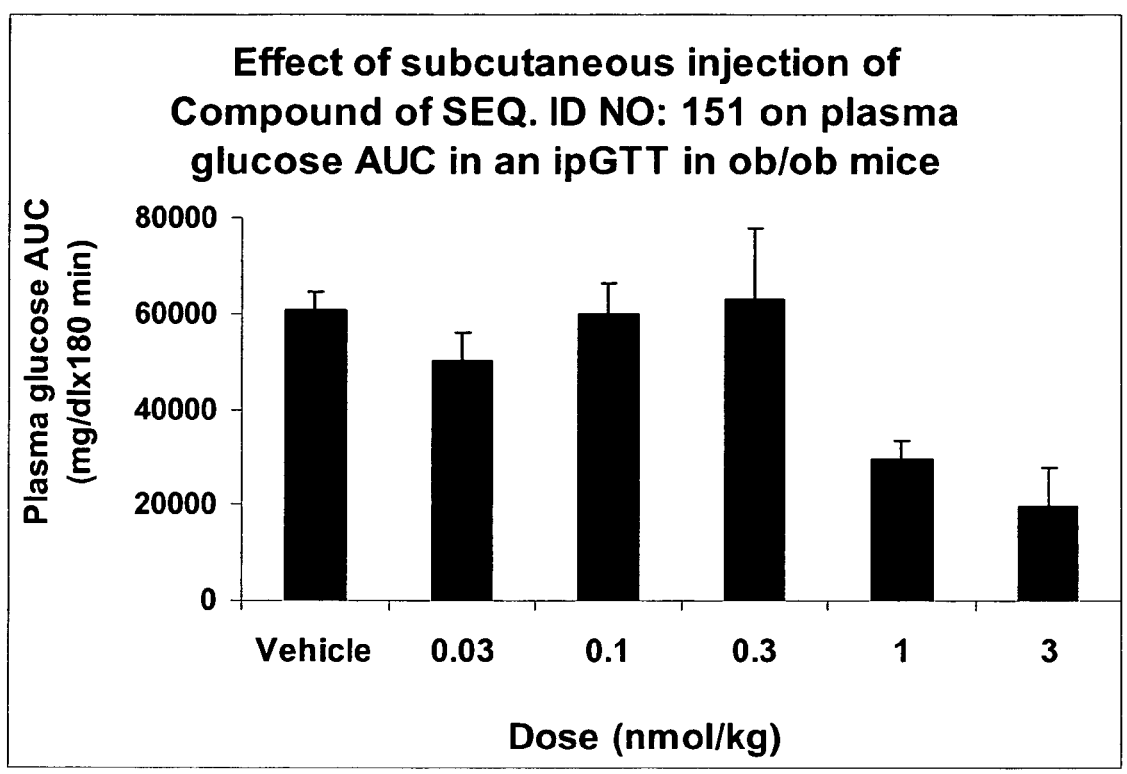
FIG. 6 illustrates the effects of subcutaneous injection of the compound of SEQ ID NO: 151 on plasma glucose in an ipGTT in ob/ob mice.
Figure 7:
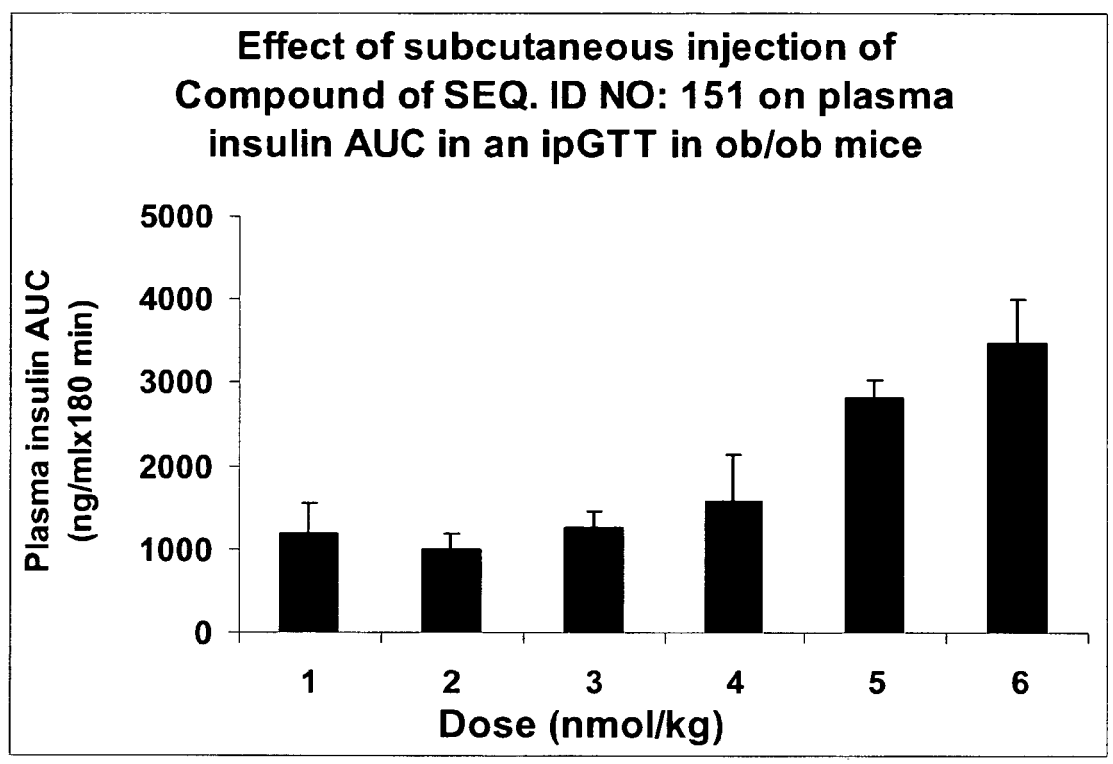
FIG. 7 illustrates the effects of subcutaneous injection of the compound of SEQ ID NO: 151 on plasma insulin in an ipGTT in ob/ob mice.
Figure 8:
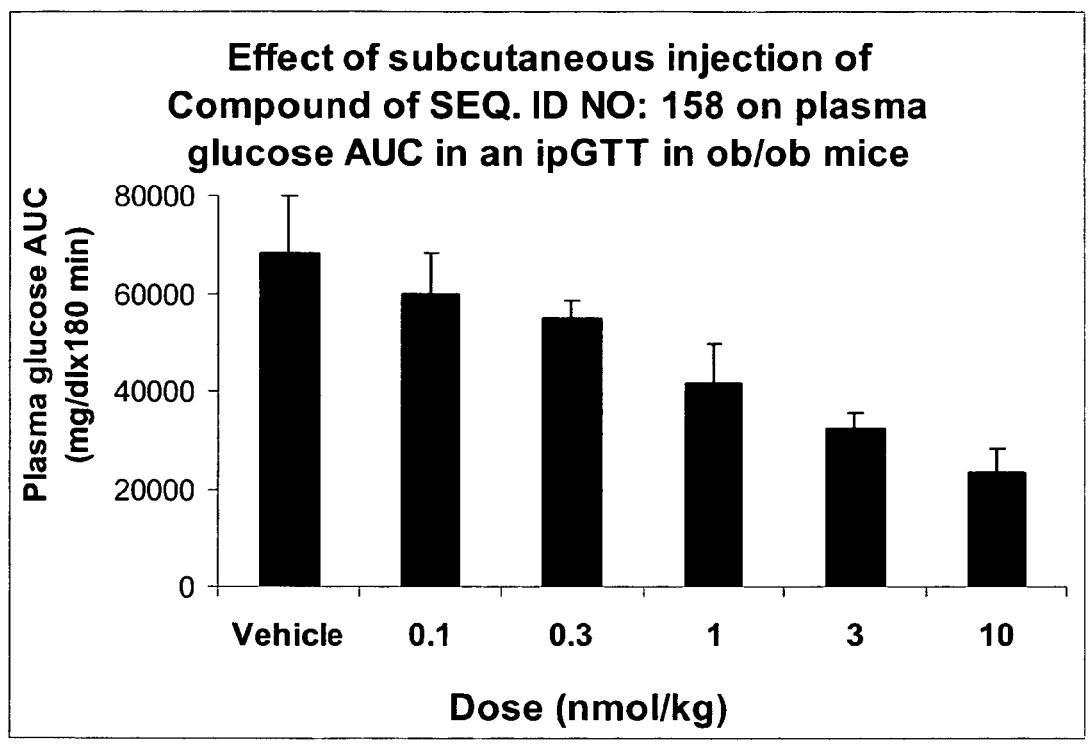
FIG. 8 illustrates the effects of subcutaneous injection of the compound of SEQ ID NO: 158 on plasma glucose in an ipGTT in ob/ob mice.
Figure 9:
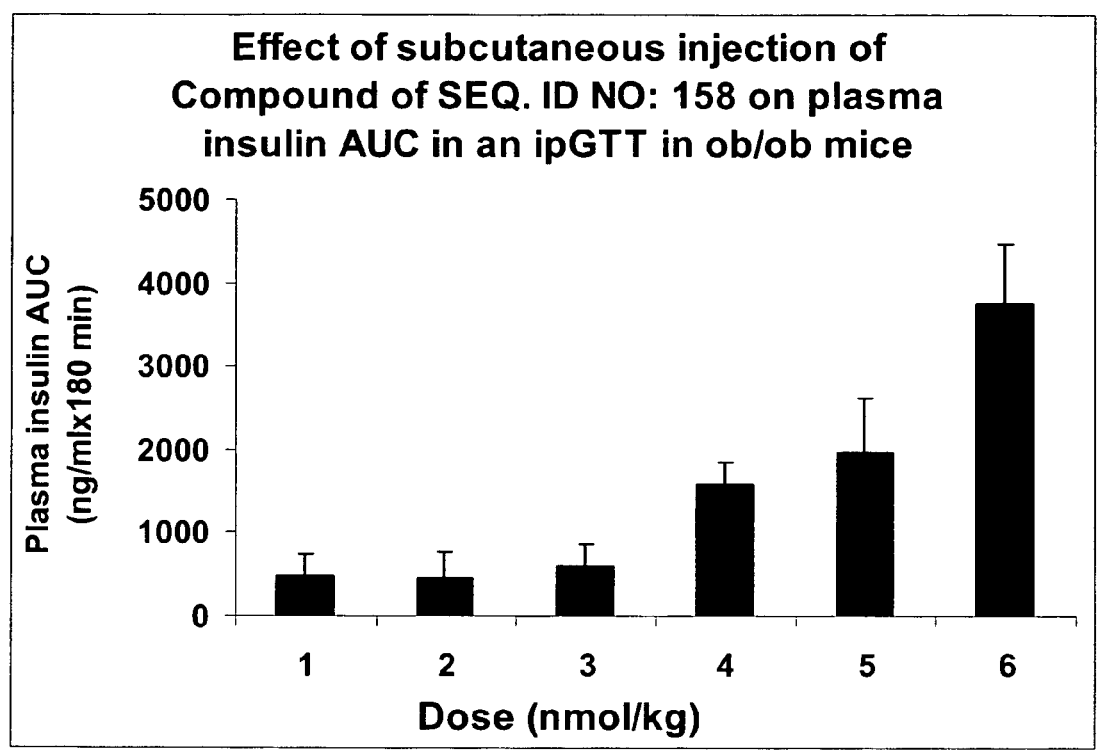
FIG. 9 illustrates the effects of subcutaneous injection of the compound of SEQ ID NO: 158 on plasma insulin in an ipGTT in ob/ob mice.
Figure 10:
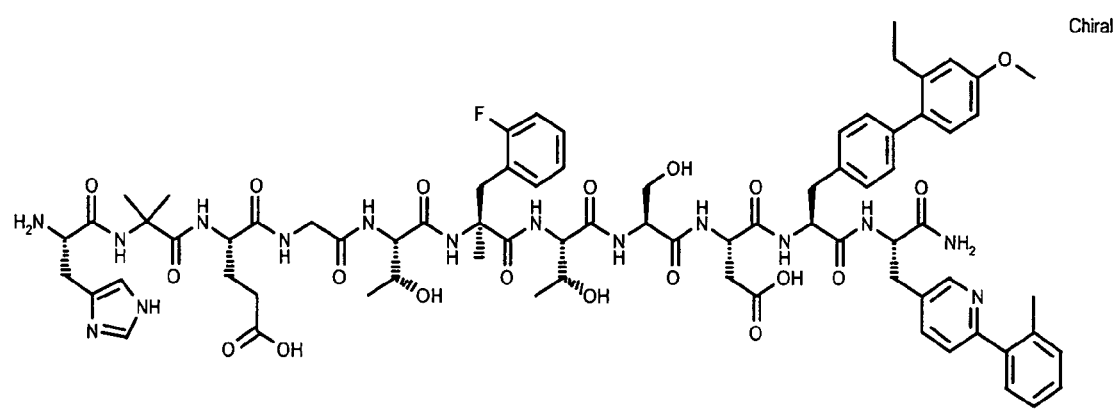
FIG. 10 illustrates the structure of the 11-mer GLP-1 receptor modulator the compound of SEQ ID NO: 9.

The effect of the compound of SEQ ID NO: 118 on postprandial glucose was dose-dependent between 1-30 nmol/kg and plasma glucose AUC decreased 81% at 30 nmol/kg dose (FIG. 5). The ED50 for the compound of SEQ ID NO: 118 was determined to be 2.5 nmoles/kg.

Example 30

Dog Pharmacokinetic Study

The pharmacokinetic parameters of the compound of SEQ ID NO:9 were determined in male beagle dogs (n=4, 14±1 kg). Following an overnight fast, each animal received the compound of SEQ ID NO:9 either as an intravenous bolus via femoral vein (67 µg/kg) or by subcutaneous injection given at near the shoulder blades (67 µg/kg). Each animal received both intravenous and subcutaneous doses with a one-week washout between doses following a crossover design. The dosing vehicle for both routes of administration was propylene glycol:phosphate buffer (50:50). Serial blood samples were collected in EDTA-containing microcentrifuge tubes at predose, 0.083, 0.25, 0.5, 0.75, 1, 2, 4, 6, 8, 24, and 30 hours post-dose after intravenous administration; at predose, 0.25, 0.5, 0.75, 1, 2, 4, 6, 8, 24, and 30 hours post-dose after subcutaneous administration. Approximately 0.3 mL of blood was collected at each time point. Blood samples were immediately centrifuged at 4° C. The obtained plasma was frozen with dry ice and stored at −20° C. Plasma drug levels were determined using the LC-MS/MS assay described above.

A. Quantitation of the Compound of SEQ ID NO:9 by LC-MS/MS

Plasma samples from in vivo dog study were prepared for analysis by precipitating plasma proteins with two volumes of acetonitrile containing an internal standard. The samples were vortex mixed and removed the precipitated proteins by centrifugation. The resulting supernatants were transferred to a 96-well plate and 10 µL were injected for analysis. Samples were prepared with the Packard Multiprobe II and Quadra 96 Liquid Handling System.

The HPLC system consisted of two Shimadzu LC10AD pumps (Columbia, Md.), a CTC PAL autosampler (Leap Technologies, Switzerland). The column used was a YMC Hydrosphere C18 (2.0×50 mm, 3 µm) (YMC, Inc., Milford, Ma.). The column temperature was maintained at 50° C. and the flow rate was 0.3 mL/minute. The mobile phase A consisted of 10 mM ammonium formate and 0.1% formic acid in water and mobile phase B consisted of 0.1% formic acid in acetonitrile. The initial mobile phase composition was 5% B, and remained at 5% B for one minute to equilibrate the column. The composition was ramped to 95% B over two minutes and held there for one additional minute. The mobile phase was then returned to initial conditions in one minute. Total analysis time was five minutes. A switching valve was used. The eluents between 0-1 minute were diverted to the waste.

The HPLC was interfaced to a Sciex API 4000 mass spectrometer, (Applied Biosystems, Foster City, Calif.) and was equipped with a TurboIonspray ionization source. Ultra high purity nitrogen was used as the nebulizing and turbo gas. The temperature of turbo gas was set at 300° C. and the interface heater was set at 60° C. Data acquisition utilized selected reaction monitoring (SRM). Ions representing the $(M+2H)^{2+}$ species for the compound of SEQ ID NO:9, and $(M+2H)^{2+}$ for BMS-501143 (IS) were selected in Q1 and were collisionally dissociated with high purity nitrogen at a pressure of $3.5\times10^{-}$ storr to form specific product ions which were subsequently monitored by Q3. The transitions and voltages are summarized in Table 4.

TABLE 4

Parameters for MS/MS Analysis of the Compound of SEQ ID NO:9 and Internal Standard

|  | Compound of SEQ ID NO:9 | Internal Standard |
|---|---|---|
| SRM transition (mz) | 765.1 -> 195.2 | 740.7 -> 210.0 |
| Declustering Potential (V) | 60 | 60 |
| Collision Energy (V) | 45 | 30 |

The standard curve concentrations, ranging from 1 to 1000 nM and from 4 to 5000 nM, were used for the in vivo samples obtained from low and high doses, respectively. The curves were fitted with a quadratic regression weighted by reciprocal concentration ($1/x^2$). Standards were analyzed in duplicate. Quality control (QC) samples, prepared in blank matrix at the same concentrations as the standard were also analyzed in each analytical set. For the compound of SEQ ID NO:9, the calculated concentrations of more than 80% of the QCs were within 20% of nominal concentration, indicating acceptable assay performance.

B. Data Analysis

The compound of SEQ ID NO:9 plasma concentration vs. time data were analyzed by noncompartmental methods using the KINETICA™ software program. The Cmax and Tmax values were recorded directly from experimental observations. The AUC0-n and AUCtot values were calculated using a combination of linear and log trapezoidal summations. The total plasma clearance ($CL_P$), terminal half life ($t_{1/2}$), mean residence time (MRT), and the steady state volume of distribution (Vss) were calculated after intra-arterial or intravenous administration. The total blood clearance ($CL_B$) was calculated using the total plasma clearance and the blood to plasma concentration ratio. $CL_B$ and Vss values were compared to standard liver blood flow and total body water values, respectively, reported in the literature. The absolute subcutaneous bioavailability (expressed as %) was estimated by taking the ratio of dose-normalized AUC values after a subcutaneous dose of the compound of SEQ ID NO:9 to that after an intravenous dose.

C. Dog Pharmacokinetics Results

The pharmacokinetic parameters of the Compound of SEQ ID NO:9 in male beagle dogs, following intravenous (IV) and subcutaneous (SC) administration are summarized in Tables 5 and 6A-6C.

The compound of SEQ ID NO:9 exhibited low systemic clearance (0.9±0.2 mL/min/kg; 3.2% of liver blood flow, 31 mL/min/kg). The steady-state volume of distribution (Vss) was 0.10±0.03 L/kg (2 times of vascular fluid, 0.05 L/kg; 71% of extracellular fluid, 0.14 L/kg), indicating limited extravascular distribution. The estimated elimination half-life was 5.1±0.5 h and the mean residence time was 3.0±1.0 h. The time to reach peak concentrations (Tmax) after a subcutaneous dose of 67 µg/kg occurred at 5.0±1.0 h. The maximum plasma concentration (Cmax) after subcutaneous administration was 90±29 nM. The subcutaneous bioavailability of the compound of SEQ ID NO:9 in dogs was 93±22%.

TABLE 5

Pharmacokinetic Parameters of the Compound of SEQ ID NO:9 in the Dog

| Parameter | Intravenous (n = 3, Mean ± SD) | Subcutaneous (n = 3, Mean ± SD) |
|---|---|---|
| Dose (μg/kg) | 67 | 67 |
| Cmax (nM) | — | 90 ± 29 |
| Tmax (h) | — | 5.0 ± 1.0 |
| AUCtot (nM × h) | 1266 ± 299 | 1223 ± 276 |
| $CL_p$ (mL/min/kg) | 0.6 ± 0.1 | — |
| $CL_B$ (mL/min/kg) | 0.9 ± 0.2 | — |
| $V_{SS}$ (L/kg) | 0.10 ± 0.03 | — |
| $t_{1/2}$ (h) | 5.1 ± 0.5 | 6.9 ± 1.3 |
| MRT (h) | 3.0 ± 1.0 | 12.5 ± 2.4 |
| Bioavailability (%) | — | 93 ± 22 |

TABLE 6A

Pharmacokinetic Parameters of the Compound of SEQ ID NO: 9 in the Dog (Dosing Vehicle: 0.2 M Tris, pH 8.0)

| Parameter | Intravenous (n = 3) | Subcutaneous (n = 3, Mean ± SD) |
|---|---|---|
| Dose (μg/kg) | 67 | 67 |
| Cmax (nM) | — | 116 ± 34 |
| Tmax (h) | — | 1.1 ± 0.6 |
| AUCtot (nM × h) | 529 ± 125 | 452 ± 153 |
| CLp (mL/min/kg) | 1.4 ± 0.4 | — |
| $V_{SS}$ (L/kg) | 0.21 ± 0.07 | — |
| $t_{1/2}$ (h) | 7.1 ± 2.1 | 2.6 ± 1.2 |
| MRT (h) | 2.4 ± 0.5 | 3.6 ± 1.0 |
| Bioavailability (%) | — | 93 ± 22 |

TABLE 6B

Pharmacokinetic Parameters of the Compound of SEQ ID NO: 151 in the Dog

| Parameter | Intravenous (n = 3, Mean ± SD) | Subcutaneous (n = 3, Mean ± SD) |
|---|---|---|
| Dose (μg/kg) | 67 | 67 |
| Cmax (nM) | — | 252 ± 15 |
| Tmax (h) | — | 1.8 ± 0.5 |
| AUCtot (nM × h) | 1519 ± 424 | 1566 ± 235 |
| CLp (mL/min/kg) | 0.49 ± 0.16 | — |
| $V_{SS}$ (L/kg) | 0.13 ± 0.05 | — |
| $t_{1/2}$ (h) | 4.0 ± 0.2 | 4.4 ± 1.4 |
| MRT (h) | 4.4 ± 0.1 | 5.8 ± 1.0 |
| Bioavailability (%) | — | 110 ± 41 |

TABLE 6C

Pharmacokinetic Parameters of the Compound of SEQ ID NO: 158 in the Dog

| Parameter | Intravenous (n = 3, Mean ± SD) | Subcutaneous (n = 3, Mean ± SD) |
|---|---|---|
| Dose (μg/kg) | 67 | 67 |
| Cmax (nM) | — | 279 ± 82 |
| Tmax (h) | — | 1.4 ± 0.7 |
| AUCtot (nM × h) | 1385 ± 227 | 1467 ± 563 |
| CLp (mL/min/kg) | 0.51 ± 0.08 | — |
| $V_{SS}$ (L/kg) | 0.15 ± 0.018 | — |
| $t_{1/2}$ (h) | 4.4 ± 0.4 | 3.9 ± 1.3 |
| MRT (h) | 4.9 ± 0.7 | 5.2 ± 1.5 |
| Bioavailability (%) | — | 110 ± 49 |

Example 31

Determining the Solubility of the Zn/Compound of SEQ ID NO:9 Adduct

Studies were performed in order to determine the solubility of the compound of SEQ ID NO:9 in the presence of the metal ion zinc acetate.

Preparation of the Zn/Compound of SEQ ID NO:9 adduct was as follows:

The compound of SEQ ID NO:9 was synthesized by and Zinc acetate and ethylenediaminetetr$_{aa}$cetic acid (EDTA) were purchased from Sigma-Aldrich (St. Louis, Mo.). HPLC grade solvents was purchased from EMD Chemicals (Bibbsons Town, N.J.).

The concentration of the compound of SEQ ID NO:9 was analyzed by a Waters HPLC system (Waters 2690 Separations Module and Waters 996 Photodiode Array Detector). A gradient method was used where solvent A is 0.05% trifluoroacetic acid (TFA, Sigma) in water, and solvent B is 0.05% TFA in acetone nitrile (ACN, Sigma). Light at a wavelength of 220 nm was used to detect the absorption of the compound of SEQ ID NO:9.

The compound of SEQ ID NO:9 and zinc acetate were dissolved separately in ethanol at concentrations of ~30 mg/ml. The two solutions were mixed at predetermined Zn:Compound of SEQ ID NO:9 molar ratio, and a white precipitation of Zn/Compound of SEQ ID NO:9 adduct was formed. The solids were isolated for different purposes so two methods were used. Method 1 was used to produce multiple, small batches of Zn/Compound of SEQ ID NO:9 adduct for characterization. With this method, the Zn/Compound of SEQ ID NO:9 methanol suspension was poured into large volume of Millipore water stirred for 2 hours before the final suspension was filtered and washed by large amount of $H_2O$. The obtained solid Zn/Compound of SEQ ID NO:9 adduct was vacuum dried at room temperature for 48 hours. Method 2 was used to produce a Zn/Compound of SEQ ID NO:9 adduct with controlled particle size for dog pharmacokinetics study. In this method, the ethanol suspension of the Zn/Compound of SEQ ID NO:9 adduct was spray dried by a Buchi B-191 mini spray dryer (Brinkmann Instruments, Westbury, N.Y.) to generate solid particles. Spray drying parameters were as follows: inlet temperature was 60° C., solution pumping rate was 3 ml/min, $N_2$ flow rate was 500Nl/hour, aspirator was set at 100%. The outlet temperature was maintained around 35° C.

Once the Zn/Compound of SEQ ID NO:9 adduct was formed, formulation development studies were conducted in order to evaluate the solubility of the compound of SEQ ID NO:9 in the presence of Zn(II). An excess amount of the compound of SEQ ID NO:9 was suspended in pH 6.8, 50 mM phosphate buffer. The suspension was then placed on an orbital shaker (Model, 100 RPM) at ambient temperature for 12 hours. The suspension was then centrifuged (Model, speed) and the saturated the clear supernatant of the compound of SEQ ID NO:9 was collected into 10 ml centrifuge tubes. A predetermined amount of zinc acetate solution (50 mM, pH 6.8 phosphate buffer) was added into the saturated solution and then precipitated. The concentration of the compound of SEQ ID NO:9 in solution was obtained by centrifuging the suspension and analyzing the clear supernatants by HPLC. A plot of the compound of SEQ ID NO:9 concentration versus molar ratio of Zn:Compound of SEQ ID NO:9 is shown in FIG. 11A.

To confirm that the Zn/Compound of SEQ ID NO:9 binding is reversible, the Zn/Compound of SEQ ID NO:9 adduct was suspended in pH 6.8, 50 mM phosphate buffer. A strong chelating agent for Zn(II), EDTA, was added into the suspension in excess amount. The Zn/Compound of SEQ ID NO:9 suspension with and without EDTA was centrifuged and the supernatants were injected into HPLC. The HPLC chromatographs are shown in FIG. 11B. As shown in FIG. 11A, with addition of Zn (II) into the compound of SEQ ID NO:9 saturated solution (concentration=17 μg/ml, pH 6.8, 50 mM phosphate buffer), the apparent solubility of the compound of SEQ ID NO:9 continued to decrease until below the detection limit of HPLC.

Figure 11:
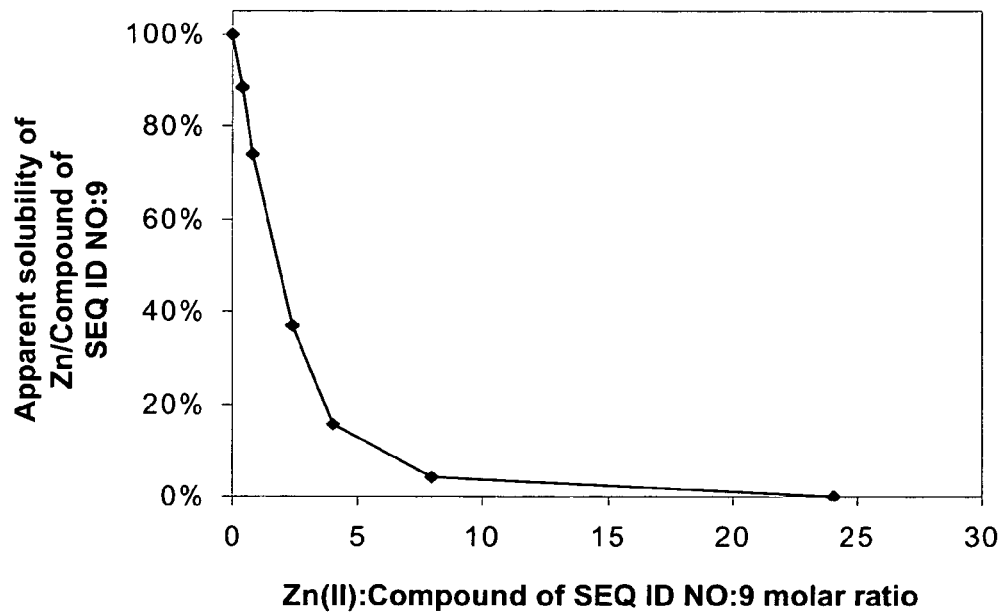
FIG. 11A illustrates the solubility of a GLP-1 receptor modulator in the presence of Zn(II).
FIG. 11B illustrates several HPLC chromatographs (from bottom to top): 1) Zn/GLP-1 receptor modulator saturated solution; 2) Free GLP-1 receptor modulator standard solution (4.3 µg/ml); 3) EDTA slurred together with Zn/GLP-1 and centrifuged; Supernatant analyzed by HPLC. The GLP-1 receptor modulator concentration in the supernatant reached the saturated value of 18 µg/ml. (Buffer used: pH 6.8, 50 mM phosphate buffer, 25° C.).
Figure 11:
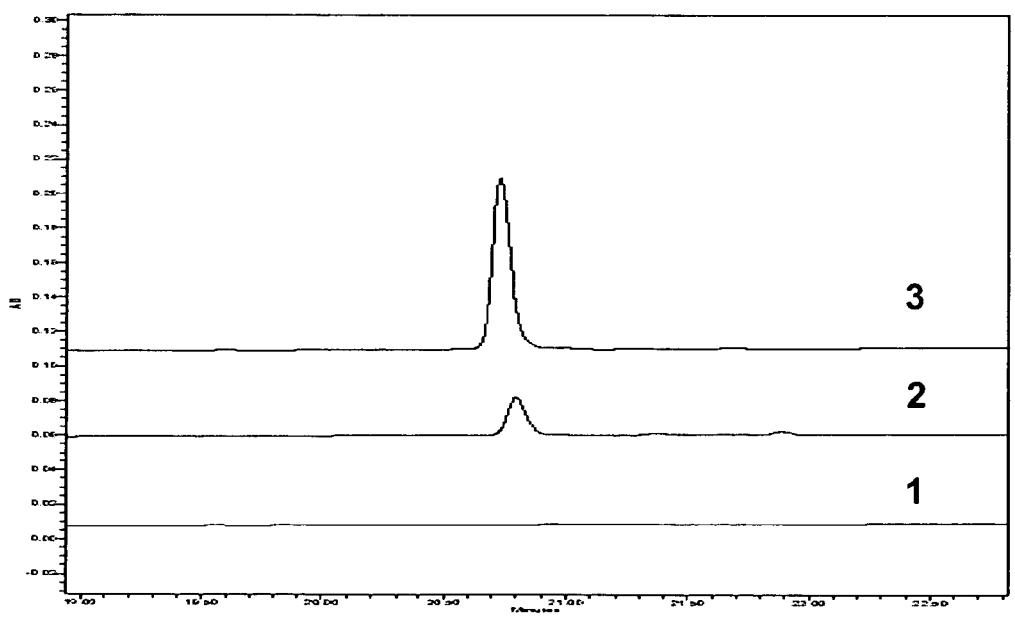

The solid Zn/Compound of SEQ ID NO:9 adduct had a solubility below the level of detection at pH 6.8, as shown in FIG. 11B-1. However, after an excess amount of EDTA (chelates strongly with metal ions) was added into the Zn/Compound of SEQ ID NO:9 suspension, free compound of SEQ ID NO:9 was released and its solution concentration reached saturation. This result demonstrated that the binding between Zn (II) and the compound of SEQ ID NO:9 is reversible, which is a prerequisite for the Zn/Compound of SEQ ID NO:9 adduct to be useful in extended release application.

Example 32

Physical Characterization of Zn/Compound of SEQ ID NO:9 Adduct

A. Atomic Absorption Analysis of Zinc Content

Approximately 20 mg of Zn/compound of SEQ ID NO:9 adduct was weighed, dissolved and diluted to 10 ml in DMSO. The sample was assayed using a Perkin-Elmer Optima 4300 ICP-AES instrument, with calibration standards of 1 ppm Zn and 5 ppm Zn. The standards were also prepared in DMSO. Results from two Zn wavelengths, 206.200 nm and 213.857 nm, were averaged as the final Zn content value.

B. Modulated Differential Scanning Calorimetry (MDSC)

The glass transition temperature ($T_g$) of the compound of SEQ ID NO:9 and Zn/Compound of SEQ ID NO:9 adduct was determined by a TA DSC Q1000 Differential Scanning Calorimeter. Approximately 3 mg of sample was placed into an Alumina pan (open) and all samples were heated from 0-250° C. The ramp rate is 2° C./minute, and modulate 0.32° C. every 60 seconds.

C. Scanning Electron Microscope (SEM)

A scanning electron microscope (Philips XL 30ESEM, FEI Philips, Hillsboro, Oreg.) was used to study the morphology of the spray dried Zn/Compound of SEQ ID NO:9 powder. Spray dried powder was mounted on the aluminum stubs by double-sided tape and sputter coated with Pd (Pelco SC-7 Auto Sputter Coater). The SEM analysis was carried out at an accelerating voltage of 15-20 kV.

D. Particle Size Distribution by Light Scattering

Spray dried Zn/Compound of SEQ ID NO:9 particles were suspended in water, slightly sonicated, and the particle size distribution was analyzed by a Horiba LA-910 laser scattering particle size distribution analyzer.

Figure 12:
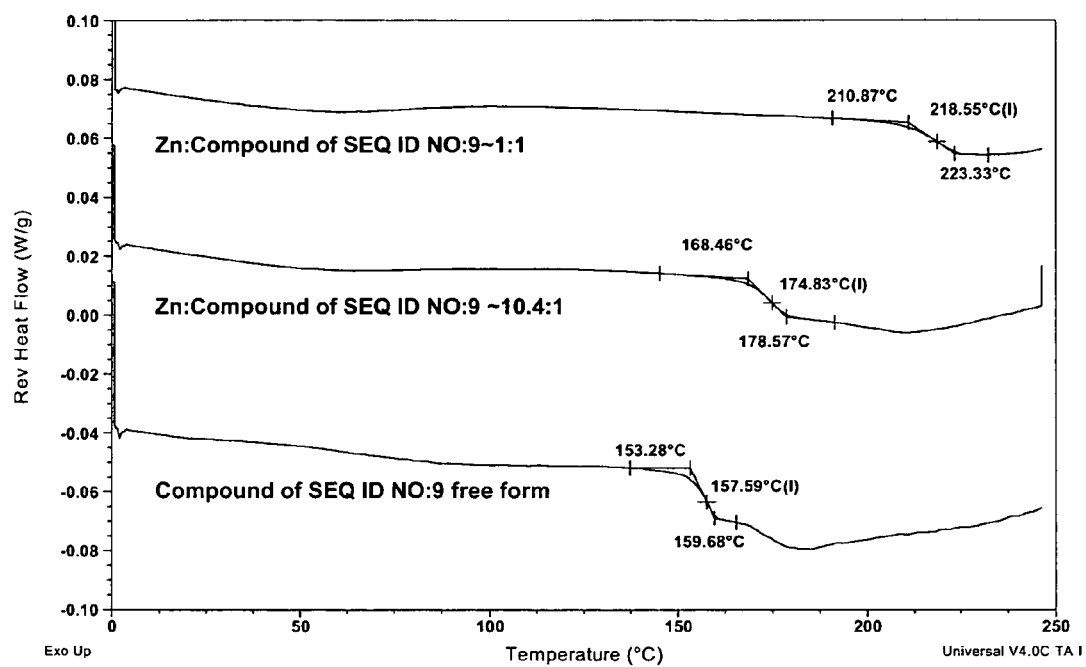
FIG. 12 illustrates the modulated temperature differential scanning calorimetry (DSC) results of Zn/Compound of SEQ ID NO:9 adducts with different Zn:GLP-1 receptor modulator molar ratio (revising signals only).

As shown in FIG. 12, with the increase of Zn in the Zn/Compound of SEQ ID NO:9 adduct, its glass transition temperature ($T_g$) increases. Free compound of SEQ ID NO:9 has a $T_g$ of 158° C., while the adducts with 0.4:1 and 1:1 Zn:Compound of SEQ ID NO:9 ratio have elevated single $T_g$ of 175° C. and 219° C., respectively. No $T_g$ of free Compound of SEQ ID NO:9 was detected in the adducts, which indicated that these adducts were not merely physical mixtures of Zn salt and free compound of SEQ ID NO:9, but rather molecular level new forms. Since higher $T_g$ is a result of lower molecular mobility, Zn (II) in the adducts acts to "bind" the compound of SEQ ID NO:9 molecule tighter than when they exist as the free form. This is also consistent with the lower solubility of Zn/Compound of SEQ ID NO:9 adducts compared with free compound of SEQ ID NO:9.

Example 33

Morphology and Particle Size of Spray Dried Zn/Compound of SEQ ID NO:9 Adduct

Figure 13:
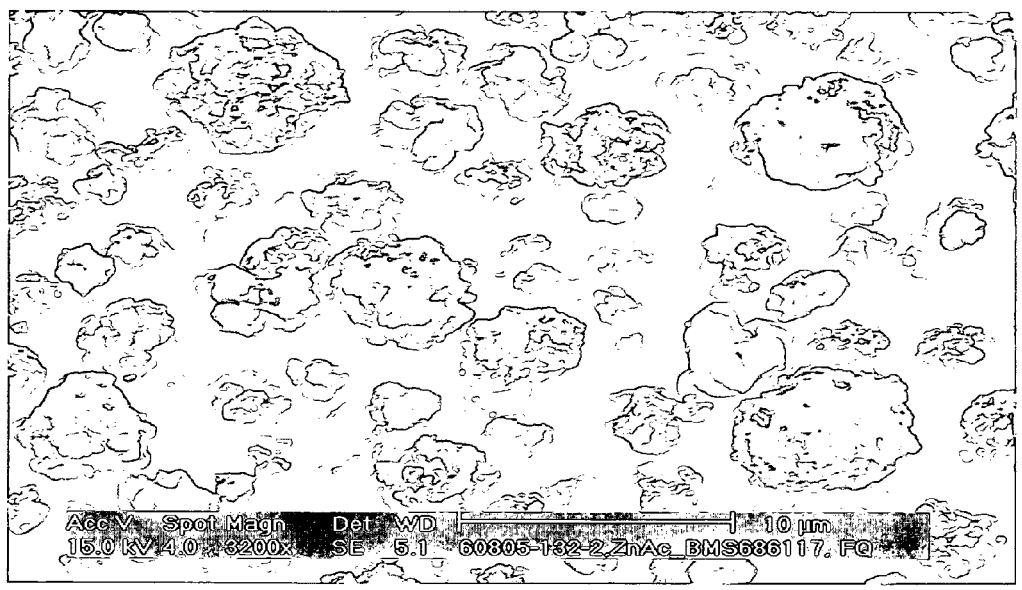
FIG. 13A illustrates an SEM picture of a spray dried Zn/GLP-1 receptor modulator adduct.
FIG. 13B illustrates the particle size distribution of a spray dried Zn/GLP-1 receptor modulator adduct.
Figure 13:
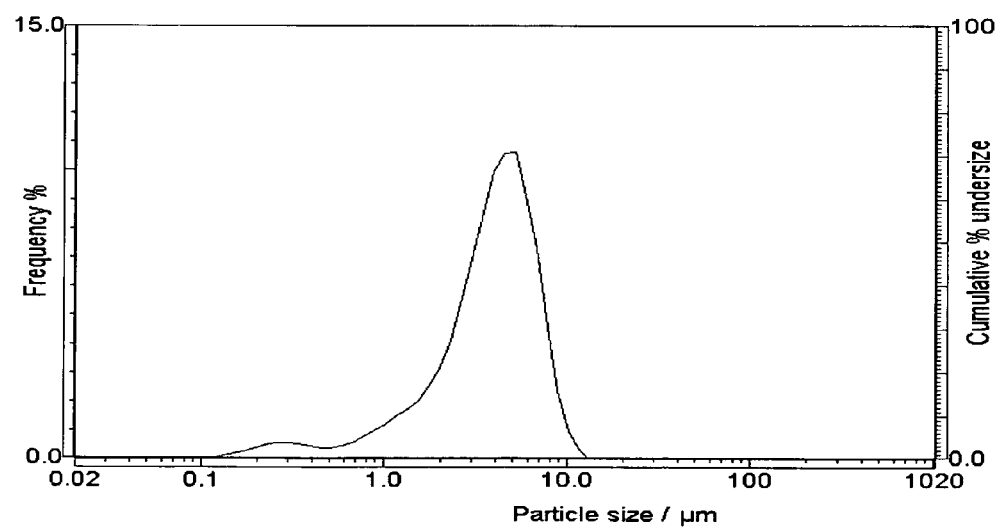
Figure 14:
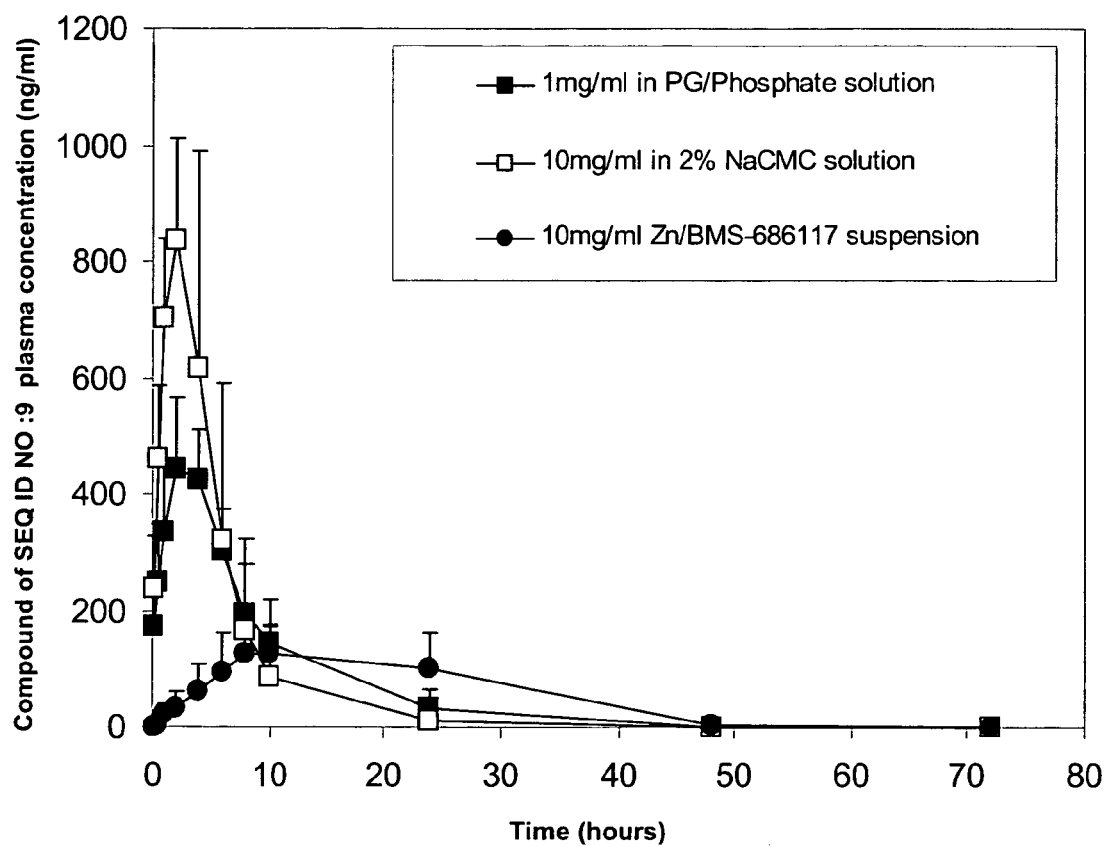
FIG. 14 illustrates the GLP-1 receptor modulator pharmacokinetic profiles following subcutaneous administration of different formulations. Doses are 0.1 mg/kg for PG/phosphate solution and 0.5 mg/kg for all the other formulations. The PK profile of PG/phosphate solution was normalized linearly to 0.5 mg/kg for comparison. (n=4 for all formulations)

Spray dried Zn/Compound of SEQ ID NO:9 adduct from ethanol suspension are spherical particles composed of finer powders (FIG. 13A). Adduct particles under SEM range from ~1-10 μm, which is consistent with the particle size distribution showed by laser scattering (FIG. 13B). Compared with the solution precipitation method (Method 1 in Example 38), spray drying generates Zn/Compound of SEQ ID NO:9 adduct with controlled particle size and relatively narrow particle size distribution, which is essential for injectable suspension formulation. Targeting a self-administered product, the small particle size of the spray dried Zn/Compound of SEQ ID NO:9 adduct also allows the suspension to be easily injected through a fine syringe needle (27 gauge or smaller) for better patient compliance. Spray drying also offered more flexibility in controlling the Zn:Compound of SEQ ID NO:9 molar ratio. As verified by elemental analysis, the maximal Zn:Compound of SEQ ID NO:9 ratio is about 1.5:1 in the precipitated adducts made by Method 1, regardless of how much Zn is in excess during the manufacturing. The unbound Zn is soluble in water and would be simply removed during the stirring, centrifuge, and wash steps. While there is no loss of Zn during a spray drying process, the excess amount of Zn can be only physically mixed with the Zn/Compound of SEQ ID NO:9 adduct. Although the unbound Zn should not decrease the molar mobility of the compound of SEQ ID NO:9, presumably more Zn in the environment could push the dissociation equilibrium of Zn/Compound of SEQ ID NO:9 to the opposite course, thereby further extending the release of free compound of SEQ ID NO:9. The spray dried Zn/Compound of SEQ ID NO:9 particles used for dog PK study in this work (FIG. 14) has excess amount of Zn, with Zn:Compound of SEQ ID NO:9 molar ratio at 2.8:1. Compared with an earlier dog PK study with Zn/Compound of SEQ ID NO:9 adduct made by Method 1 and a Zn:Compound of SEQ ID NO:9 molar ration of 1.5:1 (data not shown), the spray dried adduct showed more protracted absorption and significantly less variation.

Example 34

Dog Pharmacokinetic Profile Following Subcutaneous Injection of Zn/Compound of SEQ ID NO:9 Adduct A. Animal Experiments Pharmacokinetics of the sustained release formulations of SEQ ID NO: 9, were evaluated in purebred, male, beagle dogs. Each dog weighed approximately 8 to 12 kg. Individual doses were calculated based on body weight recorded on the day of dose administration. A subcutaneous dose was administered via syringe and needle in the dorsal thoracic region. Blood (approximately 2 to 3 mL) was collected from each animal, pre-dose and at 0.25, 0.5, 1, 2, 4, 6, 8, 24, 48, 72, and 168 hours post-dose. Blood was collected via the jugular vein into tubes containing sodium heparin anticoagulant. The blood samples were analyzed by LC/MS for concentration of the compound of SEQ ID NO: 9.

Dog pharmacokinetic results of spray dried Zn/Compound of SEQ ID NO:9 in dogs following subcutaneous injection showed a much longer Mean Residence Time (MRT) of 16 hours compared with 4-6 hours with other solution formulations with high viscosity or in situ precipitation property. The $t_{1/2}$ was prolonged to 9 hours compared with 2-4 hours of the other formulations. The relative bioavailability of Zn adduct to the compound of SEQ ID NO:9 solution formulation in PG/phosphate reached about 90%, indicating excellent exposure of the suspension formulation.

Example 35

Protamine Formulation for Sustained Release of the Compound of SEQ ED NO:9

Protamine forms a less soluble adduct with the compound of SEQ ID NO:9 thereby extending the release of the compound of SEQ ID NO:9 following subcutaneous injection. In a recent dog study, the compound of SEQ ID NO:9 that was suspended in protamine solution showed significantly protracted PK profile compared with a control formulation with "semi-crystalline" compound of SEQ ID NO:9 only. Two different methods were used to prepare the protamine formulation.

A. Pre-formed Protamine/Compound of SEQ ID NO:9 Adduct, Suspended in an Injectable Medium First, a pre-formed protamine/Compound of SEQ ID NO:9 adduct was formed as follows:

The compound of SEQ ID NO:9 was dissolved in pH 8.0, 0.1M Tris buffer at 20 mg/ml. Protamine sulfate was dissolved in the same buffer at 20 mg/ml. The protamine solution was then added into the Compound of SEQ ID NO:9 solution and a white precipitation was formed. The suspension was then centrifuged, washed with excess amount of water and vacuum dried. Instead of using Tris buffer in the above preparation, an alcohol/water (such as MeOH/H$_2$O) system can be used to make the same protamine/Compound of SEQ ID NO:9 adduct.

An analysis of the properties of the protamine/Compound of SEQ ID NO:9 adduct demonstrated that the apparent solubility of pre-formed protamine/Compound of SEQ ID NO:9 in pH 6.8 is about 10% of free Compound of SEQ ID NO:9 (both protamine/Compound of SEQ ID NO:9 and free Compound of SEQ ID NO:9 were suspended in pH 6.8, 50 mM PB buffer, and stirred for 1 hour). Modulated Differential Scanning Calorimetry (DSC) also demonstrated that the protamine/Compound of SEQ ID NO:9 adduct has a higher glass transition temperature (163° C.) than the free form (157° C.). Further, polarized optical microscopy (POM) and PXRD showed that the protamine/Compound of SEQ ID NO:9 was amorphous. The analysis also demonstrated that the solubility of protamine/Compound of SEQ ID NO:9 adduct in MeOH is less than 1 mg/ml, while that of free Compound of SEQ ID NO:9 is greater than 50mg/ml and, upon suspending in aqueous suspending medium, the protamine/Compound of SEQ ID NO:9 adduct tends to form aggregates, and stick on the glass wall. Thus, the administration of the protamine/Compound of SEQ ID NO:9 adduct may need a suitable suspending agent; or it maybe injected as dry powder.

B. Compound of SEQ ID NO:9 Suspended in Protamine Solution

The solubility of the compound of SEQ ID NO:9 in pH 6.8, 50 mM PB buffer decreases with increase of protamine in the solution. Therefore, suspension of the compound of SEQ ID NO:9 in the presence of protamine could still provide extended release effect without using pre-formed protamine/SEQ ID NO:9 adduct.

Figure 15:
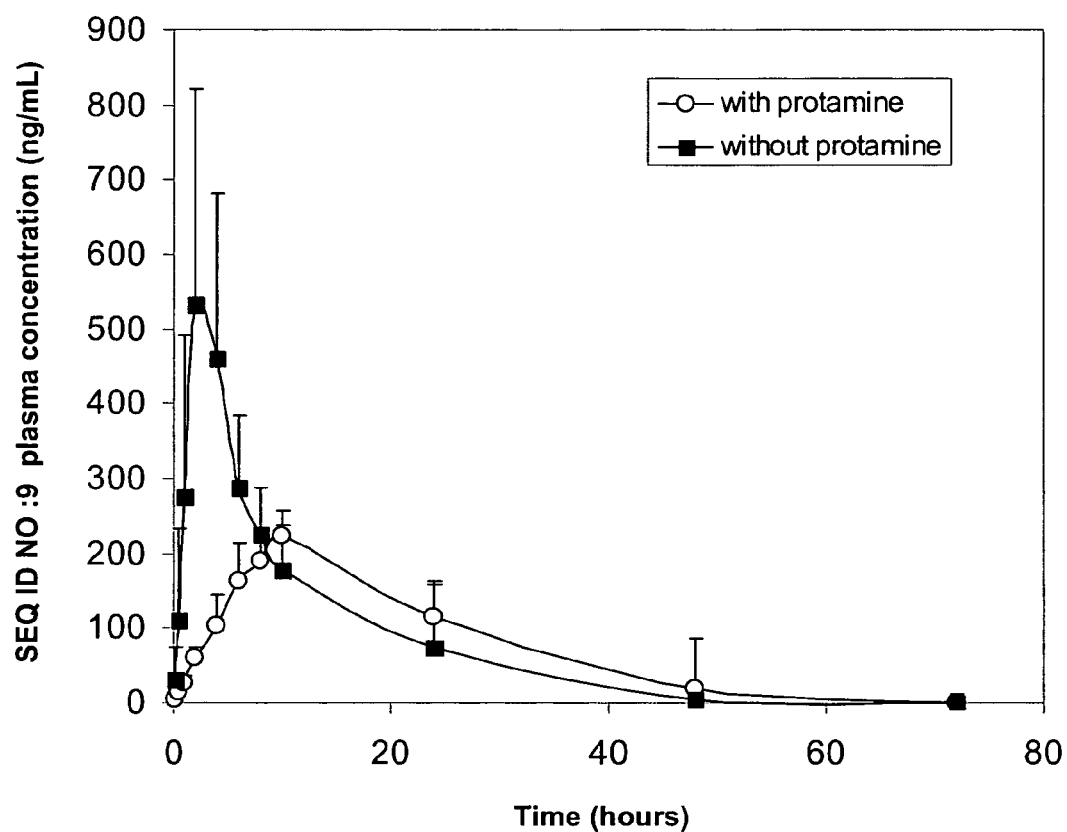
FIG. 15 represents dog pharmacokinetic profiles after subcutaneous injection of a "semi-crystalline" suspension of the compound of SEQ ID NO:9 (10 mg/ml) in 0.2% methylcellulose with (○) or without (■) 5mg/ml protamine present. The existence of protamine prolonged the $T_{max}$ and decreased the $C_{max}$.

There are two approaches that can be used to make the compound of SEQ ID NO:9 protamine suspension:

The compound of SEQ ID NO:9 ("semi-crystalline") or Zn/Compound of SEQ ID NO:9 was suspended in a protamine solution. Pure amorphous compound of SEQ ID NO:9 is difficult to suspend due to gelling of the drug in aqueous medium, while "semi-crystalline" compound of SEQ ID NO:9 or Zn/Compound of SEQ ID NO:9 adduct can form a milk, homogenous, and stable (up to 5 days) suspension. A "semi-crystalline" compound of SEQ ID NO:9 suspension in protamine solution was dosed in dogs and demonstrated extended release profile (FIG. 15).

C. Formulation Preparation

Figure 16:
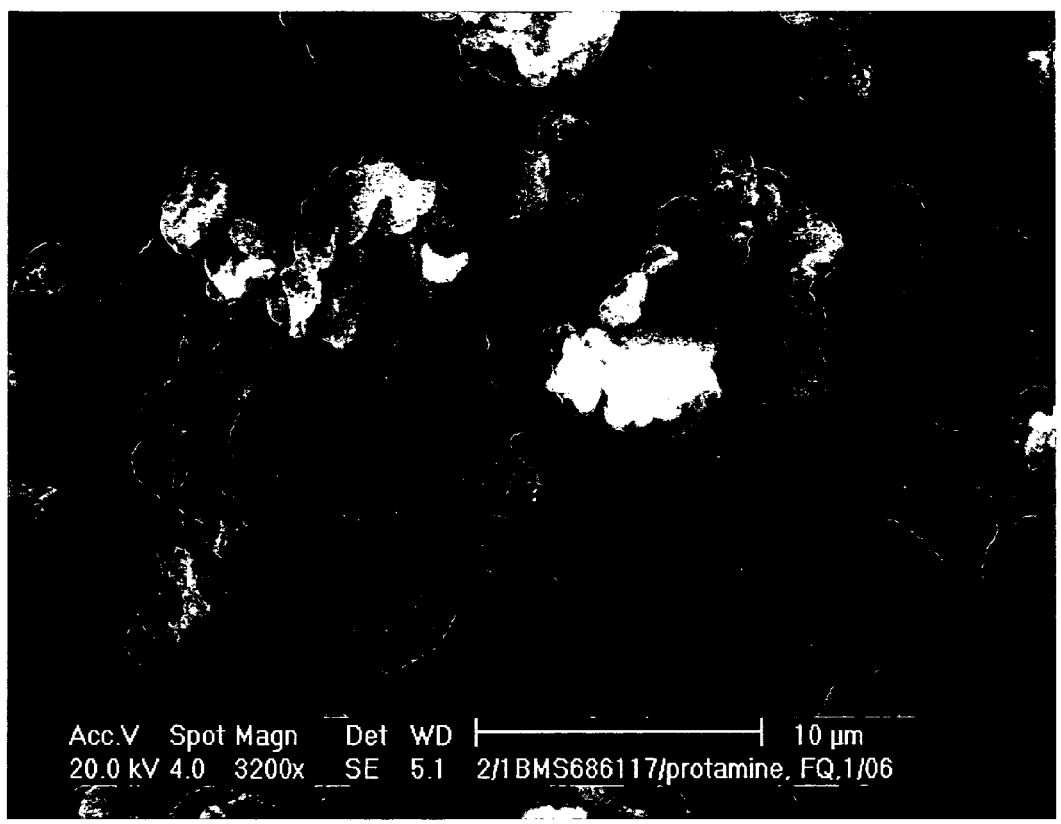
FIG. 16 represents the spray-dried protamine/Compound of SEQ ID NO:9 particles.
Figure 17:
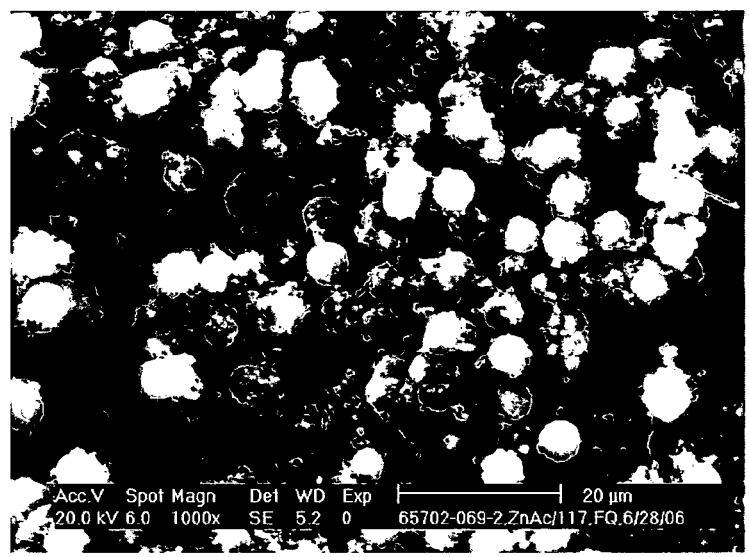
FIG. 17 provides SEM images of A: lyophilized Zn/compound of SEQ ID NO: 9 (Zn: compound of SEQ ID NO: 9=3:1), without mannitol; and B: lyophilized Zn/compound of SEQ ID NO: 9 (Zn: compound of SEQ ID NO: 9=3:1), with 2.5% w/v mannitol.
Figure 17:
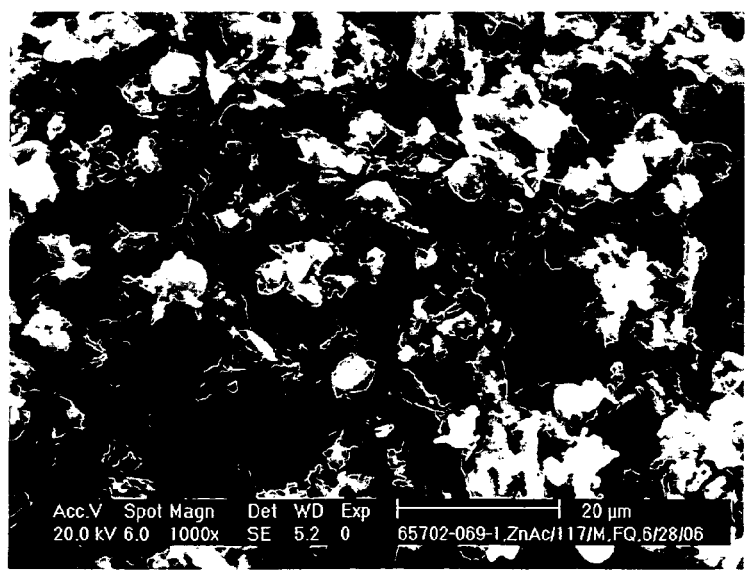

The compound of SEQ ID NO:9 and protamine were co-processed by spray dry or lyophilization to obtain a physical mixture of the two, then suspend the powder. The co-spray dried compound of SEQ ID NO:9/protamine solution (FIG. 16) can form relatively homogenous suspension but aggregates formed in the suspension after 5-day storage.

Example 36

Synthesis of Zn/Compound of SEQ ID NO: 9 by Lyophilization

The sustained GLP-1 formulations may also be made by lyophilization. To do so, first make bulk solutions of the compound of SEQ ID NO: 9, and zinc acetate in TBA/H$_2$O (50/50 v/v), respectively. Mix the two solutions to obtain a clear solution wherein the compound of SEQ ID NO: 9 concentration is 12 mg/ml, and the molar ratio of Zn: compound of SEQ ID NO: 9 is 3:1. In some instances, mannitol was added into the solution as a bulk agent. The concentration of mannitol used was 2.5% w/v. The solution was then filled in vials and subject to a lyophilization cycle in a Virtis Genesis lyophilizer. The lyophilization cycle was as follows:

The solution was frozen to −50° C. and the temperature was maintained for 6 hours followed by: primary drying: −20° C. for 36 hours at 200 mTorr; secondary drying: 0° C. for 12 hours at 200 mTorr; and then followed by 10° C. for 12 hours at 200 mTorr. FIG. 19 provides SEM images of A: lyophilized Zn/compound of SEQ ID NO: 9 (Zn: compound of SEQ ID NO: 9=3:1), without mannitol; and B: lyophilized Zn/compound of SEQ ID NO: 9 (Zn: compound of SEQ ID NO: 9=3:1), with 2.5% w/v mannitol.

Example 37

Synthesis of Zn/Compound of SEQ ID NO: 9 by co-precipitation

The sustained GLP-1 formulations may be made by co-precipitation in aqueous solution as a ready-to-use suspension. To do so, first suspend the compound of SEQ ID NO: 9 in H$_2$O and adjust pH to 8.5 by 2M NaOH to obtain a clear solution with a concentration of 10 mg/mL. Dissolve zinc acetate in H$_2$O, to obtain a concentration of 36 mg/mL and pH is 6.4. Add the zinc acetate solution dropwise into the compound of SEQ ID NO:9 solution and stir vigorously. The suspension obtained has a molar ratio of Zn: compound of SEQ ID NO: 9 of 3:1, and a final pH of about 6.0. The aqueous suspension may further comprise one or more surfactants, suspending agents and/or thickening agents.

What is claimed is:

1. A pharmaceutical composition comprising a GLP-1 receptor modulator selected from SEQ ID NOs: 9, 15, 118, 151 and 158; and a metal ion, a protamine adduct, or a combination thereof.

2. The pharmaceutical composition of claim 1 wherein said metal ion is a divalent cation.

3. The pharmaceutical composition of claim 1, wherein said composition is prepared by spray drying, precipitation, or lyophilization.

4. The pharmaceutical composition of claim 1, wherein said metal ion is a divalent metal cation selected from the group consisting of zinc, manganese, and iron.

5. The pharmaceutical composition of claim 4 wherein said divalent metal cation is zinc.

6. A method for treating a patient afflicted with diabetes, comprising administering to a patient in need thereof, the pharmaceutical composition of claim 1.

7. The method of claim 6, wherein said pharmaceutical composition is administered to a subject by subcutaneous injection or intramuscular injection.

8. The method of claim 6 wherein said composition is administered using a syringe.

9. A kit comprising the pharmaceutical composition of claim 1.

10. The pharmaceutical composition of claim 1 wherein said GLP-1 receptor modulator is the compound of SEQ ID NO: 9.

11. The pharmaceutical composition of claim 1 wherein said GLP-1 receptor modulator is the compound of SEQ ID NO: 15.

12. The pharmaceutical composition of claim 1 wherein said GLP-1 receptor modulator is the compound of SEQ ID NO: 118.

13. The pharmaceutical composition of claim 1 wherein said GLP-1 receptor modulator is the compound of SEQ ID NO: 151.

14. The pharmaceutical composition of claim 1 wherein said GLP-1 receptor modulator is the compound of SEQ ID NO: 158.

15. The pharmaceutical composition of claim 1 further comprising a co-precipitated, lyophilized, or spray dried zinc adduct, in a Zn: GLP-1 receptor modulator ratio of from about 1:10 to about 50:1.

16. The pharmaceutical composition of claim 1 further comprising a co-precipitated, lyophilized, or spray dried zinc adduct, in a Zn: GLP-1 receptor modulator ratio of from about 1:10 to about 50:1, with a weight to volume ratio of surfactants, suspending agents, and/or thickening agents, of 0% to about 30%.

17. The pharmaceutical composition of claim 16 wherein the GLP-1 receptor modulator is the compound of SEQ ID NO: 9.

18. The pharmaceutical composition of claim 16 wherein the GLP-1 receptor modulator is the compound of SEQ ID NO: 158.

19. The pharmaceutical composition of claim 16 wherein the Zn: GLP-1 receptor modulator ratio is about 0.5:1 to about 10:1, and the weight to volume ratio of surfactants, suspending agents, and/or thickening agents, is 0% to about 10%.

20. The pharmaceutical composition of claim 16 wherein the Zn: GLP-1 receptor modulator ratio is about 1.5:1 to about 5:1 and the weight to volume ratio of surfactants is 0% to about 1%, suspending agents is 0% to about 5%, and/or thickening agents is 0% to about 1%.

21. The pharmaceutical composition of claim 20 wherein the GLP-1 receptor modulator is the compound of SEQ ID NO: 9.

22. The pharmaceutical composition of claim 20 wherein the GLP-1 receptor modulator is the compound of SEQ ID NO: 158.

23. A method for making the pharmaceutical composition of claim 1 comprising:

a) obtaining a GLP-1 receptor modulator comprising at least one phenyl-heteroaryl-alanine analog, wherein said GLP-1 receptor modulator is selected from SEQ ID NOs: 9, 15, 118, 151, and 158;
b) suspending said GLP-1 receptor modulator to form a GLP-1 suspension;
c) adjusting the pH of the GLP-1 suspension to about 8.5 to obtain a GLP-1 solution;
d) dissolving zinc acetate in a solution to obtain a zinc acetate solution;
e) adding the zinc acetate solution drop wise, with stirring, to the GLP-1 solution; and
f) obtaining a composition having a molar ratio of zinc:GLP-1 receptor modulator of about 3:1, and having a final pH of about 6.0.

24. The method of claim 23 further comprising the step of adding surfactants, suspending agents, and/or thickening agents.

25. The method of claim 23 wherein said GLP-1 receptor modulator is SEQ ID NO: 9 or SEQ ID NO: 158.

* * * * *

```
                              SEQUENCE LISTING

<160> NUMBER OF SEQ ID NOS: 166

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..()
<223> OTHER INFORMATION: X is aminoisobutyric acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Phe is L-alpha-Me-Phe(2-Fluoro)
<220> FEATURE:
<221> NAME/KEY: MISC_FEATURE
<222> LOCATION: (10)..(10)
<223> OTHER INFORMATION: X is Biphenylalanine(2'-Me)
<220> FEATURE:
<221> NAME/KEY: MISC_FEATURE
<222> LOCATION: (11)..(11)
<223> OTHER INFORMATION: X is 4-(2'-pyridyl)Phenylalanine-NH2

<400> SEQUENCE: 1

His Xaa Glu Gly Thr Phe Thr Ser Asp Xaa Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(3',5'-di-Me)
<220> FEATURE:
<221> NAME/KEY: MISC_FEATURE
<222> LOCATION: (11)..(11)
<223> OTHER INFORMATION: X is 4-(2'-pyridyl)phenylalanine-NH2

<400> SEQUENCE: 2

His Xaa Glu Gly Thr Phe Thr Ser Asp Xaa Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-OBu)
<220> FEATURE:
<221> NAME/KEY: MISC_FEATURE
<222> LOCATION: (11)..(11)
<223> OTHER INFORMATION: X is 4-(2'-pyridyl)phenylalanine-NH2

<400> SEQUENCE: 3

His Xaa Glu Gly Thr Phe Thr Ser Asp Xaa Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Me)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 4

His Xaa Glu Gly Thr Phe Thr Ser Asp Xaa Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Cl)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 5

His Xaa Glu Gly Thr Phe Thr Ser Asp Xaa Xaa
1               5                   10
```

```
<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-methoxy-5'-iso-propyl)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 6

His Xaa Glu Gly Thr Phe Thr Ser Asp Xaa Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(2'-Ethylphenyl)-3-pyridylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 7

His Xaa Glu Gly Thr Phe Thr Ser Asp Xaa Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-[(2'-Ethyl-4'-methoxy)phenyl]-3-
      pyridylalanine
<220> FEATURE:
```

```
<221> NAME/KEY: MISC_FEATURE
<222> LOCATION: (11)..(11)
<223> OTHER INFORMATION: X is biphenylalanine(2'-Me)-NH2

<400> SEQUENCE: 8

His Xaa Glu Gly Thr Phe Thr Ser Asp Xaa Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 9

His Xaa Glu Gly Thr Phe Thr Ser Asp Xaa Xaa
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 10

His Xaa Glu Gly Thr Phe Thr Ser Asp Xaa Xaa
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
```

<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 11

His Xaa Glu Gly Thr Phe Thr Ser Asp Xaa Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 12

His Xaa Glu Gly Thr Phe Thr Ser Asp Xaa Xaa
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 13

His Xaa Glu Gly Thr Phe Thr Ser Asp Xaa Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 14

His Xaa Glu Gly Thr Phe Thr Ser Asp Xaa Xaa
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[3-(4-Methyl)pyridyl)phenylalanine-NH2

<400> SEQUENCE: 15

His Xaa Glu Gly Thr Phe Thr Ser Asp Xaa Xaa
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE

```
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[3-(4-Methyl)pyridyl]phenylalanine-NH2

<400> SEQUENCE: 16

His Xaa Glu Gly Thr Phe Thr Ser Asp Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3-Pyridazyl)phenylalanine-NH2

<400> SEQUENCE: 17

His Xaa Glu Gly Thr Phe Thr Ser Asp Xaa Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3-Pyridazyl)phenylalanine-NH2

<400> SEQUENCE: 18

His Xaa Glu Gly Thr Phe Thr Ser Asp Xaa Xaa
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[3-(4-Me,6-OMe)pyridyl]
      phenylalanine-NH2

<400> SEQUENCE: 19

His Xaa Glu Gly Thr Phe Thr Ser Asp Xaa Xaa
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is 4-[3-(4'-Methyl)pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 20

His Xaa Glu Gly Thr Phe Thr Ser Asp Xaa Xaa
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 21

His Xaa Glu Gly Thr Phe Thr Ser Asp Xaa Xaa
1               5                   10
```

```
<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 22

His Xaa Glu Gly Thr Phe Thr Ser Asp Xaa Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[2(1H)Pyridonyl]phenylalanine-NH2

<400> SEQUENCE: 23

His Xaa Glu Gly Thr Phe Thr Ser Asp Xaa Xaa
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
```

```
<222> LOCATION: (11)..(11)
<223> OTHER INFORMATION: X is biphenylalanine(8-Quinoline)-NH2

<400> SEQUENCE: 24

His Xaa Glu Gly Thr Phe Thr Ser Asp Xaa Xaa
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is biphenylalanine(3-Quinoline)-NH2

<400> SEQUENCE: 25

His Xaa Glu Gly Thr Phe Thr Ser Asp Xaa Xaa
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is biphenylalanine(6-Quinoline)-NH2

<400> SEQUENCE: 26

His Xaa Glu Gly Thr Phe Thr Ser Asp Xaa Xaa
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
```

```
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is biphenylalanine(5-Quinoline)-NH2

<400> SEQUENCE: 27

His Xaa Glu Gly Thr Phe Thr Ser Asp Xaa Xaa
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3-(6-OMe)pyridyl)phenylalanine-NH2

<400> SEQUENCE: 28

His Xaa Glu Gly Thr Phe Thr Ser Asp Xaa Xaa
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3-(2-Methoxy)pyridyl)phenylalanine-NH2

<400> SEQUENCE: 29

His Xaa Glu Gly Thr Phe Thr Ser Asp Xaa Xaa
1               5                   10

<210> SEQ ID NO 30
<211> LENGTH: 11
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-pyridyl)phenylalanine-NH2

<400> SEQUENCE: 30

His Xaa Glu Gly Thr Phe Thr Ser Asp Xaa Xaa
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2,6,di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 31

His Xaa Glu Gly Thr Phe Thr Ser Asp Xaa Xaa
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(5-Quinoline)phenylalanine
<220> FEATURE:
<221> NAME/KEY: MISC_FEATURE
<222> LOCATION: (11)..(11)
```

<223> OTHER INFORMATION: X is biphenylalanine(2'-Me)-NH2

<400> SEQUENCE: 32

His Xaa Glu Gly Thr Phe Thr Ser Asp Xaa Xaa
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-[3-(2'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 33

His Xaa Glu Gly Thr Phe Thr Ser Asp Xaa Xaa
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(6-Quinoline)phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 34

His Xaa Glu Gly Thr Phe Thr Ser Asp Xaa Xaa
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)

```
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is 4-(4'-pyridyl)phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 35

His Xaa Glu Gly Thr Phe Thr Ser Asp Xaa Xaa
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: 4-[4'-(3',5'-dimethylisoxazole)]phenylalanine
<220> FEATURE:
<221> NAME/KEY: MISC_FEATURE
<222> LOCATION: (11)..(11)
<223> OTHER INFORMATION: X is biphenylalanine(2'-Me)-NH2

<400> SEQUENCE: 36

His Xaa Glu Gly Thr Phe Thr Ser Asp Xaa Xaa
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2-trifluoromethylphenyl)-3-
      pyridylalanine-NH2

<400> SEQUENCE: 37

His Xaa Glu Gly Thr Phe Thr Ser Asp Xaa Xaa
1               5                   10

<210> SEQ ID NO 38
<211> LENGTH: 11
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2-methyl-5-fluorophenyl)-3-
      pyridylalanine-NH2

<400> SEQUENCE: 38

His Xaa Glu Gly Thr Phe Thr Ser Asp Xaa Xaa
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4-methanesulfonylphenyl)-3-
      pyridylalanine-NH2

<400> SEQUENCE: 39

His Xaa Glu Gly Thr Phe Thr Ser Asp Xaa Xaa
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: 4-(2'-Methylphenyl)-3-pyridylalanine-NH2
```

```
<400> SEQUENCE: 40

His Xaa Glu Gly Thr Phe Thr Ser Asp Xaa Xaa
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 41

His Xaa Glu Gly Thr Phe Thr Ser Asp Xaa Xaa
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MOD_RES
<222> LOCATION: (5)..(5)
<223> OTHER INFORMATION: Nle
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 42

His Xaa Glu Gly Leu Phe Thr Ser Asp Xaa Xaa
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
```

```
<221> NAME/KEY: MISC_FEATURE
<222> LOCATION: (6)..(6)
<223> OTHER INFORMATION: Phe is L-alpha-Me-Phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[2'-Cl, 4'-CF3)-3'-pyridyl]
      phenylalanine-NH2

<400> SEQUENCE: 43

His Xaa Glu Gly Thr Phe Thr Ser Asp Xaa Xaa
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is Biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[3'-(2'-CN-6'-Me)pyridyl]
      phenylalanine-NH2

<400> SEQUENCE: 44

His Xaa Glu Gly Thr Phe Thr Ser Asp Xaa Xaa
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Cl)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 45

His Xaa Glu Gly Thr Phe Thr Ser Asp Xaa Xaa
1               5                   10

<210> SEQ ID NO 46
```

```
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2',4'-di-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 46

His Xaa Glu Gly Thr Phe Thr Ser Asp Xaa Xaa
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(3'-pyridyl)phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 47

His Xaa Glu Gly Thr Phe Thr Ser Asp Xaa Xaa
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(4'-pyridyl)phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2
```

```
<400> SEQUENCE: 48

His Xaa Glu Gly Thr Phe Thr Ser Asp Xaa Xaa
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Me-3'-F)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 49

His Xaa Glu Gly Thr Phe Thr Ser Asp Xaa Xaa
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-F)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 50

His Xaa Glu Gly Thr Phe Thr Ser Asp Xaa Xaa
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
```

```
<220> FEATURE:
<221> NAME/KEY: MISC_FEATURE
<222> LOCATION: (10)..(10)
<223> OTHER INFORMATION: X is 4-[3'-(2'-Cl-6'-CF3)pyridyl]phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 51

His Xaa Glu Gly Thr Phe Thr Ser Asp Xaa Xaa
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is biphenylalanine(2'-Cl)-NH2

<400> SEQUENCE: 52

His Xaa Glu Gly Thr Phe Thr Ser Asp Xaa Xaa
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is biphenylalanine(3'-Cl-4'-F)-NH2

<400> SEQUENCE: 53

His Xaa Glu Gly Thr Phe Thr Ser Asp Xaa Xaa
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MOD_RES
<222> LOCATION: (5)..(5)
<223> OTHER INFORMATION: Nva
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 54

His Xaa Glu Gly Val Phe Thr Ser Asp Xaa Xaa
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is biphenylalanine(3',5'-di-Me)-NH2

<400> SEQUENCE: 55

His Xaa Glu Gly Thr Phe Thr Ser Asp Xaa Xaa
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine-NH2
<220> FEATURE:
<221> NAME/KEY: MISC_FEATURE
<222> LOCATION: (11)..(11)
<223> OTHER INFORMATION: X is 4-(2',3'-pyridazyl)phenylalanine-NH2
```

```
<400> SEQUENCE: 56

His Xaa Glu Gly Thr Phe Thr Ser Asp Xaa Xaa
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-ethylphenyl)-3-pyridylalanine-NH2

<400> SEQUENCE: 57

His Xaa Glu Gly Thr Phe Thr Ser Asp Xaa Xaa
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine-NH2
<220> FEATURE:
<221> NAME/KEY: MISC_FEATURE
<222> LOCATION: (11)..(11)
<223> OTHER INFORMATION: X is 4-[3'-(2'-Cl-6'-CF3)pyridyl]
      phenylalanine-NH2

<400> SEQUENCE: 58

His Xaa Glu Gly Thr Phe Thr Ser Asp Xaa Xaa
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
```

```
<220> FEATURE:
<221> NAME/KEY: MISC_FEATURE
<222> LOCATION: (10)..(10)
<223> OTHER INFORMATION: X is 4-(2'-ethylphenyl)-3-pyridylalanine
<220> FEATURE:
<221> NAME/KEY: MISC_FEATURE
<222> LOCATION: (11)..(11)
<223> OTHER INFORMATION: X is 4-[3'-(2'-CN-6'-Me)pyridyl]
      phenylalanine-NH2

<400> SEQUENCE: 59

His Xaa Glu Gly Thr Phe Thr Ser Asp Xaa Xaa
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(2'-Cl)-NH2

<400> SEQUENCE: 60

His Xaa Glu Gly Thr Phe Thr Ser Asp Xaa Xaa
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(3'-Cl-4'-F)-NH2

<400> SEQUENCE: 61

His Xaa Glu Gly Thr Phe Thr Ser Asp Xaa Xaa
1               5                   10

<210> SEQ ID NO 62
<211> LENGTH: 11
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(3',5'-di-Me)-NH2

<400> SEQUENCE: 62

His Xaa Glu Gly Thr Phe Thr Ser Asp Xaa Xaa
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me-4'-OMe)-NH2

<400> SEQUENCE: 63

His Xaa Glu Gly Thr Phe Thr Ser Asp Xaa Xaa
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me-3'-F)-NH2

<400> SEQUENCE: 64

His Xaa Glu Gly Thr Phe Thr Ser Asp Xaa Xaa
```

-continued

```
<210> SEQ ID NO 65
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Me)pyridyl]phenylalanine
<220> FEATURE:
<221> NAME/KEY: MISC_FEATURE
<222> LOCATION: (11)..(11)
<223> OTHER INFORMATION: X is biphenylalanine(2'-F)-NH2

<400> SEQUENCE: 65

His Xaa Glu Gly Thr Phe Thr Ser Asp Xaa Xaa
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Cl)-NH2

<400> SEQUENCE: 66

His Xaa Glu Gly Thr Phe Thr Ser Asp Xaa Xaa
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
```

```
<220> FEATURE:
<221> NAME/KEY: MISC_FEATURE
<222> LOCATION: (11)..(11)
<223> OTHER INFORMATION: X is biphenylalanine(3',4'-di-OMe)-NH2

<400> SEQUENCE: 67

His Xaa Glu Gly Thr Phe Thr Ser Asp Xaa Xaa
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is 4-(2'-pyridyl)phenylalanine-NH2

<400> SEQUENCE: 68

His Xaa Glu Gly Thr Phe Thr Ser Asp Xaa Xaa
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is biphenylalanine(2'-Me-4'-OMe)-NH2

<400> SEQUENCE: 69

His Xaa Glu Gly Thr Phe Thr Ser Asp Xaa Xaa
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
```

```
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(4'-Me-6'-OMe)-3-pyridyl]phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 70

His Xaa Glu Gly Thr Phe Thr Ser Asp Xaa Xaa
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-ethylphenyl)-3-pyridylalanine-NH2

<400> SEQUENCE: 71

His Xaa Glu Gly Thr Phe Thr Ser Asp Xaa Xaa
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[3'-(4'-Methyl)pyridyl)]phenylalanine
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 72

His Xaa Glu Gly Thr Phe Thr Ser Asp Xaa Xaa
1               5                   10

<210> SEQ ID NO 73
<211> LENGTH: 11
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-pyridyl)phenylalanine-NH2

<400> SEQUENCE: 73

His Xaa Glu Gly Thr Phe Thr Ser Asp Xaa Xaa
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-quinoline)phenylalanine-NH2

<400> SEQUENCE: 74

His Xaa Glu Gly Thr Phe Thr Ser Asp Xaa Xaa
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-(2'-Methoxy)pyridyl)
        phenylalanine-NH2
```

<400> SEQUENCE: 75

His Xaa Glu Gly Thr Phe Thr Ser Asp Xaa Xaa
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-phenyl-3-pyridylalanine-NH2

<400> SEQUENCE: 76

His Xaa Glu Gly Thr Phe Thr Ser Asp Xaa Xaa
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3',5'-dimethylphenyl)-3-pyridylalanine-
    NH2

<400> SEQUENCE: 77

His Xaa Glu Gly Thr Phe Thr Ser Asp Xaa Xaa
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)

```
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3'-chloro-4'-fluoro)phenyl]-3-
      pyridylalanine-NH2

<400> SEQUENCE: 78

His Xaa Glu Gly Thr Phe Thr Ser Asp Xaa Xaa
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3',4'-dimethoxy)phenyl]-3-
      pyridylalanine-NH2

<400> SEQUENCE: 79

His Xaa Glu Gly Thr Phe Thr Ser Asp Xaa Xaa
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(2'-ethyl-4'-methoxy)phenyl]-3-
      pyridylalanine-NH2

<400> SEQUENCE: 80

His Xaa Glu Gly Thr Phe Thr Ser Asp Xaa Xaa
1               5                   10

<210> SEQ ID NO 81
<211> LENGTH: 11
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-imidazole-lactyl
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 81

Xaa Xaa Glu Gly Thr Phe Thr Ser Asp Xaa Xaa
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 2-(5-o-Tolyl)thienylalanine-NH2

<400> SEQUENCE: 82

His Xaa Glu Gly Thr Phe Thr Ser Asp Xaa Xaa
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
```

```
<221> NAME/KEY: MISC_FEATURE
<222> LOCATION: (11)..(11)
<223> OTHER INFORMATION: X is 2-[(5-(3'-Methoxy)phenyl]thienylalanine-
      NH2

<400> SEQUENCE: 83

His Xaa Glu Gly Thr Phe Thr Ser Asp Xaa Xaa
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 2-[(5-(3',5'-di-Methyl)phenyl]
      thienylalanine-NH2

<400> SEQUENCE: 84

His Xaa Glu Gly Thr Phe Thr Ser Asp Xaa Xaa
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 2-[(5-(3'-Cl,5'-F)phenyl]thienylalanine-
      NH2

<400> SEQUENCE: 85

His Xaa Glu Gly Thr Phe Thr Ser Asp Xaa Xaa
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Isopropoxyphenyl)-3-pyridylalanine-
      NH2

<400> SEQUENCE: 86

His Xaa Glu Gly Thr Phe Thr Ser Asp Xaa Xaa
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methyl, 5'-Fluoro)phenyl)-3-
      pyridylalanine-NH2

<400> SEQUENCE: 87

His Xaa Glu Gly Thr Phe Thr Ser Asp Xaa Xaa
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Isopropoxyphenyl)-3-pyridylalanine-
      NH2

<400> SEQUENCE: 88

His Xaa Glu Gly Thr Phe Thr Ser Asp Xaa Xaa
```

```
1               5               10
```

<210> SEQ ID NO 89
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 3-(4-Br)pyridylalanine-NH2

<400> SEQUENCE: 89

His Xaa Glu Gly Thr Phe Thr Ser Asp Xaa Xaa
1               5               10

<210> SEQ ID NO 90
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Methoxyphenyl)-3-pyridylalanine-NH2

<400> SEQUENCE: 90

His Xaa Glu Gly Thr Phe Thr Ser Asp Xaa Xaa
1               5               10

<210> SEQ ID NO 91
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)

```
<220> FEATURE:
<221> NAME/KEY: MISC_FEATURE
<222> LOCATION: (11)..(11)
<223> OTHER INFORMATION: X is 4-(2'-Methyl, 4'-Fluoro)phenyl)-3-
      pyridylalanine-NH2

<400> SEQUENCE: 91

His Xaa Glu Gly Thr Phe Thr Ser Asp Xaa Xaa
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 92

His Xaa Glu Gly Thr Phe Thr Ser Asp Xaa Xaa
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Trifluoromethoxyphenyl)-3-
      pyridylalanine-NH2

<400> SEQUENCE: 93

His Xaa Glu Gly Thr Phe Thr Ser Asp Xaa Xaa
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Trifluoromethoxyphenyl)-3-
      pyridylalanine-NH2

<400> SEQUENCE: 94

His Xaa Glu Gly Thr Phe Thr Ser Asp Xaa Xaa
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 3-pyridylalanine-NH2

<400> SEQUENCE: 95

His Xaa Glu Gly Thr Phe Thr Ser Asp Xaa Xaa
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methyl,4'-Chloro)phenyl)-3-
      pyridylalanine-NH2

<400> SEQUENCE: 96

His Xaa Glu Gly Thr Phe Thr Ser Asp Xaa Xaa
1               5                   10
```

<210> SEQ ID NO 97
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Me-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 97

His Xaa Glu Gly Thr Phe Thr Ser Asp Xaa Xaa
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Trifluoromethylphenyl)-3-
      pyridylalanine-NH2

<400> SEQUENCE: 98

His Xaa Glu Gly Thr Phe Thr Ser Asp Xaa Xaa
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)

```
<220> FEATURE:
<221> NAME/KEY: MISC_FEATURE
<222> LOCATION: (11)..(11)
<223> OTHER INFORMATION: X is 4-(4'-Fluorophenyl)-3-pyridylalanine-NH2

<400> SEQUENCE: 99

His Xaa Glu Gly Thr Phe Thr Ser Asp Xaa Xaa
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Trifluoromethylphenyl)-3-
     pyridylalanine-NH2

<400> SEQUENCE: 100

His Xaa Glu Gly Thr Phe Thr Ser Asp Xaa Xaa
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Chlorophenyl)-3-pyridylalanine-NH2

<400> SEQUENCE: 101

His Xaa Glu Gly Thr Phe Thr Ser Asp Xaa Xaa
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
```

```
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Chlorophenyl)-3-pyridylalanine-NH2

<400> SEQUENCE: 102

His Xaa Glu Gly Thr Phe Thr Ser Asp Xaa Xaa
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Isopropylphenyl)-3-pyridylalanine-
      NH2

<400> SEQUENCE: 103

His Xaa Glu Gly Thr Phe Thr Ser Asp Xaa Xaa
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3',5'-dimethylisoxazol-4'-yl)-3-
      pyridylalanine-NH2

<400> SEQUENCE: 104

His Xaa Glu Gly Thr Phe Thr Ser Asp Xaa Xaa
1               5                   10
```

```
<210> SEQ ID NO 105
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(2'-Methyl-4'-methoxy)phenyl]-3-
     pyridylalanine-NH2

<400> SEQUENCE: 105

His Xaa Glu Gly Thr Phe Thr Ser Asp Xaa Xaa
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Trifluoromethylphenyl)-3-
     pyridylalanine-NH2

<400> SEQUENCE: 106

His Xaa Glu Gly Thr Phe Thr Ser Asp Xaa Xaa
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
```

```
<220> FEATURE:
<221> NAME/KEY: MISC_FEATURE
<222> LOCATION: (11)..(11)
<223> OTHER INFORMATION: X is 4-(4'-Chlorophenyl)-3-pyridylalanine-NH2

<400> SEQUENCE: 107

His Xaa Glu Gly Thr Phe Thr Ser Asp Xaa Xaa
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(4'-Pyridyl)-3-pyridylalanine-NH2

<400> SEQUENCE: 108

His Xaa Glu Gly Thr Phe Thr Ser Asp Xaa Xaa
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 109

His Xaa Glu Gly Thr Phe Thr Ser Asp Xaa Xaa
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
```

```
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(6'-Methoxypyridin-3'-yl)-3-
      pyridylalanine-NH2

<400> SEQUENCE: 110

His Xaa Glu Gly Thr Phe Thr Ser Asp Xaa Xaa
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Isopropylphenyl)-3-pyridylalanine-
      NH2

<400> SEQUENCE: 111

His Xaa Glu Gly Thr Phe Thr Ser Asp Xaa Xaa
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methoxyphenyl)-3-pyridylalanine-NH2

<400> SEQUENCE: 112

His Xaa Glu Gly Thr Phe Thr Ser Asp Xaa Xaa
1               5                   10
```

```
<210> SEQ ID NO 113
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-[(3',5'-di-Fluoro-2'-methoxy)phenyl]-3-
     pyridylalanine-NH2

<400> SEQUENCE: 113

His Xaa Glu Gly Thr Phe Thr Ser Asp Xaa Xaa
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-methylphenyl)-3-pyridylalanine-NH2

<400> SEQUENCE: 114

His Xaa Glu Gly Thr Phe Thr Ser Asp Xaa Xaa
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
```

```
<222> LOCATION: (11)..(11)
<223> OTHER INFORMATION: X is 4-(2'-fluorophenyl)-3-pyridylalanine-NH2

<400> SEQUENCE: 115

His Xaa Glu Gly Thr Phe Thr Ser Asp Xaa Xaa
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-fluorophenyl)-3-pyridylalanine-NH2

<400> SEQUENCE: 116

His Xaa Glu Gly Thr Phe Thr Ser Asp Xaa Xaa
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 117

His Xaa Glu Gly Thr Phe Thr Ser Asp Xaa Xaa
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
```

```
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 118

His Pro Glu Gly Thr Phe Thr Ser Asp Xaa Xaa
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 119

His Ala Glu Gly Thr Phe Thr Ser Asp Xaa Xaa
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 120

His Pro Glu Gly Thr Phe Thr His Asp Xaa Xaa
1               5                   10

<210> SEQ ID NO 121
<211> LENGTH: 11
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is (S)-4-(2'-Methylphenyl)-alpha-Me-3-
      pyridylalanine-NH2

<400> SEQUENCE: 121

His Pro Glu Gly Thr Phe Thr Ser Asp Xaa Xaa
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is (S)-4-(2'-Methylphenyl)-alpha-Me-3-
      pyridylalanine-NH2

<400> SEQUENCE: 122

His Xaa Glu Gly Thr Phe Thr Ser Asp Xaa Xaa
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2
```

```
<400> SEQUENCE: 123

His Pro Glu Gly Thr Phe Thr Ser Asp Xaa Xaa
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 124

His Pro Glu Gly Thr Phe Thr His Asp Xaa Xaa
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 125

His Pro Glu Gly Thr Phe Thr Ser Asp Xaa Xaa
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
```

```
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 126

His Pro Glu Gly Thr Phe Thr Ser Asp Xaa Xaa
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 127

His Pro Glu Gly Thr Phe Thr Ser Asp Xaa Xaa
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 128

His Pro Glu Gly Thr Phe Thr Ser Asp Xaa Xaa
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (2)..(2)
<223> OTHER INFORMATION: Ala is N-Me-(L)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 129

His Ala Glu Gly Thr Phe Thr Ser Asp Xaa Xaa
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3,5-pyrimidylalanine-
    NH2

<400> SEQUENCE: 130

His Xaa Glu Gly Thr Phe Thr Ser Asp Xaa Xaa
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 131

His Pro Asp Gly Thr Phe Thr Ser Asp Xaa Xaa
1               5                   10
```

```
<210> SEQ ID NO 132
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et)
<220> FEATURE:
<221> NAME/KEY: MISC_FEATURE
<222> LOCATION: (11)..(11)
<223> OTHER INFORMATION: X is 4-(2'-Ethylphenyl)-3-pyridylalanine-NH2

<400> SEQUENCE: 132

His Pro Glu Gly Thr Phe Thr Ser Asp Xaa Xaa
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 133

His Pro Glu Gly Thr Phe Thr Ser Asp Xaa Xaa
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
```

```
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 134

His Pro Glu Gly Thr Phe Thr Ser Asp Xaa Xaa
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Fluorophenyl)-3-pyridylalanine-NH2

<400> SEQUENCE: 135

His Pro Glu Gly Thr Phe Thr Ser Asp Xaa Xaa
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is Des-NH2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-Methoxyphenyl)-3-pyridylalanine-NH2

<400> SEQUENCE: 136
```

```
His Pro Glu Gly Thr Phe Thr Ser Asp Xaa Xaa
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 137

Xaa Xaa Glu Gly Thr Phe Thr Ser Asp Xaa Xaa
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 138

Xaa Xaa Glu Gly Thr Phe Thr Ser Asp Xaa Xaa
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 139

His Pro Glu Gly Thr Phe Thr Ser Asp Xaa Xaa
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 140

His Pro Glu Gly Thr Phe Thr Ser Asp Xaa Xaa
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
```

```
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 141

His Ala Glu Gly Thr Phe Thr Ser Asp Xaa Xaa
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-(D)-Ala
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 142

His Ala Glu Gly Thr Phe Thr Ser Asp Xaa Xaa
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3SO2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 143

His Pro Glu Gly Thr Phe Thr Ser Asp Xaa Xaa
1               5                   10
```

```
<210> SEQ ID NO 144
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3SO2-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 144

His Pro Glu Gly Thr Phe Thr Ser Asp Xaa Xaa
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is L-Lactyl-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 145

His Pro Glu Gly Thr Phe Thr Ser Asp Xaa Xaa
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is L-Lactyl-His
<220> FEATURE:
<221> NAME/KEY: MISC_FEATURE
```

```
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 146

His Pro Glu Gly Thr Phe Thr Ser Asp Xaa Xaa
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3',5'-di-Me)phenyl)-3-pyridylalanine-
      NH2

<400> SEQUENCE: 147

His Xaa Glu Gly Thr Phe Thr Ser Asp Xaa Xaa
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 148

His Xaa Glu Gly Thr Phe Thr His Asp Xaa Xaa
1               5                   10
```

```
<210> SEQ ID NO 149
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Ala is D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 149

His Ala Glu Gly Thr Phe Thr Ser Asp Xaa Xaa
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 150

His Xaa His Gly Thr Phe Thr Ser Asp Xaa Xaa
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
```

```
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 151

Xaa Pro Glu Gly Thr Phe Thr His Asp Xaa Xaa
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 152

Xaa Pro Glu Gly Thr Phe Thr Ser Asp Xaa Xaa
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 153

Xaa Pro Glu Gly Thr Phe Thr His Asp Xaa Xaa
1               5                   10
```

```
<210> SEQ ID NO 154
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 154

Xaa Pro Glu Gly Thr Phe Thr Ser Asp Xaa Xaa
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 155

Xaa Ala Glu Gly Thr Phe Thr His Asp Xaa Xaa
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is L-beta-Imidazole-lactyl
<220> FEATURE:
<221> NAME/KEY: MISC_FEATURE
<222> LOCATION: (2)..(2)
```

```
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 156

Xaa Ala Glu Gly Thr Phe Thr Ser Asp Xaa Xaa
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 157

His Pro Glu Gly Thr Phe Thr His Asp Xaa Xaa
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Pro is (S)-alpha-Me-Pro
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2
```

```
<400> SEQUENCE: 158

His Pro Glu Gly Thr Phe Thr Ser Asp Xaa Xaa
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 159

His Ala Glu Gly Thr Phe Thr His Asp Xaa Xaa
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: Ala is N-Me-D-Ala
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 160

His Ala Glu Gly Thr Phe Thr Ser Asp Xaa Xaa
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 161

His Xaa Glu Gly Thr Phe Thr His Asp Xaa Xaa
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: His is CH3O-CO-His
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OH)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 162

His Xaa Glu Gly Thr Phe Thr Ser Asp Xaa Xaa
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2,6-di-Fluoro)
<220> FEATURE:
<221> NAME/KEY: MISC_FEATURE
<222> LOCATION: (10)..(10)
<223> OTHER INFORMATION: X is 4-[(2'-CL1-4'-CF3)-3'-pyridyl]
      -phenylalanine
```

```
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 163

His Xaa Glu Gly Thr Phe Thr Ser Asp Xaa Xaa
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(3'-(2'-Methoxy)pyridyl)phenylalanine-
      NH2

<400> SEQUENCE: 164

His Xaa Glu Gly Thr Phe Thr Ser Asp Xaa Xaa
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (R)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 165

Xaa Xaa Glu Gly Thr Phe Thr His Asp Xaa Xaa
1               5                   10

<210> SEQ ID NO 166
<211> LENGTH: 11
<212> TYPE: PRT
<213> ORGANISM: Artificial Sequence
```

```
-continued

<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is (S)-3-(1-imidazol-4-yl)-2-methylpropionic
      acid
<220> FEATURE:
<221> NAME/KEY: MISC_FEATURE
<222> LOCATION: (2)..(2)
<223> OTHER INFORMATION: X is aminoisobutyric acid
<220> FEATURE:
<221> NAME/KEY: MISC_FEATURE
<222> LOCATION: (6)..(6)
<223> OTHER INFORMATION: Phe is L-alpha-Me-Phe(2-Fluoro)
<220> FEATURE:
<221> NAME/KEY: MISC_FEATURE
<222> LOCATION: (10)..(10)
<223> OTHER INFORMATION: X is biphenylalanine(2'-Et-4'-OMe)
<220> FEATURE:
<221> NAME/KEY: MISC_FEATURE
<222> LOCATION: (11)..(11)
<223> OTHER INFORMATION: X is 4-(2'-Methylphenyl)-3-pyridylalanine-NH2

<400> SEQUENCE: 166

Xaa Xaa Glu Gly Thr Phe Thr His Asp Xaa Xaa
1               5                   10
```